US012564632B2

(12) United States Patent
Liu et al.

(10) Patent No.: US 12,564,632 B2
(45) Date of Patent: Mar. 3, 2026

(54) CONJUGATES OF BIOMOLECULE AND USE THEREOF

(71) Applicant: YAFEI SHANGHAI BIOLOG MEDICINE SCIENCE & TECHNOLOGY CO., LTD., Shanghai (CN)

(72) Inventors: Yuan Liu, Shanghai (CN); Haiyang Wang, Shanghai (CN); Renke Li, Shanghai (CN); Rui Zhang, Shanghai (CN); Cheng Liu, Shanghai (CN)

(73) Assignee: Yafei Shanghai Biolog Medicine Science & Technology Co., Ltd., Shanghai (CN)

( * ) Notice: Subject to any disclaimer, the term of this patent is extended or adjusted under 35 U.S.C. 154(b) by 1349 days.

(21) Appl. No.: 16/761,477

(22) PCT Filed: Nov. 7, 2018

(86) PCT No.: PCT/CN2018/114266
§ 371 (c)(1),
(2) Date: May 4, 2020

(87) PCT Pub. No.: WO2019/091384
PCT Pub. Date: May 16, 2019

(65) Prior Publication Data

US 2023/0158141 A1 May 25, 2023

Related U.S. Application Data

(60) Provisional application No. 62/583,410, filed on Nov. 8, 2017.

(51) Int. Cl.

| | |
|---|---|
| ***A61K 39/395*** | (2006.01) |
| ***A61K 38/00*** | (2006.01) |
| ***A61K 39/00*** | (2006.01) |
| ***A61K 47/60*** | (2017.01) |
| ***C07K 14/52*** | (2006.01) |
| ***C07K 16/24*** | (2006.01) |
| ***C07K 16/28*** | (2006.01) |
| ***C07K 16/32*** | (2006.01) |

(52) U.S. Cl.
CPC ............ *A61K 39/395* (2013.01); *A61K 47/60* (2017.08); *C07K 16/241* (2013.01); *C07K 16/2809* (2013.01); *C07K 16/2818* (2013.01); *C07K 16/2827* (2013.01); *C07K 16/2878* (2013.01); *C07K 16/2887* (2013.01); *C07K 16/32* (2013.01); *A61K 38/00* (2013.01); *A61K 2039/505* (2013.01); *C07K 14/52* (2013.01); *C07K 2317/24* (2013.01); *C07K 2317/565* (2013.01); *C07K 2317/567* (2013.01); *C07K 2317/622* (2013.01); *C07K 2317/76* (2013.01); *C07K 2317/92* (2013.01); *C07K 2317/94* (2013.01); *C07K 2319/00* (2013.01)

(58) Field of Classification Search
None
See application file for complete search history.

(56) References Cited

U.S. PATENT DOCUMENTS

| | | | | |
|---|---|---|---|---|
| 7,635,472 | B2 * | 12/2009 | Kufer ...................... | A61P 35/02 424/130.1 |
| 2006/0063209 | A1 | 3/2006 | Meares et al. | |
| 2010/0069616 | A1 * | 3/2010 | Wu ................. | G01N 33/57492 530/391.1 |
| 2012/0009621 | A1 | 1/2012 | Yamasaki et al. | |

(Continued)

FOREIGN PATENT DOCUMENTS

| | | |
|---|---|---|
| CN | 102321239 | 1/2012 |
| CN | 104147612 | 11/2014 |

(Continued)

OTHER PUBLICATIONS

Chapman et al. PEGylated antibodies and antibody fragments for improved therapy: a review. Advanced Drug Delivery Reviews 54 (2002) 531-545. (Year: 2002).*

(Continued)

*Primary Examiner* — Julie Wu
*Assistant Examiner* — Amy M. Chattin
(74) *Attorney, Agent, or Firm* — Lewis Kohn & Walker LLP; David M. Kohn; Kari Moyer-Henry

(57) ABSTRACT

Disclosed are conjugates of biomolecule and use thereof. The disclosed conjugates of biomolecule contain a biomolecule and a functional moiety covalently linked to the biomolecule. The functional moiety contains a group that prevents the biomolecule from binding to its ligand or receptor, a cleavable linker arm that can be activated by proteolytic enzymes or can be acidically activated in a microenvironment of a disease, a linker arm that will automatically shed after the cleavable linker arm is cleaved, and a group that maintains or promotes the binding capacity of the biomolecule to its ligand or receptor. The conjugates of biomolecule of the present disclosure can effectively reduce immunogenicity of the biomolecule, increase it's half-life, and break through the immune barrier of an individual, reach a pathologic microenvironment and be activated and released in the pathologic microenvironment, selectively promoting proliferation or killing effect of T cells and the like in the tumor, thereby preventing on target off tumor toxicity or in the inflammatory microenvironment of autoimmune disease and achieving a low autoimmunity and high efficacy.

17 Claims, 17 Drawing Sheets

Specification includes a Sequence Listing.

(56) References Cited

U.S. PATENT DOCUMENTS

| | | | | |
|---|---|---|---|---|
| 2015/0031046 | A1 | 1/2015 | Dai | |
| 2017/0252458 | A1 | 9/2017 | Albone et al. | |
| 2020/0129639 | A1* | 4/2020 | Levengood | A61K 47/6809 |

FOREIGN PATENT DOCUMENTS

| | | | | |
|---|---|---|---|---|
| CN | 104177474 | | 12/2014 | |
| CN | 104829729 | A * | 8/2015 | |
| WO | 199012874 | | 4/1990 | |
| WO | 200162300 | | 8/2001 | |
| WO | 2004091517 | | 10/2004 | |
| WO | 2006121168 | | 11/2006 | |
| WO | 2007056083 | | 5/2007 | |
| WO | 2007064759 | | 6/2007 | |
| WO | 2012007880 | | 1/2012 | |
| WO | WO-2012065086 | A1 * | 5/2012 | A61K 38/2013 |
| WO | WO-2016059622 | A2 * | 4/2016 | A61K 47/6803 |

OTHER PUBLICATIONS

Dall and Brandstetter. Structure and function of legumain in health and disease. Biochimie 122 (2016) 126-150. Available online Sep. 25, 2015. (Year: 2016).*

Acchione et al. Impact of linker and conjugation chemistry on antigen binding, Fc receptor binding and thermal stability of model antibody-drug conjugates. mAbs 4:3, 362-372; May/Jun. 2012. (Year: 2009).*

Sela-Culang et al. Sela-Culang et al. The structural basis of antibody-antigen recognition. Fron. Immuno., vol. 4, Article 302, Oct. 2013. (Year: 2013).*

Koenig et al. Mutational landscape of antibody variable domains reveals a switch modulating the interdomain conformational dynamics and antigen binding. PNAS, E486-E4995, Jan. 5, 2017. (Year: 2017).*

Herold et al. Determinants of the assembly and function of antibody variable domains. Nature Scientific Reports, 7:12276, Sep. 25, 2017. (Year: 2017).*

Office Action dated Oct. 4, 2022, issued for corresponding Japanese Patent Application No. 2020-544093.

Singh et al. "Antibody-Drug Conjugates: Design, Formulation and Physiochemical Stability." (2015) Pharm Res 32:3541-3571.

Shen et al. "Conjugation site modulates the in vivo stability and therapeutic activity of antibody-drug conjugates." (2012) Nature Biotechnology 30(2):184-191.

Nunes et al. "Use of a next generation maleimide in combination with Thiomab antibody technology delivers a highly stable, potent and near homogeneous Thiomab antibody-drug conjugate." RSC Advances (2017) 7:24828-24832.

Office Action dated Mar. 29, 2023, issued for corresponding Japanese Patent Application No. 2020-544093.

Trail et al. "Cure of Xenografted Human Carcinomas by BR96-Doxorubicin Immunoconjugates." (1993) Science 261:212-215.

Shen et al. "Conjugation site modulates the in vivo stability and therapeutic activity of antibody-drug conjugates." (Feb. 2012) Nature Biotechnology 30(2):184.

* cited by examiner

| Group | CR |
|---|---|
| Saline | 0 |
| PD-1 | 16.7% |
| IL-2 | 16.7% |
| IL-2 TMEAkine | 33% |
| IL-2 TMEAkine +PD-1 | 100% |

SEQUENCE LISTING

```
<160> NUMBER OF SEQ ID NOS: 105

<210> SEQ ID NO 1
<211> LENGTH: 447
<212> TYPE: PRT
<213> ORGANISM: Artificial Sequence
<220> FEATURE:
<223> OTHER INFORMATION: heavy chain of anti-PD-1 antibody

<400> SEQUENCE: 1

Gln Val Gln Leu Val Gln Ser Gly Val Glu Val Lys Lys Pro Gly Ala
1               5                   10                  15

Ser Val Lys Val Ser Cys Lys Ala Ser Gly Tyr Thr Phe Thr Asn Tyr
            20                  25                  30

Tyr Met Tyr Trp Val Arg Gln Ala Pro Gly Gln Gly Leu Glu Trp Met
        35                  40                  45

Gly Gly Ile Asn Pro Ser Asn Gly Gly Thr Asn Phe Asn Glu Lys Phe
    50                  55                  60

Lys Asn Arg Val Thr Leu Thr Thr Asp Ser Ser Thr Thr Thr Ala Tyr
65                  70                  75                  80

Met Glu Leu Lys Ser Leu Gln Phe Asp Asp Thr Ala Val Tyr Tyr Cys
                85                  90                  95

Ala Arg Arg Asp Tyr Arg Phe Asp Met Gly Phe Asp Tyr Trp Gly Gln
            100                 105                 110

Gly Thr Thr Val Thr Val Ser Ser Ala Ser Thr Lys Gly Pro Ser Val
        115                 120                 125
```

```
Phe Pro Leu Ala Pro Cys Ser Arg Ser Thr Ser Glu Ser Thr Ala Ala
    130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
                165                 170                 175

Leu Gln Ser Ser Gly Leu Tyr Ser Leu Ser Ser Val Val Thr Val Pro
            180                 185                 190

Ser Ser Ser Leu Gly Thr Lys Thr Tyr Thr Cys Asn Val Asp His Lys
        195                 200                 205

Pro Ser Asn Thr Lys Val Asp Lys Arg Val Glu Ser Lys Tyr Gly Pro
    210                 215                 220

Pro Cys Pro Pro Cys Pro Ala Pro Glu Phe Leu Gly Gly Pro Ser Val
225                 230                 235                 240

Phe Leu Phe Pro Pro Lys Pro Lys Asp Thr Leu Met Ile Ser Arg Thr
                245                 250                 255

Pro Glu Val Thr Cys Val Val Val Asp Val Ser Gln Glu Asp Pro Glu
            260                 265                 270

Val Gln Phe Asn Trp Tyr Val Asp Gly Val Glu Val His Asn Ala Lys
        275                 280                 285

Thr Lys Pro Arg Glu Glu Gln Phe Asn Ser Thr Tyr Arg Val Val Ser
    290                 295                 300

Val Leu Thr Val Leu His Gln Asp Trp Leu Asn Gly Lys Glu Tyr Lys
305                 310                 315                 320

Cys Lys Val Ser Asn Lys Gly Leu Pro Ser Ser Ile Glu Lys Thr Ile
                325                 330                 335

Ser Lys Ala Lys Gly Gln Pro Arg Glu Pro Gln Val Tyr Thr Leu Pro
            340                 345                 350

Pro Ser Gln Glu Glu Met Thr Lys Asn Gln Val Ser Leu Thr Cys Leu
        355                 360                 365

Val Lys Gly Phe Tyr Pro Ser Asp Ile Ala Val Glu Trp Glu Ser Asn
    370                 375                 380

Gly Gln Pro Glu Asn Asn Tyr Lys Thr Thr Pro Pro Val Leu Asp Ser
385                 390                 395                 400

Asp Gly Ser Phe Phe Leu Tyr Ser Arg Leu Thr Val Asp Lys Ser Arg
                405                 410                 415

Trp Gln Glu Gly Asn Val Phe Ser Cys Ser Val Met His Glu Ala Leu
            420                 425                 430

His Asn His Tyr Thr Gln Lys Ser Leu Ser Leu Ser Leu Gly Lys
        435                 440                 445


<210> SEQ ID NO 2
<211> LENGTH: 218
<212> TYPE: PRT
<213> ORGANISM: Artificial Sequence
<220> FEATURE:
<223> OTHER INFORMATION: light chain of anti-PD-1 antibody

<400> SEQUENCE: 2

Glu Ile Val Leu Thr Gln Ser Pro Ala Thr Leu Ser Leu Ser Pro Gly
1               5                   10                  15

Glu Arg Ala Thr Leu Ser Cys Arg Ala Ser Lys Gly Val Ser Thr Ser
            20                  25                  30

Gly Tyr Ser Tyr Leu His Trp Tyr Gln Gln Lys Pro Gly Gln Ala Pro
        35                  40                  45
```

-continued

```
Arg Leu Leu Ile Tyr Leu Ala Ser Tyr Leu Glu Ser Gly Val Pro Ala
    50                  55                  60

Arg Phe Ser Gly Ser Gly Ser Gly Thr Asp Phe Thr Leu Thr Ile Ser
65                  70                  75                  80

Ser Leu Glu Pro Glu Asp Phe Ala Val Tyr Tyr Cys Gln His Ser Arg
                85                  90                  95

Asp Leu Pro Leu Thr Phe Gly Gly Gly Thr Lys Val Glu Ile Lys Arg
            100                 105                 110

Thr Val Ala Ala Pro Ser Val Phe Ile Phe Pro Pro Ser Asp Glu Gln
        115                 120                 125

Leu Lys Ser Gly Thr Ala Ser Val Val Cys Leu Leu Asn Asn Phe Tyr
    130                 135                 140

Pro Arg Glu Ala Lys Val Gln Trp Lys Val Asp Asn Ala Leu Gln Ser
145                 150                 155                 160

Gly Asn Ser Gln Glu Ser Val Thr Glu Gln Asp Ser Lys Asp Ser Thr
                165                 170                 175

Tyr Ser Leu Ser Ser Thr Leu Thr Leu Ser Lys Ala Asp Tyr Glu Lys
            180                 185                 190

His Lys Val Tyr Ala Cys Glu Val Thr His Gln Gly Leu Ser Ser Pro
        195                 200                 205

Val Thr Lys Ser Phe Asn Arg Gly Glu Cys
    210                 215


<210> SEQ ID NO 3
<211> LENGTH: 440
<212> TYPE: PRT
<213> ORGANISM: Artificial Sequence
<220> FEATURE:
<223> OTHER INFORMATION: heavy chain of anti-PD-1 antibody

<400> SEQUENCE: 3

Gln Val Gln Leu Val Glu Ser Gly Gly Gly Val Val Gln Pro Gly Arg
1               5                   10                  15

Ser Leu Arg Leu Asp Cys Lys Ala Ser Gly Ile Thr Phe Ser Asn Ser
            20                  25                  30

Gly Met His Trp Val Arg Gln Ala Pro Gly Lys Gly Leu Glu Trp Val
        35                  40                  45

Ala Val Ile Trp Tyr Asp Gly Ser Lys Arg Tyr Tyr Ala Asp Ser Val
    50                  55                  60

Lys Gly Arg Phe Thr Ile Ser Arg Asp Asn Ser Lys Asn Thr Leu Phe
65                  70                  75                  80

Leu Gln Met Asn Ser Leu Arg Ala Glu Asp Thr Ala Val Tyr Tyr Cys
                85                  90                  95

Ala Thr Asn Asp Asp Tyr Trp Gly Gln Gly Thr Leu Val Thr Val Ser
            100                 105                 110

Ser Ala Ser Thr Lys Gly Pro Ser Val Phe Pro Leu Ala Pro Cys Ser
        115                 120                 125

Arg Ser Thr Ser Glu Ser Thr Ala Ala Leu Gly Cys Leu Val Lys Asp
    130                 135                 140

Tyr Phe Pro Glu Pro Val Thr Val Ser Trp Asn Ser Gly Ala Leu Thr
145                 150                 155                 160

Ser Gly Val His Thr Phe Pro Ala Val Leu Gln Ser Ser Gly Leu Tyr
                165                 170                 175

Ser Leu Ser Ser Val Val Thr Val Pro Ser Ser Ser Leu Gly Thr Lys
            180                 185                 190
```

-continued

```
Thr Tyr Thr Cys Asn Val Asp His Lys Pro Ser Asn Thr Lys Val Asp
        195                 200                 205

Lys Arg Val Glu Ser Lys Tyr Gly Pro Pro Cys Pro Pro Cys Pro Ala
    210                 215                 220

Pro Glu Phe Leu Gly Gly Pro Ser Val Phe Leu Phe Pro Pro Lys Pro
225                 230                 235                 240

Lys Asp Thr Leu Met Ile Ser Arg Thr Pro Glu Val Thr Cys Val Val
                245                 250                 255

Val Asp Val Ser Gln Glu Asp Pro Glu Val Gln Phe Asn Trp Tyr Val
            260                 265                 270

Asp Gly Val Glu Val His Asn Ala Lys Thr Lys Pro Arg Glu Glu Gln
        275                 280                 285

Phe Asn Ser Thr Tyr Arg Val Val Ser Val Leu Thr Val Leu His Gln
    290                 295                 300

Asp Trp Leu Asn Gly Lys Glu Tyr Lys Cys Lys Val Ser Asn Lys Gly
305                 310                 315                 320

Leu Pro Ser Ser Ile Glu Lys Thr Ile Ser Lys Ala Lys Gly Gln Pro
                325                 330                 335

Arg Glu Pro Gln Val Tyr Thr Leu Pro Pro Ser Gln Glu Glu Met Thr
            340                 345                 350

Lys Asn Gln Val Ser Leu Thr Cys Leu Val Lys Gly Phe Tyr Pro Ser
        355                 360                 365

Asp Ile Ala Val Glu Trp Glu Ser Asn Gly Gln Pro Glu Asn Asn Tyr
    370                 375                 380

Lys Thr Thr Pro Pro Val Leu Asp Ser Asp Gly Ser Phe Phe Leu Tyr
385                 390                 395                 400

Ser Arg Leu Thr Val Asp Lys Ser Arg Trp Gln Glu Gly Asn Val Phe
                405                 410                 415

Ser Cys Ser Val Met His Glu Ala Leu His Asn His Tyr Thr Gln Lys
            420                 425                 430

Ser Leu Ser Leu Ser Leu Gly Lys
        435                 440


<210> SEQ ID NO 4
<211> LENGTH: 214
<212> TYPE: PRT
<213> ORGANISM: Artificial Sequence
<220> FEATURE:
<223> OTHER INFORMATION: light chain anti-PD-1 antibody

<400> SEQUENCE: 4

Glu Ile Val Leu Thr Gln Ser Pro Ala Thr Leu Ser Leu Ser Pro Gly
1               5                   10                  15

Glu Arg Ala Thr Leu Ser Cys Arg Ala Ser Gln Ser Val Ser Ser Tyr
            20                  25                  30

Leu Ala Trp Tyr Gln Gln Lys Pro Gly Gln Ala Pro Arg Leu Leu Ile
        35                  40                  45

Tyr Asp Ala Ser Asn Arg Ala Thr Gly Ile Pro Ala Arg Phe Ser Gly
    50                  55                  60

Ser Gly Ser Gly Thr Asp Phe Thr Leu Thr Ile Ser Ser Leu Glu Pro
65                  70                  75                  80

Glu Asp Phe Ala Val Tyr Tyr Cys Gln Gln Ser Ser Asn Trp Pro Arg
                85                  90                  95

Thr Phe Gly Gln Gly Thr Lys Val Glu Ile Lys Arg Thr Val Ala Ala
            100                 105                 110
```

Pro Ser Val Phe Ile Phe Pro Pro Ser Asp Glu Gln Leu Lys Ser Gly
115 120 125

Thr Ala Ser Val Val Cys Leu Leu Asn Asn Phe Tyr Pro Arg Glu Ala
130 135 140

Lys Val Gln Trp Lys Val Asp Asn Ala Leu Gln Ser Gly Asn Ser Gln
145 150 155 160

Glu Ser Val Thr Glu Gln Asp Ser Lys Asp Ser Thr Tyr Ser Leu Ser
165 170 175

Ser Thr Leu Thr Leu Ser Lys Ala Asp Tyr Glu Lys His Lys Val Tyr
180 185 190

Ala Cys Glu Val Thr His Gln Gly Leu Ser Ser Pro Val Thr Lys Ser
195 200 205

Phe Asn Arg Gly Glu Cys
210

<210> SEQ ID NO 5
<211> LENGTH: 448
<212> TYPE: PRT
<213> ORGANISM: Artificial Sequence
<220> FEATURE:
<223> OTHER INFORMATION: heavy chain of anti-CTLA-4 antibody

<400> SEQUENCE: 5

Gln Val Gln Leu Val Glu Ser Gly Gly Gly Val Val Gln Pro Gly Arg
1 5 10 15

Ser Leu Arg Leu Ser Cys Ala Ala Ser Gly Phe Thr Phe Ser Ser Tyr
20 25 30

Thr Met His Trp Val Arg Gln Ala Pro Gly Lys Gly Leu Glu Trp Val
35 40 45

Thr Phe Ile Ser Tyr Asp Gly Asn Asn Lys Tyr Tyr Ala Asp Ser Val
50 55 60

Lys Gly Arg Phe Thr Ile Ser Arg Asp Asn Ser Lys Asn Thr Leu Tyr
65 70 75 80

Leu Gln Met Asn Ser Leu Arg Ala Glu Asp Thr Ala Ile Tyr Tyr Cys
85 90 95

Ala Arg Thr Gly Trp Leu Gly Pro Phe Asp Tyr Trp Gly Gln Gly Thr
100 105 110

Leu Val Thr Val Ser Ser Ala Ser Thr Lys Gly Pro Ser Val Phe Pro
115 120 125

Leu Ala Pro Ser Ser Lys Ser Thr Ser Gly Gly Thr Ala Ala Leu Gly
130 135 140

Cys Leu Val Lys Asp Tyr Phe Pro Glu Pro Val Thr Val Ser Trp Asn
145 150 155 160

Ser Gly Ala Leu Thr Ser Gly Val His Thr Phe Pro Ala Val Leu Gln
165 170 175

Ser Ser Gly Leu Tyr Ser Leu Ser Ser Val Val Thr Val Pro Ser Ser
180 185 190

Ser Leu Gly Thr Gln Thr Tyr Ile Cys Asn Val Asn His Lys Pro Ser
195 200 205

Asn Thr Lys Val Asp Lys Arg Val Glu Pro Lys Ser Cys Asp Lys Thr
210 215 220

His Thr Cys Pro Pro Cys Pro Ala Pro Glu Leu Leu Gly Gly Pro Ser
225 230 235 240

Val Phe Leu Phe Pro Pro Lys Pro Lys Asp Thr Leu Met Ile Ser Arg
245 250 255

Thr Pro Glu Val Thr Cys Val Val Val Asp Val Ser His Glu Asp Pro
260 265 270

Glu Val Lys Phe Asn Trp Tyr Val Asp Gly Val Glu Val His Asn Ala
275 280 285

Lys Thr Lys Pro Arg Glu Glu Gln Tyr Asn Ser Thr Tyr Arg Val Val
290 295 300

Ser Val Leu Thr Val Leu His Gln Asp Trp Leu Asn Gly Lys Glu Tyr
305 310 315 320

Lys Cys Lys Val Ser Asn Lys Ala Leu Pro Ala Pro Ile Glu Lys Thr
325 330 335

Ile Ser Lys Ala Lys Gly Gln Pro Arg Glu Pro Gln Val Tyr Thr Leu
340 345 350

Pro Pro Ser Arg Asp Glu Leu Thr Lys Asn Gln Val Ser Leu Thr Cys
355 360 365

Leu Val Lys Gly Phe Tyr Pro Ser Asp Ile Ala Val Glu Trp Glu Ser
370 375 380

Asn Gly Gln Pro Glu Asn Asn Tyr Lys Thr Thr Pro Pro Val Leu Asp
385 390 395 400

Ser Asp Gly Ser Phe Phe Leu Tyr Ser Lys Leu Thr Val Asp Lys Ser
405 410 415

Arg Trp Gln Gln Gly Asn Val Phe Ser Cys Ser Val Met His Glu Ala
420 425 430

Leu His Asn His Tyr Thr Gln Lys Ser Leu Ser Leu Ser Pro Gly Lys
435 440 445

<210> SEQ ID NO 6
<211> LENGTH: 215
<212> TYPE: PRT
<213> ORGANISM: Artificial Sequence
<220> FEATURE:
<223> OTHER INFORMATION: light chain of anti-CTLA-4 antibody

<400> SEQUENCE: 6

Glu Ile Val Leu Thr Gln Ser Pro Gly Thr Leu Ser Leu Ser Pro Gly
1 5 10 15

Glu Arg Ala Thr Leu Ser Cys Arg Ala Ser Gln Ser Val Gly Ser Ser
20 25 30

Tyr Leu Ala Trp Tyr Gln Gln Lys Pro Gly Gln Ala Pro Arg Leu Leu
35 40 45

Ile Tyr Gly Ala Phe Ser Arg Ala Thr Gly Ile Pro Asp Arg Phe Ser
50 55 60

Gly Ser Gly Ser Gly Thr Asp Phe Thr Leu Thr Ile Ser Arg Leu Glu
65 70 75 80

Pro Glu Asp Phe Ala Val Tyr Tyr Cys Gln Gln Tyr Gly Ser Ser Pro
85 90 95

Trp Thr Phe Gly Gln Gly Thr Lys Val Glu Ile Lys Arg Thr Val Ala
100 105 110

Ala Pro Ser Val Phe Ile Phe Pro Pro Ser Asp Glu Gln Leu Lys Ser
115 120 125

Gly Thr Ala Ser Val Val Cys Leu Leu Asn Asn Phe Tyr Pro Arg Glu
130 135 140

Ala Lys Val Gln Trp Lys Val Asp Asn Ala Leu Gln Ser Gly Asn Ser
145 150 155 160

Gln Glu Ser Val Thr Glu Gln Asp Ser Lys Asp Ser Thr Tyr Ser Leu
165 170 175

```
Ser Ser Thr Leu Thr Leu Ser Lys Ala Asp Tyr Glu Lys His Lys Val
            180                 185                 190

Tyr Ala Cys Glu Val Thr His Gln Gly Leu Ser Ser Pro Val Thr Lys
        195                 200                 205

Ser Phe Asn Arg Gly Glu Cys
    210                 215


<210> SEQ ID NO 7
<211> LENGTH: 224
<212> TYPE: PRT
<213> ORGANISM: Artificial Sequence
<220> FEATURE:
<223> OTHER INFORMATION: heavy chain of anti-TNF   antibody

<400> SEQUENCE: 7

Glu Val Gln Leu Val Glu Ser Gly Gly Gly Leu Val Gln Pro Gly Arg
1               5                   10                  15

Ser Leu Arg Leu Ser Cys Ala Ala Ser Gly Phe Thr Phe Asp Asp Tyr
            20                  25                  30

Ala Met His Trp Val Arg Gln Ala Pro Gly Lys Gly Leu Glu Trp Val
        35                  40                  45

Ser Ala Ile Thr Trp Asn Ser Gly His Ile Asp Tyr Ala Asp Ser Val
    50                  55                  60

Glu Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Lys Val Ser Tyr Leu Ser Thr Ala Ser Ser Leu Asp Tyr Trp Gly
            100                 105                 110

Gln Gly Thr Leu Val Thr Val Ser Ser Ala Ser Thr Lys Gly Pro Ser
        115                 120                 125

Val Phe Pro Leu Ala Pro Ser Ser Lys Ser Thr Ser Gly Gly Thr Ala
    130                 135                 140

Ala Leu Gly Cys Leu Val Lys Asp Tyr Phe Pro Glu Pro Val Thr Val
145                 150                 155                 160

Ser Trp Asn Ser Gly Ala Leu Thr Ser Gly Val His Thr Phe Pro Ala
                165                 170                 175

Val Leu Gln Ser Ser Gly Leu Tyr Ser Leu Ser Ser Val Val Thr Val
            180                 185                 190

Pro Ser Ser Ser Leu Gly Thr Gln Thr Tyr Ile Cys Asn Val Asn His
        195                 200                 205

Lys Pro Ser Asn Thr Lys Val Asp Lys Lys Val Glu Pro Lys Ser Cys
    210                 215                 220


<210> SEQ ID NO 8
<211> LENGTH: 214
<212> TYPE: PRT
<213> ORGANISM: Artificial Sequence
<220> FEATURE:
<223> OTHER INFORMATION: light chain of anti-TNF   antibody

<400> SEQUENCE: 8

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Gly Ile Arg Asn Tyr
            20                  25                  30

Leu Ala Trp Tyr Gln Gln Lys Pro Gly Lys Ala Pro Lys Leu Leu Ile
```

```
        35                  40                  45

Tyr Ala Ala Ser Thr Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Val Ala Thr Tyr Tyr Cys Gln Arg Tyr Asn Arg Ala Pro Tyr
                85                  90                  95

Thr Phe Gly Gln Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210


<210> SEQ ID NO 9
<211> LENGTH: 446
<212> TYPE: PRT
<213> ORGANISM: Artificial Sequence
<220> FEATURE:
<223> OTHER INFORMATION: heavy chain of anti-CD28 antibody

<400> SEQUENCE: 9

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser Tyr
            20                  25                  30

Tyr Ile His Trp Val Arg Gln Ala Pro Gly Gln Gly Leu Glu Trp Ile
        35                  40                  45

Gly Cys Ile Tyr Pro Gly Asn Val Asn Thr Asn Tyr Asn Glu Lys Phe
    50                  55                  60

Lys Asp Arg Ala Thr Leu Thr Val Asp Thr Ser Ile Ser Thr Ala Tyr
65                  70                  75                  80

Met Glu Leu Ser Arg Leu Arg Ser Asp Asp Thr Ala Val Tyr Phe Cys
                85                  90                  95

Thr Arg Ser His Tyr Gly Leu Asp Trp Asn Phe Asp Val Trp Gly Gln
            100                 105                 110

Gly Thr Thr Val Thr Val Ser Ser Ala Ser Thr Lys Gly Pro Ser Val
        115                 120                 125

Phe Pro Leu Ala Pro Cys Ser Arg Ser Thr Ser Glu Ser Thr Ala Ala
    130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
                165                 170                 175

Leu Gln Ser Ser Gly Leu Tyr Ser Leu Ser Ser Val Val Thr Val Pro
```

```
            180                 185                 190

Ser Ser Ser Leu Gly Thr Lys Thr Tyr Thr Cys Asn Val Asp His Lys
        195                 200                 205

Pro Ser Asn Thr Lys Val Asp Lys Arg Val Glu Ser Lys Tyr Gly Pro
    210                 215                 220

Pro Cys Pro Ser Cys Pro Ala Pro Glu Phe Leu Gly Gly Pro Ser Val
225                 230                 235                 240

Phe Leu Phe Pro Pro Lys Pro Lys Asp Thr Leu Met Ile Ser Arg Thr
                245                 250                 255

Pro Glu Val Thr Cys Val Val Val Asp Val Ser Gln Glu Asp Pro Glu
            260                 265                 270

Val Gln Phe Asn Trp Tyr Val Asp Gly Val Glu Val His Asn Ala Lys
        275                 280                 285

Thr Lys Pro Arg Glu Glu Gln Phe Asn Ser Thr Tyr Arg Val Val Ser
    290                 295                 300

Val Leu Thr Val Leu His Gln Asp Trp Leu Asn Gly Lys Glu Tyr Lys
305                 310                 315                 320

Cys Lys Val Ser Asn Lys Gly Leu Pro Ser Ser Ile Glu Lys Thr Ile
                325                 330                 335

Ser Lys Ala Lys Gly Gln Pro Arg Glu Pro Gln Val Tyr Thr Leu Pro
            340                 345                 350

Pro Ser Gln Glu Glu Met Thr Lys Asn Gln Val Ser Leu Thr Cys Leu
        355                 360                 365

Val Lys Gly Phe Tyr Pro Ser Asp Ile Ala Val Glu Trp Glu Ser Asn
    370                 375                 380

Gly Gln Pro Glu Asn Asn Tyr Lys Thr Thr Pro Pro Val Leu Asp Ser
385                 390                 395                 400

Asp Gly Ser Phe Phe Leu Tyr Ser Arg Leu Thr Val Asp Lys Ser Arg
                405                 410                 415

Trp Gln Glu Gly Asn Val Phe Ser Cys Ser Val Met His Glu Ala Leu
            420                 425                 430

His Asn His Tyr Thr Gln Lys Ser Leu Ser Leu Ser Leu Gly
        435                 440                 445


<210> SEQ ID NO 10
<211> LENGTH: 214
<212> TYPE: PRT
<213> ORGANISM: Artificial Sequence
<220> FEATURE:
<223> OTHER INFORMATION: light chain of anti-CD28 antibody

<400> SEQUENCE: 10

Asp Ile Gln Met Thr Gln Ser Pro Ser Ser Leu Ser Ala Ser Val Gly
1               5                   10                  15

Asp Arg Val Thr Ile Thr Cys His Ala Ser Gln Asn Ile Tyr Val Trp
            20                  25                  30

Leu Asn Trp Tyr Gln Gln Lys Pro Gly Lys Ala Pro Lys Leu Leu Ile
        35                  40                  45

Tyr Lys Ala Ser Asn Leu His Thr Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Gly Gln Thr Tyr Pro Tyr
                85                  90                  95

Thr Phe Gly Gly Gly Thr Lys Val Glu Ile Lys Arg Thr Val Ala Ala
```

```
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210


<210> SEQ ID NO 11
<211> LENGTH: 132
<212> TYPE: PRT
<213> ORGANISM: Artificial Sequence
<220> FEATURE:
<223> OTHER INFORMATION: amino acid sequence of wild type IL2

<400> SEQUENCE: 11

Ala Pro Ala Ser Ser Thr Lys Lys Thr Gln Leu Gln Leu Glu His Leu
1               5                   10                  15

Leu Leu Asp Leu Gln Met Ile Leu Asn Gly Ile Asn Asn Tyr Lys Asn
            20                  25                  30

Pro Lys Leu Thr Arg Met Leu Thr Phe Lys Phe Tyr Met Pro Lys Lys
        35                  40                  45

Ala Thr Glu Leu Lys His Leu Gln Cys Leu Glu Glu Glu Leu Lys Pro
    50                  55                  60

Leu Glu Glu Val Leu Asn Leu Ala Gln Ser Lys Asn Phe His Leu Arg
65                  70                  75                  80

Pro Arg Asp Leu Ile Ser Asn Ile Asn Val Ile Val Leu Glu Leu Lys
                85                  90                  95

Gly Ser Glu Thr Thr Phe Met Cys Glu Tyr Ala Asp Glu Thr Ala Thr
            100                 105                 110

Ile Val Glu Phe Leu Asn Arg Trp Ile Thr Phe Ser Gln Ser Ile Ile
        115                 120                 125

Ser Thr Leu Thr
    130


<210> SEQ ID NO 12
<211> LENGTH: 131
<212> TYPE: PRT
<213> ORGANISM: Artificial Sequence
<220> FEATURE:
<223> OTHER INFORMATION: amino acid sequence of wild type IL2

<400> SEQUENCE: 12

Pro Thr Ser Ser Thr Lys Lys Thr Gln Leu Gln Leu Glu His Leu Leu
1               5                   10                  15

Leu Asp Leu Gln Met Ile Leu Asn Gly Ile Asn Asn Tyr Lys Asn Pro
            20                  25                  30

Lys Leu Thr Arg Met Leu Thr Phe Lys Phe Tyr Met Pro Lys Lys Ala
        35                  40                  45
```

```
Thr Glu Leu Lys His Leu Gln Cys Leu Glu Glu Glu Leu Lys Pro Leu
    50                  55                  60

Glu Glu Val Leu Asn Leu Ala Gln Ser Lys Asn Phe His Leu Arg Pro
65                  70                  75                  80

Arg Asp Leu Ile Ser Asn Ile Asn Val Ile Val Leu Glu Leu Lys Gly
                85                  90                  95

Ser Glu Thr Thr Phe Met Cys Glu Tyr Ala Asp Glu Thr Ala Thr Ile
            100                 105                 110

Val Glu Phe Leu Asn Arg Trp Ile Thr Phe Ser Gln Ser Ile Ile Ser
        115                 120                 125

Thr Leu Thr
    130


<210> SEQ ID NO 13
<211> LENGTH: 448
<212> TYPE: PRT
<213> ORGANISM: Artificial Sequence
<220> FEATURE:
<223> OTHER INFORMATION: Ipilimumab heavy chain

<400> SEQUENCE: 13

Gln Val Gln Leu Val Glu Ser Gly Gly Gly Val Val Gln Pro Gly Arg
1               5                   10                  15

Ser Leu Arg Leu Ser Cys Ala Ala Ser Gly Phe Thr Phe Ser Ser Tyr
            20                  25                  30

Thr Met His Trp Val Arg Gln Ala Pro Gly Lys Gly Leu Glu Trp Val
        35                  40                  45

Thr Phe Ile Ser Tyr Asp Gly Asn Asn Lys Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Ile Tyr Tyr Cys
                85                  90                  95

Ala Arg Thr Gly Trp Leu Gly Pro Phe Asp Tyr Trp Gly Gln Gly Thr
            100                 105                 110

Leu Val Thr Val Ser Ser Ala Ser Thr Lys Gly Pro Ser Val Phe Pro
        115                 120                 125

Leu Ala Pro Ser Ser Lys Ser Thr Ser Gly Gly Thr Ala Ala Leu Gly
    130                 135                 140

Cys Leu Val Lys Asp Tyr Phe Pro Glu Pro Val Thr Val Ser Trp Asn
145                 150                 155                 160

Ser Gly Ala Leu Thr Ser Gly Val His Thr Phe Pro Ala Val Leu Gln
                165                 170                 175

Ser Ser Gly Leu Tyr Ser Leu Ser Ser Val Val Thr Val Pro Ser Ser
            180                 185                 190

Ser Leu Gly Thr Gln Thr Tyr Ile Cys Asn Val Asn His Lys Pro Ser
        195                 200                 205

Asn Thr Lys Val Asp Lys Arg Val Glu Pro Lys Ser Cys Asp Lys Thr
    210                 215                 220

His Thr Cys Pro Pro Cys Pro Ala Pro Glu Leu Leu Gly Gly Pro Ser
225                 230                 235                 240

Val Phe Leu Phe Pro Pro Lys Pro Lys Asp Thr Leu Met Ile Ser Arg
                245                 250                 255

Thr Pro Glu Val Thr Cys Val Val Val Asp Val Ser His Glu Asp Pro
            260                 265                 270
```

```
Glu Val Lys Phe Asn Trp Tyr Val Asp Gly Val Glu Val His Asn Ala
        275                 280                 285

Lys Thr Lys Pro Arg Glu Glu Gln Tyr Asn Ser Thr Tyr Arg Val Val
    290                 295                 300

Ser Val Leu Thr Val Leu His Gln Asp Trp Leu Asn Gly Lys Glu Tyr
305                 310                 315                 320

Lys Cys Lys Val Ser Asn Lys Ala Leu Pro Ala Pro Ile Glu Lys Thr
                325                 330                 335

Ile Ser Lys Ala Lys Gly Gln Pro Arg Glu Pro Gln Val Tyr Thr Leu
            340                 345                 350

Pro Pro Ser Arg Asp Glu Leu Thr Lys Asn Gln Val Ser Leu Thr Cys
        355                 360                 365

Leu Val Lys Gly Phe Tyr Pro Ser Asp Ile Ala Val Glu Trp Glu Ser
    370                 375                 380

Asn Gly Gln Pro Glu Asn Asn Tyr Lys Thr Thr Pro Pro Val Leu Asp
385                 390                 395                 400

Ser Asp Gly Ser Phe Phe Leu Tyr Ser Lys Leu Thr Val Asp Lys Ser
                405                 410                 415

Arg Trp Gln Gln Gly Asn Val Phe Ser Cys Ser Val Met His Glu Ala
            420                 425                 430

Leu His Asn His Tyr Thr Gln Lys Ser Leu Ser Leu Ser Pro Gly Lys
        435                 440                 445


<210> SEQ ID NO 14
<211> LENGTH: 215
<212> TYPE: PRT
<213> ORGANISM: Artificial Sequence
<220> FEATURE:
<223> OTHER INFORMATION: Ipilimumab light chain

<400> SEQUENCE: 14

Glu Ile Val Leu Thr Gln Ser Pro Gly Thr Leu Ser Leu Ser Pro Gly
1               5                   10                  15

Glu Arg Ala Thr Leu Ser Cys Arg Ala Ser Gln Ser Val Gly Ser Ser
            20                  25                  30

Tyr Leu Ala Trp Tyr Gln Gln Lys Pro Gly Gln Ala Pro Arg Leu Leu
        35                  40                  45

Ile Tyr Gly Ala Phe Ser Arg Ala Thr Gly Ile Pro Asp Arg Phe Ser
    50                  55                  60

Gly Ser Gly Ser Gly Thr Asp Phe Thr Leu Thr Ile Ser Arg Leu Glu
65                  70                  75                  80

Pro Glu Asp Phe Ala Val Tyr Tyr Cys Gln Gln Tyr Gly Ser Ser Pro
                85                  90                  95

Trp Thr Phe Gly Gln Gly Thr Lys Val Glu Ile Lys Arg Thr Val Ala
            100                 105                 110

Ala Pro Ser Val Phe Ile Phe Pro Pro Ser Asp Glu Gln Leu Lys Ser
        115                 120                 125

Gly Thr Ala Ser Val Val Cys Leu Leu Asn Asn Phe Tyr Pro Arg Glu
    130                 135                 140

Ala Lys Val Gln Trp Lys Val Asp Asn Ala Leu Gln Ser Gly Asn Ser
145                 150                 155                 160

Gln Glu Ser Val Thr Glu Gln Asp Ser Lys Asp Ser Thr Tyr Ser Leu
                165                 170                 175

Ser Ser Thr Leu Thr Leu Ser Lys Ala Asp Tyr Glu Lys His Lys Val
            180                 185                 190
```

```
Tyr Ala Cys Glu Val Thr His Gln Gly Leu Ser Ser Pro Val Thr Lys
        195                 200                 205

Ser Phe Asn Arg Gly Glu Cys
    210                 215
```

<210> SEQ ID NO 15
<211> LENGTH: 447
<212> TYPE: PRT
<213> ORGANISM: Artificial Sequence
<220> FEATURE:
<223> OTHER INFORMATION: Pembrolizumab heavy chain

<400> SEQUENCE: 15

```
Gln Val Gln Leu Val Gln Ser Gly Val Glu Val Lys Lys Pro Gly Ala
1               5                   10                  15

Ser Val Lys Val Ser Cys Lys Ala Ser Gly Tyr Thr Phe Thr Asn Tyr
            20                  25                  30

Tyr Met Tyr Trp Val Arg Gln Ala Pro Gly Gln Gly Leu Glu Trp Met
        35                  40                  45

Gly Gly Ile Asn Pro Ser Asn Gly Gly Thr Asn Phe Asn Glu Lys Phe
    50                  55                  60

Lys Asn Arg Val Thr Leu Thr Thr Asp Ser Ser Thr Thr Thr Ala Tyr
65                  70                  75                  80

Met Glu Leu Lys Ser Leu Gln Phe Asp Asp Thr Ala Val Tyr Tyr Cys
                85                  90                  95

Ala Arg Arg Asp Tyr Arg Phe Asp Met Gly Phe Asp Tyr Trp Gly Gln
            100                 105                 110

Gly Thr Thr Val Thr Val Ser Ser Ala Ser Thr Lys Gly Pro Ser Val
        115                 120                 125

Phe Pro Leu Ala Pro Cys Ser Arg Ser Thr Ser Glu Ser Thr Ala Ala
    130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
                165                 170                 175

Leu Gln Ser Ser Gly Leu Tyr Ser Leu Ser Ser Val Val Thr Val Pro
            180                 185                 190

Ser Ser Ser Leu Gly Thr Lys Thr Tyr Thr Cys Asn Val Asp His Lys
        195                 200                 205

Pro Ser Asn Thr Lys Val Asp Lys Arg Val Glu Ser Lys Tyr Gly Pro
    210                 215                 220

Pro Cys Pro Pro Cys Pro Ala Pro Glu Phe Leu Gly Gly Pro Ser Val
225                 230                 235                 240

Phe Leu Phe Pro Pro Lys Pro Lys Asp Thr Leu Met Ile Ser Arg Thr
                245                 250                 255

Pro Glu Val Thr Cys Val Val Val Asp Val Ser Gln Glu Asp Pro Glu
            260                 265                 270

Val Gln Phe Asn Trp Tyr Val Asp Gly Val Glu Val His Asn Ala Lys
        275                 280                 285

Thr Lys Pro Arg Glu Glu Gln Phe Asn Ser Thr Tyr Arg Val Val Ser
    290                 295                 300

Val Leu Thr Val Leu His Gln Asp Trp Leu Asn Gly Lys Glu Tyr Lys
305                 310                 315                 320

Cys Lys Val Ser Asn Lys Gly Leu Pro Ser Ser Ile Glu Lys Thr Ile
                325                 330                 335
```

```
Ser Lys Ala Lys Gly Gln Pro Arg Glu Pro Gln Val Tyr Thr Leu Pro
            340                 345                 350

Pro Ser Gln Glu Glu Met Thr Lys Asn Gln Val Ser Leu Thr Cys Leu
        355                 360                 365

Val Lys Gly Phe Tyr Pro Ser Asp Ile Ala Val Glu Trp Glu Ser Asn
    370                 375                 380

Gly Gln Pro Glu Asn Asn Tyr Lys Thr Thr Pro Pro Val Leu Asp Ser
385                 390                 395                 400

Asp Gly Ser Phe Phe Leu Tyr Ser Arg Leu Thr Val Asp Lys Ser Arg
                405                 410                 415

Trp Gln Glu Gly Asn Val Phe Ser Cys Ser Val Met His Glu Ala Leu
            420                 425                 430

His Asn His Tyr Thr Gln Lys Ser Leu Ser Leu Ser Leu Gly Lys
        435                 440                 445


<210> SEQ ID NO 16
<211> LENGTH: 218
<212> TYPE: PRT
<213> ORGANISM: Artificial Sequence
<220> FEATURE:
<223> OTHER INFORMATION: Pembrolizumab light chain

<400> SEQUENCE: 16

Glu Ile Val Leu Thr Gln Ser Pro Ala Thr Leu Ser Leu Ser Pro Gly
1               5                   10                  15

Glu Arg Ala Thr Leu Ser Cys Arg Ala Ser Lys Gly Val Ser Thr Ser
            20                  25                  30

Gly Tyr Ser Tyr Leu His Trp Tyr Gln Gln Lys Pro Gly Gln Ala Pro
        35                  40                  45

Arg Leu Leu Ile Tyr Leu Ala Ser Tyr Leu Glu Ser Gly Val Pro Ala
    50                  55                  60

Arg Phe Ser Gly Ser Gly Ser Gly Thr Asp Phe Thr Leu Thr Ile Ser
65                  70                  75                  80

Ser Leu Glu Pro Glu Asp Phe Ala Val Tyr Tyr Cys Gln His Ser Arg
                85                  90                  95

Asp Leu Pro Leu Thr Phe Gly Gly Gly Thr Lys Val Glu Ile Lys Arg
            100                 105                 110

Thr Val Ala Ala Pro Ser Val Phe Ile Phe Pro Pro Ser Asp Glu Gln
        115                 120                 125

Leu Lys Ser Gly Thr Ala Ser Val Val Cys Leu Leu Asn Asn Phe Tyr
    130                 135                 140

Pro Arg Glu Ala Lys Val Gln Trp Lys Val Asp Asn Ala Leu Gln Ser
145                 150                 155                 160

Gly Asn Ser Gln Glu Ser Val Thr Glu Gln Asp Ser Lys Asp Ser Thr
                165                 170                 175

Tyr Ser Leu Ser Ser Thr Leu Thr Leu Ser Lys Ala Asp Tyr Glu Lys
            180                 185                 190

His Lys Val Tyr Ala Cys Glu Val Thr His Gln Gly Leu Ser Ser Pro
        195                 200                 205

Val Thr Lys Ser Phe Asn Arg Gly Glu Cys
    210                 215


<210> SEQ ID NO 17
<211> LENGTH: 440
<212> TYPE: PRT
<213> ORGANISM: Artificial Sequence
<220> FEATURE:
```

<223> OTHER INFORMATION: Nivolumab heavy chain

<400> SEQUENCE: 17

```
Gln Val Gln Leu Val Glu Ser Gly Gly Gly Val Val Gln Pro Gly Arg
1               5                   10                  15

Ser Leu Arg Leu Asp Cys Lys Ala Ser Gly Ile Thr Phe Ser Asn Ser
            20                  25                  30

Gly Met His Trp Val Arg Gln Ala Pro Gly Lys Gly Leu Glu Trp Val
        35                  40                  45

Ala Val Ile Trp Tyr Asp Gly Ser Lys Arg Tyr Tyr Ala Asp Ser Val
    50                  55                  60

Lys Gly Arg Phe Thr Ile Ser Arg Asp Asn Ser Lys Asn Thr Leu Phe
65                  70                  75                  80

Leu Gln Met Asn Ser Leu Arg Ala Glu Asp Thr Ala Val Tyr Tyr Cys
                85                  90                  95

Ala Thr Asn Asp Asp Tyr Trp Gly Gln Gly Thr Leu Val Thr Val Ser
            100                 105                 110

Ser Ala Ser Thr Lys Gly Pro Ser Val Phe Pro Leu Ala Pro Cys Ser
        115                 120                 125

Arg Ser Thr Ser Glu Ser Thr Ala Ala Leu Gly Cys Leu Val Lys Asp
    130                 135                 140

Tyr Phe Pro Glu Pro Val Thr Val Ser Trp Asn Ser Gly Ala Leu Thr
145                 150                 155                 160

Ser Gly Val His Thr Phe Pro Ala Val Leu Gln Ser Ser Gly Leu Tyr
                165                 170                 175

Ser Leu Ser Ser Val Val Thr Val Pro Ser Ser Ser Leu Gly Thr Lys
            180                 185                 190

Thr Tyr Thr Cys Asn Val Asp His Lys Pro Ser Asn Thr Lys Val Asp
        195                 200                 205

Lys Arg Val Glu Ser Lys Tyr Gly Pro Pro Cys Pro Pro Cys Pro Ala
    210                 215                 220

Pro Glu Phe Leu Gly Gly Pro Ser Val Phe Leu Phe Pro Pro Lys Pro
225                 230                 235                 240

Lys Asp Thr Leu Met Ile Ser Arg Thr Pro Glu Val Thr Cys Val Val
                245                 250                 255

Val Asp Val Ser Gln Glu Asp Pro Glu Val Gln Phe Asn Trp Tyr Val
            260                 265                 270

Asp Gly Val Glu Val His Asn Ala Lys Thr Lys Pro Arg Glu Glu Gln
        275                 280                 285

Phe Asn Ser Thr Tyr Arg Val Val Ser Val Leu Thr Val Leu His Gln
    290                 295                 300

Asp Trp Leu Asn Gly Lys Glu Tyr Lys Cys Lys Val Ser Asn Lys Gly
305                 310                 315                 320

Leu Pro Ser Ser Ile Glu Lys Thr Ile Ser Lys Ala Lys Gly Gln Pro
                325                 330                 335

Arg Glu Pro Gln Val Tyr Thr Leu Pro Pro Ser Gln Glu Glu Met Thr
            340                 345                 350

Lys Asn Gln Val Ser Leu Thr Cys Leu Val Lys Gly Phe Tyr Pro Ser
        355                 360                 365

Asp Ile Ala Val Glu Trp Glu Ser Asn Gly Gln Pro Glu Asn Asn Tyr
    370                 375                 380

Lys Thr Thr Pro Pro Val Leu Asp Ser Asp Gly Ser Phe Phe Leu Tyr
385                 390                 395                 400
```

```
Ser Arg Leu Thr Val Asp Lys Ser Arg Trp Gln Glu Gly Asn Val Phe
                405                 410                 415

Ser Cys Ser Val Met His Glu Ala Leu His Asn His Tyr Thr Gln Lys
            420                 425                 430

Ser Leu Ser Leu Ser Leu Gly Lys
        435                 440


<210> SEQ ID NO 18
<211> LENGTH: 214
<212> TYPE: PRT
<213> ORGANISM: Artificial Sequence
<220> FEATURE:
<223> OTHER INFORMATION: Nivolumab light chain

<400> SEQUENCE: 18

Glu Ile Val Leu Thr Gln Ser Pro Ala Thr Leu Ser Leu Ser Pro Gly
1               5                   10                  15

Glu Arg Ala Thr Leu Ser Cys Arg Ala Ser Gln Ser Val Ser Ser Tyr
            20                  25                  30

Leu Ala Trp Tyr Gln Gln Lys Pro Gly Gln Ala Pro Arg Leu Leu Ile
        35                  40                  45

Tyr Asp Ala Ser Asn Arg Ala Thr Gly Ile Pro Ala Arg Phe Ser Gly
    50                  55                  60

Ser Gly Ser Gly Thr Asp Phe Thr Leu Thr Ile Ser Ser Leu Glu Pro
65                  70                  75                  80

Glu Asp Phe Ala Val Tyr Tyr Cys Gln Gln Ser Ser Asn Trp Pro Arg
                85                  90                  95

Thr Phe Gly Gln Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210


<210> SEQ ID NO 19
<211> LENGTH: 444
<212> TYPE: PRT
<213> ORGANISM: Artificial Sequence
<220> FEATURE:
<223> OTHER INFORMATION: Anti-human PD-1 antibody (WO 2017/124050 A1)
      heavy chain

<400> SEQUENCE: 19

Gln Val Gln Leu Gln Glu Ser Gly Pro Gly Leu Val Lys Pro Ser Gln
1               5                   10                  15

Thr Leu Ser Leu Thr Cys Ser Val Ser Gly Tyr Ser Ile Thr Ser Gly
            20                  25                  30

Tyr Phe Trp Asn Trp Ile Arg Gln Phe Pro Gly Asn Lys Leu Glu Trp
```

-continued

```
        35                  40                  45

Ile Gly Tyr Ile Ser Tyr Asp Gly Ser Lys Asn Tyr Asn Pro Ser Leu
    50                  55                  60

Lys Asn Arg Val Thr Ile Ile Arg Asp Thr Ser Lys Asn Gln Phe Ser
65                  70                  75                  80

Leu Lys Leu Asn Ser Val Thr Ala Glu Asp Thr Ala Thr Tyr Tyr Cys
                85                  90                  95

Val Arg Gly Gly Leu Pro Val Met Asp Tyr Trp Gly Gln Gly Thr Ser
            100                 105                 110

Val Thr Val Ser Ser Ala Ser Thr Lys Gly Pro Ser Val Phe Pro Leu
        115                 120                 125

Ala Pro Cys Ser Arg Ser Thr Ser Glu Ser Thr Ala Ala Leu Gly Cys
    130                 135                 140

Leu Val Lys Asp Tyr Phe Pro Glu Pro Val Thr Val Ser Trp Asn Ser
145                 150                 155                 160

Gly Ala Leu Thr Ser Gly Val His Thr Phe Pro Ala Val Leu Gln Ser
                165                 170                 175

Ser Gly Leu Tyr Ser Leu Ser Ser Val Val Thr Val Pro Ser Ser Ser
            180                 185                 190

Leu Gly Thr Lys Thr Tyr Thr Cys Asn Val Asp His Lys Pro Ser Asn
        195                 200                 205

Thr Lys Val Asp Lys Arg Val Glu Ser Lys Tyr Gly Pro Pro Cys Pro
    210                 215                 220

Pro Cys Pro Ala Pro Glu Phe Leu Gly Gly Pro Ser Val Phe Leu Phe
225                 230                 235                 240

Pro Pro Lys Pro Lys Asp Thr Leu Met Ile Ser Arg Thr Pro Glu Val
                245                 250                 255

Thr Cys Val Val Val Asp Val Ser Gln Glu Asp Pro Glu Val Gln Phe
            260                 265                 270

Asn Trp Tyr Val Asp Gly Val Glu Val His Asn Ala Lys Thr Lys Pro
        275                 280                 285

Arg Glu Glu Gln Phe Asn Ser Thr Tyr Arg Val Val Ser Val Leu Thr
    290                 295                 300

Val Leu His Gln Asp Trp Leu Asn Gly Lys Glu Tyr Lys Cys Lys Val
305                 310                 315                 320

Ser Asn Lys Gly Leu Pro Ser Ser Ile Glu Lys Thr Ile Ser Lys Ala
                325                 330                 335

Lys Gly Gln Pro Arg Glu Pro Gln Val Tyr Thr Leu Pro Pro Ser Gln
            340                 345                 350

Glu Glu Met Thr Lys Asn Gln Val Ser Leu Thr Cys Leu Val Lys Gly
        355                 360                 365

Phe Tyr Pro Ser Asp Ile Ala Val Glu Trp Glu Ser Asn Gly Gln Pro
    370                 375                 380

Glu Asn Asn Tyr Lys Thr Thr Pro Pro Val Leu Asp Ser Asp Gly Ser
385                 390                 395                 400

Phe Phe Leu Tyr Ser Arg Leu Thr Val Asp Lys Ser Arg Trp Gln Glu
                405                 410                 415

Gly Asn Val Phe Ser Cys Ser Val Met His Glu Ala Leu His Asn His
            420                 425                 430

Tyr Thr Gln Lys Ser Leu Ser Leu Ser Leu Gly Lys
        435                 440

<210> SEQ ID NO 20
```

<211> LENGTH: 220
<212> TYPE: PRT
<213> ORGANISM: Artificial Sequence
<220> FEATURE:
<223> OTHER INFORMATION: Anti-human PD-1 antibody (WO 2017/124050 A1) light chain

<400> SEQUENCE: 20

Asp Ile Val Met Thr Gln Ser Pro Ser Ser Leu Ala Leu Ser Val Gly
1 5 10 15

Glu Lys Ala Thr Ile Gln Cys Lys Ser Ser Gln Ser Leu Leu Asp Asp
20 25 30

Asn Asn Gln Lys Asn Tyr Leu Ala Trp Tyr Gln Gln Lys Pro Gly Gln
35 40 45

Pro Pro Lys Leu Leu Ile Phe Phe Ala Ser Thr Arg Glu Ser Gly Val
50 55 60

Pro Asp Arg Phe Ile Gly Ser Gly Ser Gly Thr Asp Phe Thr Leu Thr
65 70 75 80

Ile Ser Ser Leu Gln Ala Glu Asp Leu Ala Asp Tyr Tyr Cys Gln Gln
85 90 95

His Tyr Thr Thr Pro Tyr Thr Phe Gly Gly Gly Thr Asn Val Glu Ile
100 105 110

Lys Arg Thr Val Ala Ala Pro Ser Val Phe Ile Phe Pro Pro Ser Asp
115 120 125

Glu Gln Leu Lys Ser Gly Thr Ala Ser Val Val Cys Leu Leu Asn Asn
130 135 140

Phe Tyr Pro Arg Glu Ala Lys Val Gln Trp Lys Val Asp Asn Ala Leu
145 150 155 160

Gln Ser Gly Asn Ser Gln Glu Ser Val Thr Glu Gln Asp Ser Lys Asp
165 170 175

Ser Thr Tyr Ser Leu Ser Ser Thr Leu Thr Leu Ser Lys Ala Asp Tyr
180 185 190

Glu Lys His Lys Val Tyr Ala Cys Glu Val Thr His Gln Gly Leu Ser
195 200 205

Ser Pro Val Thr Lys Ser Phe Asn Arg Gly Glu Cys
210 215 220

<210> SEQ ID NO 21
<211> LENGTH: 451
<212> TYPE: PRT
<213> ORGANISM: Artificial Sequence
<220> FEATURE:
<223> OTHER INFORMATION: Anti-mouse PD-1 antibody J43v2 heavy chain

<400> SEQUENCE: 21

Glu Val Arg Leu Leu Glu Ser Gly Gly Gly Leu Val Lys Pro Glu Gly
1 5 10 15

Ser Leu Lys Leu Ser Cys Val Ala Ser Gly Phe Thr Phe Ser Asp Tyr
20 25 30

Phe Met Ser Trp Val Arg Gln Ala Pro Gly Lys Gly Leu Glu Trp Val
35 40 45

Ala His Ile Tyr Thr Lys Ser Tyr Asn Tyr Ala Thr Tyr Tyr Ser Gly
50 55 60

Ser Val Lys Gly Arg Phe Thr Ile Ser Arg Asp Asp Ser Arg Ser Met
65 70 75 80

Val Tyr Leu Gln Met Asn Asn Leu Arg Thr Glu Asp Thr Ala Thr Tyr
85 90 95

-continued

```
Tyr Cys Thr Arg Asp Gly Ser Gly Tyr Pro Ser Leu Asp Phe Trp Gly
            100                 105                 110

Gln Gly Thr Gln Val Thr Val Ser Ser Ala Lys Thr Thr Ala Pro Ser
        115                 120                 125

Val Tyr Pro Leu Ala Pro Val Cys Gly Asp Thr Thr Gly Ser Ser Val
    130                 135                 140

Thr Leu Gly Cys Leu Val Lys Gly Tyr Phe Pro Glu Pro Val Thr Leu
145                 150                 155                 160

Thr Trp Asn Ser Gly Ser Leu Ser Ser Gly Val His Thr Phe Pro Ala
                165                 170                 175

Val Leu Gln Ser Asp Leu Tyr Thr Leu Ser Ser Ser Val Thr Val Thr
            180                 185                 190

Ser Ser Thr Trp Pro Ser Gln Ser Ile Thr Cys Asn Val Ala His Pro
        195                 200                 205

Ala Ser Ser Thr Lys Val Asp Lys Lys Ile Glu Pro Arg Gly Pro Thr
    210                 215                 220

Ile Lys Pro Cys Pro Pro Cys Lys Cys Pro Ala Pro Asn Leu Leu Gly
225                 230                 235                 240

Gly Pro Ser Val Phe Ile Phe Pro Pro Lys Ile Lys Asp Val Leu Met
                245                 250                 255

Ile Ser Leu Ser Pro Ile Val Thr Cys Val Val Val Asp Val Ser Glu
            260                 265                 270

Asp Asp Pro Asp Val Gln Ile Ser Trp Phe Val Asn Asn Val Glu Val
        275                 280                 285

His Thr Ala Gln Thr Gln Thr His Arg Glu Asp Tyr Asn Ser Thr Leu
    290                 295                 300

Arg Val Val Ser Ala Leu Pro Ile Gln His Gln Asp Trp Met Ser Gly
305                 310                 315                 320

Lys Glu Phe Lys Cys Lys Val Asn Asn Lys Asp Leu Pro Ala Pro Ile
                325                 330                 335

Glu Arg Thr Ile Ser Lys Pro Lys Gly Ser Val Arg Ala Pro Gln Val
            340                 345                 350

Tyr Val Leu Pro Pro Pro Glu Glu Glu Met Thr Lys Lys Gln Val Thr
        355                 360                 365

Leu Thr Cys Met Val Thr Asp Phe Met Pro Glu Asp Ile Tyr Val Glu
    370                 375                 380

Trp Thr Asn Asn Gly Lys Thr Glu Leu Asn Tyr Lys Asn Thr Glu Pro
385                 390                 395                 400

Val Leu Asp Ser Asp Gly Ser Tyr Phe Met Tyr Ser Lys Leu Arg Val
                405                 410                 415

Glu Lys Lys Asn Trp Val Glu Arg Asn Ser Tyr Ser Cys Ser Val Val
            420                 425                 430

His Glu Gly Leu His Asn His His Thr Thr Lys Ser Phe Ser Arg Thr
        435                 440                 445

Pro Gly Lys
    450
```

<210> SEQ ID NO 22
<211> LENGTH: 214
<212> TYPE: PRT
<213> ORGANISM: Artificial Sequence
<220> FEATURE:
<223> OTHER INFORMATION: Anti-mouse PD-1 antibody J43v2 light chain

<400> SEQUENCE: 22

```
Tyr Glu Leu Thr Gln Pro Pro Ser Ala Ser Val Asn Val Gly Glu Thr
1               5                   10                  15

Val Lys Ile Thr Cys Ser Gly Asp Gln Leu Pro Lys Tyr Phe Ala Asp
            20                  25                  30

Trp Phe His Gln Arg Ser Asp Gln Thr Ile Leu Gln Val Ile Tyr Asp
        35                  40                  45

Asp Asn Lys Arg Pro Ser Gly Ile Pro Glu Arg Ile Ser Gly Ser Ser
    50                  55                  60

Ser Gly Thr Thr Ala Thr Leu Thr Ile Arg Asp Val Arg Ala Glu Asp
65                  70                  75                  80

Glu Gly Asp Tyr Tyr Cys Phe Ser Gly Tyr Val Asp Ser Asp Ser Lys
                85                  90                  95

Leu Tyr Val Phe Gly Ser Gly Thr Gln Leu Thr Val Leu Gly Gly Pro
            100                 105                 110

Lys Ser Ser Pro Lys Val Thr Val Phe Pro Pro Ser Pro Glu Glu Leu
        115                 120                 125

Arg Thr Asn Lys Ala Thr Leu Val Cys Leu Val Asn Asp Phe Tyr Pro
    130                 135                 140

Gly Ser Ala Thr Val Thr Trp Lys Ala Asn Gly Ala Thr Ile Asn Asp
145                 150                 155                 160

Gly Val Lys Thr Thr Lys Pro Ser Lys Gln Gly Gln Asn Tyr Met Thr
                165                 170                 175

Ser Ser Tyr Leu Ser Leu Thr Ala Asp Gln Trp Lys Ser His Asn Arg
            180                 185                 190

Val Ser Cys Gln Val Thr His Glu Gly Glu Thr Val Glu Lys Ser Leu
        195                 200                 205

Ser Pro Ala Glu Cys Leu
    210


<210> SEQ ID NO 23
<211> LENGTH: 453
<212> TYPE: PRT
<213> ORGANISM: Artificial Sequence
<220> FEATURE:
<223> OTHER INFORMATION: Anti-mouse CTLA-4 9D9 antibody heavy chain

<400> SEQUENCE: 23

Glu Ala Lys Leu Gln Glu Ser Gly Pro Val Leu Val Lys Pro Gly Ala
1               5                   10                  15

Ser Val Lys Met Ser Cys Lys Ala Ser Gly Tyr Thr Phe Thr Asp Tyr
            20                  25                  30

Tyr Met Asn Trp Val Lys Gln Ser His Gly Lys Ser Leu Glu Trp Ile
        35                  40                  45

Gly Val Ile Asn Pro Tyr Asn Gly Asp Thr Ser Tyr Asn Gln Lys Phe
    50                  55                  60

Lys Gly Lys Ala Thr Leu Thr Val Asp Lys Ser Ser Ser Thr Ala Tyr
65                  70                  75                  80

Met Glu Leu Asn Ser Leu Thr Ser Glu Asp Ser Ala Val Tyr Tyr Cys
                85                  90                  95

Ala Arg Tyr Tyr Gly Ser Trp Phe Ala Tyr Trp Gly Gln Gly Thr Leu
            100                 105                 110

Ile Thr Val Ser Thr Ala Lys Thr Thr Pro Pro Ser Val Tyr Pro Leu
        115                 120                 125

Ala Pro Gly Cys Gly Asp Thr Thr Gly Ser Ser Val Thr Leu Gly Cys
    130                 135                 140
```

```
Leu Val Lys Gly Tyr Phe Pro Glu Ser Val Thr Val Thr Trp Asn Ser
145                 150                 155                 160

Gly Ser Leu Ser Ser Ser Val His Thr Phe Pro Ala Leu Leu Gln Ser
                165                 170                 175

Gly Leu Tyr Thr Met Ser Ser Ser Val Thr Val Pro Ser Ser Thr Trp
            180                 185                 190

Pro Ser Gln Thr Val Thr Cys Ser Val Ala His Pro Ala Ser Ser Thr
        195                 200                 205

Thr Val Asp Lys Lys Leu Glu Pro Ser Gly Pro Ile Ser Thr Ile Asn
    210                 215                 220

Pro Cys Pro Pro Cys Lys Glu Cys His Lys Cys Pro Ala Pro Asn Leu
225                 230                 235                 240

Glu Gly Gly Pro Ser Val Phe Ile Phe Pro Pro Asn Ile Lys Asp Val
                245                 250                 255

Leu Met Ile Ser Leu Thr Pro Lys Val Thr Cys Val Val Val Asp Val
            260                 265                 270

Ser Glu Asp Asp Pro Asp Val Gln Ile Ser Trp Phe Val Asn Asn Val
        275                 280                 285

Glu Val His Thr Ala Gln Thr Gln Thr His Arg Glu Asp Tyr Asn Ser
    290                 295                 300

Thr Ile Arg Val Val Ser Thr Leu Pro Ile Gln His Gln Asp Trp Met
305                 310                 315                 320

Ser Gly Lys Glu Phe Lys Cys Lys Val Asn Asn Lys Asp Leu Pro Ser
                325                 330                 335

Pro Ile Glu Arg Thr Ile Ser Lys Ile Lys Gly Leu Val Arg Ala Pro
            340                 345                 350

Gln Val Tyr Ile Leu Pro Pro Pro Ala Glu Gln Leu Ser Arg Lys Asp
        355                 360                 365

Val Ser Leu Thr Cys Leu Val Val Gly Phe Asn Pro Gly Asp Ile Ser
    370                 375                 380

Val Glu Trp Thr Ser Asn Gly His Thr Glu Glu Asn Tyr Lys Asp Thr
385                 390                 395                 400

Ala Pro Val Leu Asp Ser Asp Gly Ser Tyr Phe Ile Tyr Ser Lys Leu
                405                 410                 415

Asn Met Lys Thr Ser Lys Trp Glu Lys Thr Asp Ser Phe Ser Cys Asn
            420                 425                 430

Val Arg His Glu Gly Leu Lys Asn Tyr Tyr Leu Lys Lys Thr Ile Ser
        435                 440                 445

Arg Ser Pro Gly Lys
    450
```

<210> SEQ ID NO 24
<211> LENGTH: 219
<212> TYPE: PRT
<213> ORGANISM: Artificial Sequence
<220> FEATURE:
<223> OTHER INFORMATION: Anti-mouse CTLA-4 9D9 antibody light chain

<400> SEQUENCE: 24

```
Asp Ile Val Met Thr Gln Thr Thr Leu Ser Leu Pro Val Ser Leu Gly
1               5                   10                  15

Asp Gln Ala Ser Ile Ser Cys Arg Ser Ser Gln Ser Ile Val His Ser
            20                  25                  30

Asn Gly Asn Thr Tyr Leu Glu Trp Tyr Leu Gln Lys Pro Gly Gln Ser
        35                  40                  45
```

-continued

```
Pro Lys Leu Leu Ile Tyr Lys Val Ser Asn Arg Phe Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Leu Gly Val Tyr Tyr Cys Phe Gln Gly
                85                  90                  95

Ser His Val Pro Tyr Thr Phe Gly Gly Gly Thr Lys Leu Glu Ile Lys
            100                 105                 110

Arg Ala Asp Ala Ala Pro Thr Val Ser Ile Phe Pro Pro Ser Ser Glu
        115                 120                 125

Gln Leu Thr Ser Gly Gly Ala Ser Val Val Cys Phe Leu Asn Asn Phe
    130                 135                 140

Tyr Pro Lys Asp Ile Asn Val Lys Trp Lys Ile Asp Gly Ser Glu Arg
145                 150                 155                 160

Gln Asn Gly Val Leu Asn Ser Trp Thr Asp Gln Asp Ser Lys Asp Ser
                165                 170                 175

Thr Tyr Ser Met Ser Ser Thr Leu Thr Leu Thr Lys Asp Glu Tyr Glu
            180                 185                 190

Arg His Asn Ser Tyr Thr Cys Glu Ala Thr His Lys Thr Ser Thr Ser
        195                 200                 205

Pro Ile Val Lys Ser Phe Asn Arg Asn Glu Cys
    210                 215


<210> SEQ ID NO 25
<211> LENGTH: 442
<212> TYPE: PRT
<213> ORGANISM: Artificial Sequence
<220> FEATURE:
<223> OTHER INFORMATION: Anti-human 4-1BB antibody heavy chain

<400> SEQUENCE: 25

Glu Val Gln Leu Val Gln Ser Gly Ala Glu Val Lys Lys Pro Gly Glu
1               5                   10                  15

Ser Leu Arg Ile Ser Cys Lys Gly Ser Gly Tyr Ser Phe Ser Thr Tyr
            20                  25                  30

Trp Ile Ser Trp Val Arg Gln Met Pro Gly Lys Gly Leu Glu Trp Met
        35                  40                  45

Gly Lys Ile Tyr Pro Gly Asp Ser Tyr Thr Asn Tyr Ser Pro Ser Phe
    50                  55                  60

Gln Gly Gln Val Thr Ile Ser Ala Asp Lys Ser Ile Ser Thr Ala Tyr
65                  70                  75                  80

Leu Gln Trp Ser Ser Leu Lys Ala Ser Asp Thr Ala Met Tyr Tyr Cys
                85                  90                  95

Ala Arg Gly Tyr Gly Ile Phe Asp Tyr Trp Gly Gln Gly Thr Leu Val
            100                 105                 110

Thr Val Ser Ser Ala Ser Thr Lys Gly Pro Ser Val Phe Pro Leu Ala
        115                 120                 125

Pro Cys Ser Arg Ser Thr Ser Glu Ser Thr Ala Ala Leu Gly Cys Leu
    130                 135                 140

Val Lys Asp Tyr Phe Pro Glu Pro Val Thr Val Ser Trp Asn Ser Gly
145                 150                 155                 160

Ala Leu Thr Ser Gly Val His Thr Phe Pro Ala Val Leu Gln Ser Ser
                165                 170                 175

Gly Leu Tyr Ser Leu Ser Ser Val Val Thr Val Pro Ser Ser Asn Phe
            180                 185                 190
```

-continued

```
Gly Thr Gln Thr Tyr Thr Cys Asn Val Asp His Lys Pro Ser Asn Thr
        195                 200                 205

Lys Val Asp Lys Thr Val Glu Arg Lys Cys Cys Val Glu Cys Pro Pro
    210                 215                 220

Cys Pro Ala Pro Pro Val Ala Gly Pro Ser Val Phe Leu Phe Pro Pro
225                 230                 235                 240

Lys Pro Lys Asp Thr Leu Met Ile Ser Arg Thr Pro Glu Val Thr Cys
                245                 250                 255

Val Val Val Asp Val Ser His Glu Asp Pro Glu Val Gln Phe Asn Trp
            260                 265                 270

Tyr Val Asp Gly Val Glu Val His Asn Ala Lys Thr Lys Pro Arg Glu
        275                 280                 285

Glu Gln Phe Asn Ser Thr Phe Arg Val Val Ser Val Leu Thr Val Val
    290                 295                 300

His Gln Asp Trp Leu Asn Gly Lys Glu Tyr Lys Cys Lys Val Ser Asn
305                 310                 315                 320

Lys Gly Leu Pro Ala Pro Ile Glu Lys Thr Ile Ser Lys Thr Lys Gly
                325                 330                 335

Gln Pro Arg Glu Pro Gln Val Tyr Thr Leu Pro Pro Ser Arg Glu Glu
            340                 345                 350

Met Thr Lys Asn Gln Val Ser Leu Thr Cys Leu Val Lys Gly Phe Tyr
        355                 360                 365

Pro Ser Asp Ile Ala Val Glu Trp Glu Ser Asn Gly Gln Pro Glu Asn
    370                 375                 380

Asn Tyr Lys Thr Thr Pro Pro Met Leu Asp Ser Asp Gly Ser Phe Phe
385                 390                 395                 400

Leu Tyr Ser Lys Leu Thr Val Asp Lys Ser Arg Trp Gln Gln Gly Asn
                405                 410                 415

Val Phe Ser Cys Ser Val Met His Glu Ala Leu His Asn His Tyr Thr
            420                 425                 430

Gln Lys Ser Leu Ser Leu Ser Pro Gly Lys
        435                 440


<210> SEQ ID NO 26
<211> LENGTH: 214
<212> TYPE: PRT
<213> ORGANISM: Artificial Sequence
<220> FEATURE:
<223> OTHER INFORMATION: Anti-human 4-1BB antibody light chain

<400> SEQUENCE: 26

Ser Tyr Glu Leu Thr Gln Pro Pro Ser Val Ser Val Ser Pro Gly Gln
1               5                   10                  15

Thr Ala Ser Ile Thr Cys Ser Gly Asp Asn Ile Gly Asp Gln Tyr Ala
            20                  25                  30

His Trp Tyr Gln Gln Lys Pro Gly Gln Ser Pro Val Leu Val Ile Tyr
        35                  40                  45

Gln Asp Lys Asn Arg Pro Ser Gly Ile Pro Glu Arg Phe Ser Gly Ser
    50                  55                  60

Asn Ser Gly Asn Thr Ala Thr Leu Thr Ile Ser Gly Thr Gln Ala Met
65                  70                  75                  80

Asp Glu Ala Asp Tyr Tyr Cys Ala Thr Tyr Thr Gly Phe Gly Ser Leu
                85                  90                  95

Ala Val Phe Gly Gly Gly Thr Lys Leu Thr Val Leu Gly Gln Pro Lys
            100                 105                 110
```

-continued

```
Ala Ala Pro Ser Val Thr Leu Phe Pro Pro Ser Ser Glu Glu Leu Gln
        115                 120                 125

Ala Asn Lys Ala Thr Leu Val Cys Leu Ile Ser Asp Phe Tyr Pro Gly
    130                 135                 140

Ala Val Thr Val Ala Trp Lys Ala Asp Ser Ser Pro Val Lys Ala Gly
145                 150                 155                 160

Val Glu Thr Thr Thr Pro Ser Lys Gln Ser Asn Asn Lys Tyr Ala Ala
                165                 170                 175

Ser Ser Tyr Leu Ser Leu Thr Pro Glu Gln Trp Lys Ser His Arg Ser
            180                 185                 190

Tyr Ser Cys Gln Val Thr His Glu Gly Ser Thr Val Glu Lys Thr Val
        195                 200                 205

Ala Pro Thr Glu Cys Ser
    210


<210> SEQ ID NO 27
<211> LENGTH: 450
<212> TYPE: PRT
<213> ORGANISM: Artificial Sequence
<220> FEATURE:
<223> OTHER INFORMATION: Trastuzumab heavy chain

<400> SEQUENCE: 27

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Asn Ile Lys Asp Thr
            20                  25                  30

Tyr Ile His Trp Val Arg Gln Ala Pro Gly Lys Gly Leu Glu Trp Val
        35                  40                  45

Ala Arg Ile Tyr Pro Thr Asn Gly Tyr Thr Arg Tyr Ala Asp Ser Val
    50                  55                  60

Lys Gly Arg Phe Thr Ile Ser Ala Asp Thr Ser Lys Asn Thr Ala Tyr
65                  70                  75                  80

Leu Gln Met Asn Ser Leu Arg Ala Glu Asp Thr Ala Val Tyr Tyr Cys
                85                  90                  95

Ser Arg Trp Gly Gly Asp Gly Phe Tyr Ala Met Asp Tyr Trp Gly Gln
            100                 105                 110

Gly Thr Leu Val Thr Val Ser Ser Ala Ser Thr Lys Gly Pro Ser Val
        115                 120                 125

Phe Pro Leu Ala Pro Ser Ser Lys Ser Thr Ser Gly Gly Thr Ala Ala
    130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
                165                 170                 175

Leu Gln Ser Ser Gly Leu Tyr Ser Leu Ser Ser Val Val Thr Val Pro
            180                 185                 190

Ser Ser Ser Leu Gly Thr Gln Thr Tyr Ile Cys Asn Val Asn His Lys
        195                 200                 205

Pro Ser Asn Thr Lys Val Asp Lys Lys Val Glu Pro Lys Ser Cys Asp
    210                 215                 220

Lys Thr His Thr Cys Pro Pro Cys Pro Ala Pro Glu Leu Leu Gly Gly
225                 230                 235                 240

Pro Ser Val Phe Leu Phe Pro Pro Lys Pro Lys Asp Thr Leu Met Ile
                245                 250                 255
```

```
Ser Arg Thr Pro Glu Val Thr Cys Val Val Val Asp Val Ser His Glu
            260                 265                 270

Asp Pro Glu Val Lys Phe Asn Trp Tyr Val Asp Gly Val Glu Val His
        275                 280                 285

Asn Ala Lys Thr Lys Pro Arg Glu Glu Gln Tyr Asn Ser Thr Tyr Arg
    290                 295                 300

Val Val Ser Val Leu Thr Val Leu His Gln Asp Trp Leu Asn Gly Lys
305                 310                 315                 320

Glu Tyr Lys Cys Lys Val Ser Asn Lys Ala Leu Pro Ala Pro Ile Glu
                325                 330                 335

Lys Thr Ile Ser Lys Ala Lys Gly Gln Pro Arg Glu Pro Gln Val Tyr
            340                 345                 350

Thr Leu Pro Pro Ser Arg Glu Glu Met Thr Lys Asn Gln Val Ser Leu
        355                 360                 365

Thr Cys Leu Val Lys Gly Phe Tyr Pro Ser Asp Ile Ala Val Glu Trp
    370                 375                 380

Glu Ser Asn Gly Gln Pro Glu Asn Asn Tyr Lys Thr Thr Pro Pro Val
385                 390                 395                 400

Leu Asp Ser Asp Gly Ser Phe Phe Leu Tyr Ser Lys Leu Thr Val Asp
                405                 410                 415

Lys Ser Arg Trp Gln Gln Gly Asn Val Phe Ser Cys Ser Val Met His
            420                 425                 430

Glu Ala Leu His Asn His Tyr Thr Gln Lys Ser Leu Ser Leu Ser Pro
        435                 440                 445

Gly Lys
    450


<210> SEQ ID NO 28
<211> LENGTH: 214
<212> TYPE: PRT
<213> ORGANISM: Artificial Sequence
<220> FEATURE:
<223> OTHER INFORMATION: Trastuzumab light chain

<400> SEQUENCE: 28

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Val Asn Thr Ala
            20                  25                  30

Val Ala Trp Tyr Gln Gln Lys Pro Gly Lys Ala Pro Lys Leu Leu Ile
        35                  40                  45

Tyr Ser Ala Ser Phe Leu Tyr Ser Gly Val Pro Ser Arg Phe Ser Gly
    50                  55                  60

Ser Arg Ser Gly Thr Asp Phe Thr Leu Thr Ile Ser Ser Leu Gln Pro
65                  70                  75                  80

Glu Asp Phe Ala Thr Tyr Tyr Cys Gln Gln His Tyr Thr Thr Pro Pro
                85                  90                  95

Thr Phe Gly Gln Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160
```

```
Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210


<210> SEQ ID NO 29
<211> LENGTH: 451
<212> TYPE: PRT
<213> ORGANISM: Artificial Sequence
<220> FEATURE:
<223> OTHER INFORMATION: Adalimumab heavy chain

<400> SEQUENCE: 29

Glu Val Gln Leu Val Glu Ser Gly Gly Gly Leu Val Gln Pro Gly Arg
1               5                   10                  15

Ser Leu Arg Leu Ser Cys Ala Ala Ser Gly Phe Thr Phe Asp Asp Tyr
            20                  25                  30

Ala Met His Trp Val Arg Gln Ala Pro Gly Lys Gly Leu Glu Trp Val
        35                  40                  45

Ser Ala Ile Thr Trp Asn Ser Gly His Ile Asp Tyr Ala Asp Ser Val
    50                  55                  60

Glu Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Lys Val Ser Tyr Leu Ser Thr Ala Ser Ser Leu Asp Tyr Trp Gly
            100                 105                 110

Gln Gly Thr Leu Val Thr Val Ser Ser Ala Ser Thr Lys Gly Pro Ser
        115                 120                 125

Val Phe Pro Leu Ala Pro Ser Ser Lys Ser Thr Ser Gly Gly Thr Ala
    130                 135                 140

Ala Leu Gly Cys Leu Val Lys Asp Tyr Phe Pro Glu Pro Val Thr Val
145                 150                 155                 160

Ser Trp Asn Ser Gly Ala Leu Thr Ser Gly Val His Thr Phe Pro Ala
                165                 170                 175

Val Leu Gln Ser Ser Gly Leu Tyr Ser Leu Ser Ser Val Val Thr Val
            180                 185                 190

Pro Ser Ser Ser Leu Gly Thr Gln Thr Tyr Ile Cys Asn Val Asn His
        195                 200                 205

Lys Pro Ser Asn Thr Lys Val Asp Lys Lys Val Glu Pro Lys Ser Cys
    210                 215                 220

Asp Lys Thr His Thr Cys Pro Pro Cys Pro Ala Pro Glu Leu Leu Gly
225                 230                 235                 240

Gly Pro Ser Val Phe Leu Phe Pro Pro Lys Pro Lys Asp Thr Leu Met
                245                 250                 255

Ile Ser Arg Thr Pro Glu Val Thr Cys Val Val Val Asp Val Ser His
            260                 265                 270

Glu Asp Pro Glu Val Lys Phe Asn Trp Tyr Val Asp Gly Val Glu Val
        275                 280                 285

His Asn Ala Lys Thr Lys Pro Arg Glu Glu Gln Tyr Asn Ser Thr Tyr
    290                 295                 300
```

-continued

```
Arg Val Val Ser Val Leu Thr Val Leu His Gln Asp Trp Leu Asn Gly
305                 310                 315                 320

Lys Glu Tyr Lys Cys Lys Val Ser Asn Lys Ala Leu Pro Ala Pro Ile
                325                 330                 335

Glu Lys Thr Ile Ser Lys Ala Lys Gly Gln Pro Arg Glu Pro Gln Val
            340                 345                 350

Tyr Thr Leu Pro Pro Ser Arg Asp Glu Leu Thr Lys Asn Gln Val Ser
        355                 360                 365

Leu Thr Cys Leu Val Lys Gly Phe Tyr Pro Ser Asp Ile Ala Val Glu
    370                 375                 380

Trp Glu Ser Asn Gly Gln Pro Glu Asn Asn Tyr Lys Thr Thr Pro Pro
385                 390                 395                 400

Val Leu Asp Ser Asp Gly Ser Phe Phe Leu Tyr Ser Lys Leu Thr Val
                405                 410                 415

Asp Lys Ser Arg Trp Gln Gln Gly Asn Val Phe Ser Cys Ser Val Met
            420                 425                 430

His Glu Ala Leu His Asn His Tyr Thr Gln Lys Ser Leu Ser Leu Ser
        435                 440                 445

Pro Gly Lys
    450


<210> SEQ ID NO 30
<211> LENGTH: 214
<212> TYPE: PRT
<213> ORGANISM: Artificial Sequence
<220> FEATURE:
<223> OTHER INFORMATION: Adalimumab light chain

<400> SEQUENCE: 30

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Gly Ile Arg Asn Tyr
            20                  25                  30

Leu Ala Trp Tyr Gln Gln Lys Pro Gly Lys Ala Pro Lys Leu Leu Ile
        35                  40                  45

Tyr Ala Ala Ser Thr Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Val Ala Thr Tyr Tyr Cys Gln Arg Tyr Asn Arg Ala Pro Tyr
                85                  90                  95

Thr Phe Gly Gln Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205
```

Phe Asn Arg Gly Glu Cys
    210

<210> SEQ ID NO 31
<211> LENGTH: 448
<212> TYPE: PRT
<213> ORGANISM: Artificial Sequence
<220> FEATURE:
<223> OTHER INFORMATION: Atezolizumab heavy chain

<400> SEQUENCE: 31

```
Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Asp Ser
            20                  25                  30

Trp Ile His Trp Val Arg Gln Ala Pro Gly Lys Gly Leu Glu Trp Val
        35                  40                  45

Ala Trp Ile Ser Pro Tyr Gly Gly Ser Thr Tyr Tyr Ala Asp Ser Val
    50                  55                  60

Lys Gly Arg Phe Thr Ile Ser Ala Asp Thr Ser Lys Asn Thr Ala Tyr
65                  70                  75                  80

Leu Gln Met Asn Ser Leu Arg Ala Glu Asp Thr Ala Val Tyr Tyr Cys
                85                  90                  95

Ala Arg Arg His Trp Pro Gly Gly Phe Asp Tyr Trp Gly Gln Gly Thr
            100                 105                 110

Leu Val Thr Val Ser Ser Ala Ser Thr Lys Gly Pro Ser Val Phe Pro
        115                 120                 125

Leu Ala Pro Ser Ser Lys Ser Thr Ser Gly Gly Thr Ala Ala Leu Gly
    130                 135                 140

Cys Leu Val Lys Asp Tyr Phe Pro Glu Pro Val Thr Val Ser Trp Asn
145                 150                 155                 160

Ser Gly Ala Leu Thr Ser Gly Val His Thr Phe Pro Ala Val Leu Gln
                165                 170                 175

Ser Ser Gly Leu Tyr Ser Leu Ser Ser Val Val Thr Val Pro Ser Ser
            180                 185                 190

Ser Leu Gly Thr Gln Thr Tyr Ile Cys Asn Val Asn His Lys Pro Ser
        195                 200                 205

Asn Thr Lys Val Asp Lys Lys Val Glu Pro Lys Ser Cys Asp Lys Thr
    210                 215                 220

His Thr Cys Pro Pro Cys Pro Ala Pro Glu Leu Leu Gly Gly Pro Ser
225                 230                 235                 240

Val Phe Leu Phe Pro Pro Lys Pro Lys Asp Thr Leu Met Ile Ser Arg
                245                 250                 255

Thr Pro Glu Val Thr Cys Val Val Val Asp Val Ser His Glu Asp Pro
            260                 265                 270

Glu Val Lys Phe Asn Trp Tyr Val Asp Gly Val Glu Val His Asn Ala
        275                 280                 285

Lys Thr Lys Pro Arg Glu Glu Gln Tyr Ala Ser Thr Tyr Arg Val Val
    290                 295                 300

Ser Val Leu Thr Val Leu His Gln Asp Trp Leu Asn Gly Lys Glu Tyr
305                 310                 315                 320

Lys Cys Lys Val Ser Asn Lys Ala Leu Pro Ala Pro Ile Glu Lys Thr
                325                 330                 335

Ile Ser Lys Ala Lys Gly Gln Pro Arg Glu Pro Gln Val Tyr Thr Leu
            340                 345                 350
```

```
Pro Pro Ser Arg Glu Glu Met Thr Lys Asn Gln Val Ser Leu Thr Cys
        355                 360                 365

Leu Val Lys Gly Phe Tyr Pro Ser Asp Ile Ala Val Glu Trp Glu Ser
    370                 375                 380

Asn Gly Gln Pro Glu Asn Asn Tyr Lys Thr Thr Pro Pro Val Leu Asp
385                 390                 395                 400

Ser Asp Gly Ser Phe Phe Leu Tyr Ser Lys Leu Thr Val Asp Lys Ser
                405                 410                 415

Arg Trp Gln Gln Gly Asn Val Phe Ser Cys Ser Val Met His Glu Ala
            420                 425                 430

Leu His Asn His Tyr Thr Gln Lys Ser Leu Ser Leu Ser Pro Gly Lys
        435                 440                 445


<210> SEQ ID NO 32
<211> LENGTH: 214
<212> TYPE: PRT
<213> ORGANISM: Artificial Sequence
<220> FEATURE:
<223> OTHER INFORMATION: Atezolizumab light chain

<400> SEQUENCE: 32

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Val Ser Thr Ala
            20                  25                  30

Val Ala Trp Tyr Gln Gln Lys Pro Gly Lys Ala Pro Lys Leu Leu Ile
        35                  40                  45

Tyr Ser Ala Ser Phe Leu Tyr Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Tyr Leu Tyr His Pro Ala
                85                  90                  95

Thr Phe Gly Gln Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210


<210> SEQ ID NO 33
<211> LENGTH: 446
<212> TYPE: PRT
<213> ORGANISM: Artificial Sequence
<220> FEATURE:
<223> OTHER INFORMATION: Anti-human CD28 antibody heavy chain

<400> SEQUENCE: 33
```

-continued

```
Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser Tyr
            20                  25                  30

Tyr Ile His Trp Val Arg Gln Ala Pro Gly Gln Gly Leu Glu Trp Ile
        35                  40                  45

Gly Cys Ile Tyr Pro Gly Asn Val Asn Thr Asn Tyr Asn Glu Lys Phe
    50                  55                  60

Lys Asp Arg Ala Thr Leu Thr Val Asp Thr Ser Ile Ser Thr Ala Tyr
65                  70                  75                  80

Met Glu Leu Ser Arg Leu Arg Ser Asp Asp Thr Ala Val Tyr Phe Cys
                85                  90                  95

Thr Arg Ser His Tyr Gly Leu Asp Trp Asn Phe Asp Val Trp Gly Gln
            100                 105                 110

Gly Thr Thr Val Thr Val Ser Ser Ala Ser Thr Lys Gly Pro Ser Val
        115                 120                 125

Phe Pro Leu Ala Pro Cys Ser Arg Ser Thr Ser Glu Ser Thr Ala Ala
    130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
                165                 170                 175

Leu Gln Ser Ser Gly Leu Tyr Ser Leu Ser Ser Val Val Thr Val Pro
            180                 185                 190

Ser Ser Ser Leu Gly Thr Lys Thr Tyr Thr Cys Asn Val Asp His Lys
        195                 200                 205

Pro Ser Asn Thr Lys Val Asp Lys Arg Val Glu Ser Lys Tyr Gly Pro
    210                 215                 220

Pro Cys Pro Ser Cys Pro Ala Pro Glu Phe Leu Gly Gly Pro Ser Val
225                 230                 235                 240

Phe Leu Phe Pro Pro Lys Pro Lys Asp Thr Leu Met Ile Ser Arg Thr
                245                 250                 255

Pro Glu Val Thr Cys Val Val Val Asp Val Ser Gln Glu Asp Pro Glu
            260                 265                 270

Val Gln Phe Asn Trp Tyr Val Asp Gly Val Glu Val His Asn Ala Lys
        275                 280                 285

Thr Lys Pro Arg Glu Glu Gln Phe Asn Ser Thr Tyr Arg Val Val Ser
    290                 295                 300

Val Leu Thr Val Leu His Gln Asp Trp Leu Asn Gly Lys Glu Tyr Lys
305                 310                 315                 320

Cys Lys Val Ser Asn Lys Gly Leu Pro Ser Ser Ile Glu Lys Thr Ile
                325                 330                 335

Ser Lys Ala Lys Gly Gln Pro Arg Glu Pro Gln Val Tyr Thr Leu Pro
            340                 345                 350

Pro Ser Gln Glu Glu Met Thr Lys Asn Gln Val Ser Leu Thr Cys Leu
        355                 360                 365

Val Lys Gly Phe Tyr Pro Ser Asp Ile Ala Val Glu Trp Glu Ser Asn
    370                 375                 380

Gly Gln Pro Glu Asn Asn Tyr Lys Thr Thr Pro Pro Val Leu Asp Ser
385                 390                 395                 400

Asp Gly Ser Phe Phe Leu Tyr Ser Arg Leu Thr Val Asp Lys Ser Arg
                405                 410                 415
```

-continued

```
Trp Gln Glu Gly Asn Val Phe Ser Cys Ser Val Met His Glu Ala Leu
            420                 425                 430

His Asn His Tyr Thr Gln Lys Ser Leu Ser Leu Ser Leu Gly
        435                 440                 445


<210> SEQ ID NO 34
<211> LENGTH: 214
<212> TYPE: PRT
<213> ORGANISM: Artificial Sequence
<220> FEATURE:
<223> OTHER INFORMATION: Anti-human CD28 antibody light chain

<400> SEQUENCE: 34

Asp Ile Gln Met Thr Gln Ser Pro Ser Ser Leu Ser Ala Ser Val Gly
1               5                   10                  15

Asp Arg Val Thr Ile Thr Cys His Ala Ser Gln Asn Ile Tyr Val Trp
            20                  25                  30

Leu Asn Trp Tyr Gln Gln Lys Pro Gly Lys Ala Pro Lys Leu Leu Ile
        35                  40                  45

Tyr Lys Ala Ser Asn Leu His Thr Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Gly Gln Thr Tyr Pro Tyr
                85                  90                  95

Thr Phe Gly Gly Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210


<210> SEQ ID NO 35
<211> LENGTH: 215
<212> TYPE: PRT
<213> ORGANISM: Artificial Sequence
<220> FEATURE:
<223> OTHER INFORMATION: Ipi-se008 light chain

<400> SEQUENCE: 35

Glu Ile Val Leu Thr Gln Ser Pro Gly Thr Leu Ser Leu Ser Pro Gly
1               5                   10                  15

Glu Arg Ala Thr Leu Ser Cys Arg Ala Ser Gln Ser Val Gly Ser Ser
            20                  25                  30

Tyr Leu Ala Trp Tyr Gln Gln Lys Pro Gly Gln Ala Pro Arg Leu Leu
        35                  40                  45

Ile Cys Gly Ala Phe Ser Arg Ala Thr Gly Ile Pro Asp Arg Phe Ser
    50                  55                  60
```

```
Gly Ser Gly Ser Gly Thr Asp Phe Thr Leu Thr Ile Ser Arg Leu Glu
65                  70                  75                  80

Pro Glu Asp Phe Ala Val Tyr Tyr Cys Gln Gln Tyr Gly Ser Ser Pro
                85                  90                  95

Trp Thr Phe Gly Gln Gly Thr Lys Val Glu Ile Lys Arg Thr Val Ala
            100                 105                 110

Ala Pro Ser Val Phe Ile Phe Pro Pro Ser Asp Glu Gln Leu Lys Ser
        115                 120                 125

Gly Thr Ala Ser Val Val Cys Leu Leu Asn Asn Phe Tyr Pro Arg Glu
    130                 135                 140

Ala Lys Val Gln Trp Lys Val Asp Asn Ala Leu Gln Ser Gly Asn Ser
145                 150                 155                 160

Gln Glu Ser Val Thr Glu Gln Asp Ser Lys Asp Ser Thr Tyr Ser Leu
                165                 170                 175

Ser Ser Thr Leu Thr Leu Ser Lys Ala Asp Tyr Glu Lys His Lys Val
            180                 185                 190

Tyr Ala Cys Glu Val Thr His Gln Gly Leu Ser Ser Pro Val Thr Lys
        195                 200                 205

Ser Phe Asn Arg Gly Glu Cys
    210                 215


<210> SEQ ID NO 36
<211> LENGTH: 215
<212> TYPE: PRT
<213> ORGANISM: Artificial Sequence
<220> FEATURE:
<223> OTHER INFORMATION: Ipi-se010 light chain

<400> SEQUENCE: 36

Glu Ile Val Leu Thr Gln Ser Pro Gly Thr Leu Ser Leu Ser Pro Gly
1               5                   10                  15

Glu Arg Ala Thr Leu Ser Cys Arg Ala Ser Gln Ser Val Gly Ser Ser
            20                  25                  30

Tyr Leu Ala Trp Tyr Gln Gln Lys Pro Gly Gln Ala Pro Arg Leu Leu
        35                  40                  45

Ile Tyr Gly Ala Phe Ser Arg Ala Thr Gly Ile Pro Asp Arg Phe Ser
    50                  55                  60

Gly Ser Gly Cys Gly Thr Asp Phe Thr Leu Thr Ile Ser Arg Leu Glu
65                  70                  75                  80

Pro Glu Asp Phe Ala Val Tyr Tyr Cys Gln Gln Tyr Gly Ser Ser Pro
                85                  90                  95

Trp Thr Phe Gly Gln Gly Thr Lys Val Glu Ile Lys Arg Thr Val Ala
            100                 105                 110

Ala Pro Ser Val Phe Ile Phe Pro Pro Ser Asp Glu Gln Leu Lys Ser
        115                 120                 125

Gly Thr Ala Ser Val Val Cys Leu Leu Asn Asn Phe Tyr Pro Arg Glu
    130                 135                 140

Ala Lys Val Gln Trp Lys Val Asp Asn Ala Leu Gln Ser Gly Asn Ser
145                 150                 155                 160

Gln Glu Ser Val Thr Glu Gln Asp Ser Lys Asp Ser Thr Tyr Ser Leu
                165                 170                 175

Ser Ser Thr Leu Thr Leu Ser Lys Ala Asp Tyr Glu Lys His Lys Val
            180                 185                 190

Tyr Ala Cys Glu Val Thr His Gln Gly Leu Ser Ser Pro Val Thr Lys
        195                 200                 205
```

```
Ser Phe Asn Arg Gly Glu Cys
    210                 215


<210> SEQ ID NO 37
<211> LENGTH: 215
<212> TYPE: PRT
<213> ORGANISM: Artificial Sequence
<220> FEATURE:
<223> OTHER INFORMATION: Ipi-se009 light chain

<400> SEQUENCE: 37

Glu Ile Val Leu Thr Gln Ser Pro Gly Thr Leu Ser Leu Ser Pro Gly
1               5                   10                  15

Glu Arg Ala Thr Leu Ser Cys Arg Ala Ser Gln Ser Val Gly Ser Ser
            20                  25                  30

Tyr Leu Ala Trp Tyr Gln Gln Lys Pro Gly Gln Ala Pro Arg Leu Leu
        35                  40                  45

Ile Tyr Gly Ala Phe Cys Arg Ala Thr Gly Ile Pro Asp Arg Phe Ser
    50                  55                  60

Gly Ser Gly Ser Gly Thr Asp Phe Thr Leu Thr Ile Ser Arg Leu Glu
65                  70                  75                  80

Pro Glu Asp Phe Ala Val Tyr Tyr Cys Gln Gln Tyr Gly Ser Ser Pro
                85                  90                  95

Trp Thr Phe Gly Gln Gly Thr Lys Val Glu Ile Lys Arg Thr Val Ala
            100                 105                 110

Ala Pro Ser Val Phe Ile Phe Pro Pro Ser Asp Glu Gln Leu Lys Ser
        115                 120                 125

Gly Thr Ala Ser Val Val Cys Leu Leu Asn Asn Phe Tyr Pro Arg Glu
    130                 135                 140

Ala Lys Val Gln Trp Lys Val Asp Asn Ala Leu Gln Ser Gly Asn Ser
145                 150                 155                 160

Gln Glu Ser Val Thr Glu Gln Asp Ser Lys Asp Ser Thr Tyr Ser Leu
                165                 170                 175

Ser Ser Thr Leu Thr Leu Ser Lys Ala Asp Tyr Glu Lys His Lys Val
            180                 185                 190

Tyr Ala Cys Glu Val Thr His Gln Gly Leu Ser Ser Pro Val Thr Lys
        195                 200                 205

Ser Phe Asn Arg Gly Glu Cys
    210                 215


<210> SEQ ID NO 38
<211> LENGTH: 217
<212> TYPE: PRT
<213> ORGANISM: Artificial Sequence
<220> FEATURE:
<223> OTHER INFORMATION: Pem-se010 light chain

<400> SEQUENCE: 38

Glu Ile Val Leu Thr Gln Ser Pro Ala Thr Leu Ser Leu Ser Pro Gly
1               5                   10                  15

Glu Arg Ala Thr Leu Ser Cys Arg Ala Ser Lys Gly Val Ser Thr Ser
            20                  25                  30

Gly Tyr Ser Tyr Leu His Trp Tyr Gln Gln Lys Pro Gly Gln Ala Pro
        35                  40                  45

Arg Leu Leu Ile Tyr Leu Ala Ser Cys Glu Ser Gly Val Pro Ala Arg
    50                  55                  60

Phe Ser Gly Ser Gly Ser Gly Thr Asp Phe Thr Leu Thr Ile Ser Ser
```

```
65                  70                  75                  80

Leu Glu Pro Glu Asp Phe Ala Val Tyr Tyr Cys Gln His Ser Arg Asp
                85                  90                  95

Leu Pro Leu Thr Phe Gly Gly Gly Thr Lys Val Glu Ile Lys Arg Thr
            100                 105                 110

Val Ala Ala Pro Ser Val Phe Ile Phe Pro Pro Ser Asp Glu Gln Leu
        115                 120                 125

Lys Ser Gly Thr Ala Ser Val Val Cys Leu Leu Asn Asn Phe Tyr Pro
    130                 135                 140

Arg Glu Ala Lys Val Gln Trp Lys Val Asp Asn Ala Leu Gln Ser Gly
145                 150                 155                 160

Asn Ser Gln Glu Ser Val Thr Glu Gln Asp Ser Lys Asp Ser Thr Tyr
                165                 170                 175

Ser Leu Ser Ser Thr Leu Thr Leu Ser Lys Ala Asp Tyr Glu Lys His
            180                 185                 190

Lys Val Tyr Ala Cys Glu Val Thr His Gln Gly Leu Ser Ser Pro Val
        195                 200                 205

Thr Lys Ser Phe Asn Arg Gly Glu Cys
    210                 215


<210> SEQ ID NO 39
<211> LENGTH: 218
<212> TYPE: PRT
<213> ORGANISM: Artificial Sequence
<220> FEATURE:
<223> OTHER INFORMATION: Pem-se009 light chain

<400> SEQUENCE: 39

Glu Ile Val Leu Thr Gln Ser Pro Ala Thr Leu Ser Leu Ser Pro Gly
1               5                   10                  15

Glu Arg Ala Thr Leu Ser Cys Arg Ala Ser Lys Gly Val Ser Thr Ser
            20                  25                  30

Gly Tyr Ser Cys Leu His Trp Tyr Gln Gln Lys Pro Gly Gln Ala Pro
        35                  40                  45

Arg Leu Leu Ile Tyr Leu Ala Ser Tyr Leu Glu Ser Gly Val Pro Ala
    50                  55                  60

Arg Phe Ser Gly Ser Gly Ser Gly Thr Asp Phe Thr Leu Thr Ile Ser
65                  70                  75                  80

Ser Leu Glu Pro Glu Asp Phe Ala Val Tyr Tyr Cys Gln His Ser Arg
                85                  90                  95

Asp Leu Pro Leu Thr Phe Gly Gly Gly Thr Lys Val Glu Ile Lys Arg
            100                 105                 110

Thr Val Ala Ala Pro Ser Val Phe Ile Phe Pro Pro Ser Asp Glu Gln
        115                 120                 125

Leu Lys Ser Gly Thr Ala Ser Val Val Cys Leu Leu Asn Asn Phe Tyr
    130                 135                 140

Pro Arg Glu Ala Lys Val Gln Trp Lys Val Asp Asn Ala Leu Gln Ser
145                 150                 155                 160

Gly Asn Ser Gln Glu Ser Val Thr Glu Gln Asp Ser Lys Asp Ser Thr
                165                 170                 175

Tyr Ser Leu Ser Ser Thr Leu Thr Leu Ser Lys Ala Asp Tyr Glu Lys
            180                 185                 190

His Lys Val Tyr Ala Cys Glu Val Thr His Gln Gly Leu Ser Ser Pro
        195                 200                 205

Val Thr Lys Ser Phe Asn Arg Gly Glu Cys
```

210                 215

<210> SEQ ID NO 40
<211> LENGTH: 218
<212> TYPE: PRT
<213> ORGANISM: Artificial Sequence
<220> FEATURE:
<223> OTHER INFORMATION: Pem-se007 light chain

<400> SEQUENCE: 40

```
Glu Ile Val Leu Thr Gln Ser Pro Ala Thr Leu Ser Leu Ser Pro Gly
1               5                   10                  15

Glu Arg Ala Thr Leu Ser Cys Arg Ala Ser Lys Cys Val Ser Thr Ser
            20                  25                  30

Gly Tyr Ser Tyr Leu His Trp Tyr Gln Gln Lys Pro Gly Gln Ala Pro
        35                  40                  45

Arg Leu Leu Ile Tyr Leu Ala Ser Tyr Leu Glu Ser Gly Val Pro Ala
    50                  55                  60

Arg Phe Ser Gly Ser Gly Ser Gly Thr Asp Phe Thr Leu Thr Ile Ser
65                  70                  75                  80

Ser Leu Glu Pro Glu Asp Phe Ala Val Tyr Tyr Cys Gln His Ser Arg
                85                  90                  95

Asp Leu Pro Leu Thr Phe Gly Gly Gly Thr Lys Val Glu Ile Lys Arg
            100                 105                 110

Thr Val Ala Ala Pro Ser Val Phe Ile Phe Pro Pro Ser Asp Glu Gln
        115                 120                 125

Leu Lys Ser Gly Thr Ala Ser Val Val Cys Leu Leu Asn Asn Phe Tyr
    130                 135                 140

Pro Arg Glu Ala Lys Val Gln Trp Lys Val Asp Asn Ala Leu Gln Ser
145                 150                 155                 160

Gly Asn Ser Gln Glu Ser Val Thr Glu Gln Asp Ser Lys Asp Ser Thr
                165                 170                 175

Tyr Ser Leu Ser Ser Thr Leu Thr Leu Ser Lys Ala Asp Tyr Glu Lys
            180                 185                 190

His Lys Val Tyr Ala Cys Glu Val Thr His Gln Gly Leu Ser Ser Pro
        195                 200                 205

Val Thr Lys Ser Phe Asn Arg Gly Glu Cys
    210                 215
```

<210> SEQ ID NO 41
<211> LENGTH: 440
<212> TYPE: PRT
<213> ORGANISM: Artificial Sequence
<220> FEATURE:
<223> OTHER INFORMATION: Niv-se001 heavy chain variable domain

<400> SEQUENCE: 41

```
Gln Val Gln Leu Val Glu Ser Gly Gly Gly Val Val Gln Pro Gly Arg
1               5                   10                  15

Ser Leu Arg Leu Asp Cys Cys Ala Ser Gly Ile Thr Phe Ser Asn Ser
            20                  25                  30

Gly Met His Trp Val Arg Gln Ala Pro Gly Lys Gly Leu Glu Trp Val
        35                  40                  45

Ala Val Ile Trp Tyr Asp Gly Ser Lys Arg Tyr Tyr Ala Asp Ser Val
    50                  55                  60

Lys Gly Arg Phe Thr Ile Ser Arg Asp Asn Ser Lys Asn Thr Leu Phe
65                  70                  75                  80
```

-continued

```
Leu Gln Met Asn Ser Leu Arg Ala Glu Asp Thr Ala Val Tyr Tyr Cys
                85                  90                  95

Ala Thr Asn Asp Asp Tyr Trp Gly Gln Gly Thr Leu Val Thr Val Ser
            100                 105                 110

Ser Ala Ser Thr Lys Gly Pro Ser Val Phe Pro Leu Ala Pro Cys Ser
        115                 120                 125

Arg Ser Thr Ser Glu Ser Thr Ala Ala Leu Gly Cys Leu Val Lys Asp
    130                 135                 140

Tyr Phe Pro Glu Pro Val Thr Val Ser Trp Asn Ser Gly Ala Leu Thr
145                 150                 155                 160

Ser Gly Val His Thr Phe Pro Ala Val Leu Gln Ser Ser Gly Leu Tyr
                165                 170                 175

Ser Leu Ser Ser Val Val Thr Val Pro Ser Ser Ser Leu Gly Thr Lys
            180                 185                 190

Thr Tyr Thr Cys Asn Val Asp His Lys Pro Ser Asn Thr Lys Val Asp
        195                 200                 205

Lys Arg Val Glu Ser Lys Tyr Gly Pro Pro Cys Pro Pro Cys Pro Ala
    210                 215                 220

Pro Glu Phe Leu Gly Gly Pro Ser Val Phe Leu Phe Pro Pro Lys Pro
225                 230                 235                 240

Lys Asp Thr Leu Met Ile Ser Arg Thr Pro Glu Val Thr Cys Val Val
                245                 250                 255

Val Asp Val Ser Gln Glu Asp Pro Glu Val Gln Phe Asn Trp Tyr Val
            260                 265                 270

Asp Gly Val Glu Val His Asn Ala Lys Thr Lys Pro Arg Glu Glu Gln
        275                 280                 285

Phe Asn Ser Thr Tyr Arg Val Val Ser Val Leu Thr Val Leu His Gln
    290                 295                 300

Asp Trp Leu Asn Gly Lys Glu Tyr Lys Cys Lys Val Ser Asn Lys Gly
305                 310                 315                 320

Leu Pro Ser Ser Ile Glu Lys Thr Ile Ser Lys Ala Lys Gly Gln Pro
                325                 330                 335

Arg Glu Pro Gln Val Tyr Thr Leu Pro Pro Ser Gln Glu Glu Met Thr
            340                 345                 350

Lys Asn Gln Val Ser Leu Thr Cys Leu Val Lys Gly Phe Tyr Pro Ser
        355                 360                 365

Asp Ile Ala Val Glu Trp Glu Ser Asn Gly Gln Pro Glu Asn Asn Tyr
    370                 375                 380

Lys Thr Thr Pro Pro Val Leu Asp Ser Asp Gly Ser Phe Phe Leu Tyr
385                 390                 395                 400

Ser Arg Leu Thr Val Asp Lys Ser Arg Trp Gln Glu Gly Asn Val Phe
                405                 410                 415

Ser Cys Ser Val Met His Glu Ala Leu His Asn His Tyr Thr Gln Lys
            420                 425                 430

Ser Leu Ser Leu Ser Leu Gly Lys
        435                 440
```

<210> SEQ ID NO 42
<211> LENGTH: 214
<212> TYPE: PRT
<213> ORGANISM: Artificial Sequence
<220> FEATURE:
<223> OTHER INFORMATION: Niv-se005 light chain

<400> SEQUENCE: 42

-continued

```
Glu Ile Val Leu Thr Gln Ser Pro Ala Thr Leu Ser Leu Ser Pro Gly
1               5                   10                  15

Glu Arg Ala Thr Leu Ser Cys Arg Ala Ser Gln Ser Val Ser Ser Tyr
            20                  25                  30

Leu Ala Trp Tyr Gln Gln Lys Pro Gly Gln Ala Pro Arg Leu Leu Ile
        35                  40                  45

Cys Asp Ala Ser Asn Arg Ala Thr Gly Ile Pro Ala Arg Phe Ser Gly
    50                  55                  60

Ser Gly Ser Gly Thr Asp Phe Thr Leu Thr Ile Ser Ser Leu Glu Pro
65                  70                  75                  80

Glu Asp Phe Ala Val Tyr Tyr Cys Gln Gln Ser Ser Asn Trp Pro Arg
                85                  90                  95

Thr Phe Gly Gln Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210


<210> SEQ ID NO 43
<211> LENGTH: 214
<212> TYPE: PRT
<213> ORGANISM: Artificial Sequence
<220> FEATURE:
<223> OTHER INFORMATION: Niv-se007 light chain

<400> SEQUENCE: 43

Glu Ile Val Leu Thr Gln Ser Pro Ala Thr Leu Ser Leu Ser Pro Gly
1               5                   10                  15

Glu Arg Ala Thr Leu Ser Cys Arg Ala Ser Gln Ser Val Ser Ser Tyr
            20                  25                  30

Leu Ala Trp Tyr Gln Gln Lys Pro Gly Gln Ala Pro Arg Leu Leu Ile
        35                  40                  45

Tyr Asp Ala Ser Asn Arg Ala Thr Gly Ile Pro Ala Arg Phe Ser Gly
    50                  55                  60

Ser Gly Ser Gly Thr Asp Phe Thr Leu Thr Ile Ser Ser Leu Glu Pro
65                  70                  75                  80

Glu Asp Phe Ala Val Tyr Tyr Cys Gln Gln Cys Ser Asn Trp Pro Arg
                85                  90                  95

Thr Phe Gly Gln Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140
```

-continued

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210

<210> SEQ ID NO 44
<211> LENGTH: 133
<212> TYPE: PRT
<213> ORGANISM: Artificial Sequence
<220> FEATURE:
<223> OTHER INFORMATION: Interleukin-2 with mutation

<400> SEQUENCE: 44

Ala Pro Thr Ser Ser Ser Thr Lys Lys Thr Gln Leu Gln Leu Glu His
1               5                   10                  15

Leu Leu Leu Asp Leu Gln Met Ile Leu Asn Gly Ile Asn Asn Tyr Lys
            20                  25                  30

Asn Pro Lys Leu Thr Arg Met Leu Cys Phe Lys Phe Tyr Met Pro Lys
        35                  40                  45

Lys Ala Thr Glu Leu Lys His Leu Gln Cys Leu Glu Glu Glu Leu Lys
    50                  55                  60

Pro Leu Glu Glu Val Leu Asn Leu Ala Gln Ser Lys Asn Phe His Leu
65                  70                  75                  80

Arg Pro Arg Asp Leu Ile Ser Asn Ile Asn Val Ile Val Leu Glu Leu
                85                  90                  95

Lys Gly Ser Glu Thr Thr Phe Met Cys Glu Tyr Ala Asp Glu Thr Ala
            100                 105                 110

Thr Ile Val Glu Phe Leu Asn Arg Trp Ile Thr Phe Ser Gln Ser Ile
        115                 120                 125

Ile Ser Thr Leu Thr
    130

<210> SEQ ID NO 45
<211> LENGTH: 133
<212> TYPE: PRT
<213> ORGANISM: Artificial Sequence
<220> FEATURE:
<223> OTHER INFORMATION: Interleukin-2 with mutation

<400> SEQUENCE: 45

Ala Pro Thr Ser Ser Ser Thr Lys Lys Thr Gln Leu Gln Leu Glu His
1               5                   10                  15

Leu Leu Leu Asp Leu Gln Met Ile Leu Asn Gly Ile Asn Asn Tyr Lys
            20                  25                  30

Asn Pro Lys Leu Cys Arg Met Leu Thr Phe Lys Phe Tyr Met Pro Lys
        35                  40                  45

Lys Ala Thr Glu Leu Lys His Leu Gln Cys Leu Glu Glu Glu Leu Lys
    50                  55                  60

Pro Leu Glu Glu Val Leu Asn Leu Ala Gln Ser Lys Asn Phe His Leu
65                  70                  75                  80

Arg Pro Arg Asp Leu Ile Ser Asn Ile Asn Val Ile Val Leu Glu Leu
                85                  90                  95

```
Lys Gly Ser Glu Thr Thr Phe Met Cys Glu Tyr Ala Asp Glu Thr Ala
            100                 105                 110

Thr Ile Val Glu Phe Leu Asn Arg Trp Ile Thr Phe Ser Gln Ser Ile
        115                 120                 125

Ile Ser Thr Leu Thr
    130


<210> SEQ ID NO 46
<211> LENGTH: 133
<212> TYPE: PRT
<213> ORGANISM: Artificial Sequence
<220> FEATURE:
<223> OTHER INFORMATION: Interleukin-2 with mutation

<400> SEQUENCE: 46

Ala Pro Thr Ser Ser Ser Thr Lys Lys Thr Gln Leu Gln Leu Glu His
1               5                   10                  15

Leu Leu Leu Asp Leu Gln Met Ile Leu Asn Gly Ile Asn Asn Tyr Lys
            20                  25                  30

Asn Pro Lys Leu Thr Arg Met Leu Thr Phe Lys Phe Cys Met Pro Lys
        35                  40                  45

Lys Ala Thr Glu Leu Lys His Leu Gln Cys Leu Glu Glu Glu Leu Lys
    50                  55                  60

Pro Leu Glu Glu Val Leu Asn Leu Ala Gln Ser Lys Asn Phe His Leu
65                  70                  75                  80

Arg Pro Arg Asp Leu Ile Ser Asn Ile Asn Val Ile Val Leu Glu Leu
                85                  90                  95

Lys Gly Ser Glu Thr Thr Phe Met Cys Glu Tyr Ala Asp Glu Thr Ala
            100                 105                 110

Thr Ile Val Glu Phe Leu Asn Arg Trp Ile Thr Phe Ser Gln Ser Ile
        115                 120                 125

Ile Ser Thr Leu Thr
    130


<210> SEQ ID NO 47
<211> LENGTH: 133
<212> TYPE: PRT
<213> ORGANISM: Artificial Sequence
<220> FEATURE:
<223> OTHER INFORMATION: Interleukin-2 with mutation

<400> SEQUENCE: 47

Ala Pro Thr Ser Ser Ser Thr Lys Lys Thr Gln Leu Gln Leu Glu His
1               5                   10                  15

Leu Leu Leu Asp Leu Gln Met Ile Leu Asn Gly Ile Asn Asn Tyr Lys
            20                  25                  30

Asn Pro Lys Leu Thr Arg Met Leu Cys Phe Lys Phe Tyr Met Pro Lys
        35                  40                  45

Lys Ala Thr Glu Leu Lys His Leu Gln Cys Leu Glu Glu Glu Leu Lys
    50                  55                  60

Pro Leu Glu Glu Val Leu Asn Leu Ala Gln Ser Lys Asn Phe His Leu
65                  70                  75                  80

Arg Pro Arg Asp Leu Ile Cys Asn Ile Asn Val Ile Val Leu Glu Leu
                85                  90                  95

Lys Gly Ser Glu Thr Thr Phe Met Cys Glu Tyr Ala Asp Glu Thr Ala
            100                 105                 110

Thr Ile Val Glu Phe Leu Asn Arg Trp Ile Thr Phe Ser Gln Ser Ile
```

```
        115                 120                 125

Ile Ser Thr Leu Thr
    130


<210> SEQ ID NO 48
<211> LENGTH: 133
<212> TYPE: PRT
<213> ORGANISM: Artificial Sequence
<220> FEATURE:
<223> OTHER INFORMATION: Interleukin-2 with mutation

<400> SEQUENCE: 48

Ala Pro Thr Ser Ser Ser Thr Lys Lys Thr Gln Leu Gln Leu Glu His
1               5                   10                  15

Leu Leu Cys Asp Leu Gln Met Ile Leu Asn Gly Ile Asn Asn Tyr Lys
            20                  25                  30

Asn Pro Lys Leu Cys Arg Met Leu Thr Phe Lys Phe Tyr Met Pro Lys
        35                  40                  45

Lys Ala Thr Glu Leu Lys His Leu Gln Cys Leu Glu Glu Glu Leu Lys
    50                  55                  60

Pro Leu Glu Glu Val Leu Asn Leu Ala Gln Ser Lys Asn Phe His Leu
65                  70                  75                  80

Arg Pro Arg Asp Leu Ile Ser Asn Ile Asn Val Ile Val Leu Glu Leu
                85                  90                  95

Lys Gly Ser Glu Thr Thr Phe Met Cys Glu Tyr Ala Asp Glu Thr Ala
            100                 105                 110

Thr Ile Val Glu Phe Leu Asn Arg Trp Ile Thr Phe Ser Gln Ser Ile
        115                 120                 125

Ile Ser Thr Leu Thr
    130


<210> SEQ ID NO 49
<211> LENGTH: 133
<212> TYPE: PRT
<213> ORGANISM: Artificial Sequence
<220> FEATURE:
<223> OTHER INFORMATION: Interleukin-2 with mutation

<400> SEQUENCE: 49

Ala Pro Thr Ser Ser Ser Thr Lys Lys Thr Gln Leu Gln Leu Glu His
1               5                   10                  15

Leu Leu Leu Asp Leu Gln Met Ile Leu Asn Gly Ile Asn Asn Tyr Lys
            20                  25                  30

Asn Pro Lys Leu Thr Arg Met Leu Cys Phe Lys Phe Tyr Met Pro Lys
        35                  40                  45

Lys Ala Thr Glu Leu Lys His Leu Gln Cys Leu Glu Glu Glu Leu Lys
    50                  55                  60

Pro Leu Glu Glu Val Leu Asn Leu Ala Gln Ser Lys Asn Phe His Leu
65                  70                  75                  80

Arg Pro Arg Cys Leu Ile Ser Asn Ile Asn Val Ile Val Leu Glu Leu
                85                  90                  95

Lys Gly Ser Glu Thr Thr Phe Met Cys Glu Tyr Ala Asp Glu Thr Ala
            100                 105                 110

Thr Ile Val Glu Phe Leu Asn Arg Trp Ile Thr Phe Ser Gln Ser Ile
        115                 120                 125

Ile Ser Thr Leu Thr
    130
```

<210> SEQ ID NO 50
<211> LENGTH: 133
<212> TYPE: PRT
<213> ORGANISM: Artificial Sequence
<220> FEATURE:
<223> OTHER INFORMATION: Interleukin-2 with mutation

<400> SEQUENCE: 50

```
Ala Pro Thr Ser Ser Ser Thr Lys Lys Thr Gln Leu Gln Leu Glu His
1               5                   10                  15

Leu Leu Leu Asp Leu Gln Met Ile Leu Asn Gly Ile Asn Asn Tyr Lys
            20                  25                  30

Asn Pro Lys Leu Thr Asp Met Leu Cys Phe Lys Phe Tyr Met Pro Lys
        35                  40                  45

Lys Ala Thr Glu Leu Lys His Leu Gln Cys Leu Glu Glu Glu Leu Lys
    50                  55                  60

Pro Leu Glu Glu Val Leu Asn Leu Ala Gln Ser Lys Asn Phe His Leu
65                  70                  75                  80

Arg Pro Arg Asp Leu Ile Cys Asn Ile Asn Val Ile Val Leu Glu Leu
                85                  90                  95

Lys Gly Ser Glu Thr Thr Phe Met Cys Glu Tyr Ala Asp Glu Thr Ala
            100                 105                 110

Thr Ile Val Glu Phe Leu Asn Arg Trp Ile Thr Phe Ser Gln Ser Ile
        115                 120                 125

Ile Ser Thr Leu Thr
    130
```

<210> SEQ ID NO 51
<211> LENGTH: 133
<212> TYPE: PRT
<213> ORGANISM: Artificial Sequence
<220> FEATURE:
<223> OTHER INFORMATION: Interleukin-2 with mutation

<400> SEQUENCE: 51

```
Ala Pro Thr Ser Ser Ser Thr Lys Lys Thr Gln Leu Gln Leu Glu His
1               5                   10                  15

Leu Leu Leu Asp Leu Gln Met Ile Leu Asn Gly Ile Asn Asn Tyr Lys
            20                  25                  30

Asn Pro Lys Leu Thr Asp Met Leu Cys Phe Lys Phe Tyr Met Pro Lys
        35                  40                  45

Lys Ala Thr Glu Leu Lys His Leu Gln Cys Leu Glu Arg Glu Leu Lys
    50                  55                  60

Pro Leu Glu Glu Val Leu Asn Leu Ala Gln Ser Lys Asn Phe His Leu
65                  70                  75                  80

Arg Pro Arg Asp Leu Ile Cys Asn Ile Asn Val Ile Val Leu Glu Leu
                85                  90                  95

Lys Gly Ser Glu Thr Thr Phe Met Cys Glu Tyr Ala Asp Glu Thr Ala
            100                 105                 110

Thr Ile Val Glu Phe Leu Asn Arg Trp Ile Thr Phe Ser Gln Ser Ile
        115                 120                 125

Ile Ser Thr Leu Thr
    130
```

<210> SEQ ID NO 52
<211> LENGTH: 133
<212> TYPE: PRT
<213> ORGANISM: Artificial Sequence
<220> FEATURE:
<223> OTHER INFORMATION: Interleukin-2 with mutation

<400> SEQUENCE: 52

```
Ala Pro Thr Ser Ser Ser Thr Lys Lys Thr Gln Leu Gln Leu Glu His
1               5                   10                  15

Leu Leu Cys Asp Leu Gln Met Ile Leu Asn Gly Ile Asn Asn Tyr Lys
            20                  25                  30

Asn Pro Lys Leu Thr Asp Met Leu Cys Phe Lys Phe Tyr Met Pro Lys
        35                  40                  45

Lys Ala Thr Glu Leu Lys His Leu Gln Cys Leu Glu Arg Glu Leu Lys
    50                  55                  60

Pro Leu Glu Glu Val Leu Asn Leu Ala Gln Ser Lys Asn Phe His Leu
65                  70                  75                  80

Arg Pro Arg Asp Leu Ile Ser Asn Ile Asn Val Ile Val Leu Glu Leu
                85                  90                  95

Lys Gly Ser Glu Thr Thr Phe Met Cys Glu Tyr Ala Asp Glu Thr Ala
            100                 105                 110

Thr Ile Val Glu Phe Leu Asn Arg Trp Ile Thr Phe Ser Gln Ser Ile
        115                 120                 125

Ile Ser Thr Leu Thr
    130
```

<210> SEQ ID NO 53
<211> LENGTH: 133
<212> TYPE: PRT
<213> ORGANISM: Artificial Sequence
<220> FEATURE:
<223> OTHER INFORMATION: Interleukin-2 with mutation

<400> SEQUENCE: 53

```
Ala Pro Thr Ser Ser Ser Thr Lys Lys Thr Gln Leu Gln Leu Glu His
1               5                   10                  15

Leu Leu Leu Asp Leu Gln Met Ile Leu Asn Gly Ile Asn Asn Tyr Lys
            20                  25                  30

Asn Pro Lys Leu Thr Asp Met Leu Cys Phe Lys Phe Tyr Met Pro Lys
        35                  40                  45

Lys Ala Thr Glu Leu Lys His Leu Gln Cys Leu Glu Arg Glu Leu Lys
    50                  55                  60

Pro Leu Glu Glu Val Leu Asn Leu Ala Gln Ser Lys Asn Phe His Leu
65                  70                  75                  80

Arg Pro Arg Cys Leu Ile Ser Asn Ile Asn Val Ile Val Leu Glu Leu
                85                  90                  95

Lys Gly Ser Glu Thr Thr Phe Met Cys Glu Tyr Ala Asp Glu Thr Ala
            100                 105                 110

Thr Ile Val Glu Phe Leu Asn Arg Trp Ile Thr Phe Ser Gln Ser Ile
        115                 120                 125

Ile Ser Thr Leu Thr
    130
```

<210> SEQ ID NO 54
<211> LENGTH: 159
<212> TYPE: PRT
<213> ORGANISM: Artificial Sequence
<220> FEATURE:
<223> OTHER INFORMATION: Interleukin-10 with mutation

<400> SEQUENCE: 54

-continued

Ser Pro Gly Gln Gly Thr Gln Ser Glu Asn Ser Cys Thr His Phe Pro
1 5 10 15

Gly Asn Leu Pro Asn Met Leu Arg Asp Leu Arg Asp Ala Phe Ser Arg
20 25 30

Val Lys Thr Phe Phe Gln Met Lys Asp Gln Leu Asp Asn Leu Leu Leu
35 40 45

Lys Glu Ser Leu Leu Glu Asp Phe Lys Gly Tyr Leu Gly Cys Gln Ala
50 55 60

Leu Ser Glu Met Ile Gln Phe Tyr Leu Glu Glu Val Met Pro Gln Ala
65 70 75 80

Glu Asn Gln Asp Pro Asp Ile Lys Ala His Val Asn Ser Leu Gly Glu
85 90 95

Asn Leu Lys Thr Leu Arg Leu Arg Leu Arg Arg Cys His Arg Phe Leu
100 105 110

Pro Cys Glu Asn Lys Ser Lys Ala Val Glu Gln Val Lys Asn Ala Phe
115 120 125

Asn Lys Leu Gln Glu Lys Gly Ile Tyr Lys Ala Met Ser Glu Phe Asp
130 135 140

Ile Phe Ile Asn Tyr Ile Glu Tyr Met Thr Met Lys Ile Arg Asn
145 150 155

<210> SEQ ID NO 55
<211> LENGTH: 159
<212> TYPE: PRT
<213> ORGANISM: Artificial Sequence
<220> FEATURE:
<223> OTHER INFORMATION: Interleukin-10 with mutation

<400> SEQUENCE: 55

Ser Pro Gly Gln Gly Thr Gln Ser Glu Asn Ser Cys Thr His Phe Pro
1 5 10 15

Gly Asn Leu Pro Asn Met Leu Arg Asp Leu Arg Asp Ala Phe Cys Arg
20 25 30

Val Lys Thr Phe Phe Gln Met Lys Asp Gln Leu Asp Asn Leu Leu Leu
35 40 45

Lys Glu Ser Leu Leu Glu Asp Phe Lys Gly Tyr Leu Gly Cys Gln Ala
50 55 60

Leu Ser Glu Met Ile Gln Phe Tyr Leu Glu Glu Val Met Pro Gln Ala
65 70 75 80

Glu Asn Gln Asp Pro Asp Ile Lys Ala His Val Asn Ser Leu Gly Glu
85 90 95

Asn Leu Lys Thr Leu Arg Leu Arg Leu Arg Arg Cys His Arg Phe Leu
100 105 110

Pro Cys Glu Asn Lys Ser Lys Ala Val Glu Gln Val Lys Asn Ala Phe
115 120 125

Asn Lys Leu Gln Glu Lys Gly Ile Tyr Lys Ala Met Ser Glu Phe Asp
130 135 140

Ile Phe Ile Asn Tyr Ile Glu Tyr Met Thr Met Lys Ile Arg Asn
145 150 155

<210> SEQ ID NO 56
<211> LENGTH: 159
<212> TYPE: PRT
<213> ORGANISM: Artificial Sequence
<220> FEATURE:
<223> OTHER INFORMATION: Interleukin-10 with mutation

<400> SEQUENCE: 56

```
Ser Pro Gly Gln Gly Thr Gln Ser Glu Asn Ser Cys Thr His Phe Pro
1               5                   10                  15

Gly Asn Leu Pro Asn Met Leu Arg Asp Leu Arg Asp Ala Phe Ser Arg
            20                  25                  30

Val Cys Thr Phe Phe Gln Met Lys Asp Gln Leu Asp Asn Leu Leu Leu
        35                  40                  45

Lys Glu Ser Leu Leu Glu Asp Phe Lys Gly Tyr Leu Gly Cys Gln Ala
    50                  55                  60

Leu Ser Glu Met Ile Gln Phe Tyr Leu Glu Glu Val Met Pro Gln Ala
65                  70                  75                  80

Glu Asn Gln Asp Pro Asp Ile Lys Ala His Val Asn Ser Leu Gly Glu
                85                  90                  95

Asn Leu Lys Thr Leu Arg Leu Arg Leu Arg Arg Cys His Arg Phe Leu
            100                 105                 110

Pro Cys Glu Asn Lys Ser Lys Ala Val Glu Gln Val Lys Asn Ala Phe
        115                 120                 125

Asn Lys Leu Gln Glu Lys Gly Ile Tyr Lys Ala Met Ser Glu Phe Asp
    130                 135                 140

Ile Phe Ile Asn Tyr Ile Glu Tyr Met Thr Met Lys Ile Arg Asn
145                 150                 155


<210> SEQ ID NO 57
<211> LENGTH: 159
<212> TYPE: PRT
<213> ORGANISM: Artificial Sequence
<220> FEATURE:
<223> OTHER INFORMATION: Interleukin-10 with mutation

<400> SEQUENCE: 57

Ser Pro Gly Gln Gly Thr Gln Ser Glu Asn Ser Cys Thr His Phe Pro
1               5                   10                  15

Gly Asn Leu Pro Asn Met Leu Arg Asp Leu Arg Asp Ala Phe Ser Arg
            20                  25                  30

Val Lys Thr Phe Phe Gln Met Lys Asp Gln Leu Cys Asn Leu Leu Leu
        35                  40                  45

Lys Glu Ser Leu Leu Glu Asp Phe Lys Gly Tyr Leu Gly Cys Gln Ala
    50                  55                  60

Leu Ser Glu Met Ile Gln Phe Tyr Leu Glu Glu Val Met Pro Gln Ala
65                  70                  75                  80

Glu Asn Gln Asp Pro Asp Ile Lys Ala His Val Asn Ser Leu Gly Glu
                85                  90                  95

Asn Leu Lys Thr Leu Arg Leu Arg Leu Arg Arg Cys His Arg Phe Leu
            100                 105                 110

Pro Cys Glu Asn Lys Ser Lys Ala Val Glu Gln Val Lys Asn Ala Phe
        115                 120                 125

Asn Lys Leu Gln Glu Lys Gly Ile Tyr Lys Ala Met Ser Glu Phe Asp
    130                 135                 140

Ile Phe Ile Asn Tyr Ile Glu Tyr Met Thr Met Lys Ile Arg Asn
145                 150                 155


<210> SEQ ID NO 58
<211> LENGTH: 159
<212> TYPE: PRT
<213> ORGANISM: Artificial Sequence
<220> FEATURE:
<223> OTHER INFORMATION: Interleukin-10 with mutation
```

<400> SEQUENCE: 58

Ser Pro Gly Gln Gly Thr Gln Ser Glu Asn Ser Cys Thr His Phe Pro
1               5                   10                  15

Gly Asn Leu Pro Asn Met Leu Arg Asp Leu Arg Asp Ala Phe Ser Cys
            20                  25                  30

Val Lys Thr Phe Phe Gln Met Lys Asp Gln Leu Asp Asn Leu Leu Leu
        35                  40                  45

Lys Glu Ser Leu Leu Glu Asp Phe Lys Gly Tyr Leu Gly Cys Gln Ala
    50                  55                  60

Leu Ser Glu Met Ile Gln Phe Tyr Leu Glu Glu Val Met Pro Gln Ala
65                  70                  75                  80

Glu Asn Gln Asp Pro Asp Ile Lys Ala His Val Asn Ser Leu Gly Glu
                85                  90                  95

Asn Leu Lys Thr Leu Arg Leu Arg Leu Arg Arg Cys His Arg Phe Leu
            100                 105                 110

Pro Cys Glu Asn Lys Ser Lys Ala Val Glu Gln Val Lys Asn Ala Phe
        115                 120                 125

Asn Lys Leu Gln Glu Lys Gly Ile Tyr Lys Ala Met Ser Glu Phe Asp
    130                 135                 140

Ile Phe Ile Asn Tyr Ile Glu Tyr Met Thr Met Lys Ile Arg Asn
145                 150                 155

<210> SEQ ID NO 59
<211> LENGTH: 159
<212> TYPE: PRT
<213> ORGANISM: Artificial Sequence
<220> FEATURE:
<223> OTHER INFORMATION: Interleukin-10 with mutation

<400> SEQUENCE: 59

Ser Pro Gly Gln Gly Thr Gln Ser Glu Asn Ser Cys Thr His Phe Pro
1               5                   10                  15

Gly Asn Leu Pro Asn Met Leu Arg Asp Leu Arg Asp Ala Phe Ser Arg
            20                  25                  30

Val Lys Cys Phe Phe Gln Met Lys Asp Gln Leu Asp Asn Leu Leu Leu
        35                  40                  45

Lys Glu Ser Leu Leu Glu Asp Phe Lys Gly Tyr Leu Gly Cys Gln Ala
    50                  55                  60

Leu Ser Glu Met Ile Gln Phe Tyr Leu Glu Glu Val Met Pro Gln Ala
65                  70                  75                  80

Glu Asn Gln Asp Pro Asp Ile Lys Ala His Val Asn Ser Leu Gly Glu
                85                  90                  95

Asn Leu Lys Thr Leu Arg Leu Arg Leu Arg Arg Cys His Arg Phe Leu
            100                 105                 110

Pro Cys Glu Asn Lys Ser Lys Ala Val Glu Gln Val Lys Asn Ala Phe
        115                 120                 125

Asn Lys Leu Gln Glu Lys Gly Ile Tyr Lys Ala Met Ser Glu Phe Asp
    130                 135                 140

Ile Phe Ile Asn Tyr Ile Glu Tyr Met Thr Met Lys Ile Arg Asn
145                 150                 155

<210> SEQ ID NO 60
<211> LENGTH: 453
<212> TYPE: PRT
<213> ORGANISM: Artificial Sequence
<220> FEATURE:
<223> OTHER INFORMATION: Anti-human VEGF antibody heavy chain

<400> SEQUENCE: 60

Glu Val Gln Leu Val Glu Ser Gly Gly Gly Leu Val Gln Pro Gly Gly
1               5                   10                  15

Ser Leu Arg Leu Ser Cys Ala Ala Ser Gly Tyr Thr Phe Thr Asn Tyr
            20                  25                  30

Gly Met Asn Trp Val Arg Gln Ala Pro Gly Lys Gly Leu Glu Trp Val
        35                  40                  45

Gly Trp Ile Asn Thr Tyr Thr Gly Glu Pro Thr Tyr Ala Ala Asp Phe
    50                  55                  60

Lys Arg Arg Phe Thr Phe Ser Leu Asp Thr Ser Lys Ser Thr Ala Tyr
65                  70                  75                  80

Leu Gln Met Asn Ser Leu Arg Ala Glu Asp Thr Ala Val Tyr Tyr Cys
                85                  90                  95

Ala Lys Tyr Pro His Tyr Tyr Gly Ser Ser His Trp Tyr Phe Asp Val
            100                 105                 110

Trp Gly Gln Gly Thr Leu Val Thr Val Ser Ser Ala Ser Thr Lys Gly
        115                 120                 125

Pro Ser Val Phe Pro Leu Ala Pro Ser Ser Lys Ser Thr Ser Gly Gly
    130                 135                 140

Thr Ala Ala Leu Gly Cys Leu Val Lys Asp Tyr Phe Pro Glu Pro Val
145                 150                 155                 160

Thr Val Ser Trp Asn Ser Gly Ala Leu Thr Ser Gly Val His Thr Phe
                165                 170                 175

Pro Ala Val Leu Gln Ser Ser Gly Leu Tyr Ser Leu Ser Ser Val Val
            180                 185                 190

Thr Val Pro Ser Ser Ser Leu Gly Thr Gln Thr Tyr Ile Cys Asn Val
        195                 200                 205

Asn His Lys Pro Ser Asn Thr Lys Val Asp Lys Lys Val Glu Pro Lys
    210                 215                 220

Ser Cys Asp Lys Thr His Thr Cys Pro Pro Cys Pro Ala Pro Glu Leu
225                 230                 235                 240

Leu Gly Gly Pro Ser Val Phe Leu Phe Pro Pro Lys Pro Lys Asp Thr
                245                 250                 255

Leu Met Ile Ser Arg Thr Pro Glu Val Thr Cys Val Val Val Asp Val
            260                 265                 270

Ser His Glu Asp Pro Glu Val Lys Phe Asn Trp Tyr Val Asp Gly Val
        275                 280                 285

Glu Val His Asn Ala Lys Thr Lys Pro Arg Glu Glu Gln Tyr Asn Ser
    290                 295                 300

Thr Tyr Arg Val Val Ser Val Leu Thr Val Leu His Gln Asp Trp Leu
305                 310                 315                 320

Asn Gly Lys Glu Tyr Lys Cys Lys Val Ser Asn Lys Ala Leu Pro Ala
                325                 330                 335

Pro Ile Glu Lys Thr Ile Ser Lys Ala Lys Gly Gln Pro Arg Glu Pro
            340                 345                 350

Gln Val Tyr Thr Leu Pro Pro Ser Arg Glu Glu Met Thr Lys Asn Gln
        355                 360                 365

Val Ser Leu Thr Cys Leu Val Lys Gly Phe Tyr Pro Ser Asp Ile Ala
    370                 375                 380

Val Glu Trp Glu Ser Asn Gly Gln Pro Glu Asn Asn Tyr Lys Thr Thr
385                 390                 395                 400

Pro Pro Val Leu Asp Ser Asp Gly Ser Phe Phe Leu Tyr Ser Lys Leu

```
                405                 410                 415

Thr Val Asp Lys Ser Arg Trp Gln Gln Gly Asn Val Phe Ser Cys Ser
            420                 425                 430

Val Met His Glu Ala Leu His Asn His Tyr Thr Gln Lys Ser Leu Ser
        435                 440                 445

Leu Ser Pro Gly Lys
    450


<210> SEQ ID NO 61
<211> LENGTH: 214
<212> TYPE: PRT
<213> ORGANISM: Artificial Sequence
<220> FEATURE:
<223> OTHER INFORMATION: Anti-human VEGF antibody light chain

<400> SEQUENCE: 61

Asp Ile Gln Met Thr Gln Ser Pro Ser Ser Leu Ser Ala Ser Val Gly
1               5                   10                  15

Asp Arg Val Thr Ile Thr Cys Ser Ala Ser Gln Asp Ile Ser Asn Tyr
            20                  25                  30

Leu Asn Trp Tyr Gln Gln Lys Pro Gly Lys Ala Pro Lys Val Leu Ile
        35                  40                  45

Tyr Phe Thr Ser Ser Leu His Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Tyr Ser Thr Val Pro Trp
                85                  90                  95

Thr Phe Gly Gln Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210


<210> SEQ ID NO 62
<211> LENGTH: 451
<212> TYPE: PRT
<213> ORGANISM: Artificial Sequence
<220> FEATURE:
<223> OTHER INFORMATION: Anti-human CD20 antibody heavy chain

<400> SEQUENCE: 62

Gln Val Gln Leu Gln Gln Pro Gly Ala Glu Leu Val Lys Pro Gly Ala
1               5                   10                  15

Ser Val Lys Met Ser Cys Lys Ala Ser Gly Tyr Thr Phe Thr Ser Tyr
            20                  25                  30
```

-continued

```
Asn Met His Trp Val Lys Gln Thr Pro Gly Arg Gly Leu Glu Trp Ile
        35                  40                  45

Gly Ala Ile Tyr Pro Gly Asn Gly Asp Thr Ser Tyr Asn Gln Lys Phe
    50                  55                  60

Lys Gly Lys Ala Thr Leu Thr Ala Asp Lys Ser Ser Ser Thr Ala Tyr
65                  70                  75                  80

Met Gln Leu Ser Ser Leu Thr Ser Glu Asp Ser Ala Val Tyr Tyr Cys
                85                  90                  95

Ala Arg Ser Thr Tyr Tyr Gly Gly Asp Trp Tyr Phe Asn Val Trp Gly
            100                 105                 110

Ala Gly Thr Thr Val Thr Val Ser Ala Ala Ser Thr Lys Gly Pro Ser
        115                 120                 125

Val Phe Pro Leu Ala Pro Ser Ser Lys Ser Thr Ser Gly Gly Thr Ala
    130                 135                 140

Ala Leu Gly Cys Leu Val Lys Asp Tyr Phe Pro Glu Pro Val Thr Val
145                 150                 155                 160

Ser Trp Asn Ser Gly Ala Leu Thr Ser Gly Val His Thr Phe Pro Ala
                165                 170                 175

Val Leu Gln Ser Ser Gly Leu Tyr Ser Leu Ser Ser Val Val Thr Val
            180                 185                 190

Pro Ser Ser Ser Leu Gly Thr Gln Thr Tyr Ile Cys Asn Val Asn His
        195                 200                 205

Lys Pro Ser Asn Thr Lys Val Asp Lys Lys Ala Glu Pro Lys Ser Cys
    210                 215                 220

Asp Lys Thr His Thr Cys Pro Pro Cys Pro Ala Pro Glu Leu Leu Gly
225                 230                 235                 240

Gly Pro Ser Val Phe Leu Phe Pro Pro Lys Pro Lys Asp Thr Leu Met
                245                 250                 255

Ile Ser Arg Thr Pro Glu Val Thr Cys Val Val Val Asp Val Ser His
            260                 265                 270

Glu Asp Pro Glu Val Lys Phe Asn Trp Tyr Val Asp Gly Val Glu Val
        275                 280                 285

His Asn Ala Lys Thr Lys Pro Arg Glu Glu Gln Tyr Asn Ser Thr Tyr
    290                 295                 300

Arg Val Val Ser Val Leu Thr Val Leu His Gln Asp Trp Leu Asn Gly
305                 310                 315                 320

Lys Glu Tyr Lys Cys Lys Val Ser Asn Lys Ala Leu Pro Ala Pro Ile
                325                 330                 335

Glu Lys Thr Ile Ser Lys Ala Lys Gly Gln Pro Arg Glu Pro Gln Val
            340                 345                 350

Tyr Thr Leu Pro Pro Ser Arg Asp Glu Leu Thr Lys Asn Gln Val Ser
        355                 360                 365

Leu Thr Cys Leu Val Lys Gly Phe Tyr Pro Ser Asp Ile Ala Val Glu
    370                 375                 380

Trp Glu Ser Asn Gly Gln Pro Glu Asn Asn Tyr Lys Thr Thr Pro Pro
385                 390                 395                 400

Val Leu Asp Ser Asp Gly Ser Phe Phe Leu Tyr Ser Lys Leu Thr Val
                405                 410                 415

Asp Lys Ser Arg Trp Gln Gln Gly Asn Val Phe Ser Cys Ser Val Met
            420                 425                 430

His Glu Ala Leu His Asn His Tyr Thr Gln Lys Ser Leu Ser Leu Ser
        435                 440                 445

Pro Gly Lys
```

450

<210> SEQ ID NO 63
<211> LENGTH: 213
<212> TYPE: PRT
<213> ORGANISM: Artificial Sequence
<220> FEATURE:
<223> OTHER INFORMATION: Anti-human CD20 antibody light chain

<400> SEQUENCE: 63

Gln Ile Val Leu Ser Gln Ser Pro Ala Ile Leu Ser Ala Ser Pro Gly
1 5 10 15

Glu Lys Val Thr Met Thr Cys Arg Ala Ser Ser Ser Val Ser Tyr Ile
20 25 30

His Trp Phe Gln Gln Lys Pro Gly Ser Ser Pro Lys Pro Trp Ile Tyr
35 40 45

Ala Thr Ser Asn Leu Ala Ser Gly Val Pro Val Arg Phe Ser Gly Ser
50 55 60

Gly Ser Gly Thr Ser Tyr Ser Leu Thr Ile Ser Arg Val Glu Ala Glu
65 70 75 80

Asp Ala Ala Thr Tyr Tyr Cys Gln Gln Trp Thr Ser Asn Pro Pro Thr
85 90 95

Phe Gly Gly Gly Thr Lys Leu Glu Ile Lys Arg Thr Val Ala Ala Pro
100 105 110

Ser Val Phe Ile Phe Pro Pro Ser Asp Glu Gln Leu Lys Ser Gly Thr
115 120 125

Ala Ser Val Val Cys Leu Leu Asn Asn Phe Tyr Pro Arg Glu Ala Lys
130 135 140

Val Gln Trp Lys Val Asp Asn Ala Leu Gln Ser Gly Asn Ser Gln Glu
145 150 155 160

Ser Val Thr Glu Gln Asp Ser Lys Asp Ser Thr Tyr Ser Leu Ser Ser
165 170 175

Thr Leu Thr Leu Ser Lys Ala Asp Tyr Glu Lys His Lys Val Tyr Ala
180 185 190

Cys Glu Val Thr His Gln Gly Leu Ser Ser Pro Val Thr Lys Ser Phe
195 200 205

Asn Arg Gly Glu Cys
210

<210> SEQ ID NO 64
<211> LENGTH: 118
<212> TYPE: PRT
<213> ORGANISM: Artificial Sequence
<220> FEATURE:
<223> OTHER INFORMATION: VH of Atezolizumab

<400> SEQUENCE: 64

Glu Val Gln Leu Val Glu Ser Gly Gly Gly Leu Val Gln Pro Gly Gly
1 5 10 15

Ser Leu Arg Leu Ser Cys Ala Ala Ser Gly Phe Thr Phe Ser Asp Ser
20 25 30

Trp Ile His Trp Val Arg Gln Ala Pro Gly Lys Gly Leu Glu Trp Val
35 40 45

Ala Trp Ile Ser Pro Tyr Gly Gly Ser Thr Tyr Tyr Ala Asp Ser Val
50 55 60

Lys Gly Arg Phe Thr Ile Ser Ala Asp Thr Ser Lys Asn Thr Ala Tyr
65 70 75 80

-continued

```
Leu Gln Met Asn Ser Leu Arg Ala Glu Asp Thr Ala Val Tyr Tyr Cys
                85                  90                  95

Ala Arg Arg His Trp Pro Gly Gly Phe Asp Tyr Trp Gly Gln Gly Thr
            100                 105                 110

Leu Val Thr Val Ser Ser
        115


<210> SEQ ID NO 65
<211> LENGTH: 107
<212> TYPE: PRT
<213> ORGANISM: Artificial Sequence
<220> FEATURE:
<223> OTHER INFORMATION: VL of Atezolizumab

<400> SEQUENCE: 65

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Val Ser Thr Ala
            20                  25                  30

Val Ala Trp Tyr Gln Gln Lys Pro Gly Lys Ala Pro Lys Leu Leu Ile
        35                  40                  45

Cys Ser Ala Ser Phe Leu Tyr Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Tyr Leu Tyr His Pro Ala
                85                  90                  95

Thr Phe Gly Gln Gly Thr Lys Val Glu Ile Lys
            100                 105


<210> SEQ ID NO 66
<211> LENGTH: 119
<212> TYPE: PRT
<213> ORGANISM: Artificial Sequence
<220> FEATURE:
<223> OTHER INFORMATION: VH of Cetuximab with mutation

<400> SEQUENCE: 66

Gln Val Gln Leu Lys Gln Ser Gly Pro Gly Leu Val Gln Pro Ser Gln
1               5                   10                  15

Ser Leu Ser Ile Thr Cys Thr Val Ser Gly Phe Ser Leu Thr Asn Tyr
            20                  25                  30

Gly Val His Trp Val Arg Gln Ser Pro Gly Lys Gly Leu Glu Trp Leu
        35                  40                  45

Gly Val Ile Trp Ser Gly Gly Asn Thr Asp Tyr Asn Thr Pro Phe Thr
    50                  55                  60

Ser Arg Leu Ser Ile Asn Lys Asp Asn Ser Lys Ser Gln Val Phe Phe
65                  70                  75                  80

Lys Met Asn Ser Leu Gln Ser Asn Asp Thr Ala Ile Tyr Tyr Cys Ala
                85                  90                  95

Arg Ala Leu Thr Tyr Tyr Asp Tyr Glu Phe Ala Tyr Trp Gly Gln Gly
            100                 105                 110

Thr Leu Val Thr Val Ser Ala
        115


<210> SEQ ID NO 67
<211> LENGTH: 107
<212> TYPE: PRT
<213> ORGANISM: Artificial Sequence
```

<220> FEATURE:
<223> OTHER INFORMATION: VL of Cetuximab with mutation

<400> SEQUENCE: 67

Asp Ile Leu Leu Thr Gln Ser Pro Val Ile Leu Ser Val Ser Pro Gly
1 5 10 15

Glu Arg Val Ser Phe Ser Cys Arg Ala Ser Gln Ser Ile Gly Thr Asn
20 25 30

Ile His Trp Tyr Gln Gln Arg Thr Asn Gly Ser Pro Arg Leu Leu Ile
35 40 45

Cys Tyr Ala Ser Glu Ser Ile Ser Gly Ile Pro Ser Arg Phe Ser Gly
50 55 60

Ser Gly Ser Gly Thr Asp Phe Thr Leu Ser Ile Asn Ser Val Glu Ser
65 70 75 80

Glu Asp Ile Ala Asp Tyr Tyr Cys Gln Gln Asn Asn Asn Trp Pro Thr
85 90 95

Thr Phe Gly Ala Gly Thr Lys Leu Glu Leu Lys
100 105

<210> SEQ ID NO 68
<211> LENGTH: 116
<212> TYPE: PRT
<213> ORGANISM: Artificial Sequence
<220> FEATURE:
<223> OTHER INFORMATION: VH of Ramucirumab with mutation

<400> SEQUENCE: 68

Glu Val Gln Leu Val Gln Ser Gly Gly Gly Leu Val Lys Pro Gly Gly
1 5 10 15

Ser Leu Arg Leu Ser Cys Ala Ala Ser Gly Phe Thr Phe Ser Ser Tyr
20 25 30

Ser Met Asn Trp Val Arg Gln Ala Pro Gly Lys Gly Leu Glu Trp Val
35 40 45

Ser Ser Ile Ser Ser Ser Ser Ser Tyr Ile Tyr Tyr Ala Asp Ser Val
50 55 60

Lys Gly Arg Phe Thr Ile Ser Arg Asp Asn Ala Lys Asn Ser Leu Tyr
65 70 75 80

Leu Gln Met Asn Ser Leu Arg Ala Glu Asp Thr Ala Val Tyr Tyr Cys
85 90 95

Ala Arg Val Thr Asp Ala Phe Asp Ile Trp Gly Gln Gly Thr Met Val
100 105 110

Thr Val Ser Ser
115

<210> SEQ ID NO 69
<211> LENGTH: 107
<212> TYPE: PRT
<213> ORGANISM: Artificial Sequence
<220> FEATURE:
<223> OTHER INFORMATION: VL of Ramucirumab with mutation

<400> SEQUENCE: 69

Asp Ile Gln Met Thr Gln Ser Pro Ser Ser Val Ser Ala Ser Ile Gly
1 5 10 15

Asp Arg Val Thr Ile Thr Cys Arg Ala Ser Gln Gly Ile Asp Asn Trp
20 25 30

Leu Gly Trp Tyr Gln Gln Lys Pro Gly Lys Ala Pro Lys Leu Leu Ile
35 40 45

-continued

```
Cys Asp Ala Ser Asn Leu Asp Thr Gly Val Pro Ser Arg Phe Ser Gly
    50                  55                  60

Ser Gly Ser Gly Thr Tyr Phe Thr Leu Thr Ile Ser Ser Leu Gln Ala
65                  70                  75                  80

Glu Asp Phe Ala Val Tyr Phe Cys Gln Gln Ala Lys Ala Phe Pro Pro
                85                  90                  95

Thr Phe Gly Gly Gly Thr Lys Val Asp Ile Lys
            100                 105


<210> SEQ ID NO 70
<211> LENGTH: 496
<212> TYPE: PRT
<213> ORGANISM: Artificial Sequence
<220> FEATURE:
<223> OTHER INFORMATION: Fusion protein of scFv of anti-Her2 antibody
      with CD3, with mutation

<400> SEQUENCE: 70

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Val Asn Thr Ala
            20                  25                  30

Val Ala Trp Tyr Gln Gln Lys Pro Gly Lys Ala Pro Lys Leu Leu Ile
        35                  40                  45

Cys Ser Ala Ser Phe Leu Tyr Ser Gly Val Pro Ser Arg Phe Ser Gly
    50                  55                  60

Ser Arg Ser Gly Thr Asp Phe Thr Leu Thr Ile Ser Ser Leu Gln Pro
65                  70                  75                  80

Glu Asp Phe Ala Thr Tyr Tyr Cys Gln Gln His Tyr Thr Thr Pro Pro
                85                  90                  95

Thr Phe Gly Gln Gly Thr Lys Val Glu Ile Lys Gly Gly Gly Gly Ser
            100                 105                 110

Gly Gly Gly Gly Ser Gly Gly Gly Gly Ser Glu Val Gln Leu Val Glu
        115                 120                 125

Ser Gly Gly Gly Leu Val Gln Pro Gly Gly Ser Leu Arg Leu Ser Cys
    130                 135                 140

Ala Ala Ser Gly Phe Asn Ile Lys Asp Thr Tyr Ile His Trp Val Arg
145                 150                 155                 160

Gln Ala Pro Gly Lys Gly Leu Glu Trp Val Ala Arg Ile Tyr Pro Thr
                165                 170                 175

Asn Gly Tyr Thr Arg Tyr Ala Asp Ser Val Lys Gly Arg Phe Thr Ile
            180                 185                 190

Ser Ala Asp Thr Ser Lys Asn Thr Ala Tyr Leu Gln Met Asn Ser Leu
        195                 200                 205

Arg Ala Glu Asp Thr Ala Val Tyr Tyr Cys Ser Arg Trp Gly Gly Asp
    210                 215                 220

Gly Phe Tyr Ala Met Asp Tyr Trp Gly Gln Gly Thr Leu Val Thr Val
225                 230                 235                 240

Ser Ser Gly Gly Gly Gly Ser Asp Ile Lys Leu Gln Gln Ser Gly Ala
                245                 250                 255

Glu Leu Ala Arg Pro Gly Ala Ser Val Lys Met Ser Cys Lys Thr Ser
            260                 265                 270

Gly Tyr Thr Phe Thr Arg Tyr Thr Met His Trp Val Lys Gln Arg Pro
        275                 280                 285

Gly Gln Gly Leu Glu Trp Ile Gly Tyr Ile Asn Pro Ser Arg Gly Tyr
    290                 295                 300
```

Thr Asn Tyr Asn Gln Lys Phe Lys Asp Lys Ala Thr Leu Thr Thr Asp
305 310 315 320

Lys Ser Ser Ser Thr Ala Tyr Met Gln Leu Ser Ser Leu Thr Ser Glu
325 330 335

Asp Ser Ala Val Tyr Tyr Cys Ala Arg Tyr Tyr Asp Asp His Tyr Cys
340 345 350

Leu Asp Tyr Trp Gly Gln Gly Thr Thr Leu Thr Val Ser Ser Val Glu
355 360 365

Gly Gly Ser Gly Gly Ser Gly Gly Ser Gly Gly Ser Gly Gly Val Asp
370 375 380

Asp Ile Gln Leu Thr Gln Ser Pro Ala Ile Met Ser Ala Ser Pro Gly
385 390 395 400

Glu Lys Val Thr Met Thr Cys Arg Ala Ser Ser Ser Val Ser Tyr Met
405 410 415

Asn Trp Tyr Gln Gln Lys Ser Gly Thr Ser Pro Lys Arg Trp Ile Tyr
420 425 430

Asp Thr Ser Lys Val Ala Ser Gly Val Pro Tyr Arg Phe Ser Gly Ser
435 440 445

Gly Ser Gly Thr Ser Tyr Ser Leu Thr Ile Ser Ser Met Glu Ala Glu
450 455 460

Asp Ala Ala Thr Tyr Tyr Cys Gln Gln Trp Ser Ser Asn Pro Leu Thr
465 470 475 480

Phe Gly Ala Gly Thr Lys Leu Glu Leu Lys His His His His His His
485 490 495

<210> SEQ ID NO 71
<211> LENGTH: 120
<212> TYPE: PRT
<213> ORGANISM: Artificial Sequence
<220> FEATURE:
<223> OTHER INFORMATION: VH of anti Her2 antibody with mutation

<400> SEQUENCE: 71

Glu Val Gln Leu Val Glu Ser Gly Gly Gly Leu Val Gln Pro Gly Gly
1 5 10 15

Ser Leu Arg Leu Ser Cys Ala Ala Ser Gly Phe Asn Ile Lys Asp Thr
20 25 30

Tyr Ile His Trp Val Arg Gln Ala Pro Gly Lys Gly Leu Glu Trp Val
35 40 45

Ala Arg Ile Tyr Pro Thr Asn Gly Tyr Thr Arg Tyr Ala Asp Ser Val
50 55 60

Lys Gly Arg Phe Thr Ile Ser Ala Asp Thr Ser Lys Asn Thr Ala Tyr
65 70 75 80

Leu Gln Met Asn Ser Leu Arg Ala Glu Asp Thr Ala Val Tyr Tyr Cys
85 90 95

Ser Arg Trp Gly Gly Asp Gly Phe Tyr Ala Met Asp Tyr Trp Gly Gln
100 105 110

Gly Thr Leu Val Thr Val Ser Ser
115 120

<210> SEQ ID NO 72
<211> LENGTH: 107
<212> TYPE: PRT
<213> ORGANISM: Artificial Sequence
<220> FEATURE:
<223> OTHER INFORMATION: VL of anti Her2 antibody with mutation

```
<400> SEQUENCE: 72

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Val Asn Thr Ala
            20                  25                  30

Val Ala Trp Tyr Gln Gln Lys Pro Gly Lys Ala Pro Lys Leu Leu Ile
        35                  40                  45

Cys Ser Ala Ser Phe Leu Tyr Ser Gly Val Pro Ser Arg Phe Ser Gly
    50                  55                  60

Ser Arg Ser Gly Thr Asp Phe Thr Leu Thr Ile Ser Ser Leu Gln Pro
65                  70                  75                  80

Glu Asp Phe Ala Thr Tyr Tyr Cys Gln Gln His Tyr Thr Thr Pro Pro
                85                  90                  95

Thr Phe Gly Gln Gly Thr Lys Val Glu Ile Lys
            100                 105


<210> SEQ ID NO 73
<211> LENGTH: 590
<212> TYPE: PRT
<213> ORGANISM: Artificial Sequence
<220> FEATURE:
<223> OTHER INFORMATION: Fusion protein of scFvs of anti-Her2 antibody
      with anti-CD3 antibody

<400> SEQUENCE: 73

Gln Val Gln Leu Val Glu Ser Gly Gly Gly Val Val Gln Pro Gly Arg
1               5                   10                  15

Ser Leu Arg Leu Asp Cys Lys Ala Ser Gly Ile Thr Phe Ser Asn Ser
            20                  25                  30

Gly Met His Trp Val Arg Gln Ala Pro Gly Lys Gly Leu Glu Trp Val
        35                  40                  45

Ala Val Ile Trp Tyr Asp Gly Ser Lys Arg Tyr Tyr Ala Asp Ser Val
    50                  55                  60

Lys Gly Arg Phe Thr Ile Ser Arg Asp Asn Ser Lys Asn Thr Leu Phe
65                  70                  75                  80

Leu Gln Met Asn Ser Leu Arg Ala Glu Asp Thr Ala Val Tyr Tyr Cys
                85                  90                  95

Ala Thr Asn Asp Asp Tyr Trp Gly Gln Gly Thr Leu Val Thr Val Ser
            100                 105                 110

Ser Ala Ser Thr Lys Gly Pro Ser Val Phe Pro Leu Ala Pro Ser Ser
        115                 120                 125

Lys Ser Thr Ser Gly Gly Thr Ala Ala Leu Gly Cys Leu Val Lys Asp
    130                 135                 140

Tyr Phe Pro Glu Pro Val Thr Val Ser Trp Asn Ser Gly Ala Leu Thr
145                 150                 155                 160

Ser Gly Val His Thr Phe Pro Ala Val Leu Gln Ser Ser Gly Leu Tyr
                165                 170                 175

Ser Leu Ser Ser Val Val Thr Val Pro Ser Ser Ser Leu Gly Thr Gln
            180                 185                 190

Thr Tyr Ile Cys Asn Val Asn His Lys Pro Ser Asn Thr Lys Val Asp
        195                 200                 205

Lys Lys Val Glu Pro Lys Ser Cys Asp Lys Thr His Thr Cys Pro Pro
    210                 215                 220

Cys Pro Ala Pro Glu Ala Ala Gly Gly Pro Ser Val Phe Leu Phe Pro
225                 230                 235                 240
```

```
Pro Lys Pro Lys Asp Thr Leu Met Ile Ser Arg Thr Pro Glu Val Thr
                245                 250                 255

Cys Val Val Val Asp Val Ser His Glu Asp Pro Glu Val Lys Phe Asn
            260                 265                 270

Trp Tyr Val Asp Gly Val Glu Val His Asn Ala Lys Thr Lys Pro Arg
        275                 280                 285

Glu Glu Gln Tyr Asn Ser Thr Tyr Arg Val Val Ser Val Leu Thr Val
    290                 295                 300

Leu His Gln Asp Trp Leu Asn Gly Lys Glu Tyr Lys Cys Lys Val Ser
305                 310                 315                 320

Asn Lys Ala Leu Gly Ala Pro Ile Glu Lys Thr Ile Ser Lys Ala Lys
                325                 330                 335

Gly Gln Pro Arg Glu Pro Gln Val Tyr Thr Leu Pro Pro Cys Arg Asp
            340                 345                 350

Glu Leu Thr Lys Asn Gln Val Ser Leu Trp Cys Leu Val Lys Gly Phe
        355                 360                 365

Tyr Pro Ser Asp Ile Ala Val Glu Trp Glu Ser Asn Gly Gln Pro Glu
    370                 375                 380

Asn Asn Tyr Lys Thr Thr Pro Pro Val Leu Asp Ser Asp Gly Ser Phe
385                 390                 395                 400

Phe Leu Tyr Ser Lys Leu Thr Val Asp Lys Ser Arg Trp Gln Gln Gly
                405                 410                 415

Asn Val Phe Ser Cys Ser Val Met His Glu Ala Leu His Asn His Tyr
            420                 425                 430

Thr Gln Lys Ser Leu Ser Leu Ser Pro Gly Gly Gly Ser Gly Gly Gly
        435                 440                 445

Ser Gly Gly Gly Ser Gly Gly Gly Ser Ala Pro Ala Ser Ser Ser Thr
    450                 455                 460

Lys Lys Thr Gln Leu Gln Leu Glu His Leu Leu Leu Asp Leu Gln Met
465                 470                 475                 480

Ile Leu Asn Gly Ile Asn Asn Tyr Lys Asn Pro Lys Leu Thr Arg Met
                485                 490                 495

Leu Cys Phe Lys Phe Tyr Met Pro Lys Lys Ala Thr Glu Leu Lys His
            500                 505                 510

Leu Gln Cys Leu Glu Glu Glu Leu Lys Pro Leu Glu Glu Val Leu Asn
        515                 520                 525

Leu Ala Gln Ser Lys Asn Phe His Leu Arg Pro Arg Asp Leu Ile Ser
    530                 535                 540

Asn Ile Asn Val Ile Val Leu Glu Leu Lys Gly Ser Glu Thr Thr Phe
545                 550                 555                 560

Met Cys Glu Tyr Ala Asp Glu Thr Ala Thr Ile Val Glu Phe Leu Asn
                565                 570                 575

Arg Trp Ile Thr Phe Ser Gln Ser Ile Ile Ser Thr Leu Thr
            580                 585                 590
```

<210> SEQ ID NO 74
<211> LENGTH: 595
<212> TYPE: PRT
<213> ORGANISM: Artificial Sequence
<220> FEATURE:
<223> OTHER INFORMATION: Fusion protein of scFvs of anti-Her2 antibody with anti-CD3 antibody

<400> SEQUENCE: 74

```
Glu Val Gln Leu Val Glu Ser Gly Gly Gly Leu Val Gln Pro Gly Gly
1               5                   10                  15
```

-continued

```
Ser Leu Arg Leu Ser Cys Ala Ala Ser Gly Phe Thr Phe Ser Asp Ser
            20                  25                  30

Trp Ile His Trp Val Arg Gln Ala Pro Gly Lys Gly Leu Glu Trp Val
        35                  40                  45

Ala Trp Ile Ser Pro Tyr Gly Gly Ser Thr Tyr Tyr Ala Asp Ser Val
    50                  55                  60

Lys Gly Arg Phe Thr Ile Ser Ala Asp Thr Ser Lys Asn Thr Ala Tyr
65                  70                  75                  80

Leu Gln Met Asn Ser Leu Arg Ala Glu Asp Thr Ala Val Tyr Tyr Cys
                85                  90                  95

Ala Arg Arg His Trp Pro Gly Gly Phe Asp Tyr Trp Gly Gln Gly Thr
            100                 105                 110

Leu Val Thr Val Ser Ser Ala Ser Thr Lys Gly Pro Ser Val Phe Pro
        115                 120                 125

Leu Ala Pro Ser Ser Lys Ser Thr Ser Gly Gly Thr Ala Ala Leu Gly
    130                 135                 140

Cys Leu Val Lys Asp Tyr Phe Pro Glu Pro Val Thr Val Ser Trp Asn
145                 150                 155                 160

Ser Gly Ala Leu Thr Ser Gly Val His Thr Phe Pro Ala Val Leu Gln
                165                 170                 175

Ser Ser Gly Leu Tyr Ser Leu Ser Ser Val Val Thr Val Pro Ser Ser
            180                 185                 190

Ser Leu Gly Thr Gln Thr Tyr Ile Cys Asn Val Asn His Lys Pro Ser
        195                 200                 205

Asn Thr Lys Val Asp Lys Lys Val Glu Pro Lys Ser Cys Asp Lys Thr
    210                 215                 220

His Thr Cys Pro Pro Cys Pro Ala Pro Glu Ala Ala Gly Gly Pro Ser
225                 230                 235                 240

Val Phe Leu Phe Pro Pro Lys Pro Lys Asp Thr Leu Met Ile Ser Arg
                245                 250                 255

Thr Pro Glu Val Thr Cys Val Val Val Asp Val Ser His Glu Asp Pro
            260                 265                 270

Glu Val Lys Phe Asn Trp Tyr Val Asp Gly Val Glu Val His Asn Ala
        275                 280                 285

Lys Thr Lys Pro Arg Glu Glu Gln Tyr Ala Ser Thr Tyr Arg Val Val
    290                 295                 300

Ser Val Leu Thr Val Leu His Gln Asp Trp Leu Asn Gly Lys Glu Tyr
305                 310                 315                 320

Lys Cys Lys Val Ser Asn Lys Ala Leu Gly Ala Pro Ile Glu Lys Thr
                325                 330                 335

Ile Ser Lys Ala Lys Gly Gln Pro Arg Glu Pro Gln Val Tyr Thr Leu
            340                 345                 350

Pro Pro Ser Arg Glu Glu Met Thr Lys Asn Gln Val Ser Leu Trp Cys
        355                 360                 365

Leu Val Lys Gly Phe Tyr Pro Ser Asp Ile Ala Val Glu Trp Glu Ser
    370                 375                 380

Asn Gly Gln Pro Glu Asn Asn Tyr Lys Thr Thr Pro Pro Val Leu Asp
385                 390                 395                 400

Ser Asp Gly Ser Phe Phe Leu Tyr Ser Lys Leu Thr Val Asp Lys Ser
                405                 410                 415

Arg Trp Gln Gln Gly Asn Val Phe Ser Cys Ser Val Met His Glu Ala
            420                 425                 430
```

```
Leu His Asn His Tyr Thr Gln Lys Ser Leu Ser Leu Ser Pro Gly Gly
        435                 440                 445

Gly Ser Gly Gly Gly Ser Gly Gly Gly Ser Gly Gly Gly Ser Ala Pro
    450                 455                 460

Ala Ser Ser Ser Thr Lys Lys Thr Gln Leu Gln Leu Glu His Leu Leu
465                 470                 475                 480

Leu Asp Leu Gln Met Ile Leu Asn Gly Ile Asn Asn Tyr Lys Asn Pro
                485                 490                 495

Lys Leu Thr Arg Met Leu Cys Phe Lys Phe Tyr Met Pro Lys Lys Ala
            500                 505                 510

Thr Glu Leu Lys His Leu Gln Cys Leu Glu Glu Glu Leu Lys Pro Leu
        515                 520                 525

Glu Glu Val Leu Asn Leu Ala Gln Ser Lys Asn Phe His Leu Arg Pro
    530                 535                 540

Arg Asp Leu Ile Ser Asn Ile Asn Val Ile Val Leu Glu Leu Lys Gly
545                 550                 555                 560

Ser Glu Thr Thr Phe Met Cys Glu Tyr Ala Asp Glu Thr Ala Thr Ile
                565                 570                 575

Val Glu Phe Leu Asn Arg Trp Ile Thr Phe Ser Gln Ser Ile Ile Ser
            580                 585                 590

Thr Leu Thr
        595


<210> SEQ ID NO 75
<211> LENGTH: 243
<212> TYPE: PRT
<213> ORGANISM: Artificial Sequence
<220> FEATURE:
<223> OTHER INFORMATION: anti CD3 antibody

<400> SEQUENCE: 75

Asp Ile Lys Leu Gln Gln Ser Gly Ala Glu Leu Ala Arg Pro Gly Ala
1               5                   10                  15

Ser Val Lys Met Ser Cys Lys Thr Ser Gly Tyr Thr Phe Thr Arg Tyr
            20                  25                  30

Thr Met His Trp Val Lys Gln Arg Pro Gly Gln Gly Leu Glu Trp Ile
        35                  40                  45

Gly Tyr Ile Asn Pro Ser Arg Gly Tyr Thr Asn Tyr Asn Gln Lys Phe
    50                  55                  60

Lys Asp Lys Ala Thr Leu Thr Thr Asp Lys Ser Ser Ser Thr Ala Tyr
65                  70                  75                  80

Met Gln Leu Ser Ser Leu Thr Ser Glu Asp Ser Ala Val Tyr Tyr Cys
                85                  90                  95

Ala Arg Tyr Tyr Asp Asp His Tyr Cys Leu Asp Tyr Trp Gly Gln Gly
            100                 105                 110

Thr Thr Leu Thr Val Ser Ser Val Glu Gly Gly Ser Gly Gly Ser Gly
        115                 120                 125

Gly Ser Gly Gly Ser Gly Gly Val Asp Asp Ile Gln Leu Thr Gln Ser
    130                 135                 140

Pro Ala Ile Met Ser Ala Ser Pro Gly Glu Lys Val Thr Met Thr Cys
145                 150                 155                 160

Arg Ala Ser Ser Ser Val Ser Tyr Met Asn Trp Tyr Gln Gln Lys Ser
                165                 170                 175

Gly Thr Ser Pro Lys Arg Trp Ile Tyr Asp Thr Ser Lys Val Ala Ser
            180                 185                 190
```

```
Gly Val Pro Tyr Arg Phe Ser Gly Ser Gly Ser Gly Thr Ser Tyr Ser
        195                 200                 205

Leu Thr Ile Ser Ser Met Glu Ala Glu Asp Ala Ala Thr Tyr Tyr Cys
    210                 215                 220

Gln Gln Trp Ser Ser Asn Pro Leu Thr Phe Gly Ala Gly Thr Lys Leu
225                 230                 235                 240

Glu Leu Lys


<210> SEQ ID NO 76
<211> LENGTH: 119
<212> TYPE: PRT
<213> ORGANISM: Artificial Sequence
<220> FEATURE:
<223> OTHER INFORMATION: VH of Cetuximab

<400> SEQUENCE: 76

Gln Val Gln Leu Lys Gln Ser Gly Pro Gly Leu Val Gln Pro Ser Gln
1               5                   10                  15

Ser Leu Ser Ile Thr Cys Thr Val Ser Gly Phe Ser Leu Thr Asn Tyr
            20                  25                  30

Gly Val His Trp Val Arg Gln Ser Pro Gly Lys Gly Leu Glu Trp Leu
        35                  40                  45

Gly Val Ile Trp Ser Gly Gly Asn Thr Asp Tyr Asn Thr Pro Phe Thr
    50                  55                  60

Ser Arg Leu Ser Ile Asn Lys Asp Asn Ser Lys Ser Gln Val Phe Phe
65                  70                  75                  80

Lys Met Asn Ser Leu Gln Ser Asn Asp Thr Ala Ile Tyr Tyr Cys Ala
                85                  90                  95

Arg Ala Leu Thr Tyr Tyr Asp Tyr Glu Phe Ala Tyr Trp Gly Gln Gly
            100                 105                 110

Thr Leu Val Thr Val Ser Ala
        115


<210> SEQ ID NO 77
<211> LENGTH: 107
<212> TYPE: PRT
<213> ORGANISM: Artificial Sequence
<220> FEATURE:
<223> OTHER INFORMATION: VL of Cetuximab

<400> SEQUENCE: 77

Asp Ile Leu Leu Thr Gln Ser Pro Val Ile Leu Ser Val Ser Pro Gly
1               5                   10                  15

Glu Arg Val Ser Phe Ser Cys Arg Ala Ser Gln Ser Ile Gly Thr Asn
            20                  25                  30

Ile His Trp Tyr Gln Gln Arg Thr Asn Gly Ser Pro Arg Leu Leu Ile
        35                  40                  45

Lys Tyr Ala Ser Glu Ser Ile Ser Gly Ile Pro Ser Arg Phe Ser Gly
    50                  55                  60

Ser Gly Ser Gly Thr Asp Phe Thr Leu Ser Ile Asn Ser Val Glu Ser
65                  70                  75                  80

Glu Asp Ile Ala Asp Tyr Tyr Cys Gln Gln Asn Asn Asn Trp Pro Thr
                85                  90                  95

Thr Phe Gly Ala Gly Thr Lys Leu Glu Leu Lys
            100                 105


<210> SEQ ID NO 78
<211> LENGTH: 116
```

-continued

<212> TYPE: PRT
<213> ORGANISM: Artificial Sequence
<220> FEATURE:
<223> OTHER INFORMATION: VH of Ramucirumab

<400> SEQUENCE: 78

```
Glu Val Gln Leu Val Gln Ser Gly Gly Gly Leu Val Lys Pro Gly Gly
1               5                   10                  15

Ser Leu Arg Leu Ser Cys Ala Ala Ser Gly Phe Thr Phe Ser Ser Tyr
            20                  25                  30

Ser Met Asn Trp Val Arg Gln Ala Pro Gly Lys Gly Leu Glu Trp Val
        35                  40                  45

Ser Ser Ile Ser Ser Ser Ser Ser Tyr Ile Tyr Tyr Ala Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Arg Val Thr Asp Ala Phe Asp Ile Trp Gly Gln Gly Thr Met Val
            100                 105                 110

Thr Val Ser Ser
        115
```

<210> SEQ ID NO 79
<211> LENGTH: 107
<212> TYPE: PRT
<213> ORGANISM: Artificial Sequence
<220> FEATURE:
<223> OTHER INFORMATION: VL of Ramucirumab

<400> SEQUENCE: 79

```
Asp Ile Gln Met Thr Gln Ser Pro Ser Ser Val Ser Ala Ser Ile Gly
1               5                   10                  15

Asp Arg Val Thr Ile Thr Cys Arg Ala Ser Gln Gly Ile Asp Asn Trp
            20                  25                  30

Leu Gly Trp Tyr Gln Gln Lys Pro Gly Lys Ala Pro Lys Leu Leu Ile
        35                  40                  45

Tyr Asp Ala Ser Asn Leu Asp Thr Gly Val Pro Ser Arg Phe Ser Gly
    50                  55                  60

Ser Gly Ser Gly Thr Tyr Phe Thr Leu Thr Ile Ser Ser Leu Gln Ala
65                  70                  75                  80

Glu Asp Phe Ala Val Tyr Phe Cys Gln Gln Ala Lys Ala Phe Pro Pro
                85                  90                  95

Thr Phe Gly Gly Gly Thr Lys Val Asp Ile Lys
            100                 105
```

<210> SEQ ID NO 80
<211> LENGTH: 120
<212> TYPE: PRT
<213> ORGANISM: Artificial Sequence
<220> FEATURE:
<223> OTHER INFORMATION: VH of anti Her2 antibody

<400> SEQUENCE: 80

```
Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Asn Ile Lys Asp Thr
            20                  25                  30

Tyr Ile His Trp Val Arg Gln Ala Pro Gly Lys Gly Leu Glu Trp Val
```

```
        35                  40                  45

Ala Arg Ile Tyr Pro Thr Asn Gly Tyr Thr Arg Tyr Ala Asp Ser Val
    50                  55                  60

Lys Gly Arg Phe Thr Ile Ser Ala Asp Thr Ser Lys Asn Thr Ala Tyr
65                  70                  75                  80

Leu Gln Met Asn Ser Leu Arg Ala Glu Asp Thr Ala Val Tyr Tyr Cys
                85                  90                  95

Ser Arg Trp Gly Gly Asp Gly Phe Tyr Ala Met Asp Tyr Trp Gly Gln
            100                 105                 110

Gly Thr Leu Val Thr Val Ser Ser
        115                 120


<210> SEQ ID NO 81
<211> LENGTH: 107
<212> TYPE: PRT
<213> ORGANISM: Artificial Sequence
<220> FEATURE:
<223> OTHER INFORMATION: VL of Her2 antibody

<400> SEQUENCE: 81

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Val Asn Thr Ala
            20                  25                  30

Val Ala Trp Tyr Gln Gln Lys Pro Gly Lys Ala Pro Lys Leu Leu Ile
        35                  40                  45

Tyr Ser Ala Ser Phe Leu Tyr Ser Gly Val Pro Ser Arg Phe Ser Gly
    50                  55                  60

Ser Arg Ser Gly Thr Asp Phe Thr Leu Thr Ile Ser Ser Leu Gln Pro
65                  70                  75                  80

Glu Asp Phe Ala Thr Tyr Tyr Cys Gln Gln His Tyr Thr Thr Pro Pro
                85                  90                  95

Thr Phe Gly Gln Gly Thr Lys Val Glu Ile Lys
            100                 105


<210> SEQ ID NO 82
<211> LENGTH: 496
<212> TYPE: PRT
<213> ORGANISM: Artificial Sequence
<220> FEATURE:
<223> OTHER INFORMATION: Fusion protein of scFvs of anti-Her2 antibody
      with anti-CD3 antibody, with mutation

<400> SEQUENCE: 82

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Val Asn Thr Ala
            20                  25                  30

Val Ala Trp Tyr Gln Gln Lys Pro Gly Lys Ala Pro Lys Leu Leu Ile
        35                  40                  45

Tyr Ser Ala Ser Phe Leu Tyr Ser Gly Val Pro Ser Arg Phe Ser Gly
    50                  55                  60

Ser Arg Ser Gly Thr Asp Phe Thr Leu Thr Ile Ser Ser Leu Gln Pro
65                  70                  75                  80

Glu Asp Phe Ala Thr Tyr Tyr Cys Gln Gln His Tyr Thr Thr Pro Pro
                85                  90                  95

Thr Phe Gly Gln Gly Thr Lys Val Glu Ile Lys Gly Gly Gly Gly Ser
            100                 105                 110
```

```
Gly Gly Gly Gly Ser Gly Gly Gly Gly Ser Glu Val Gln Leu Val Glu
        115                 120                 125

Ser Gly Gly Gly Leu Val Gln Pro Gly Gly Ser Leu Arg Leu Ser Cys
    130                 135                 140

Ala Ala Ser Gly Phe Asn Ile Lys Asp Thr Tyr Ile His Trp Val Arg
145                 150                 155                 160

Gln Ala Pro Gly Lys Gly Leu Glu Trp Val Ala Arg Ile Tyr Pro Thr
                165                 170                 175

Asn Gly Tyr Thr Arg Tyr Ala Asp Ser Val Lys Gly Arg Phe Thr Ile
            180                 185                 190

Ser Ala Asp Thr Ser Lys Asn Thr Ala Tyr Leu Gln Met Asn Ser Leu
        195                 200                 205

Arg Ala Glu Asp Thr Ala Val Tyr Tyr Cys Ser Arg Trp Gly Gly Asp
    210                 215                 220

Gly Phe Tyr Ala Met Asp Tyr Trp Gly Gln Gly Thr Leu Val Thr Val
225                 230                 235                 240

Ser Ser Gly Gly Gly Gly Ser Asp Ile Lys Leu Gln Gln Ser Gly Ala
                245                 250                 255

Glu Leu Ala Arg Pro Gly Ala Ser Val Lys Met Ser Cys Lys Thr Ser
            260                 265                 270

Gly Tyr Thr Phe Thr Arg Tyr Thr Met His Trp Val Lys Gln Arg Pro
        275                 280                 285

Gly Gln Gly Leu Glu Trp Ile Gly Tyr Ile Asn Pro Ser Arg Gly Tyr
    290                 295                 300

Thr Asn Tyr Asn Gln Lys Phe Lys Asp Lys Ala Thr Leu Thr Thr Asp
305                 310                 315                 320

Lys Ser Ser Ser Thr Ala Tyr Met Gln Leu Ser Ser Leu Thr Ser Glu
                325                 330                 335

Asp Ser Ala Val Tyr Tyr Cys Ala Arg Tyr Tyr Asp Asp His Tyr Cys
            340                 345                 350

Leu Asp Tyr Trp Gly Gln Gly Thr Thr Leu Thr Val Ser Ser Val Glu
        355                 360                 365

Gly Gly Ser Gly Gly Ser Gly Gly Ser Gly Gly Ser Gly Gly Val Asp
    370                 375                 380

Asp Ile Gln Leu Thr Gln Ser Pro Ala Ile Met Ser Ala Ser Pro Gly
385                 390                 395                 400

Glu Lys Val Thr Met Thr Cys Arg Ala Ser Ser Ser Val Ser Tyr Met
                405                 410                 415

Asn Trp Tyr Gln Gln Lys Ser Gly Thr Ser Pro Lys Arg Trp Ile Cys
            420                 425                 430

Asp Thr Ser Lys Val Ala Ser Gly Val Pro Tyr Arg Phe Ser Gly Ser
        435                 440                 445

Gly Ser Gly Thr Ser Tyr Ser Leu Thr Ile Ser Ser Met Glu Ala Glu
    450                 455                 460

Asp Ala Ala Thr Tyr Tyr Cys Gln Gln Trp Ser Ser Asn Pro Leu Thr
465                 470                 475                 480

Phe Gly Ala Gly Thr Lys Leu Glu Leu Lys His His His His His His
                485                 490                 495
```

<210> SEQ ID NO 83
<211> LENGTH: 496
<212> TYPE: PRT
<213> ORGANISM: Artificial Sequence
<220> FEATURE:

<223> OTHER INFORMATION: Fusion protein of scFvs of anti-Her2 antibody with anti-CD3 antibody, with mutation

<400> SEQUENCE: 83

```
Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Val Asn Thr Ala
            20                  25                  30

Val Ala Trp Tyr Gln Gln Lys Pro Gly Lys Ala Pro Lys Leu Leu Ile
        35                  40                  45

Cys Ser Ala Ser Phe Leu Tyr Ser Gly Val Pro Ser Arg Phe Ser Gly
    50                  55                  60

Ser Arg Ser Gly Thr Asp Phe Thr Leu Thr Ile Ser Ser Leu Gln Pro
65                  70                  75                  80

Glu Asp Phe Ala Thr Tyr Tyr Cys Gln Gln His Tyr Thr Thr Pro Pro
                85                  90                  95

Thr Phe Gly Gln Gly Thr Lys Val Glu Ile Lys Gly Gly Gly Gly Ser
            100                 105                 110

Gly Gly Gly Gly Ser Gly Gly Gly Gly Ser Glu Val Gln Leu Val Glu
        115                 120                 125

Ser Gly Gly Gly Leu Val Gln Pro Gly Gly Ser Leu Arg Leu Ser Cys
    130                 135                 140

Ala Ala Ser Gly Phe Asn Ile Lys Asp Thr Tyr Ile His Trp Val Arg
145                 150                 155                 160

Gln Ala Pro Gly Lys Gly Leu Glu Trp Val Ala Arg Ile Tyr Pro Thr
                165                 170                 175

Asn Gly Tyr Thr Arg Tyr Ala Asp Ser Val Lys Gly Arg Phe Thr Ile
            180                 185                 190

Ser Ala Asp Thr Ser Lys Asn Thr Ala Tyr Leu Gln Met Asn Ser Leu
        195                 200                 205

Arg Ala Glu Asp Thr Ala Val Tyr Tyr Cys Ser Arg Trp Gly Gly Asp
    210                 215                 220

Gly Phe Tyr Ala Met Asp Tyr Trp Gly Gln Gly Thr Leu Val Thr Val
225                 230                 235                 240

Ser Ser Gly Gly Gly Gly Ser Asp Ile Lys Leu Gln Gln Ser Gly Ala
                245                 250                 255

Glu Leu Ala Arg Pro Gly Ala Ser Val Lys Met Ser Cys Lys Thr Ser
            260                 265                 270

Gly Tyr Thr Phe Thr Arg Tyr Thr Met His Trp Val Lys Gln Arg Pro
        275                 280                 285

Gly Gln Gly Leu Glu Trp Ile Gly Tyr Ile Asn Pro Ser Arg Gly Tyr
    290                 295                 300

Thr Asn Tyr Asn Gln Lys Phe Lys Asp Lys Ala Thr Leu Thr Thr Asp
305                 310                 315                 320

Lys Ser Ser Ser Thr Ala Tyr Met Gln Leu Ser Ser Leu Thr Ser Glu
                325                 330                 335

Asp Ser Ala Val Tyr Tyr Cys Ala Arg Tyr Tyr Asp Asp His Tyr Cys
            340                 345                 350

Leu Asp Tyr Trp Gly Gln Gly Thr Thr Leu Thr Val Ser Ser Val Glu
        355                 360                 365

Gly Gly Ser Gly Gly Ser Gly Gly Ser Gly Gly Ser Gly Gly Val Asp
    370                 375                 380

Asp Ile Gln Leu Thr Gln Ser Pro Ala Ile Met Ser Ala Ser Pro Gly
385                 390                 395                 400
```

Glu Lys Val Thr Met Thr Cys Arg Ala Ser Ser Ser Val Ser Tyr Met
405 410 415

Asn Trp Tyr Gln Gln Lys Ser Gly Thr Ser Pro Lys Arg Trp Ile Cys
420 425 430

Asp Thr Ser Lys Val Ala Ser Gly Val Pro Tyr Arg Phe Ser Gly Ser
435 440 445

Gly Ser Gly Thr Ser Tyr Ser Leu Thr Ile Ser Ser Met Glu Ala Glu
450 455 460

Asp Ala Ala Thr Tyr Tyr Cys Gln Gln Trp Ser Ser Asn Pro Leu Thr
465 470 475 480

Phe Gly Ala Gly Thr Lys Leu Glu Leu Lys His His His His His His
485 490 495

<210> SEQ ID NO 84
<211> LENGTH: 10
<212> TYPE: PRT
<213> ORGANISM: Artificial Sequence
<220> FEATURE:
<223> OTHER INFORMATION: sequence of R2

<400> SEQUENCE: 84

Leu Thr Pro Arg Leu Gly Pro Ala Ala Asn
1 5 10

<210> SEQ ID NO 85
<211> LENGTH: 5
<212> TYPE: PRT
<213> ORGANISM: Artificial Sequence
<220> FEATURE:
<223> OTHER INFORMATION: sequence of R2

<400> SEQUENCE: 85

Gly Pro Ala Ala Asn
1 5

<210> SEQ ID NO 86
<211> LENGTH: 7
<212> TYPE: PRT
<213> ORGANISM: Artificial Sequence
<220> FEATURE:
<223> OTHER INFORMATION: sequence of R2

<400> SEQUENCE: 86

Leu Ser Gly Arg Ser Asp Asn
1 5

<210> SEQ ID NO 87
<211> LENGTH: 21
<212> TYPE: DNA
<213> ORGANISM: Artificial Sequence
<220> FEATURE:
<223> OTHER INFORMATION: forward primer

<400> SEQUENCE: 87
gaactccctc gatgttaacc a 21

<210> SEQ ID NO 88
<211> LENGTH: 21
<212> TYPE: DNA
<213> ORGANISM: Artificial Sequence
<220> FEATURE:
<223> OTHER INFORMATION: reverse primer

<400> SEQUENCE: 88

```
ttcaatcccc aaatcctagc c                                              21


<210> SEQ ID NO 89
<211> LENGTH: 214
<212> TYPE: PRT
<213> ORGANISM: Artificial Sequence
<220> FEATURE:
<223> OTHER INFORMATION: Light chain of Cetuximab

<400> SEQUENCE: 89

Asp Ile Leu Leu Thr Gln Ser Pro Val Ile Leu Ser Val Ser Pro Gly
1               5                   10                  15

Glu Arg Val Ser Phe Ser Cys Arg Ala Ser Gln Ser Ile Gly Thr Asn
            20                  25                  30

Ile His Trp Tyr Gln Gln Arg Thr Asn Gly Ser Pro Arg Leu Leu Ile
        35                  40                  45

Lys Tyr Ala Ser Glu Ser Ile Ser Gly Ile Pro Ser Arg Phe Ser Gly
    50                  55                  60

Ser Gly Ser Gly Thr Asp Phe Thr Leu Ser Ile Asn Ser Val Glu Ser
65                  70                  75                  80

Glu Asp Ile Ala Asp Tyr Tyr Cys Gln Gln Asn Asn Asn Trp Pro Thr
                85                  90                  95

Thr Phe Gly Ala Gly Thr Lys Leu Glu Leu Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210


<210> SEQ ID NO 90
<211> LENGTH: 214
<212> TYPE: PRT
<213> ORGANISM: Artificial Sequence
<220> FEATURE:
<223> OTHER INFORMATION: Light chain of Pertuzumab

<400> SEQUENCE: 90

Asp Ile Gln Met Thr Gln Ser Pro Ser Ser Leu Ser Ala Ser Val Gly
1               5                   10                  15

Asp Arg Val Thr Ile Thr Cys Lys Ala Ser Gln Asp Val Ser Ile Gly
            20                  25                  30

Val Ala Trp Tyr Gln Gln Lys Pro Gly Lys Ala Pro Lys Leu Leu Ile
        35                  40                  45

Tyr Ser Ala Ser Tyr Arg Tyr Thr Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80
```

```
Glu Asp Phe Ala Thr Tyr Tyr Cys Gln Gln Tyr Tyr Ile Tyr Pro Tyr
                85                  90                  95

Thr Phe Gly Gln Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210


<210> SEQ ID NO 91
<211> LENGTH: 448
<212> TYPE: PRT
<213> ORGANISM: Artificial Sequence
<220> FEATURE:
<223> OTHER INFORMATION: Heavy chain of Pertuzumab

<400> SEQUENCE: 91

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Thr Asp Tyr
            20                  25                  30

Thr Met Asp Trp Val Arg Gln Ala Pro Gly Lys Gly Leu Glu Trp Val
        35                  40                  45

Ala Asp Val Asn Pro Asn Ser Gly Gly Ser Ile Tyr Asn Gln Arg Phe
    50                  55                  60

Lys Gly Arg Phe Thr Leu Ser Val Asp Arg Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Asn Leu Gly Pro Ser Phe Tyr Phe Asp Tyr Trp Gly Gln Gly
            100                 105                 110

Thr Leu Val Thr Val Ser Ser Ala Ser Thr Lys Gly Pro Ser Val Phe
        115                 120                 125

Pro Leu Ala Pro Ser Ser Lys Ser Thr Ser Gly Gly Thr Ala Ala Leu
    130                 135                 140

Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
                165                 170                 175

Gln Ser Ser Gly Leu Tyr Ser Leu Ser Ser Val Val Thr Val Pro Ser
            180                 185                 190

Ser Ser Leu Gly Thr Gln Thr Tyr Ile Cys Asn Val Asn His Lys Pro
        195                 200                 205

Ser Asn Thr Lys Val Asp Lys Lys Val Glu Pro Lys Ser Cys Asp Lys
    210                 215                 220
```

```
Thr His Thr Cys Pro Pro Cys Pro Ala Pro Glu Leu Leu Gly Gly Pro
225                 230                 235                 240

Ser Val Phe Leu Phe Pro Pro Lys Pro Lys Asp Thr Leu Met Ile Ser
                245                 250                 255

Arg Thr Pro Glu Val Thr Cys Val Val Val Asp Val Ser His Glu Asp
            260                 265                 270

Pro Glu Val Lys Phe Asn Trp Tyr Val Asp Gly Val Glu Val His Asn
        275                 280                 285

Ala Lys Thr Lys Pro Arg Glu Glu Gln Tyr Asn Ser Thr Tyr Arg Val
    290                 295                 300

Val Ser Val Leu Thr Val Leu His Gln Asp Trp Leu Asn Gly Lys Glu
305                 310                 315                 320

Tyr Lys Cys Lys Val Ser Asn Lys Ala Leu Pro Ala Pro Ile Glu Lys
                325                 330                 335

Thr Ile Ser Lys Ala Lys Gly Gln Pro Arg Glu Pro Gln Val Tyr Thr
            340                 345                 350

Leu Pro Pro Ser Arg Glu Glu Met Thr Lys Asn Gln Val Ser Leu Thr
        355                 360                 365

Cys Leu Val Lys Gly Phe Tyr Pro Ser Asp Ile Ala Val Glu Trp Glu
    370                 375                 380

Ser Asn Gly Gln Pro Glu Asn Asn Tyr Lys Thr Thr Pro Pro Val Leu
385                 390                 395                 400

Asp Ser Asp Gly Ser Phe Phe Leu Tyr Ser Lys Leu Thr Val Asp Lys
                405                 410                 415

Ser Arg Trp Gln Gln Gly Asn Val Phe Ser Cys Ser Val Met His Glu
            420                 425                 430

Ala Leu His Asn His Tyr Thr Gln Lys Ser Leu Ser Leu Ser Pro Gly
        435                 440                 445


<210> SEQ ID NO 92
<211> LENGTH: 113
<212> TYPE: PRT
<213> ORGANISM: Artificial Sequence
<220> FEATURE:
<223> OTHER INFORMATION: VH of Opdivo

<400> SEQUENCE: 92

Gln Val Gln Leu Val Glu Ser Gly Gly Gly Val Val Gln Pro Gly Arg
1               5                   10                  15

Ser Leu Arg Leu Asp Cys Lys Ala Ser Gly Ile Thr Phe Ser Asn Ser
            20                  25                  30

Gly Met His Trp Val Arg Gln Ala Pro Gly Lys Gly Leu Glu Trp Val
        35                  40                  45

Ala Val Ile Trp Tyr Asp Gly Ser Lys Arg Tyr Tyr Ala Asp Ser Val
    50                  55                  60

Lys Gly Arg Phe Thr Ile Ser Arg Asp Asn Ser Lys Asn Thr Leu Phe
65                  70                  75                  80

Leu Gln Met Asn Ser Leu Arg Ala Glu Asp Thr Ala Val Tyr Tyr Cys
                85                  90                  95

Ala Thr Asn Asp Asp Tyr Trp Gly Gln Gly Thr Leu Val Thr Val Ser
            100                 105                 110

Ser


<210> SEQ ID NO 93
<211> LENGTH: 107
```

<212> TYPE: PRT
<213> ORGANISM: Artificial Sequence
<220> FEATURE:
<223> OTHER INFORMATION: VL of Opdivo

<400> SEQUENCE: 93

```
Glu Ile Val Leu Thr Gln Ser Pro Ala Thr Leu Ser Leu Ser Pro Gly
1               5                   10                  15

Glu Arg Ala Thr Leu Ser Cys Arg Ala Ser Gln Ser Val Ser Ser Tyr
            20                  25                  30

Leu Ala Trp Tyr Gln Gln Lys Pro Gly Gln Ala Pro Arg Leu Leu Ile
        35                  40                  45

Tyr Asp Ala Ser Asn Arg Ala Thr Gly Ile Pro Ala Arg Phe Ser Gly
    50                  55                  60

Ser Gly Ser Gly Thr Asp Phe Thr Leu Thr Ile Ser Ser Leu Glu Pro
65                  70                  75                  80

Glu Asp Phe Ala Val Tyr Tyr Cys Gln Gln Ser Ser Asn Trp Pro Arg
                85                  90                  95

Thr Phe Gly Gln Gly Thr Lys Val Glu Ile Lys
            100                 105
```

<210> SEQ ID NO 94
<211> LENGTH: 120
<212> TYPE: PRT
<213> ORGANISM: Artificial Sequence
<220> FEATURE:
<223> OTHER INFORMATION: VH of Keytruda

<400> SEQUENCE: 94

```
Gln Val Gln Leu Val Gln Ser Gly Val Glu Val Lys Lys Pro Gly Ala
1               5                   10                  15

Ser Val Lys Val Ser Cys Lys Ala Ser Gly Tyr Thr Phe Thr Asn Tyr
            20                  25                  30

Tyr Met Tyr Trp Val Arg Gln Ala Pro Gly Gln Gly Leu Glu Trp Met
        35                  40                  45

Gly Gly Ile Asn Pro Ser Asn Gly Gly Thr Asn Phe Asn Glu Lys Phe
    50                  55                  60

Lys Asn Arg Val Thr Leu Thr Thr Asp Ser Ser Thr Thr Thr Ala Tyr
65                  70                  75                  80

Met Glu Leu Lys Ser Leu Gln Phe Asp Asp Thr Ala Val Tyr Tyr Cys
                85                  90                  95

Ala Arg Arg Asp Tyr Arg Phe Asp Met Gly Phe Asp Tyr Trp Gly Gln
            100                 105                 110

Gly Thr Thr Val Thr Val Ser Ser
        115                 120
```

<210> SEQ ID NO 95
<211> LENGTH: 111
<212> TYPE: PRT
<213> ORGANISM: Artificial Sequence
<220> FEATURE:
<223> OTHER INFORMATION: VL of Keytruda

<400> SEQUENCE: 95

```
Glu Ile Val Leu Thr Gln Ser Pro Ala Thr Leu Ser Leu Ser Pro Gly
1               5                   10                  15

Glu Arg Ala Thr Leu Ser Cys Arg Ala Ser Lys Gly Val Ser Thr Ser
            20                  25                  30

Gly Tyr Ser Tyr Leu His Trp Tyr Gln Gln Lys Pro Gly Gln Ala Pro
```

-continued

```
        35                  40                  45

Arg Leu Leu Ile Tyr Leu Ala Ser Tyr Leu Glu Ser Gly Val Pro Ala
    50                  55                  60

Arg Phe Ser Gly Ser Gly Ser Gly Thr Asp Phe Thr Leu Thr Ile Ser
65                  70                  75                  80

Ser Leu Glu Pro Glu Asp Phe Ala Val Tyr Tyr Cys Gln His Ser Arg
                85                  90                  95

Asp Leu Pro Leu Thr Phe Gly Gly Gly Thr Lys Val Glu Ile Lys
            100                 105                 110


<210> SEQ ID NO 96
<211> LENGTH: 108
<212> TYPE: PRT
<213> ORGANISM: Artificial Sequence
<220> FEATURE:
<223> OTHER INFORMATION: VL of Ipilimumab

<400> SEQUENCE: 96

Glu Ile Val Leu Thr Gln Ser Pro Gly Thr Leu Ser Leu Ser Pro Gly
1               5                   10                  15

Glu Arg Ala Thr Leu Ser Cys Arg Ala Ser Gln Ser Val Gly Ser Ser
            20                  25                  30

Tyr Leu Ala Trp Tyr Gln Gln Lys Pro Gly Gln Ala Pro Arg Leu Leu
        35                  40                  45

Ile Tyr Gly Ala Phe Ser Arg Ala Thr Gly Ile Pro Asp Arg Phe Ser
    50                  55                  60

Gly Ser Gly Ser Gly Thr Asp Phe Thr Leu Thr Ile Ser Arg Leu Glu
65                  70                  75                  80

Pro Glu Asp Phe Ala Val Tyr Tyr Cys Gln Gln Tyr Gly Ser Ser Pro
                85                  90                  95

Trp Thr Phe Gly Gln Gly Thr Lys Val Glu Ile Lys
            100                 105


<210> SEQ ID NO 97
<211> LENGTH: 118
<212> TYPE: PRT
<213> ORGANISM: Artificial Sequence
<220> FEATURE:
<223> OTHER INFORMATION: VH of Ipilimumab

<400> SEQUENCE: 97

Gln Val Gln Leu Val Glu Ser Gly Gly Gly Val Val Gln Pro Gly Arg
1               5                   10                  15

Ser Leu Arg Leu Ser Cys Ala Ala Ser Gly Phe Thr Phe Ser Ser Tyr
            20                  25                  30

Thr Met His Trp Val Arg Gln Ala Pro Gly Lys Gly Leu Glu Trp Val
        35                  40                  45

Thr Phe Ile Ser Tyr Asp Gly Asn Asn Lys Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Ile Tyr Tyr Cys
                85                  90                  95

Ala Arg Thr Gly Trp Leu Gly Pro Phe Asp Tyr Trp Gly Gln Gly Thr
            100                 105                 110

Leu Val Thr Val Ser Ser
        115
```

-continued

<210> SEQ ID NO 98
<211> LENGTH: 108
<212> TYPE: PRT
<213> ORGANISM: Artificial Sequence
<220> FEATURE:
<223> OTHER INFORMATION: VL of Anti-human 4-1BB antibody

<400> SEQUENCE: 98

```
Ser Thr Glu Leu Thr Gln Pro Pro Ser Val Ser Val Ser Pro Gly Gln
1               5                   10                  15

Thr Ala Ser Ile Thr Cys Ser Gly Asp Asn Ile Gly Asp Gln Thr Ala
            20                  25                  30

His Trp Thr Gln Gln Leu Pro Gly Gln Ser Pro Val Leu Val Ile Thr
        35                  40                  45

Gln Asp Leu Asn Arg Pro Ser Gly Ile Pro Glu Arg Phe Ser Gly Ser
    50                  55                  60

Asn Ser Gly Asn Thr Ala Thr Leu Thr Ile Ser Gly Thr Gln Ala Met
65                  70                  75                  80

Asp Glu Ala Asp Thr Thr Cys Ala Thr Thr Thr Gly Phe Gly Ser Leu
                85                  90                  95

Ala Val Phe Gly Gly Gly Thr Leu Leu Thr Val Leu
            100                 105
```

<210> SEQ ID NO 99
<211> LENGTH: 116
<212> TYPE: PRT
<213> ORGANISM: Artificial Sequence
<220> FEATURE:
<223> OTHER INFORMATION: VH of Anti-human 4-1BB antibody

<400> SEQUENCE: 99

```
Glu Val Gln Leu Val Gln Ser Gly Ala Glu Val Leu Leu Pro Gly Glu
1               5                   10                  15

Ser Leu Arg Ile Ser Cys Leu Gly Ser Gly Thr Ser Phe Ser Thr Thr
            20                  25                  30

Trp Ile Ser Trp Val Arg Gln Met Pro Gly Leu Gly Leu Glu Trp Met
        35                  40                  45

Gly Leu Ile Thr Pro Gly Asp Ser Thr Thr Asn Thr Ser Pro Ser Phe
    50                  55                  60

Gln Gly Gln Val Thr Ile Ser Ala Asp Leu Ser Ile Ser Thr Ala Thr
65                  70                  75                  80

Leu Gln Trp Ser Ser Leu Leu Ala Ser Asp Thr Ala Met Thr Thr Cys
                85                  90                  95

Ala Arg Gly Thr Gly Ile Phe Asp Thr Trp Gly Gln Gly Thr Leu Val
            100                 105                 110

Thr Val Ser Ser
        115
```

<210> SEQ ID NO 100
<211> LENGTH: 107
<212> TYPE: PRT
<213> ORGANISM: Artificial Sequence
<220> FEATURE:
<223> OTHER INFORMATION: VL of Adalimumab

<400> SEQUENCE: 100

```
Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Gly Ile Arg Asn Tyr
```

```
            20                  25                  30

Leu Ala Trp Tyr Gln Gln Lys Pro Gly Lys Ala Pro Lys Leu Leu Ile
        35                  40                  45

Tyr Ala Ala Ser Thr Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Val Ala Thr Tyr Tyr Cys Gln Arg Tyr Asn Arg Ala Pro Tyr
                85                  90                  95

Thr Phe Gly Gln Gly Thr Lys Val Glu Ile Lys
            100                 105


<210> SEQ ID NO 101
<211> LENGTH: 121
<212> TYPE: PRT
<213> ORGANISM: Artificial Sequence
<220> FEATURE:
<223> OTHER INFORMATION: VH of Adalimumab

<400> SEQUENCE: 101

Glu Val Gln Leu Val Glu Ser Gly Gly Gly Leu Val Gln Pro Gly Arg
1               5                   10                  15

Ser Leu Arg Leu Ser Cys Ala Ala Ser Gly Phe Thr Phe Asp Asp Tyr
            20                  25                  30

Ala Met His Trp Val Arg Gln Ala Pro Gly Lys Gly Leu Glu Trp Val
        35                  40                  45

Ser Ala Ile Thr Trp Asn Ser Gly His Ile Asp Tyr Ala Asp Ser Val
    50                  55                  60

Glu Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Lys Val Ser Tyr Leu Ser Thr Ala Ser Ser Leu Asp Tyr Trp Gly
            100                 105                 110

Gln Gly Thr Leu Val Thr Val Ser Ser
        115                 120


<210> SEQ ID NO 102
<211> LENGTH: 120
<212> TYPE: PRT
<213> ORGANISM: Artificial Sequence
<220> FEATURE:
<223> OTHER INFORMATION: VH of Pembrolizumab

<400> SEQUENCE: 102

Gln Val Gln Leu Val Gln Ser Gly Val Glu Val Lys Lys Pro Gly Ala
1               5                   10                  15

Ser Val Lys Val Ser Cys Lys Ala Ser Gly Tyr Thr Phe Thr Asn Tyr
            20                  25                  30

Tyr Met Tyr Trp Val Arg Gln Ala Pro Gly Gln Gly Leu Glu Trp Met
        35                  40                  45

Gly Gly Ile Asn Pro Ser Asn Gly Gly Thr Asn Phe Asn Glu Lys Phe
    50                  55                  60

Lys Asn Arg Val Thr Leu Thr Thr Asp Ser Ser Thr Thr Thr Ala Tyr
65                  70                  75                  80

Met Glu Leu Lys Ser Leu Gln Phe Asp Asp Thr Ala Val Tyr Tyr Cys
                85                  90                  95
```

```
Ala Arg Arg Asp Tyr Arg Phe Asp Met Gly Phe Asp Tyr Trp Gly Gln
            100                 105                 110

Gly Thr Thr Val Thr Val Ser Ser
        115                 120


<210> SEQ ID NO 103
<211> LENGTH: 111
<212> TYPE: PRT
<213> ORGANISM: Artificial Sequence
<220> FEATURE:
<223> OTHER INFORMATION: VL of Pembrolizumab

<400> SEQUENCE: 103

Glu Ile Val Leu Thr Gln Ser Pro Ala Thr Leu Ser Leu Ser Pro Gly
1               5                   10                  15

Glu Arg Ala Thr Leu Ser Cys Arg Ala Ser Lys Gly Val Ser Thr Ser
            20                  25                  30

Gly Tyr Ser Tyr Leu His Trp Tyr Gln Gln Lys Pro Gly Gln Ala Pro
        35                  40                  45

Arg Leu Leu Ile Tyr Leu Ala Ser Tyr Leu Glu Ser Gly Val Pro Ala
    50                  55                  60

Arg Phe Ser Gly Ser Gly Ser Gly Thr Asp Phe Thr Leu Thr Ile Ser
65                  70                  75                  80

Ser Leu Glu Pro Glu Asp Phe Ala Val Tyr Tyr Cys Gln His Ser Arg
                85                  90                  95

Asp Leu Pro Leu Thr Phe Gly Gly Gly Thr Lys Val Glu Ile Lys
            100                 105                 110


<210> SEQ ID NO 104
<211> LENGTH: 105
<212> TYPE: PRT
<213> ORGANISM: Artificial Sequence
<220> FEATURE:
<223> OTHER INFORMATION: VL of Trastuzumab

<400> SEQUENCE: 104

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Val Asn Thr Ala
            20                  25                  30

Val Ala Trp Tyr Gln Gln Lys Pro Gly Lys Ala Pro Lys Leu Leu Ile
        35                  40                  45

Tyr Ser Ala Ser Phe Leu Gly Val Pro Ser Arg Phe Ser Gly Ser Arg
    50                  55                  60

Ser Gly Thr Asp Phe Thr Leu Thr Ile Ser Ser Leu Gln Pro Glu Asp
65                  70                  75                  80

Phe Ala Thr Tyr Tyr Cys Gln Gln His Tyr Thr Thr Pro Pro Thr Phe
                85                  90                  95

Gly Gln Gly Thr Lys Val Glu Ile Lys
            100                 105


<210> SEQ ID NO 105
<211> LENGTH: 120
<212> TYPE: PRT
<213> ORGANISM: Artificial Sequence
<220> FEATURE:
<223> OTHER INFORMATION: VH of Trastuzumab

<400> SEQUENCE: 105

Glu Val Gln Leu Val Glu Ser Gly Gly Gly Leu Val Gln Pro Gly Gly
```

-continued

```
1               5                   10                  15

Ser Leu Arg Leu Ser Cys Ala Ala Ser Gly Phe Asn Ile Lys Asp Thr
            20                  25                  30

Tyr Ile His Trp Val Arg Gln Ala Pro Gly Lys Gly Leu Glu Trp Val
        35                  40                  45

Ala Arg Ile Tyr Pro Thr Asn Gly Tyr Thr Arg Tyr Ala Asp Ser Val
    50                  55                  60

Lys Gly Arg Phe Thr Ile Ser Ala Asp Thr Ser Lys Asn Thr Ala Tyr
65                  70                  75                  80

Leu Gln Met Asn Ser Leu Arg Ala Glu Asp Thr Ala Val Tyr Tyr Cys
                85                  90                  95

Ser Arg Trp Gly Gly Asp Gly Phe Tyr Ala Met Asp Tyr Trp Gly Gln
            100                 105                 110

Gly Thr Leu Val Thr Val Ser Ser
        115                 120
```

CONJUGATES OF BIOMOLECULE AND USE THEREOF

RELATED APPLICATIONS

This application is a U.S. National Stage application under 35 U.S.C. § 371 from International Patent Application No. PCT/CN2018/114266 filed Nov. 7, 2018, which claims the benefit of priority from U.S. Patent Application No. 62/583,410 filed Nov. 8, 2017.

TECHNICAL FIELD

The present invention relates to conjugates of biomolecules and use thereof.

REFERENCE TO SEQUENCE LISTING

The Sequence Listing submitted as an XML filed named "863.203US_final.xml," created on Jul. 26, 2023, and having a size of 152 kB is hereby incorporated by reference pursuant to 37 C.F.R. § 1.835(a)(2).

TECHNICAL BACKGROUND

Conjugating agents to antibodies by linking to native cystine has been used to further advance the use of antibody. Molecules such as toxins and drugs have been conjugated to antibodies to generate antibody-drug conjugates (ADCs). Fusion of a cleaving, masking peptide sequence to an antibody to generate a probody has been used for a local activation in Tumor. But the peptides are limited in terminal of antibody, and the activation sequence is limited with peptide with low activation rate and high immunogenicity from masking peptide.

The common side effect of the currently commercial macromolecular drugs is immunotoxicity. Immunotoxicity includes immunosuppression, generation of immunogenicity, hypersensitivity, autoreaction and adverse immune stimulation. These side effects are mainly caused by extraneous macromolecules. After entering into the body, heterogenous macromolecules will elicit an immune response in the patient due to its immunogenicity. In normal tissues, immunity also will be stimulated and autoimmunity response will be generated after a macromolecule drug, such as antibody or cytokine, binds to the antigens or receptors. At this time it is very dangerous to the patient. For example, during the treatment of non-small cell lung cancer with the current PD-1 antibodies, Keytruda® (pembrolizumab) and Opdivo® (nivolumab), serious pneumonia may occur, which may even lead to death of patients. Similar effects were also reported in the clinical use of CTLA4 antibodies (Yervoy®; ipilimumab), 41BB, IL-2, IL-10 etc. In combination therapy of Opdivo® (nivolumab) and Yervoy® (ipilimumab) to non-small cell lung cancer, 55% patients showed the high grade 3-4 AEs and 36% patients had to stop drug treatment due to drug toxicity. Therefore, intelligent conjugates of biomolecule with new functions are required in this field to decrease the overall toxicity and immunotoxicity by blocking drug activity in blood and normal tissue and to enhance the active drug in pathologic microenvironment, to adjust DMPK and half-life in serum, to decrease immunogenicity of Fab of antibody, to adjust the binding affinity of active biomolecule, and to enhance the efficacy.

SUMMARY OF INVENTION

The present disclosure provides conjugates of a biomolecule having the following structure:

R1-R2-R3-R4-S-cys-R5 wherein,

R5 represents a biomolecule with one or more cysteine residues introduced by mutation;

cys represents the cysteine residue(s) contained in R5;

S represents sulfur atom(s) of the cysteine residue(s);

R1 is a group that prevents R5 from binding to its antigen, ligand or receptor;

R2 is absent, or R2 is a cleavable linker arm capable of being activated by one or more proteolytic enzymes or a chemical bond capable of being acidically activated in a pathologic microenvironment;

R3 is absent, or R3 is a linker arm capable of automatically shedding after R2 is cleaved or a chemical bond capable of being acidically activated in a pathologic microenvironment; with the proviso that when R2 is absent, R3 is the chemical bond capable of being acidically activated in a pathologic microenvironment; and R4 is a group covalently linked to R5 via the sulfur atom(s) of the cysteine residue(s) contained in R5 that recovers, maintains or promotes the binding capacity of R5 to its antigen, ligand or receptor after the moiety R1-R2-R3 is cleaved.

In the above formula, when R1-R2 is cleaved from R3-R4-S-cys-R5 by a proteolytic enzyme or under an acid condition in the pathologic microenvironment, R3-R4-S-cys-R5 is released. And the binding capacity of R4-S-cys-R5 to the antigen, ligand or receptor of R5 will be recovered, maintained or improved after R3 automatically sheds and R4-S-cys-R5 is released.

In one or more embodiments of the present disclosure, R1, R2, R3, R4 and R5 of the conjugates of biomolecule are described as in other parts of the present disclosure.

The present disclosure also provides a compound having the following structure:

R4-S-cys-R5 wherein,

R4 is represented by $R_{4\text{-}a}$-$R_{4\text{-}b}$-$R_{4\text{-}c}$-, wherein R4 is represented by $R_{4\text{-}a}$-$R_{4\text{-}b}$-$R_{4\text{-}c}$-, wherein $R_{4\text{-}a}$ is selected from the group consisting of:

$R_4$-$a_1$

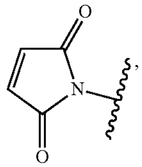

, $R_4$-$a_2$

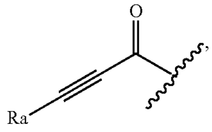

, $R_4$-$a_3$

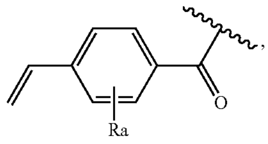

,

-continued $R_4$-$a_4$

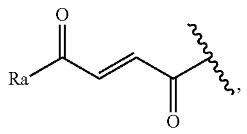

and $R_4$-$a_5$

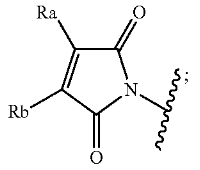

wherein Ra and Rb are each independently selected from the group consisting of H and $C_{1-6}$ alkyl or $C_{1-6}$ alkoxyl;

$R_{4-b}$ is selected from the group consisting of:

$R_{4-b1}$

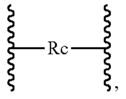

$R_{4-b2}$

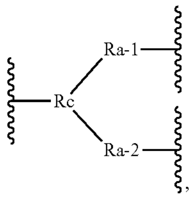

and $R_{4-b3}$

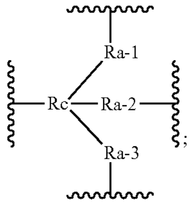

wherein in formula R4-b1, Rc is absent, or is selected from the group consisting of $C_{1-12}$ alkyl, $C_{1-12}$alkoxy-$C_{1-12}$alkyl, $C_{1-12}$alkyl-$C_{3-8}$cycloalkyl, $(C_{1-4}$alkyl-$O)_p$—$C_{1-12}$alkyl, $C_{1-12}$alkylcarbonylamino-$(C_{1-4}$alkyl-$O)_p$—$C_{1-12}$alkyl, phenyl-$C_{1-12}$alkyl, $C_{3-8}$cycloalkyl, $C_{1-12}$alkyl-$C_{3-8}$cycloalkyl-$C_{1-12}$alkyl, and $C_{1-12}$alkyl-phenyl-$C_{1-12}$alkyl; in formula R4-b2, Rc is a $C_{1-12}$alkylamino with Ra-1 and Ra-2 substituted at N atom of the amino group, and in formula 4-b3, Rc is a $C_{1-12}$alkyl with the last C atom at the end of the alkyl being substituted by Ra-1, Ra-2 and R2-3, wherein Ra-1, Ra-2 and Ra-3 are each independently selected from the group consisting of $C_{1-12}$alkyl, $C_{1-12}$alkyl-OH, and $C_{1-12}$alkyl-NR"R'", wherein R" and R'" are each independently selected from the group consisting of H and $C_{1-12}$alkyl; wherein in formulae R4-b2 and R4-b3, R4-b links to R4-c via at least one of the Ra-1, Ra-2 and Ra-3;

$R_{4-c}$ is selected from the group consisting of $R_{4c}$-I

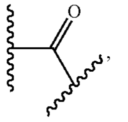

$R_{4c}$-II

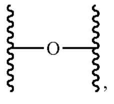

$R_{4c}$-III

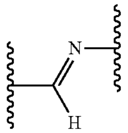

$R_{4c}$-IV

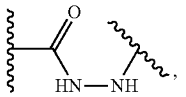

$R_{4c}$-V

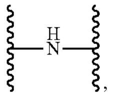

$R_{4c}$-VI

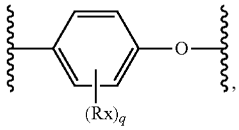

and $R_{4c}$-VII

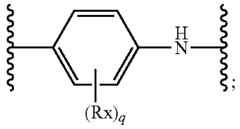

wherein Rx is selected from the group consisting of H, halo and $C_{1-4}$alkyl; p is an integer in a range of 1 to 10, such as an integer in a range of 1 to 5; and q is an integer in a range of 1 to 4, such as an integer in a range of 1 to 2; with the proviso that R4-c is absent when R4-a is selected from the group consisting of formulae R4-a2, R4-a3 and R4-a4; wherein R3 links to R4 via the R4-c of R4, and the wave line shown in each formula of R4-a indicates the position at which R4-a links to R4-b.

Also provided is a compound represented by R1-R2-R3-R4, wherein R1, R2, R3 and R4 are defined as in any embodiments of the present disclosure.

The present disclosure provides use of the conjugates of biomolecule or the R4-S-cys-R5 compound as described herein in the manufacture of an anti-tumor drug.

The present disclosure provides a pharmaceutical composition comprising the conjugates of biomolecule as described herein.

The present disclosure provides a method for treating or preventing tumor, comprising providing to a subject in need thereof a therapeutically effective amount of the conjugates of biomolecule or the R4-S-cys-R5 compound as described herein.

The present disclosure also provides compounds, including compounds S1-S64 and compounds described in other parts of the present disclosure, and antibodies and cytokines containing mutation as described herein.

EMBODIMENTS

Figure 1:
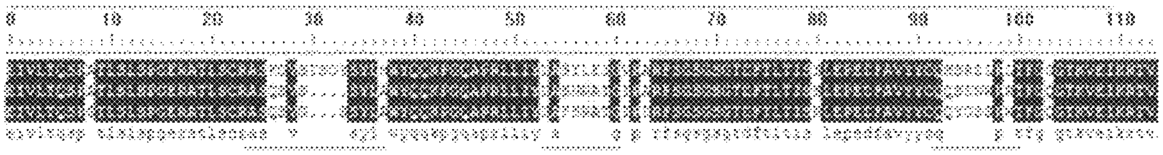
FIG. 1: Alignment of the amino acid sequences of the light chains of antibodies (From top to bottom: SEQ ID NO:95, SEQ ID NO: 93 and SEQ ID NO: 96).

It should be understood that, within the scope of the present disclosure, each of the technical features mentioned above and each of those mentioned hereinafter, such as in the Examples, can be combined with each other to constitute preferred technical solutions. Additionally, the present disclosure is not limited to particular embodiments described, as such may, of course, vary. It is also to be understood that, unless defined otherwise, all technical and scientific terms used herein have the same meaning as commonly understood by one of ordinary skill in the art to which this invention belongs. Although any methods and materials similar or equivalent to those described herein can also be used in the practice or testing of the present invention, the preferred methods and materials are now described. All publications mentioned herein are incorporated herein by reference to disclose and describe the methods and/or materials in connection with which the publications are cited.

It must be noted that as used herein and in the appended claims, the singular forms “a,” “an,” “and,” and “the” include plural referents unless the context clearly dictates otherwise. Thus, for example, reference to “an antibody” includes a plurality of antibodies and reference to “the antibody” includes reference to one or more antibodies and equivalents thereof known to those skilled in the art, and so forth. It is further noted that the claims may be drafted to exclude any optional element. As such, this statement is intended to serve as antecedent basis for use of such exclusive terminology as “solely”, “only” and the like in connection with the recitation of claim elements, or use of a “negative” limitation.

One of the purposes of the present disclosure is to provide modified biomolecules, which are only activated in a pathologic microenvironment, such as in a tumor microenvironment or an inflammatory environment, to release a biomolecule (R5) in the pathologic microenvironment which has the same or even improved binding capacity to its ligand, thereby improving the targeting and efficacy of the biomolecule, overcoming drug resistance and reducing toxicity.

In the present disclosure, the modified biomolecule is a conjugate, which comprises a biomolecule and a functional moiety covalently linked to the biomolecule. Biomolecules suitable for use in the present disclosure may be biomolecules having a biological function or activity of interest, including but not limited to various functional proteins. Biological function or activity of interest includes but is not limited to functions or activities in enzymology and immunology. Therefore, biomolecules suitable for use in the present disclosure include but are not limited to antibodies or functional fragments thereof, enzymes, fusion proteins (such as protein-antibody fusions), antibody drug conjugates, cytokines, and any other genetically engineered biological molecules.

As used herein, the term “antibody” is used in the broadest sense and specifically covers monoclonal antibodies, polyclonal antibodies, dimers, multimers, multispecific antibodies (e.g., bispecific antibodies), and antibody fragments, so long as they exhibit the desired biological activity (Miller et al (2003) Jour. of Immunology 170:4854-4861). In the context and in the Figures, an antibody is abbreviated as “Ab”.

The basic antibody structural unit is known to comprise a tetramer composed of two identical pairs of polypeptide chains, each pair having one light and one heavy chain. The N terminal portion of each chain includes a variable region of about 100 to 110 or more amino acids primarily responsible for antigen recognition. The C terminal portion of each chain defines a constant region primarily responsible for effector function. The variable region of heavy chain (VH) and the variable region of light chain (VL) each contain 3 complementarity determining region (CDR), including HCDR1, HCDR2, HCDR3 and LCDR1, LCDR2 and LCDR3. These six CDRs form antigen-binding site of an antibody. The remaining amino acids of the variable region are relatively conservative and are termed as framework region (FR). VH and VL each contain 4 framework regions, called FR1, FR2, FR3 and FR4, respectively.

Antibodies may be murine, human, humanized, chimeric, or derived from other species. The immunoglobulin disclosed herein can be of any type (e.g., IgG, IgE, IgM, IgD, and IgA), class (e.g., IgG1, IgG2, IgG3, IgG4, IgA1 and IgA2) or subclass of immunoglobulin molecule. The immunoglobulins can be derived from any species. In one aspect, however, the immunoglobulin is of human, murine, or rabbit origin.

Antibody fragment comprise a portion of a full length antibody, generally the antigen binding or variable region thereof. Preferably, fragment of an antibody is a functional fragment, i.e., retaining the antigen-binding capability of the intact antibody. Examples of antibody fragments or functional fragments include Fab, Fab', F(ab')2, and Fv fragments; diabodies; linear antibodies; and single chain antibody molecules (scFv); etc.

Fusion protein used herein may contain an antigen binding domain of an antibody and optionally a cytokine. The antigen binding domain of an antibody contained in fusion protein may be an antigen binding domain to an antigen selected from the group consisting of HER2, CD19, EGFR, CD22, CD3, TROP2, Glycoprotein NMB, Guanylyl cyclase C, CEA, CD79b, PSMA, ENPP3, Mesothelin, CD138, NaPi2b, CD56, CD74, FOLR1, DLL3, CEACAM5, CD142, SLAMF7, CD25, SLTRK6, CD37, CD70, AGS-22, C4.4A, FGFR2, Ly6E, MUC16, BCMA, pCadherin, Ephrin-A, LAMP1, MUC1, CD19, PDL1, HER2, NY-ESO-1, BCMA, WT1, MUC1, CD20, CD23, ROR1, CD123, CD33, CD44v6, CD174, CD30, CD133, cMet, EGFR, FAP, EphA2, GD2, GPC3, IL-13Ra2, LewisY, Mesothelin, SS1, CEA, CD171, EGFR, EGFRvIII, VEGFR2, NY-ESO-1, MUC-1 and MAGE-A3, or may be an antigen binding domain of any antibodies as described herein. In some embodiments, the fusion protein is a bispecific antibody, which contain an antigen binding domain to an antigen selected from the group consisting of HER2, CD19, EGFR, CD22, CD3, TROP2, Glycoprotein NMB, Guanylyl cyclase C, CEA, CD79b, PSMA, ENPP3, Mesothelin, CD138, NaPi2b, CD56, CD74, FOLR1, DLL3, CEACAM5, CD142, SLAMF7, CD25, SLTRK6, CD37, CD70, AGS-22, C4.4A, FGFR2, Ly6E, MUC16, BCMA, pCadherin, Ephrin-A, LAMP1, MUC1, CD19, PDL1, HER2, NY-ESO-1, BCMA, WT1, MUC1, CD20, CD23, ROR1, CD123, CD33, CD44v6, CD174, CD30, CD133, cMet, EGFR, FAP, EphA2, GD2, GPC3, IL-13Ra2, LewisY, Mesothelin, SS1, CEA, CD171, EGFR, EGFRvIII, VEGFR2, NY-ESO-1, MUC-1 and MAGE-A3, or which contain an antigen binding domain from any antibodies as described herein. Preferably, the bispecific antibody is a single chain bispecific antibody, which contains two scFv from the same or different antibodies.

In some embodiments, the fusion protein is an antibody-cytokine fusion protein, which contains an antibody or functional fragment thereof and a cytokine selected from the group consisting of IL-2, IL-7, IL-10, IL-11, IL-12, IL-15, IL-21, IFN-α, IFN-β, IFN-γ, G-CSF, GM-CSF, TNF-α, TRAP, and TRAIL. An example of such fusion protein is a fusion protein of anti-PD-1 antibody or anti-CD3 antibody or antigen binding domain thereof with IL2.

Antibody used herein may be any antibodies known in the art and functional fragments thereof. For example, antibody used herein may be an antibody or functional fragment thereof selected from the group consisting of anti-Her2 antibody, anti-EGFR antibody, anti-VEGFR antibody, anti-CD20 antibody, anti-CD33 antibody, anti-PD-L1 antibody, anti-PD-1 antibody, anti-CTLA-4 antibody, anti-TNFα antibody, anti-CD28 antibody, anti-4-1BB antibody, anti-OX40 antibody, anti-GITR antibody, anti-CD27 antibody, antib-CD40 antibody, or anti-ICOS antibody, anti-CD25 antibody, anti-CD30 antibody, anti-CD3 antibody, anti-CD22 antibody, anti-CCR4 antibody, anti-CD38 antibody, anti-CD52 antibody, anti-Complement C5 antibody, anti-F protein of RSV, anti-GD2 antibody, anti-GITR antibody, anti-Glycoprotein receptor lib/Illa antibody, anti-ICOS antibody, anti-IL2R antibody, anti-LAG3 antibody, anti-Integrinα4 antibody, anti-lgE antibody, anti-PDGFRa antibody, anti-RANKL antibody, anti-SLAMF7 antibody, anti-LTIGIT antibody, anti-TIM-3 antibody, anti-VEGFR2 antibody, anti-VISTA antibody.

In preferred embodiments, antibody used herein may be an antibody or functional fragment thereof selected from the group consisting of utomilumab, urelumab, ADG106, Poteligeo® (mogamulizumab), Bexxar™ (tositumomab), Zevalin™ (ibritumomab tiuxetan), Rituxan® (rituximab), Arzerra® (ofatumumab), Gazyva® (obinutuzumab), Besponsa® (inotuzumab ozogamicin), Zenapax® (daclizumab), varlilumab, theralizumab, Adcetris® (brentuximab vedotin), Myelotarg™ (gemtuzumab), Darzalex® (daratumumab), CDX-1140, SEA-CD40, RO7009789, JNJ-64457107, APX-005M, Chi Lob 7/4, Campath™ (alemtuzumab), Raptiva™ (efalizumab), Soliris® (eculizumab), Yervoy® (ipilimumab), tremelimumab, Erbitux® (cetuximab), Vectibix® (panitumumab), Portrazza™ (necitumumab), TheraCIM® (nimotuzumab), Synagis® (palivizumab), Unituxin® (dinutuximab), TRX-518, MK-4166, MK-1248, GWN-323, INCAGN0186, BMS-986156, AMG-228, ReoPro® (abiciximab), Herceptin® (trastuzumab), Perjeta® (pertuzumab), Kadcyla® (ado-trastuzumab emtansine), GSK-3359609, JTX-2011, Simulect™ (basiliximab), Tysabri® (natalizumab), BMS-986016, REGN3767, LAG525, Xolair® (omalizumab), tavolimab, PF-04518600, BMS-986178, MOXR-0916, GSK-3174998, INCAGN01949, IBI-101, Keytruda® (pembrolizumab), Opdivo® (nivolumab), Lartruvo™ (olaratumab), Tecentriq® (atezolizumab), BMS-936559, Bavencio® (avelumab), Imfinzi® (duralumab), Prolia® (denosumab), Empliciti® (elotuzumab), MTIG7192A, TSR-022, MBG-453, Remicade® (infliximab), Humira® (adalimumab), Avastin® (bevacizumab), Lucentis® (ranibizumab), Cyramza® (ramucirumab), and JNJ-61610588.

In the present disclosure, cytokine may have a meaning and structure commonly used in the art. It generally refers to a kind of small proteins having wide biological activities, which are synthesized and secreted by stimulating immunocytes, such as monocytes, macrophages, T cells, B cells, NK cells, etc., or nonimmune cells, such as endothelial cells, epidermal cells, fibroblasts, etc. Cytokine may regulate cell growth, differentiation and effect, and immune response through binding to a corresponding receptor. Suitable cytokines include interleukins, interferons, tumor necrosis factor superfamily, colony stimulating factors, chemotactic factors and growth factors, etc.

Exemplary cytokines include but are not limited to IL-2, IL-7, IL-10, IL-11, IL-12, IL-15, IL-21, IFN-α, IFN-β, IFN-γ, G-CSF, GM-CSF, TNF-α, TRAP, and TRAIL.

In the present disclosure, one or more (such as 5 or less or 3 or less) amino acids in suitable position(s) of the amino acid sequence of the biomolecule are mutated to cysteine and the biomolecule is covalently linked to the functional moiety of the present disclosure (R1-R2-R3-R4) via the thiol group of the cysteine. For example, one or two amino acids of interest in the biomolecule of interest are mutated to cysteine for conjugation to the functional moiety. For an antibody, the mutation position may be present in a complementarity determining region or a non-complementarity determining region of a variable region. Preferably, the mutation is a mutation by substitution. More preferably, the mutation occurs in a variable region of the light chain of antibody. Generally, a mutant can be prepared and then its binding activity to a corresponding antigen is tested. If a mutant retains 70% or more, preferably 80% or more, more preferably 90% or more of binding activity as compared to the wild-type antibody, it is believed that the amino acid residue at the mutation position may be mutated to cysteine to covalently link to a functional moiety. Alternatively, in certain embodiments, if a conjugate produced by linking a mutant to R4 retains 80% or more, preferably 90% or more, more preferably 95% or more of binding activity, it is believed that the amino acid residue at the mutation position may be mutated to cysteine to covalently link to a functional moiety.

In general, one or more of G, A, S, T, L, I, F, E, K, D and Y, etc., more preferably one or more of G, A, S, T, L, I, K and Y, more preferably one or more of G, A, T, L and S, in a CDR of a variable region of a light chain of an antibody may be mutated to cysteine. In some embodiments, one or more of G, A, S, T, L, I, F, E, K, D and Y, etc., more preferably one or more of G, A, S, T, L, I, K and Y, more preferably one or more of G, A, T, L, Y and S, in a CDR of a variable region of a heavy chain of an antibody may be mutated to cysteine. If mutation occurs in a non-CDR of a light chain of an antibody, one or more of G, A, S, T, L, I, F, E, K, D and Y, etc., preferably G, A, S, T, K, I, Y and L, more preferably one or more of G, A, T, Y and S, in the non-CDR in the variable region of a light chain or a heavy chain may be mutated to cysteine. In some embodiments, one or more of S, T, L, I, F, E, K, D, N, Q, R and Y residues, etc., in non-complementarity determining region (such as in FR1, FR2 or FR3) of a variable region of a light chain or a heavy chain may be mutated to cysteine. In some embodiments, substitution mutation may be introduced into one or more the following conservative sites: Gln3, Ser7, Ser26, Glu46, Thr68 and Asp72 in non-complementarity determining region (FR1, FR2 or FR3) of VH, and Thr5, Tyr49, Arg61, Ser63, Ser65, Ser67, Thr72, Thr74, Ser76 and Asp82 in non-complementarity determining region (FR1, FR2 or FR3) of VL.

For example, in some embodiments of the present disclosure, the mutation position in a heavy chain of anti-PD-1 antibody (such as Pembrolizumab) may be selected from the group consisting of: Ser7, Gly8, Gly15, Ala16, Ser17, Ala24, Ser25, Gly26, Tyr27, Thr28, Thr30, Asn31, Tyr32, Tyr33, Tyr35, Ala40, Gly42, Gly44, Leu45, Gly49, Gly50, Ile51, Asn52, Ser54, Asn55, Gly56, Gly57, Thr58, Asn59, Lys63, Lys65, Thr69, Leu70, Thr71, Thr72, Asp73, Ser74, Ser75, Thr76, Thr77, Thr78, Ala79, Leu83, Ser85, Leu86, Thr91, Ala92, Arg99, Asp100, Tyr101, Arg102, Asp104, Gly106, Gly111, Gly113, Thr114, 115Thr, 117Thr, Ser119, Ser120, Ala121, Ser122, Thr123, Lys124, Gly125 and Ser127; and the mutation position in a light chain may be selected from the group consisting of: Ile2, Thr5, Ser7, Ala9, Thr10, Leu11, Ser12, Leu13, Ser14, Gly16, Ala19, Thr20, Ala25, Ser26, Lys27, Gly28, Ser30, Thr31, Ser32, Gly33, Tyr34, Ser35, Tyr36, Leu37, Gly45, Ala47, Leu50, Leu51, Ile52, Tyr53, Leu54, Ala55, Ser56, Tyr57, Leu58, Ser60, Gly61, Ala64, Ser67, Gly68, Ser69, Gly70, Ser71, Gly72, Thr73, Ala76, Thr78, Ser80, Ser81, Ser95, Arg96, Asp97, Leu98, Leu100, Thr101, Phe102, Gly104, Ile110, Lys111 and K130.

Alternatively, the mutation position in a heavy chain of anti-PD-1 antibody (such as Nivolumab) may be selected from the group consisting of: Gln3, Ser7, Gly8, Gly9, Gly10, Gly15, Ser17, Lys23, Ala24, Ser25, Gly26, Ile27, Asn31, Thr28, Ser30, Ser32, Gly33, Ala40, Gly42, Gly44, Leu45, Ala49, Ile51, Tyr53, Asp54, Gly55, Ser56, Lys57, Tyr59, Tyr60, Ala61, Asp62, Ser63, Lys65, Gly66, Thr69, Ile70, Ser71, Arg72, Asp73, Asn74, Ser75, Lys76, Asn77, Thr78, Leu79, Leu81, Ser85, Leu86, Ala88, Thr91, Ala92, Thr98, Asn99, Asp100, Asp101, Tyr102, Gly104, Gly106, Thr107, Leu108, Thr110, Ser112, Ser113, Ala114, Ser115, Thr116, Lys117, Gly118 and Ser120; and the mutation position in a light chain may be selected from the group consisting of: Ile2, Leu4, Thr5, Ser7, Ala9, Thr10, Leu11, Ser12, Leu13, Ser14, Gly16, Ala19, Thr20, Leu21, Ala25, Ser26, Ser28, Ser30, Ser31, Tyr32, Leu33, Ala34, Tyr36, Gly41, Ala43, Leu46, Leu47, Ile48, Tyr49, Asp50, Ala51, Ser52, Asn53, Arg54, Ala55, Thr56, Gly57, Ile58, Ala60, Arg61, Ser63, Gly64, Ser65, Gly66, Ser67, Gly68, Thr69, Thr72, Leu73, Thr74, Ile75, Ser76, Ser77, Leu78, Ala84, Ser91, Ser92, Asn93, Arg96, Thr97, Phe98, Gly99, Gly101, Thr102, Ile106, Lys107, Thr109, Ala111, Ala112, Ser114, Ile117 and Ser121.

The mutation position in a heavy chain of anti-CTLA-4 antibody may be selected from the group consisting of: Ser7, Gly8, Gly9, Gly10, Gly15, Ser17, Leu18, Leu20, Ala24, Ser25, Gly26, Phe27, Thr28, Phe29, Ser30, Ser31, Tyr32, Thr33, Ala40, Gly42, Lys43, Gly44, Leu45, Glu46, Thr49, Phe50, Ile51, Ser52, Tyr53, Asp54, Gly55, Lys58, Tyr59, Tyr60, Ala61, Asp62, Ser63, Lys65, Gly66, Thr69, Ile70, Ser71, Ser75, Lys76, Thr78, Leu79, Leu81, Ser85, Leu86, Ala88, Gly89, Asp90, Thr91, Ala92, Tyr94, Tyr95, Ala97, Phe98, Thr99, Gly100, Leu102, Gly103, Asp106, Tyr107, Gly109, Gly111, Thr112, Leu113, Thr115, Ser117, Ser118, Ala119, Ser120, Thr121 and Lys122; and the mutation position in a light chain may be selected from the group consisting of: Ile2, Leu4, Thr5, Ser7, Gly9, Thr10, Leu11, Ser12, Leu13, Ser14, Gly16, Ala19, Thr20, Leu21, Ala25, Ser26, Ser28, Gly30, Ser31, Ser32, Tyr33, Leu34, Ala35, Tyr37, Lys40, Gly42, Ala44, Leu47, Leu48, Ile49, Tyr50, Gly51, Ala52, Phe53, Ser54, Ala56, Thr57, Gly58, Ile59, Ser64, Gly65, Ser66, Gly67, Ser68, Gly69, Thr70, Asp71, Thr73, Leu74, Thr75, Ile76, Ser77, Leu79, Ala85, Tyr92, Gly93, Ser94, Ser95, Thr98, Phe99, Gly100, Gly102, Thr103, Lys104, Ile107, Lys108, Thr110, Ala112, Ala113, Ser115, Ser128, Gly129 and Thr130.

The mutation position in a heavy chain of the anti-CTLA-4 antibody Ipilimumab may be selected from the group consisting of: Gln3, Arg19, Leu20, Ser25, Gly26, Phe27, Thr28, Phe29, Ser30, Ser31, Tyr32, Thr33, Met34, His35, Gly44, Phe50, Ile51, Ser52, Tyr53, Asp54, Gly55, Asn56, Asn57, Lys58, Tyr59, Tyr60, Thr69, Ser71, Arg72, Asp73, Asn74, Ser75, Lys76, Asn77, Thr99, Gly100, Trp101, Leu102, Gly103 and Pro104; the mutation position in a light chain is selected from the group consisting of: Gln6, Arg24, Ala25, Ser26, Gln27, Ser28, Val29, Gly30, Ser31, Ser32, Tyr33, Ile49, Tyr50, Gly51, Ala52, Phe53, Ser54, Arg55, Ala56, Phe53, Ser54, Arg55, Ala56, Thr57, Gly58, Ile59, Pro60, Asp61, Arg62, Ser68, Gly69, Thr70, Gln90, Gln91, Tyr92, Gly93, Ser94, Ser95, Pro96 and Trp 97.

The mutation position in a heavy chain of anti-TNFα antibody may be selected from the group consisting of: Ser7, Gly8, Gly9, Gly10, Leu11, Gly15, Ser17, Leu18, Leu20, Ala24, Ser25, Gly26, Thr28, Asp30, Asp31, Tyr32, Ala33, Ala40, Gly42, Gly44, Leu45, Ser49, Ala50, Ile51, Thr52, Asn54, Ser55, Gly56, Ile58, Asp59, Tyr60, Ala61, Asp62, Ser63, Glu65, Gly66, Phe68, Thr69, Ile70, Ser71, Asp73, Asn74, Ala75, Lys76, Ser78, Leu79, Tyr80, Leu81, Ser85, Leu86, Ala88, Thr91, Ala92, Lys98, Ser100, Tyr101, Leu102, Ser103, Thr104, Ala105, Ser106, Ser107, Leu108, Asp109, Tyr110, Gly112, Gly114, Thr115, Leu116, thr118, Ser120, Ser121, Ala122, Ser123 and Thr124; and the mutation position in a light chain may be selected from the group consisting of: Asp1, Thr5, Ser7, Ser9, Ser10, Leu11, Ser12, Ala13, Ser14, Gly16, Thr20, Ile21, Ala25, Ser26, Gln27, Gly28, Ile29, Arg30, Asn31, Tyr32, Leu33, Ala34, Tyr36, Lys39, Gly41, Lys42, Ala43, Leu48, Leu47, Ile48, Tyr49, Ala50, Ala51, Ser52, Thr53, Leu54, Gln55, Ser56, Gly57, Ser60, Ser63, Gly64, Ser65, Gly66, Ser67, Gly68, Thr69, Asp70, Thr72, Leu73, Thr74, Ile75, Ser76, Ser77, Leu78, Ala84, Thr85, Tyr91, Asn92, Arg93, Ala94, Tyr96, Thr97, Phe98, Gly99, Gly101, Thr102, Ile106, Lys107, Thr109 and Ala111.

The mutation position in a heavy chain of anti-CD28 antibody may be selected from the group consisting of: Ser7, Gly8, Gly15, Ala16, Ser17, Ser21, Ala24, Ser25, Gly26, Tyr27, Thr28, Thr30, Ser31, Tyr32, Ala40, Gly42, Gly44, Gly49, Tyr52, Gly54, Thr58, Ala68, Thr69, Thr71, Thr74, Ser75, Ser77, Thr78, Ala79, Ser84, Leu86, Ser88, Thr91, Ala92, Thr97, Ser99, Tyr101, Gly102, Leu103, Gly113, Thr114, Thr115, Thr117, Ser119, Ser120, Ala121, Ser122 and Thr123; and the mutation position in a light chain may be selected from the group consisting of: Thr5, Ser7, Ser9, Ser1O, Ser11, Ser12, Ala13, Ser14, Gly16, Thr20, Thr22, Ala25, Ser26, Ser27, Ile29, Tyr30, Ala43, Leu46, Leu47, Tyr49, Lys50, Ala51, Ser52, Leu54, Thr56, Gly57, Ser60, Ser63, Gly64, Ser65, Gly66, Ser67, Gly68, Thr69, Asp70, Thr72, Thr74, Ser76, Ser77, Ala84, Thr85, Gly91, Thr93, Tyr94, Tyr96, Thr97, Phe98, Gly99, Gly100, Gly101, Thr102, Thr109 and Ala111.

The mutation position in a heavy chain of the anti-4-1BB antibody may be selected from the group consisting of: Thr31, Tyr32, Ser35, Lys50, Tyr52, Asp55, Ser56, Tyr57, Thr58, Asn59, Tyr60, Ser61, Gln65, Gly66, Gly99, Tyr100, Gly101, Asp104 and Tyr105; the mutation position in a light chain may be selected from the group consisting of: Ser23, Gly24, Asp25, Asn26, Gly28, Asp29, Gln30, Tyr31, Gln49, Asp50, Lys51, Asn52, Arg53, Ser55, Gly56, Thr89, Tyr90, Thr91, Gly92, Gly94 and Ser95.

The mutation position in a heavy chain of the anti-Her2 antibody (such as Trastuzumab) may be selected from the group consisting of: Arg19, Lys30, Asp31, Tyr33, Arg50, Tyr62, Asn55, Tyr57, Arg59, Tyr60, Asp62, Lys65, Asp102 and Tyr105; the mutation position in a light chain is selected from the group consisting of: Asp1, Gln3, Gln27, Asp28, Asn30, Tyr49, Tyr55, Arg66, Asp70 and Tyr92.

The mutation position in a heavy chain of the anti-PD-L1 antibody (such as Atezolizumab) is selected from the group consisting of: Gln3, Asp31, Tyr54, Tyr59, Tyr60, Asp62, Lys65, Asp73, Lys76, Asn77 and Arg99; the mutation position in a light chain is selected from the group consisting of: Arg24, Gln27, Asp28, Tyr49, Tyr55, Asp70, Gln89, Gln90, Tyr91 and Tyr93.

In some preferred embodiments, the mutation positions of various antibodies are preferably selected from the positions listed in Tables 5 to 19 which retain 70% or more, preferably 80% or more, more preferably 90% or more of binding activity after mutation or retain 80% or more, preferably 90% or more of binding activity after conjugating to R4. These mutation positions include those in CDR and non-CDR. For example, preferred mutation positions of a light chain of anti-PD-1 antibody 1 may include Ala25, Ser26, Gly28, Ser30, Thr31, Ser32, Gly33, Ser35, Tyr36, Leu37, Leu54, Ala55, Ser56, Tyr57, Ser60, Gly61, Ser95, Thr101 and Gly104; more preferably, the mutation positions include Ser26, Gly28, Ser30, Ser32, Gly33, Ser35, Ala55, Ser56, Ser60, Gly61 and Ser95. Preferred mutation positions of a light chain of anti-PD-1 antibody 2 may include Ala25, Ser26, Ser28, Ser30, Ser31, Ala34, Ala51, Ser52, Ser54, Ala55, Thr56, Gly57, Ile58, Ala60, Ser91, Ser92, Thr97 and Gly99; more preferably, the mutation positions include Ser26, Ser28, Ser30, Ser31, Ala34, Ser52, Ser54, Thr56, Gly57, Ser91, Ser92, Thr97 and Gly99. Preferred mutation positions of a light chain of anti-CTLA-4 antibody may include Ala25, Ser26, Ser28, Gly30, Ser31, Ser32, Leu34, Ala35, Gly51, Ala52, Ser54, Ala56, Thr57, Gly58, Gly93, Ser94, Ser95, Thr98 and Gly100; more preferably, the mutation positions include Ala25, Ser26, Ser28, Gly30, Ser31, Ser32, Gly51, Ser54, Thr57, Gly58, Gly93, Ser94, Ser95 and Gly100. Preferred mutation positions of a light chain of anti-CD28 antibody may include Ser26, Ile29, Tyr30, Lys50, Ala51, Ser52, Gly91, Thr93, Tyr94, Tyr96, Thr97 and Gly99; more preferably, the mutation positions include Tyr30, Ala51, Tyr96, Thr97 and Gly99. Preferred mutation positions of a light chain of anti-TNFα antibody may include Ala25, Ser26, Gly28, Ile29, Tyr32, Leu33, Ala34, Ala50, Ala51, Ser52, Thr53, Leu54, Ser56, Gly57, Tyr91, Ala94 and Thr97; more preferably, the mutation positions include Ser26, Gly28, Ala51, Ser56, Gly57, Tyr91 and Ala94.

Preferred mutation positions of a heavy chain of anti-PD-1 antibody 1 may include Thr30, Tyr32, Tyr35, Gly50, Ile51, Ser54, Gly56, Gly57, Thr58, Lys63, Tyr101 and Gly106; more preferably, the mutation positions include Thr30, Gly50, Ser54, Gly56, Gly57, Thr58, Lys63 and Gly106. Preferred mutation positions of a heavy chain of anti-PD-1 antibody 2 may include Ser30, Ser32, Gly33, Ile51, Tyr53, Asp54, Gly55, Ser56, Lys57, Ala61, Ser63, Lys65, Gly66, Asp101, Gly104, Gly106, Thr107 and Leu108; more preferably, the mutation positions include Ser30, Ser32, Gly33, Tyr53, Gly55, Ser56, Ser63, Lys65, Gly66, Gly104, Gly106 and Thr107. Preferred mutation positions of a heavy chain of anti-CTLA-4 antibody may include Ser30, Ser31, Tyr32, Thr33, Ile51, Asp54, Gly55, Lys58, Tyr59, Tyr60, Ala61, Asp62, Ser63, Lys65, Gly66, Gly100, Leu102, Gly103, Asp106 and Tyr107; more preferably, the mutation positions include Ser30, Ser31, Thr33, Gly55, Tyr60, Ala61, Ser63, Lys65, Gly66, Gly100, and Gly103. Preferred mutation positions of a heavy chain of anti-CD28 antibody may include Ser25, Gly26, Tyr27, Thr28, Thr30, Ser31, Tyr32, Tyr33, Tyr52, Gly54, Thr58, Ser99, Tyr101, Gly102 and Leu103; more preferably, the mutation positions include Gly26, Tyr27, Thr28, Thr30, Ser31, Tyr52, Gly54 and Leu103. Preferred mutation positions of a heavy chain of anti-TNFα antibody may include Tyr32, Ala33, Ile51, Thr52, Ser55, Gly56, Ile58, Tyr60, Ala61, Ser63, Gly66, Ser100, Tyr101, Leu102, Ser103, Thr104, Ala105, Ser106, Ser107, Leu108 and Tyr110; more preferably, the mutation positions include Ala33, Ile51, Ala61, Ser63, Gly66, Ser100, Thr104 and Ser106.

Similarly, when the mutation occurs in a non-CDR, i.e., in a framework region of a variable region of a light chain, mutation positions of various antibodies may be preferably selected from those listed in Tables 7 and 8 which retain 80% or more, preferably 90% or more of binding activity after mutation. For example, for the light chain of the anti-PD-1 antibody 1 as disclosed herein, the preferred mutation positions in the framework region include Thr5, Ser7, Ala9, Thr10, Leu11, Ser12, Leu13, Ser14, Gly16, Ala19, Thr20, Gly45, Ala47, Leu50, Leu51, Ile52, Ala64, Ser67, Gly68, Ser69, Gly70, Ser71, Gly72, Thr73, Ala76, Thr78, Ser80, Ser81, Ile110 and Lys111; more preferably, the mutation positions include Thr5, Ser7, Ala9, Leu11, Leu13, Ser14, Ala47, Leu50, Ala64, Gly68, Ser69, Ser71, Gly72, Thr73, Ser80 and Ile 110. For the heavy chain of anti-PD-1 antibody 2 as disclosed herein, the preferred mutation positions of the framework region include Ser7, Gly8, Gly9, Gly10, Gly15, Ser17, Ala24, Ser25, Gly26, Thr28, Ser30, Ala40, Gly42, Gly44, Thr68, Ser71, Ser75, Thr78, Thr85, Ala88, Thr91, Ala92, Thr98, Thr110, Ser112, Ser113, Ala114, Ser115, Thr116, Lys117, Gly118 and Ser120; more preferably, the mutation positions include Ser7, Gly8, Gly9, Ala24, Ser25, Gly26, Gly44, Thr68, Ser75, Thr78, Thr85, Thr110, Ser112, Ser113, Ser115, Thr116, Lys117, Gly118 and Ser120.

With respect to other functional proteins, such as cytokines, if its mutant retains 70% or more, preferably 80% or more, more preferably 90% or more of binding activity (e.g., binding capacity to its nature ligand) of a wild-type protein, it is believed that the amino acid residue at the position may be mutated to cysteine to link to a functional moiety. For example, the mutation position of IL2 may be selected from the group consisting of Lys32, Lys35, Thr37, Met39, Thr41, Lys43, Lys48, Lys49, Lys64, Leu72, Ala73, Ser75, Lys76, Leu94, Thr101, Thr102, Tyr107, Ala108, Thr11 and Ala112, so as to block an alpha receptor; or is selected from the group consisting of Leu12, His16, Leu19, Met23, Gly27, Ser75, Arg81, Leu85, Ser87, Leu94, Gly98, Ser99, Thr101 and Thr133, so as to block a beta receptor; or is selected from the group consisting of Leu36, Ala50, Thr51, Thr123, Ser126, Ser127 and Ser130, so as to block a gamma receptor. In some embodiments, the mutation position of the IL2 may be selected from the group consisting of: Lys32, Lys35, Thr37, Thr41, Lys43, Lys48, Lys49, Ala50, Leu72, Ala73, Ser75, Lys76, Leu94, Thr101, Thr102, Ala108, Thr111 and Ala112, so as to block alpha receptor of IL2; or may be selected from the group consisting of Leu19, Gly27, Ser75, Leu80, Ser87, Leu94, Gly98, Ser99, Thr101 and Thr133, so as to block beta receptor of IL2; or is selected from the group consisting of Leu36, Ala50, Thr51, Thr123, Ser126, Ser127 and Ser130, so as to block gamma receptor of IL2.

One or more of Ala, Gly, Ser, Thr, Leu, Lys, Tyr, Phe, Asp, Glu and Ile of cytokines, such as IL2, IL10 and IL15, may be mutated to cysteine. Preferably, any of Thr, Leu, Ala, Gly and Ser in the amino acid sequence of cytokines is mutated to cysteine.

In some embodiments, the mutation position in a Human IL10 may be selected from the group consisting of: Thr6, Ser8, Ser11, Thr13, Gly17, Arg24, Ser31, Arg32, Lys34, Thr35, Lys40, Leu46, Lys49, Ser51, Lys57, Gly58, Ser66, Tyr72, Lys88, His90, Ser93, Lys99, Thr100, Arg104, Lys117, Ser118, Lys119, Lys125, Lys130, Lys134, Gly135, Tyr137, Tyr149, Thr155, Lys157 and Arg159.

For the fusion protein of the present disclosure, one or more cysteines may be introduced into any protein of the fusion protein. For example, for a bispecific antibody, the mutation(s) may be introduced into the CDR or non-CDR of either or both of the scFv, or into the either or both of the antigen binding domain. For a fusion protein of an antibody and a cytokine, either or both of the antibody and cytokine may contain the mutation(s).

Exemplified sequences may be referred to SEQ ID NO: 13-83.

Mutation, transfection, expression and purification of a biomolecule may be performed by the methods known in the art. For example, a nucleic acid of a biomolecule having a mutation position may be directly synthesized, then nucleic acid molecules of different fragments obtained by enzyme digestion may be ligated into an expression vector and the expression vector is transformed into bacteria or eukaryotic host cells. The biomolecule containing the cysteine mutation may be obtained through recombination in the host cells.

Bacteria or eukaryotic host cells suitable for use in the present disclosure may be host cells commonly used in the art, including but not limited to bacteria, yeast and mammal cells. Useful eukaryotic host cells include CHO cells, HEK293T cells, or *Pichia pastoris.*

Expression vectors suitable for use in the present disclosure may be virus-based expression vectors known in the art, including but not limited to baculovirus, simian virus (SV40), retrovirus or vaccinia based viral vectors. Expression vectors containing suitable regulatory elements and selecting markers may be used to prepare mammal cell lines which stably express a mutant. For example, GS Eukaryotic Expression System (Lonza), DHFR Eukaryotic Expression System (Invitrogen) and *Pichia pastoris* Expression System (Invitrogen) may be used in the expression and preparation.

Biomolecules of the present disclosure may be purified by the isolation methods known in the art. These methods include but are not limited to DEAE ionic exchange, gel filtration and hydroxyapatite chromatography. For example, protein G column may be used to isolate biomolecules in the supernatant of cell cultures or in extracts of cytoplasm. In some embodiments, the biomolecules may be subjected to "engineering modification" to make them to contain an amino acid sequence that allows the biomolecules to be captured to an affinity matrix. For example, a tag may be used to facilitate purification of a polypeptide. The tag includes but is not limited to c-myc, hemagonium, poly-His (e.g., 6His) or Flag™ (Kodak). Such kind of tags may be inserted to any position within a polypeptide, including a carboxyl terminus or an amino terminus. Biomolecules of the present disclosure may also be purified by immunoaffinity chromatography.

The functional moiety suitable for use in the present disclosure may be represented by formula R1-R2-R3-R4. In the functional moiety, R1, R2, R3 and R4 are linked together via any suitable linkage manner, including but not limited to amide, ester, carbamate, urea or hydrazone bond. In the present disclosure, amide bond may be represented by "—CO—NH—", ester bond may be represented by "—C(O)—O—", carbamate bond may be represented by "—NH—C(O)—O—", urea bond may be represented by "—NH—CO—NH—", and hydrazone bond may be represented by "—CH=N—NH—".

R1 is a protective group for the biomolecule R5. It may be selected from any group that can prevent the biomolecule from binding to its ligand or receptor, so as to prevent it from being interfered by other molecules, for example, those that prevent it from binding to its ligand or receptor, before it reaches a pathologic microenvironment, such as tumor or inflammatory microenvironment. Suitable R1 may be selected from the group consisting of polyethylene glycol-$C_{1-5}$ alkylcarbonyl, naphthylcarbonyl, quinolylcarbonyl, fluorenylcarbonyl, adamantylcarbonyl,

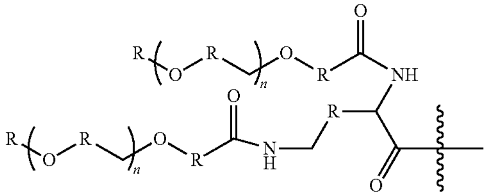
,
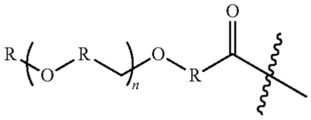
,
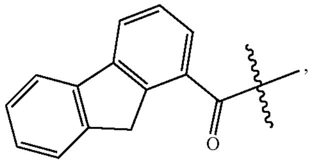
,
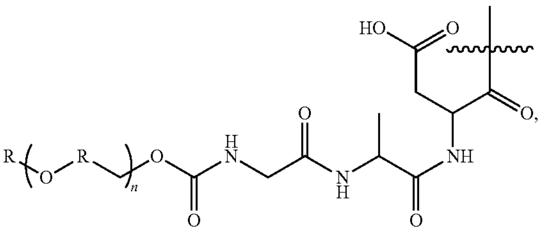
,
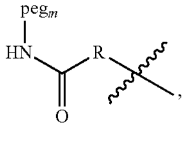
, or
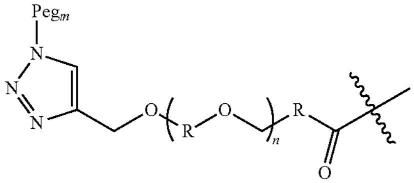
,
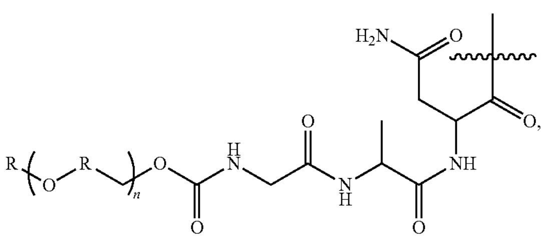
,
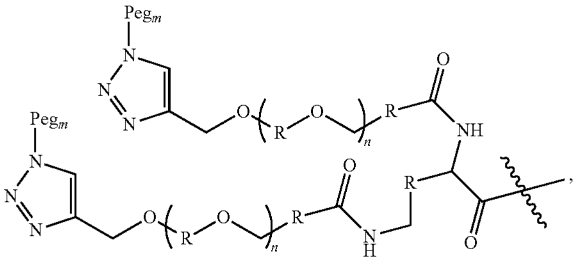
, -continued

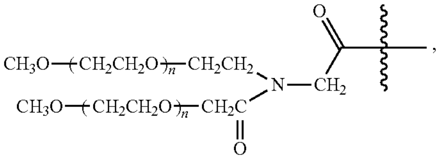

,

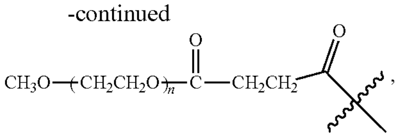

, and

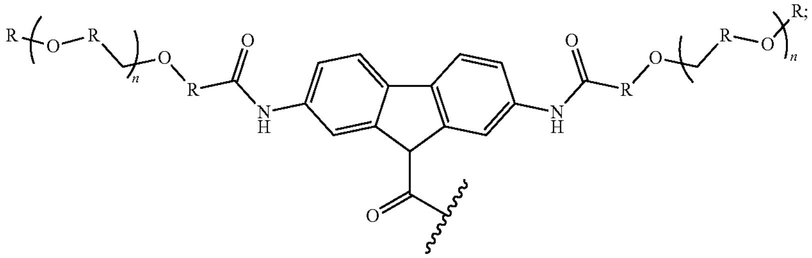

wherein each R is independently a $C_{1-4}$alkyl; each n is independently an integer in a range of 1 to 30000, such as an integer in a range of 1 to 15000, 1 to 5000, 1 to 2000, 1 to 300, 1 to 150, 1 to 50, 1 to 20 or 3 to 12; polyethylene glycol or $peg_m$ represents a polyethylene glycol having a molecular weight in a range of 44 to 132000, such as that in a range of 1000 to 50000 or 10000 to 30000; m represents the molecular weight of the polyethylene glycol; and the wave line indicates the position of R1 linking to R2.

In some embodiments, R1 is selected from the group consisting of:

R1-1

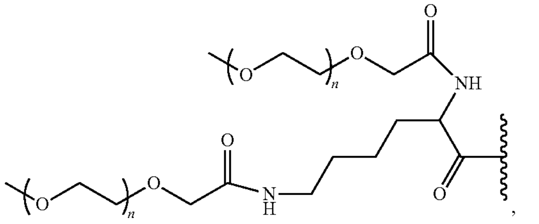

n = 5

,

R1-2

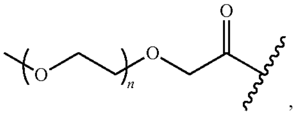

n = 12

,

R1-3

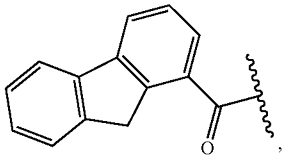

,

R1-4

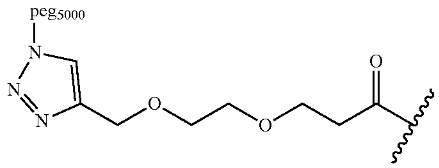

,

R1-5

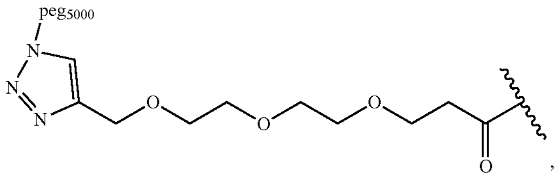

,

R1-6

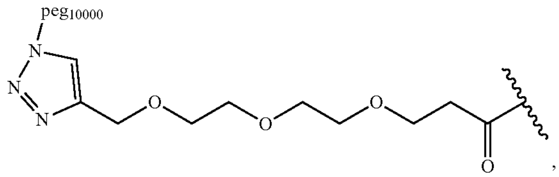

,

R1-7

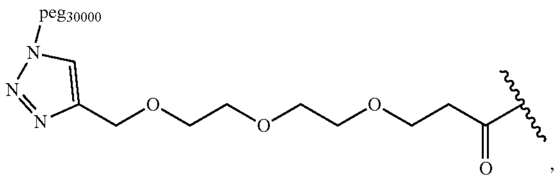

,

R1-8

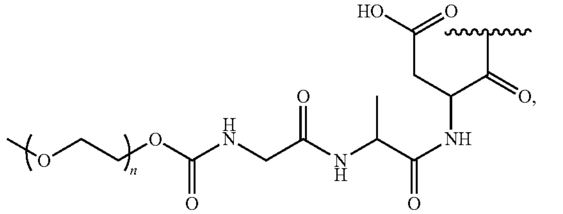

n = 12

-continued
R1-9
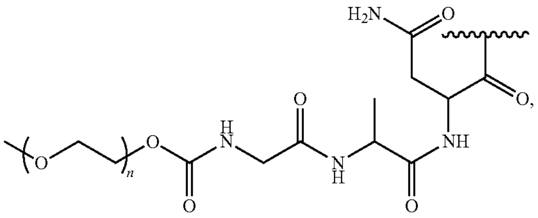
n = 12
R1-10
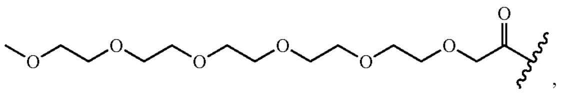
R1-11
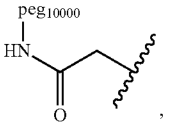
R1-12
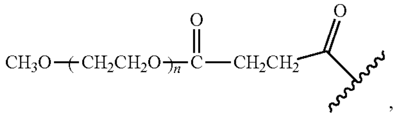
n = 112
R1-13
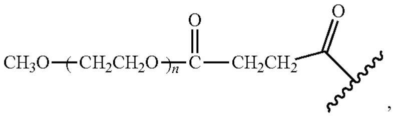
n = 232
R1-14
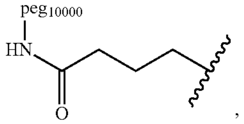
R1-15
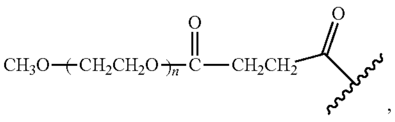
n = 480
R1-16
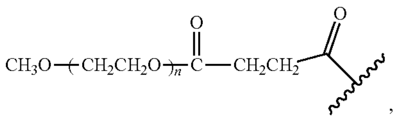
n = 930
R1-17
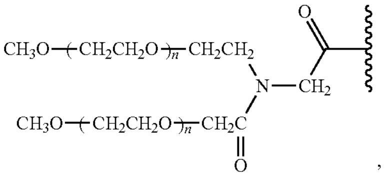
n = 528
R1-18
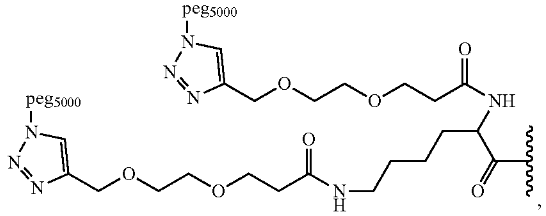
R1-19
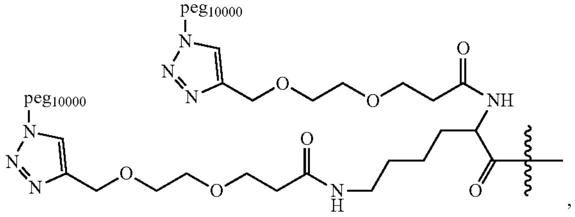
R1-20
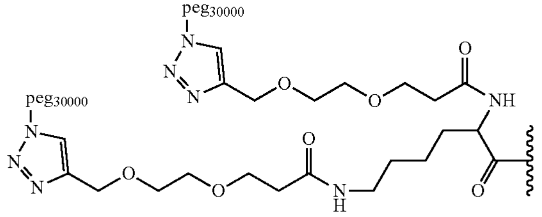
R1-21
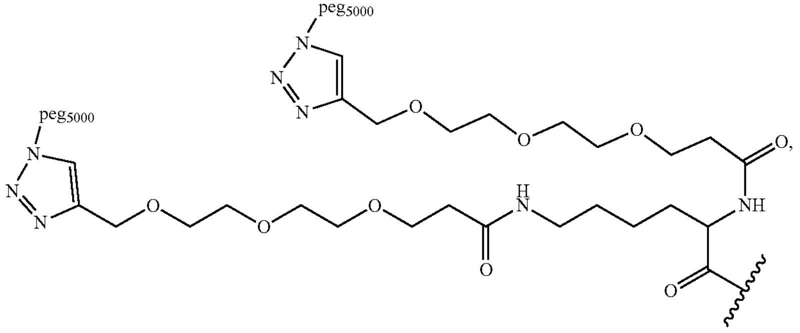

-continued
R1-22
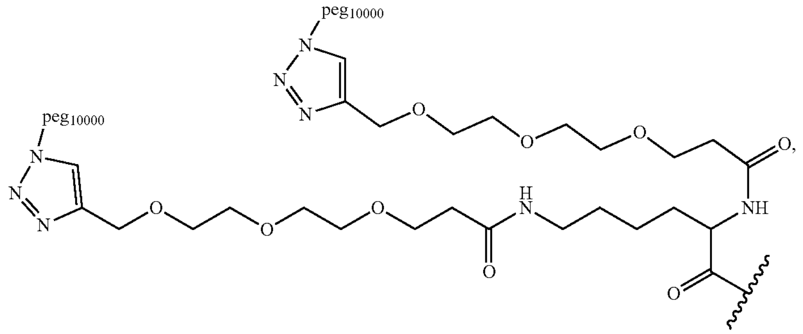
R1-23
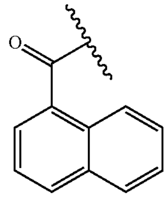
,
R1-24
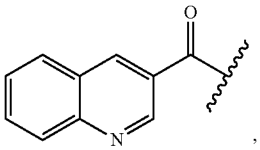
,
R1-25
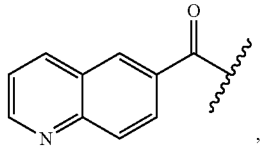
,
R1-26
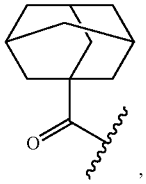
,
R1-27
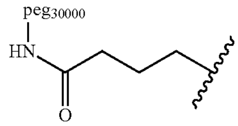
,
R1-28
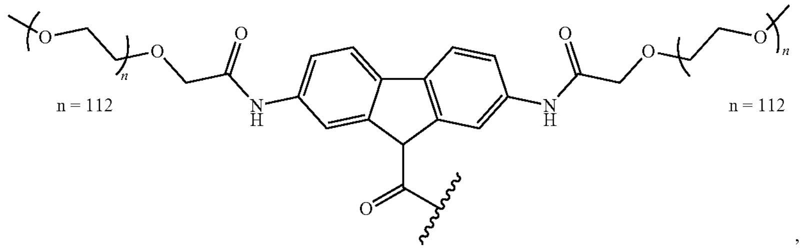
n = 112
n = 112
,
R1-29
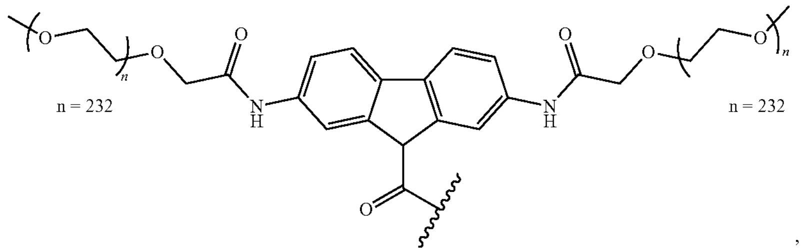
n = 232
n = 232
, -continued

R1-30

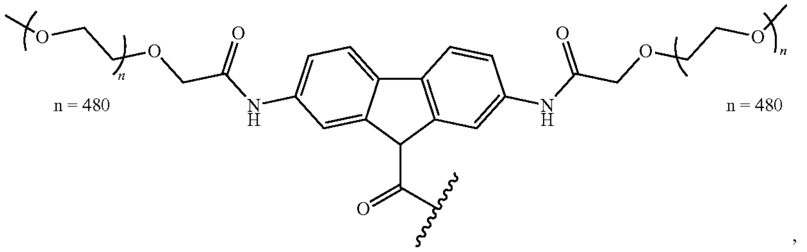

, and

R1-31

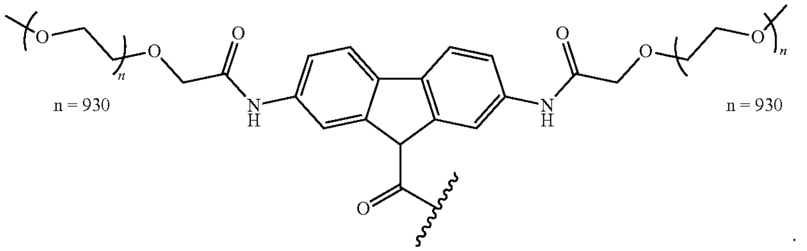

.

Generally, if a mutation position is present in the functional domain of a biomolecule, for example, in a CDR of an antibody, there is no specific limitation on the molecular weight of R1 and R1 may have a relatively low molecular weight. If a mutation position is present outside the functional domain of a biomolecule, for example, in a non-CDR of an antibody, R1 is preferably selected to make the molecular weight of R1-R2-R3-R4 to be higher than 200, preferably higher than 500, more preferably to be higher than 1000, so as to make the molecular weight of the conjugate of biomolecule to be 5000 or more, preferably 8000 or more, more preferably 10000 or more, thereby better preventing the biomolecule from binding to its ligand or receptor before arriving at a pathologic microenvironment.

In the present disclosure, R2 is a cleavable linker arm. It may be a peptide capable of being activated by a proteolytic enzyme, protease or peptidase or a chemical bond capable of being acidically activated in a pathologic microenvironment. In the present disclosure, the proteolytic enzyme, protease or peptidase may be various proteolytic enzymes, proteases or peptidases present in a pathologic microenvironment. For example, protease may be cysteine protease, aspartate protease, glutamic acid protease, threonine protease, gelatinase, metallopro-teinase, or asparagine peptide lyase. In some embodiments, R2 may be cleaved by at least one of a Legumain, Cathepsin B, Cathepsin C, Cathepsin D, Cathepsin E, Cathepsin K, Cathepsin L, kallikrein, hKl, hKlO, hK15, plasmin, collagenase, Type IV collagenase, astromelysin, Factor Xa, chymotrypsin-like protease, trypsin-like protease, elastase-like protease, subtilisin-like protease, actinidain, bromelain, calpain, caspase, caspase-3, Mirl-CP, papain, HIV-1 protease, HSV protease, CMV protease, chymosm, pepsm, matriptase, legumain, plasmepsm, nepenthesin, metalloexopeptidase, metalloendopeptidase, matrix metalloprotease (MMP), MMPI, MMP2, MMP3, MMP8, MMP9, MMPlO, MMP11, MMP12, MMP13, MMP14, ADAMlO, ADAM12, urokinase plasminogen activator (uPA), nenterokinase, prostate-specific antigen (PSA, hK3), interleukin-113 converting enzyme, thrombin, FAP (FAP-a), meprin, granzyme, dipeptidyl peptidase, and dipeptidyl peptidase IV (DPPIV/CD26). In preferred embodiments, the present disclosure specifically relates to Legumain, which is largely expressed and secreted by tumor cells in a tumor microenvironment. Tumor-associated macrophage (M2 type) is also different from monocyte and inflammatory macrophage (M1 type) by the expression of Legumain. In the present disclosure, the peptide is a substrate of the proteolytic enzyme. It can be recognized and cleaved by the proteolytic enzyme.

R2 of the present disclosure may be represented by -R2a-, -R2b-, -R2a-N—, -R2a-D-, -R2a-AAN—, -R2a-AAD-, or -R2a-R2b-; wherein R2a is a peptide capable of being cleaved at amide bond by one or more proteolytic enzymes; R2b is a kind of peptide with its nitrogen in side chain forming a carbamate with R3 and the carbamate can be cleaved by one or more proteolytic enzymes; A is alanine; N is asparagine with its nitrogen in side chain forming a carbamate with R3 and the carbamate can be cleaved by Legumain; D is aspartic acid with its nitrogen in side chain forming a carbamate with R3 and the carbamate can be cleaved by Granzyme B. R2a and R2b can be linked by forming an amide bond. After legumain, granzyme B cleaving the bonds (such as carbamate) between R2 and R3, R3 can quickly undergo auto-releasing. Then the R4 moiety may be retained. The other enzymes may cleave at amide bond of R2, which may cause some amino acid residues remaining in the linker and thus auto-releasing of R3 will not occur. Examples of such R2 include but are limited to LTPRLGPAAN (SEQ ID NO:84), GPAAN (SEQ ID NO:85) and LSGRSDN (SEQ ID NO:86).

In some embodiments, suitable peptide capable of being activated by a proteolytic enzyme may be a tripeptide. Any substrate peptide capable of being recognized and cleaved (activated) by a proteolytic enzyme in a pathologic microenvironment known in the art may be used as R2 as disclosed herein. Such peptides may have structures disclosed in WO 2016/026458, the entity of which is incorporated in the present disclosure by reference. In some embodiments, in the tripeptide structure suitable for use in the present disclosure, the amino acid residue linked to Ri may be selected from the group consisting of Ala, Thr, Val and Ile, the middle amino acid residue may be selected from the group consisting of Ala, Thr, Val and Asn, and the amino acid residue linked to R3 may be selected from the group consisting of Asn and Asp. Generally, R2 links to R1 via an amino group of its amino acid residue in a linkage manner of amide, ester, carbamate, urea or hydrazone bond, and links to R3 via a carboxyl group of its amino acid residue in a linkage manner of amide, ester, carbamate, urea or hydrazone bond. In some preferred embodiments of the present disclosure, the tripeptide is selected from the group consisting of Ala-Ala-Asn and Ala-Ala-Asp. Ala-Ala-Asn may be recognized and cleaved by Legumain, and Ala-Ala-Asp may be recognized and cleaved by granzyme.

In some embodiments, R2 may be a chemical bond capable of being acidically activated in a pathologic microenvironment. Such bond includes but is not limited to amide bond, ester bond, carbamate bond, urea bond or hydrazone bond. When R2 is a chemical bond, the functional moiety as disclosed herein may be represented by formula R1-R2-R3-R4, wherein R1 links to R3 by the chemical bond capable of being acidically activated in a pathologic microenvironment. For example, in some embodiments, the structure of R1-R2-R3-R4 may be represented as follows:

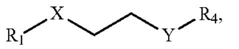

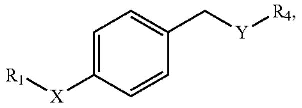

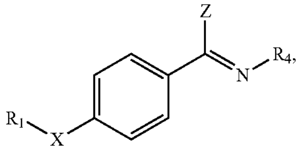
or

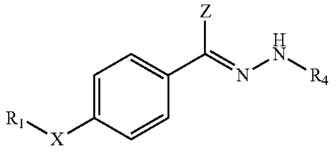

wherein X and Y are each independently NR' or O, Z is H or $C_{1-10}$alkyl, preferably $C_{1-4}$alkyl, and R' is H or $C_{1-4}$alkyl; R3 links to R1 and R4, respectively, via X and Y in a linkage manner of amide, ester, carbamate, urea or hydrazone bond.

In some embodiments, the structure of R1-R2-R3-R4 may be represented as follows:

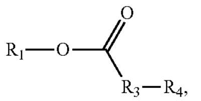

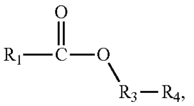

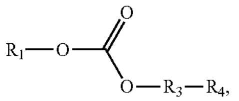

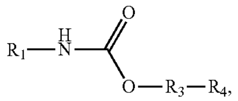

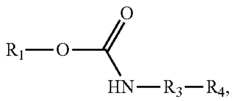

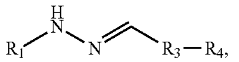
and

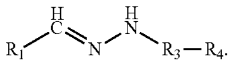

In the present disclosure, R3 may be an automatically cleavable linker arm capable of automatically shedding after cleavage of R2 to release R4-S-cys-R5. For example, such linker arm includes but is not limited to:

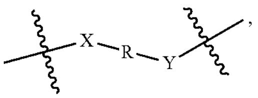

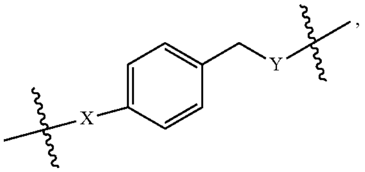

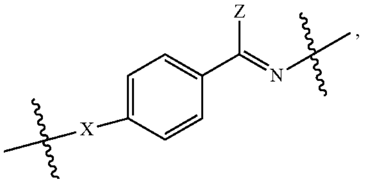
and

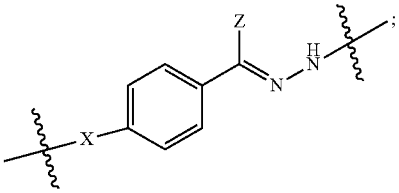

wherein X and Y are each independently NR' or O, Z is H or $C_{1-10}$alkyl, preferably $C_{1-4}$alkyl; R is $C_{1-4}$alkyl; and R' is H or $C_{1-4}$alkyl; wherein R4 links to R3 via Y or N in above formula in a manner of, such as amide bond, ester bond, carbamate bond, urea bond and hydrazone bond. In some embodiments, R3 is selected from the group consisting of —NH-phenyl-$CH_2O$—, —NH-phenyl-CH═N—, —NH-phenyl-C($CH_3$)═N—, —O-phenyl-CH═N— and —O-phenyl-C($CH_3$)═N—.

In some embodiments, R3 is a chemical bond capable of being acidically activated in a pathologic microenvironment. The chemical bond may be selected from the group consisting of amide bond, ester bond, carbamate bond, urea bond and hydrazone bond.

When R3 is a chemical bond capable of being acidically activated, R2 may be absent, such that the R1-R3-R4-S-cys-R5 can merely be acidically activated. On the other hand, when R2 is absent, R3 must be a chemical bond capable of being acidically activated.

In some embodiments, R3 is represented by any of the following structures:

R3-1

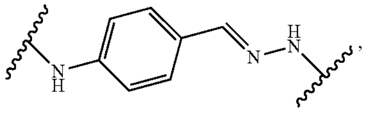

R3-2

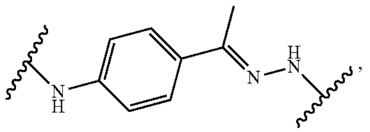

-continued

R3-3

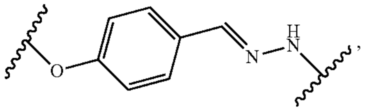

R3-4

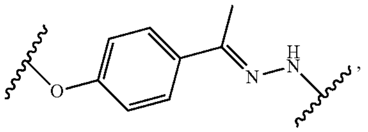

R3-5

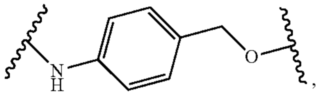

R3-6

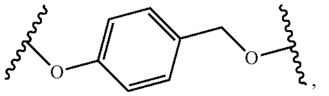

R3-7

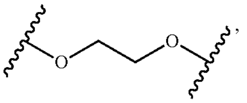

R3-8

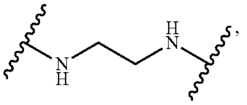

R3-9

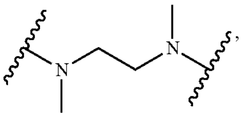

R3-10

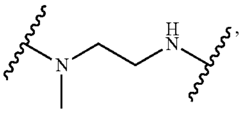

R3-11

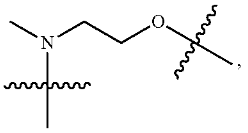

and

R3-12

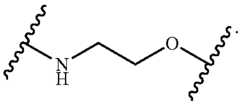

In the above formulae R3-1 to R3-12, R2 or R1 if R2 is absent may link to either end of the formulae as long as they form amide bond, ester bond, carbamate bond, urea bond and hydrazone bond.

In the present disclosure, R4 is a binding group capable of recovering, maintaining, reducing or promoting the binding capacity of a biomolecule to its antigen, ligand or receptor after cleavage of R2 and R3. In some embodiments, the resultant R4-s-Cys-R5 exhibits>60% affinity of native R5 to its antigen, ligand or receptor after cleavage of R2 and R3.

Suitable R4 may be represented by $-R_{4\text{-}a}\text{-}R_{4\text{-}b}\text{-}R_{4\text{-}c}\text{-}$, wherein $R_{4\text{-}a}$ is selected from the group consisting of:

$R_4$-$a_1$

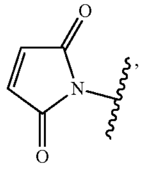

$R_4$-$a_2$

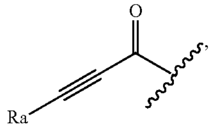

$R_4$-$a_3$

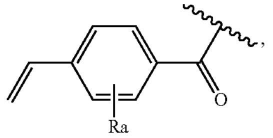

$R_4$-$a_4$

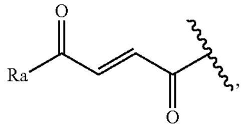

and $R_4$-$a_5$

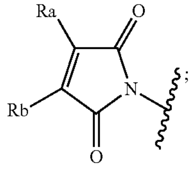

wherein Ra and Rb are each independently selected from the group consisting of H and $C_{1\text{-}6}$ alkyl or $C_{1\text{-}6}$ alkoxyl;

$R_{4\text{-}b}$ is selected from the group consisting of:

$R_4$-$b1$

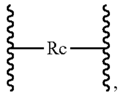

$R_4$-$b2$

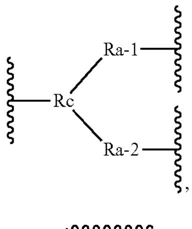

and $R_4$-$b3$

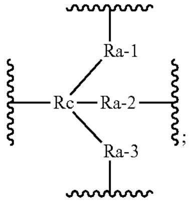

wherein in formula R4-b1, Rc is absent, or is selected from the group consisting of $C_{1\text{-}12}$ alkyl, $C_{1\text{-}12}$alkoxy-$C_{1\text{-}12}$alkyl, $C_{1\text{-}12}$alkyl-$C_{3\text{-}8}$cycloalkyl, $(C_{1\text{-}4}\text{alkyl-O})_p$—$C_{1\text{-}12}$alkyl, $C_{1\text{-}12}$alkylcarbonylamino-$(C_{1\text{-}4}\text{alkyl-O})_p$—$C_{1\text{-}12}$alkyl, phenyl-$C_{1\text{-}12}$alkyl, $C_{3\text{-}8}$cycloalkyl, $C_{1\text{-}12}$alkyl-$C_{3\text{-}8}$cycloalkyl- $C_{1-12}$alkyl, and $C_{1-12}$alkyl-phenyl-$C_{1-12}$alkyl; in formula R4-b2, Rc is a $C_{1-12}$alkylamino with Ra-1 and Ra-2 substituted at N atom of the amino group, and in formula 4-b3, Rc is a $C_{1-12}$alkyl with the last C atom at the end of the alkyl being substituted by Ra-1, Ra-2 and R2-3, wherein Ra-1, Ra-2 and Ra-3 are each independently selected from the group consisting of $C_{1-12}$alkyl, $C_{1-12}$alkyl-OH, and $C_{1-12}$alkyl-NR"R'", wherein R" and R'" are each independently selected from the group consisting of H and $C_{1-12}$alkyl; wherein in formulae R4-b2 and R4-b3, R4-b links to R4-c via at least one of the Ra-1, Ra-2 and Ra-3;

$R_{4-c}$ is selected from the group consisting of:

$R_{4c}$-I

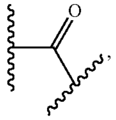

, $R_{4c}$-II

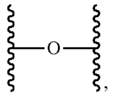

, $R_{4c}$-III

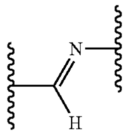

$R_{4c}$-IV

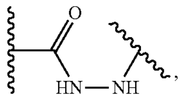

,

-continued $R_{4c}$-V

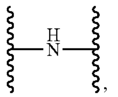

, $R_{4c}$-VI

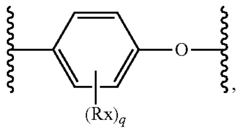

, and $R_{4c}$-VII

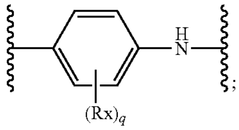

;

wherein Rx is selected from the group consisting of H, halo and $C_{1-4}$alkyl; p is an integer in a range of 1 to 10, such as an integer in a range of 1 to 5; and q is an integer in a range of 1 to 4, such as an integer in a range of 1 to 2; with the proviso that R4-c is absent when R4-a is selected from the group consisting of formulae R4-a2, R4-a3 and R4-a4;

wherein R3 links to R4 via the $R_{4-c\ of R}4$, and the wave line shown in each formula of R4-a indicates the position at which R4-a links to R4-b. Preferably, in formulae R4c-III, Rc4-IV, R4c-VI and R4c-VII, R3 links to the carbon atom of these groups.

Generally, R4 links to the S atom of the cysteine of R5 via maleimide (R4-a1), acetylene (R4-a2), vinyl (R4-a3), mono-substituted butenedioic acid (R4-a4), or di-substituted maleimide (R4-a4).

In some embodiments, R4 is selected from the group consisting of:

R4-1

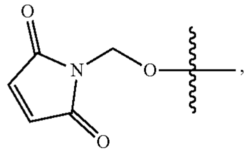

,

R4-2

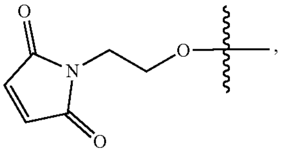

,

R4-3

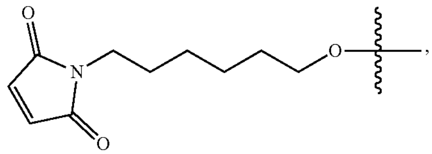

,

R4-4

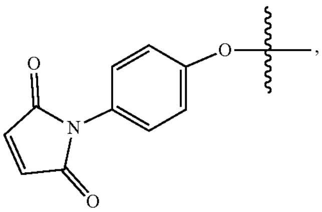

,

R4-5

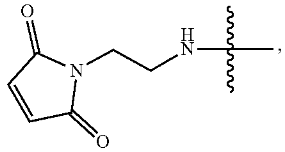

,

R4-6

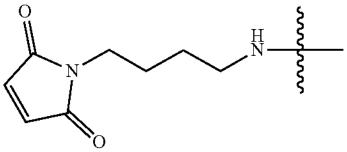

,

-continued
R4-7
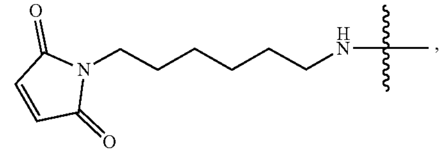
R4-8
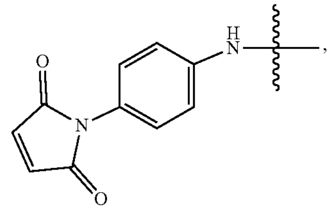
R4-9
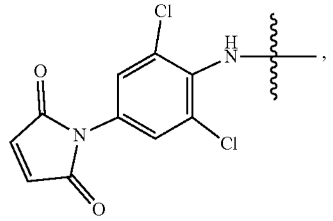
R4-10
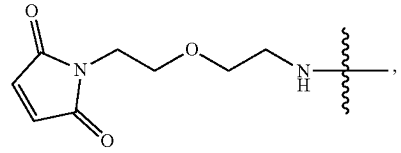
R4-11
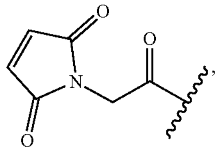
R4-12
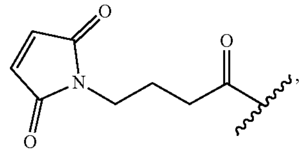
R4-13
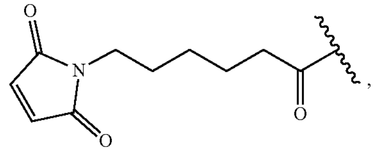
R4-14
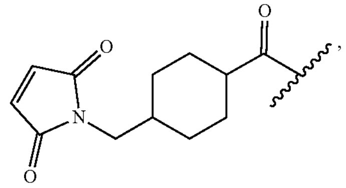
R4-15
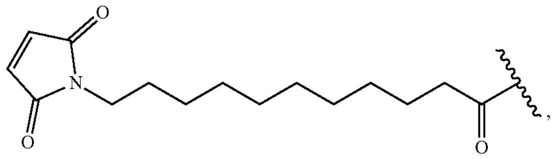
R4-16
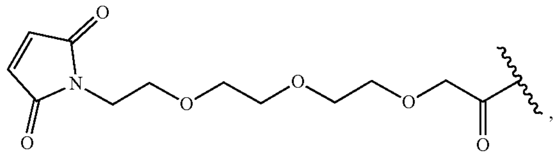
R4-17
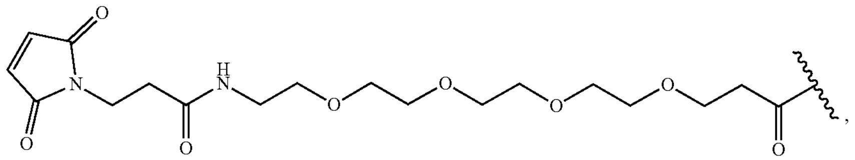
R4-18
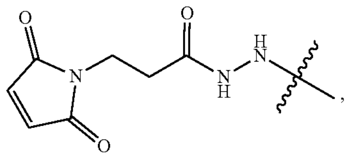
R4-19
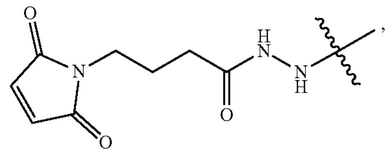
R4-20
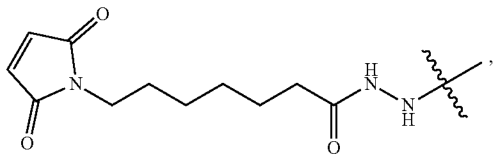
R4-21
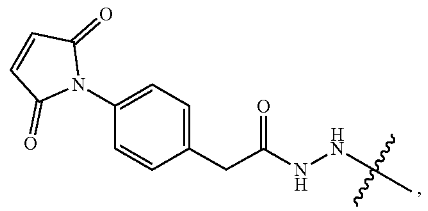

-continued
R4-22
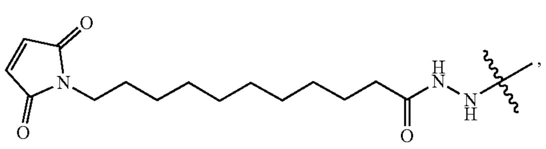
R4-23
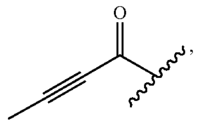
R4-24
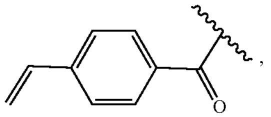
R4-25
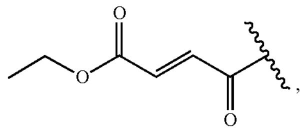
R4-26
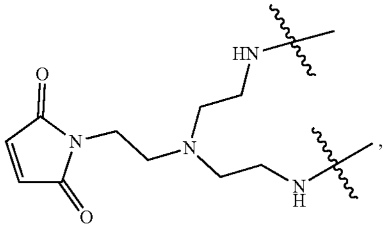
R4-27
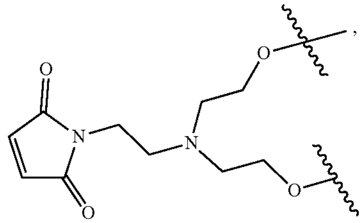
R4-28
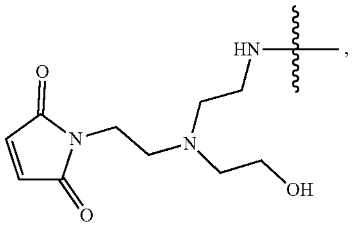
R4-29
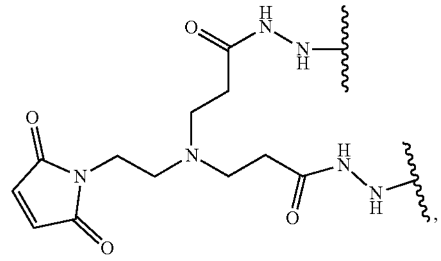
R4-30
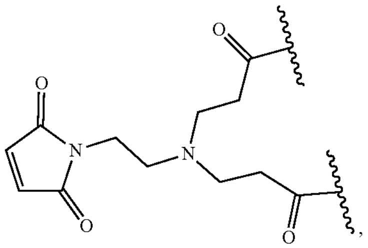
R4-31
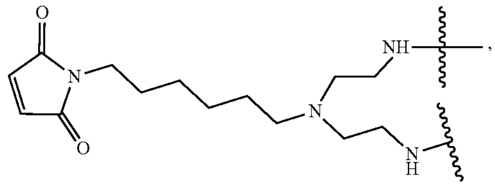
R4-32
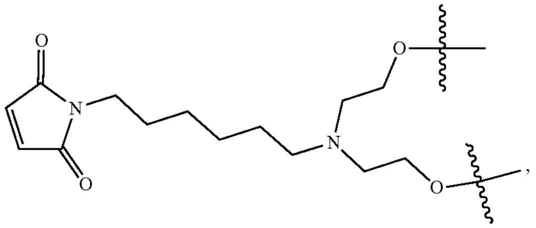
R4-33
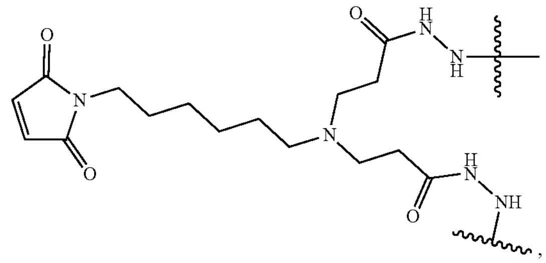
R4-34
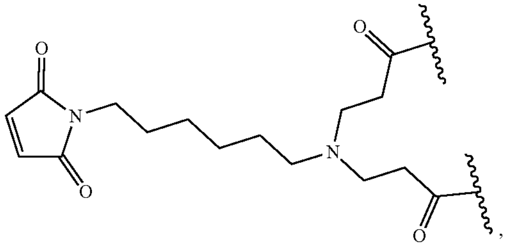
R4-35
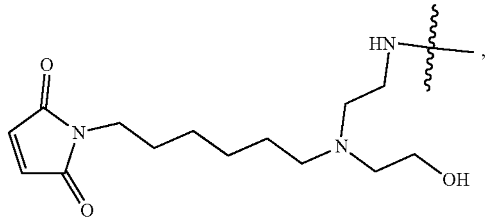

-continued
R4-36
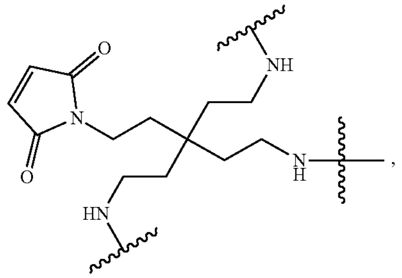
R4-37
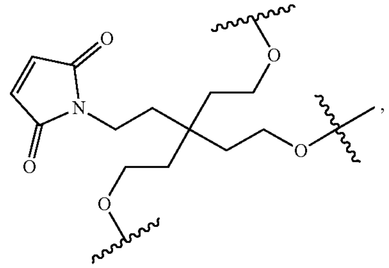
R4-38a
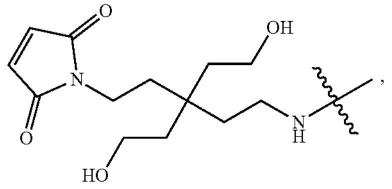
R4-38b
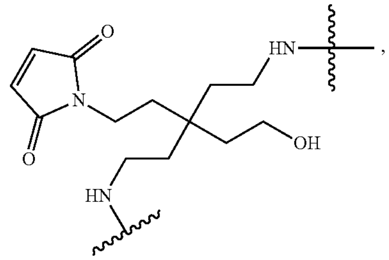
R4-39
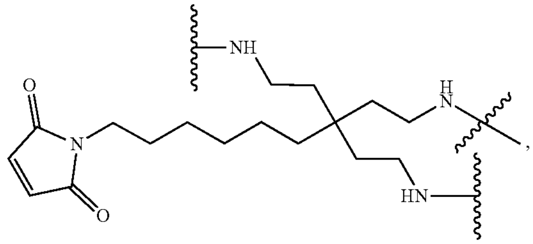
R4-40
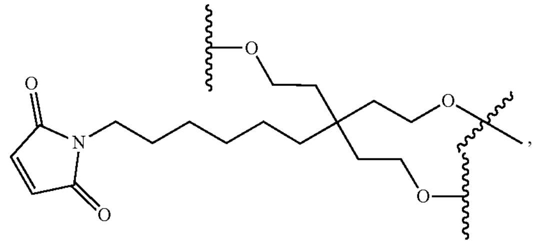
R4-41
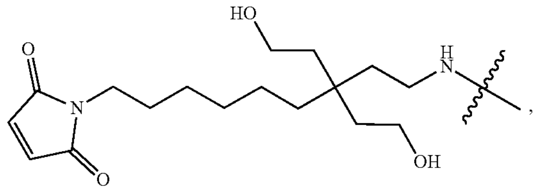
R4-42
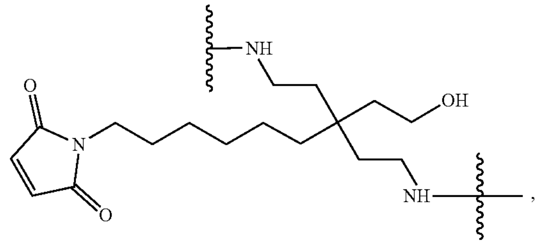
R4-43
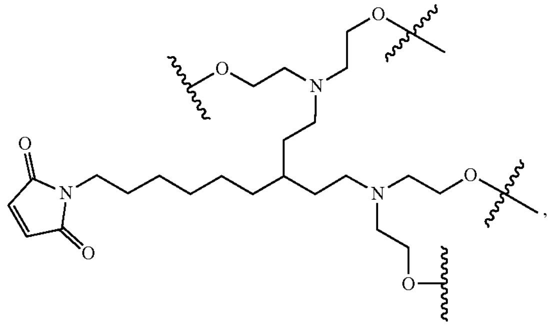

-continued
R4-44
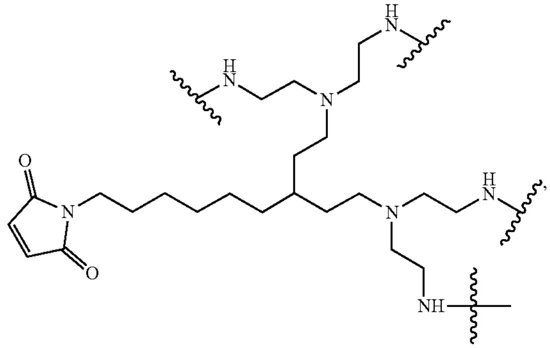
R4-45
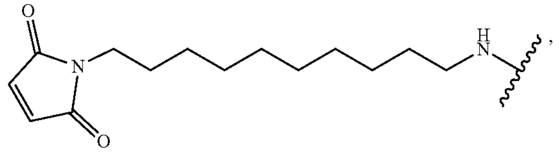
R4-46
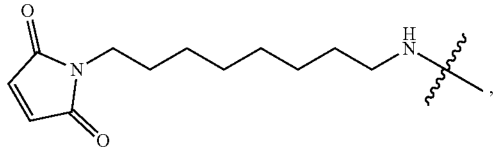
R4-47
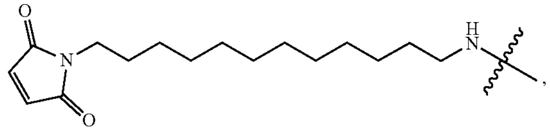
R4-48
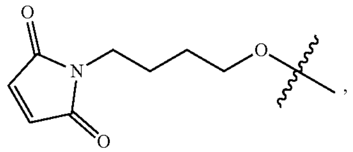
R4-49
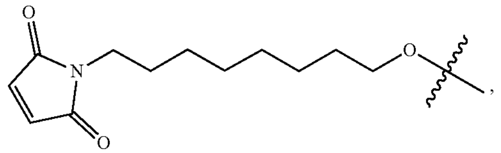
R4-50
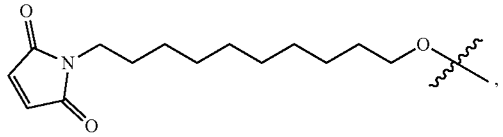
R4-51
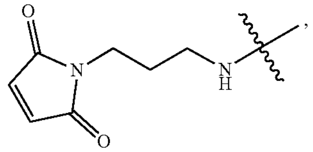
R4-52
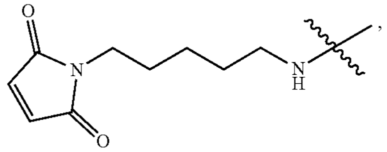
R4-53
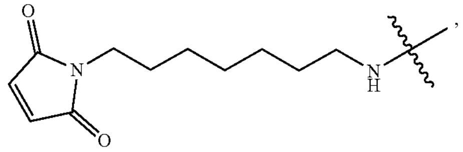
R4-54
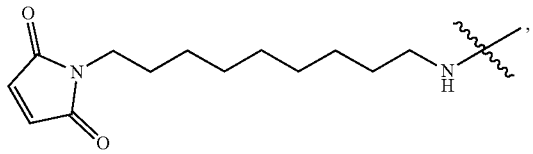
R4-55
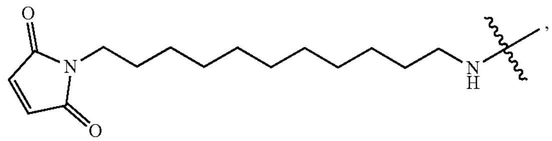
R4-56
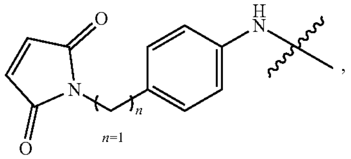
R4-57
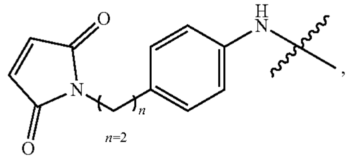
R4-58
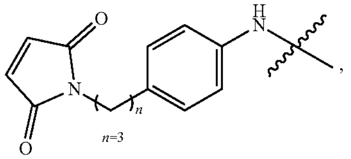
R4-59
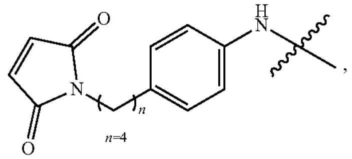

-continued
R4-60
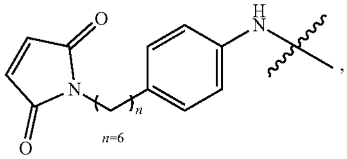
R4-61
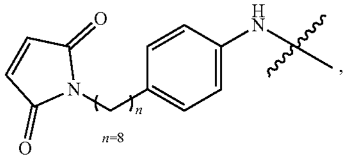
R4-62
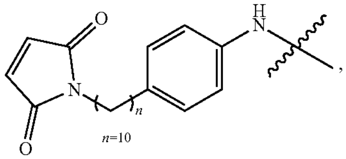
R4-63
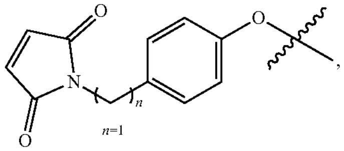
R4-64
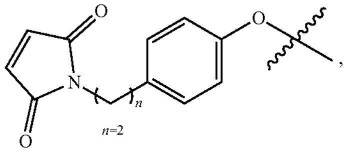
R4-65
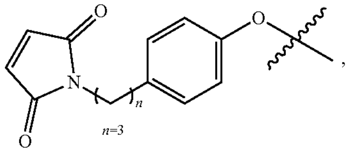
R4-66
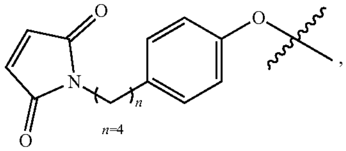
R4-67
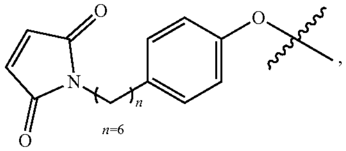
R4-68
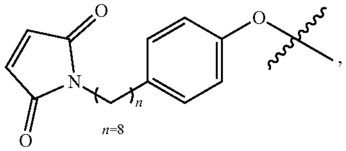
R4-69
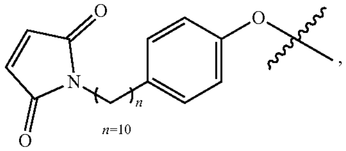
R4-70
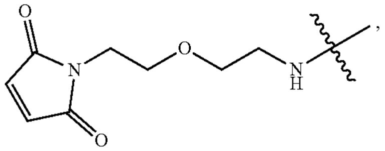
R4-71
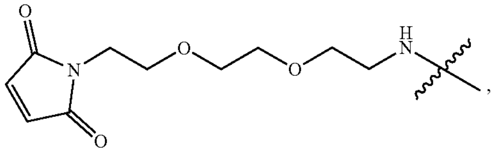
R4-72
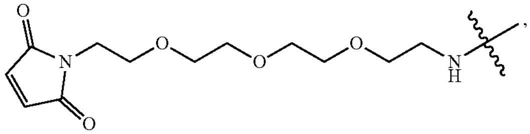
R4-73
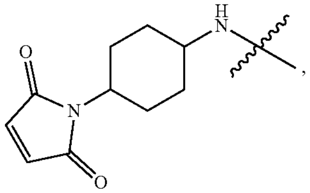
R4-74
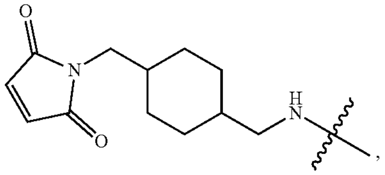
R4-75
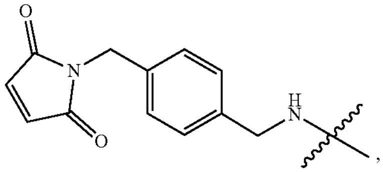
and
R4-76
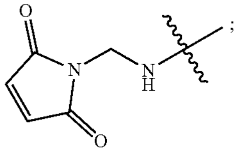

wherein the wave line indicates the position of R4 linking to R3.

In some embodiments, R4 is represented by:

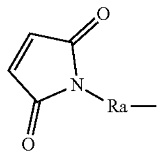

wherein:

Ra is selected from the group consisting of $C_{1-12}$ alkyl, $C_{1-12}$ alkoxy, $C_{1-12}$alkylcarbonyl, phenoxy or phenyl amino optionally substituted by one or two halogens, $C_{1-12}$alkylamino, $C_{1-12}$alkoxy-$C_{1-12}$alkylamino, $C_{1-12}$alkylcarbonyloxy, $C_{1-12}$alkyl-$C_3$-scycloalkylcarbonyloxy, $(C_{1-4}alkyl-O)_p$-$C_{1-12}$alkylcarbonyloxy, $C_{1-12}$alkylcarbonylamino-$(C_{1-4}alkyl-O)_p$-$C_{1-12}$alkylcarbonyloxy, $C_{1-12}$alkylcarbonylamino and phenyl-$C_{1-12}$alkylcarbonylamino;

p is an integer in a range of 1 to 10, such as an integer in a range of 1 to 5;

wherein R3 links to R4 via the Ra of R4, and to th thiol group of the cysteine of R5 via the maleimide group of R4.

In the conjugate of the present disclosure, R4 covalently links to R5 via the S of cysteine contained in R5. RT-R2 is cleaved from R3-R4-S-cys-R5 by a proteolytic enzyme or under an acidic condition of a pathologic microenvironment, and R3-R4-S-cys-R5 is released. Then R3 automatically sheds and R4-S-cys-R5 is released. The R4-S-cys-R5 can recover or promote the binding capacity of R5 to its ligand or receptor.

It should be understood that in the present disclosure, the wave line(s) used in each of the indicated formulae indicate the linking position of the group containing the wave line(s) to other groups, and all position numbers of the amino acid mentioned for amino acid residue of an antibody is based on Kabat numbering.

R5, as described above, represents a biomolecule with one or more amino acid residues mutated to cysteine. R5 in fact is a moiety of the biomolecule without the hydrogen atom of the thiol group of the introduced cysteine. Absence of the hydrogen atom of the thiol group allows R5 being regarded as a group to link to R4 of the present disclosure.

Conjugates of the present disclosure may be prepared by a method comprising reducing the mutant biomolecule by DTT, TCEP or other reducing agent; oxidizing by $Cu_2SO_4$, dehydroascorbic acid or other oxidizing agent; and then conjugating the oxidized biomolecule (R5) to R1-R2-R3-R4 in a liquid phase or solid phase condition. The final product may be collected in a liquid phase.

Therefore, in addition to the conjugate, the present disclosure also comprises the functional moiety, i.e., RT-R2-R3-R4; R2-R3-R4; R3-R4-S-cys-R5; R4-S-cys-R5; and the mutated biomolecule; wherein R1, R2, R3, R3, R5 and their linkage manner and the mutated biomolecule are defined as in any part or any embodiments of the present disclosure. In some embodiments, the functional moieties are shown by S1-S64. In the present disclosure, the -S-cys-indicates that R4 covalently links to R5 via the thiol group of cysteine introduced by mutation in R5. The R3-R4-S-cys-R5 is a conjugate produced by cleavage of R1-R2 by a proteolytic enzyme or under an acidic condition of a pathologic microenvironment. Generally, after separation of R3 from R2, the group of R3 previously linked to R2 forms a hydroxyl (—OH) or an amino group (—$NH_2$). R4-S-cys-R5 is a conjugate formed after automatic shedding of R3. Generally, after automatic shedding of R3, the group of R4 previously linked to R3 forms a hydroxyl (—OH) or an amino group (—$NH_2$).

The conjugate, the functional moiety, R2-R3-R4, R3-R4-S-cys-R5 and R4-S-cys-R5 as described herein may be synthesized by the methods known in the art. For example, they may be prepared according to the method described in Example 1 of the present application.

The present disclosure also includes a pharmaceutical composition which comprises the conjugate as described herein. The pharmaceutical composition may further comprise a pharmaceutically acceptable carrier. The carrier may be any pharmaceutically acceptable carrier or excipient, which may be varied according to the dosage form and administration mode. The pharmaceutically acceptable carrier is generally safe and non-toxic, and may comprise any known substance used in formulating a pharmaceutical composition in the pharmaceutical industry, including filler, diluent, coagulant, adhesive, lubricant, glidant, stabilizer, colorant, wetting agent, and disintegrant, etc. Suitable pharmaceutically acceptable carrier include sugars, such as lactose or sucrose, mannitol or sorbitol; cellulose formulation and/or calcium phosphate, such as tricalcium phosphate or calcium hydrogen phosphate; amylum, including corn starch, wheat starch, rice starch, potato starch, gelatin, tragacanth, methyl cellulose, hydroxylpropylmethyl cellulose, sodium carboxyl methyl cellulose and/or polyvinylpyrrolidone; silica, talc, stearic acid or salt thereof, such as magnesium stearate or calcium stearate; and/or polyethylene glycol; and the like. When selecting a pharmaceutically acceptable carrier, the main consideration is the administration mode of the pharmaceutical composition. This is well known in the art.

The pharmaceutical composition may comprise a conjugate in a therapeutically or in a prophylactically effective amount. The "effective amount" indicates that the amount of an ingredient is sufficient to produce a desired reaction. The specific effective amount will depend on various factors, such as the specific disease to be treated, the physical condition of the patient, such as body weight, age and sex, the duration time of treatment, the therapy co-administered (if any), and the specific formulation used. Generally, the "effective amount" as described herein is a conventional amount of the biomolecule. However, in some embodiments, the therapeutically or prophylactically effective amount of the conjugate contained in the present pharmaceutical composition may be lower than the conventional amount of the biomolecule but may produce better treatment or prevention effect, because the biomolecule is protected by a protective group from binding to its ligand or receptor before arriving at a pathologic microenvironment.

The pharmaceutical composition of the present disclosure may be formulated into various suitable dosage forms, including but not limited to tablet, capsule, injection, etc., and it can be administered via any suitable route to achieve the expected purpose. For example, it can be administered parenterally, subcutaneously, intravenously, muscularly, intraperitoneally, transdermally, orally, intrathecally, intracranially, nasally or externally. The dose of a drug may depend on age, health status and body weight of a patient, treatment carried out in parallel, and frequency of treatment, etc. The pharmaceutical composition of the present disclosure may be administered to any subject in need thereof, such as a mammal, especially a human being.

In a tumor patient, tumor cells or antigen-presenting cells (APC) bearing a tumor antigen partially or fully inhibit immunological killing of the tumor by a host via binding to T cells. However, the conjugate of the present disclosure is activated and released by a proteolytic enzyme, especially Legumain or granzyme, or under an acidic condition, in a pathologic microenvironment. For example, the conjugate of the present disclosure in which the biomolecule is IL2, anti-CD28 antibody or anti-PD-1 antibody and the like can selectively stimulate proliferation of T cell or enhance its function to secrete anti-tumor cytokines. Therefore, the conjugate of the present disclosure can effectively break through the immune barrier of an individual, arrive at a pathologic microenvironment and then be activated and released in the pathologic microenvironment. As a result, it can selectively promote proliferation or killing effect of T cells, etc., in a tumor or inflammatory microenvironment, thereby realizing low autoimmunity and high efficacy.

Therefore, each of the conjugates, R4-S-cys-R5 or mutated biomolecules disclosed in the present disclosure may be used for treating tumor or inflammation or can be used as an active ingredient for preparing a medicament for treating tumor or inflammation. The tumor or inflammation described herein can be any tumor or inflammation which is known to be treated by the biomolecule as described herein, including but not limited to a cancer in bladder, brain, breast, cervix, colon-rectum, esophagus, kidney, liver, lung, nasopharynx, pancreas, prostate, skin, stomach, uterus, ovary, testiculus and blood, etc. Specifically, the cancer includes bladder cancer, brain cancer, breast cancer, cervical cancer, colorectal cancer, esophageal cancer, renal cancer, liver cancer, lung cancer, nasopharyngeal cancer, pancreatic cancer, prostate cancer, skin cancer, gastric cancer, uterus cancer, ovarian cancer, testicular cancer and blood cancer.

Further included is a method for treating or preventing tumor or inflammation, comprising administering a subject in need thereof a therapeutically or prophylactically effective amount of a conjugate as described herein or a pharmaceutical composition thereof. The method may be used in combination with any known radiotherapy or immunotherapy.

It should be understood that the term "comprising" and "including" or similar expressions used in the present disclosure also means "consisting of" or the like. The sum of all weight percentages or volume percentages should be equal to 100%. Unless otherwise specified, various reagents and products used in the Examples are commercial products. Unless otherwise specified, the methods mentioned in the Examples were implemented according to the conventional technique. The following examples are not intended to limit the scope of the present disclosure.

Information of sequence is summarized below:

| SEQ ID NO: | Description |
|---|---|
| 1 | heavy chain of anti-PD-1 antibody |
| 2 | light chain of anti-PD-1 antibody |
| 3 | heavy chain of anti-PD-1 antibody |
| 4 | light chain anti-PD-1 antibody |
| 5 | heavy chain of anti-CTLA-4 antibody |
| 6 | light chain of anti-CTLA-4 antibody |
| 7 | heavy chain of anti-TNFα antibody |
| 8 | light chain of anti-TNFα antibody |
| 9 | heavy chain of anti-CD28 antibody |
| 10 | light chain of anti-CD28 antibody |
| 11 | amino acid sequence of wild type IL2 |
| 12 | amino acid sequence of wild type IL2 |
| 13 | Ipilimumab heavy chain |
| 14 | Ipilimumab light chain |
| 15 | Pembrolizumab heavy chain |
| 16 | Pembrolizumab light chain |
| 17 | Nivolumab heavy chain |
| 18 | Nivolumab light chain |
| 19 | Anti-human PD-1 antibody (WO 2017/124050 A1) heavy chain |
| 20 | Anti-human PD-1 antibody (WO 2017/124050 A1) light chain |
| 21 | Anti-mouse PD-1 antibody J43v2 heavy chain |
| 22 | Anti-mouse PD-1 antibody J43v2 light chain |
| 23 | Anti-mouse CTLA-4 9D9 antibody heavy chain |
| 24 | Anti-mouse CTLA-4 9D9 antibody light chain |
| 25 | Anti-human 4-1BB antibody heavy chain |
| 26 | Anti-human 4-1BB antibody light chain |
| 27 | Trastuzumab heavy chain |
| 28 | Trastuzumab light chain |
| 29 | Adalimumab heavy chain |
| 30 | Adalimumab light chain |
| 31 | Atezolizumab heavy chain |
| 32 | Atezolizumab light chain |
| 33 | Anti-human CD28 antibody heavy chain |
| 34 | Anti-human CD28 antibody light chain |
| 35 | Ipi-se008 light chain |
| 36 | Ipi-se010 light chain |
| 37 | Ipi-se009 light chain |
| 38 | Pem-se010 light chain |
| 39 | Pem-se009 light chain |
| 40 | Pem-se007 light chain |
| 41 | Niv-se001 heavy chain variable domain |
| 42 | Niv-se005 light chain |
| 43 | Niv-se007 light chain |
| 44 | Interleukin-2 with mutation |
| 45 | Interleukin-2 with mutation |
| 46 | Interleukin-2 with mutation |
| 47 | Interleukin-2 with mutation |
| 48 | Interleukin-2 with mutation |
| 49 | Interleukin-2 with mutation |
| 50 | Interleukin-2 with mutation |
| 51 | Interleukin-2 with mutation |
| 52 | Interleukin-2 with mutation |
| 53 | Interleukin-2 with mutation |
| 54 | Interleukin-10 with mutation |
| 55 | Interleukin-10 with mutation |
| 56 | Interleukin-10 with mutation |
| 57 | Interleukin-10 with mutation |
| 58 | Interleukin-10 with mutation |
| 59 | Interleukin-10 with mutation |
| 60 | Anti-human VEGF antibody heavy chain |
| 61 | Anti-human VEGF antibody light chain |
| 62 | Anti-human CD20 antibody heavy chain |
| 63 | Anti-human CD20 antibody light chain |
| 64 | VH of Atezolizumab |
| 65 | VL of Atezolizumab |
| 66 | VH of Cetuximab with mutation |
| 67 | VL of Cetuximab with mutation |
| 68 | VH of Ramucirumab with mutation |
| 69 | VL of Ramucirumab with mutation |
| 70 | Fusion protein of scFv of anti-Her2 antibody with CD3, with mutation |
| 71 | VH of anti Her2 antibody with mutation |
| 72 | VL of anti Her2 antibody with mutation |
| 73 | Fusion protein of scFvs of anti-Her2 antibody with anti-CD3 antibody |
| 74 | Fusion protein of scFvs of anti-Her2 antibody with anti-CD3 antibody |
| 75 | anti CD3 antibody |
| 76 | VH of Cetuximab |
| 77 | VL of Cetuximab |
| 78 | VH of Ramucirumab |
| 79 | VL of Ramucirumab |
| 80 | VH of anti Her2 antibody |
| 81 | VL of Her2 antibody |

-continued

| SEQ ID NO: | Description |
|---|---|
| 82 | Fusion protein of scFvs of anti-Her2 antibody with anti-CD3 antibody, with mutation |
| 83 | Fusion protein of scFvs of anti-Her2 antibody with anti-CD3 antibody, with mutation |
| 84 | Sequence of R2 |
| 85 | Sequence of R2 |
| 86 | Sequence of R2 |
| 87 | forward primer |
| 88 | reverse primer |
| 89 | Light chain of Cetuximab |
| 90 | Light chain of Pertuzumab |
| 91 | Heavy chain of Pertuzumab |
| 92 | VH of Opdivo ® (nivolumab) |
| 93 | VL of Opdivo ® (nivolumab) |
| 94 | VH of Keytruda ® (pembrolizumab) |
| 95 | VL of Keytruda ® (pembrolizumab) |
| 96 | VL of Ipilimumab |
| 97 | VH of Ipilimumab |
| 98 | VL of Anti-human 4-1BB antibody |
| 99 | VH of Anti-human 4-1BB antibody |
| 100 | VL of Adalimumab |
| 101 | VH of Adalimumab |
| 102 | VH of Pembrolizumab |
| 103 | VL of Pembrolizumab |
| 104 | VL of Trastuzumab |
| 105 | VH of Trastuzumab |

Example 1: Synthesis of Chemical Structure of Activatable and Binding Arms

When R2 has an amino acid sequence of Ala-Ala-Asn and R3 is PABC (R3-5), the synthetic scheme is shown below:

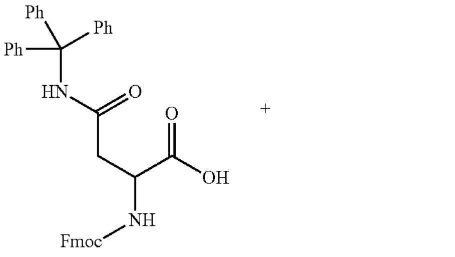

Fmoc-ASN(Trt)-OH

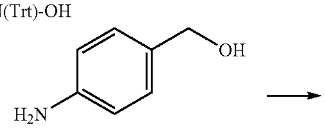

R3 = PABC

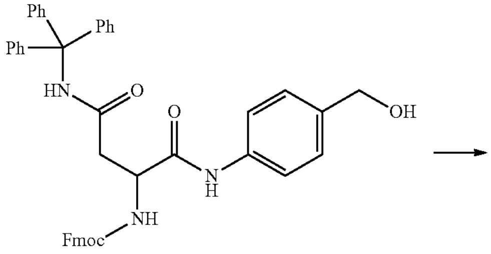

Fmoc-ASN(Trt)-PABC

-continued

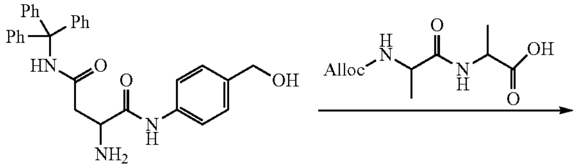

NH2-ASN(Trt)-PABC

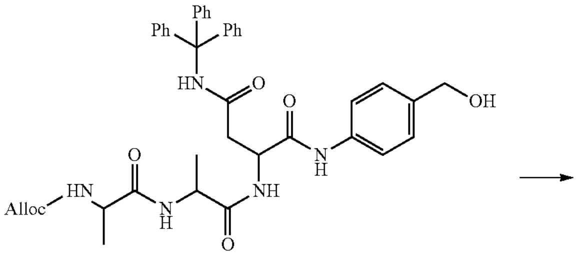

Alloc-AAN(Trt)-PABC

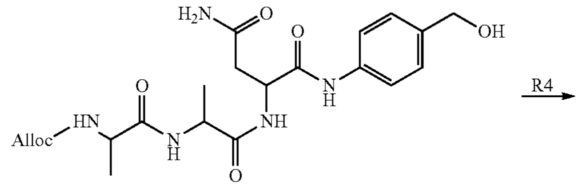

Alloc-AAN-PABC

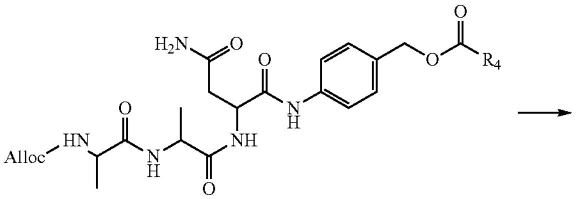

Alloc-AAN-PABC-R4

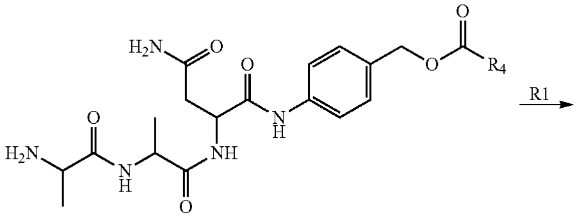

NH2-AAN-PABC-R4

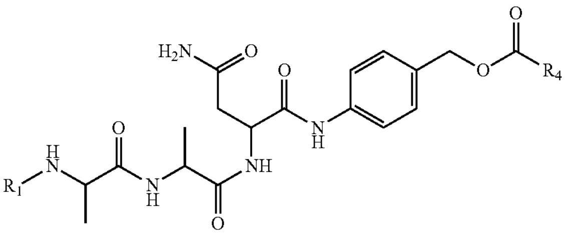

R1-AAN-PABC-R4

When R1 and R4 are different substituents, the following compounds shown in Table 1 were obtained.

TABLE 1
| R1 | R4 | Compound |
|---|---|---|
| 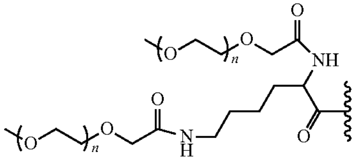 n = 5 R1-1 | 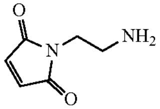 R4-5 | 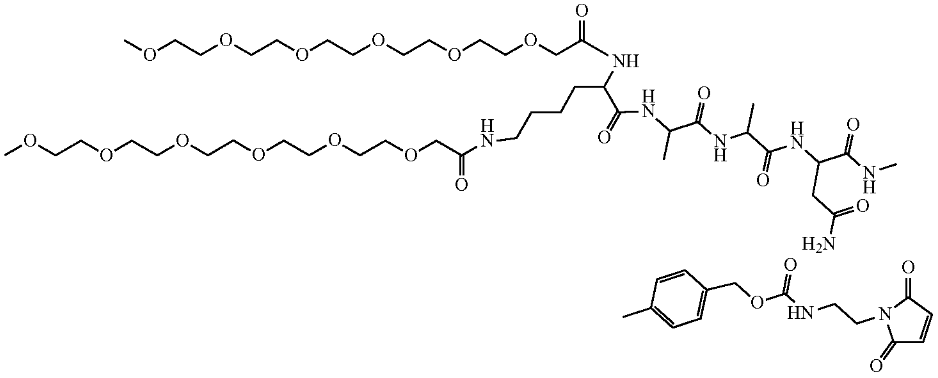 S1 |
| 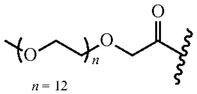 n = 12 R1-2 | 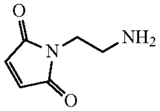 R4-5 | 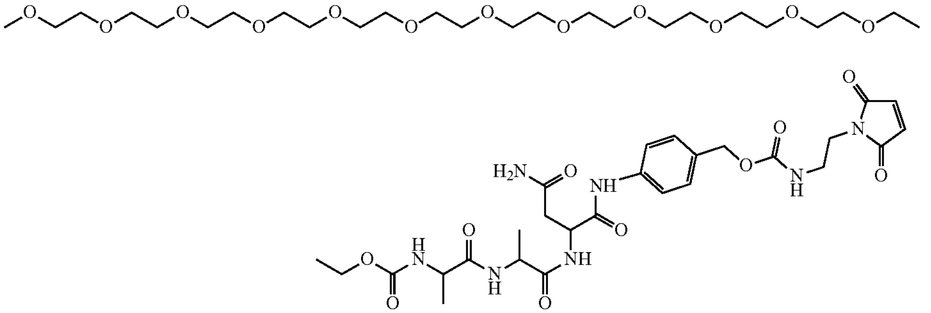 S3 |

TABLE 1-continued
| R1 | R4 | Compound |
|---|---|---|
| 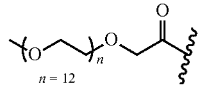 R1-2 | 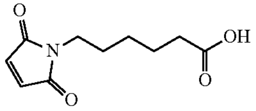 R4-13 | 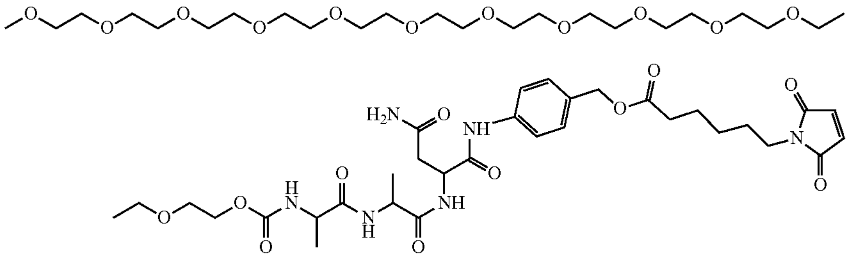 S7 |
| 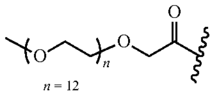 R1-2 | 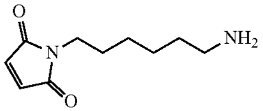 R4-7 | 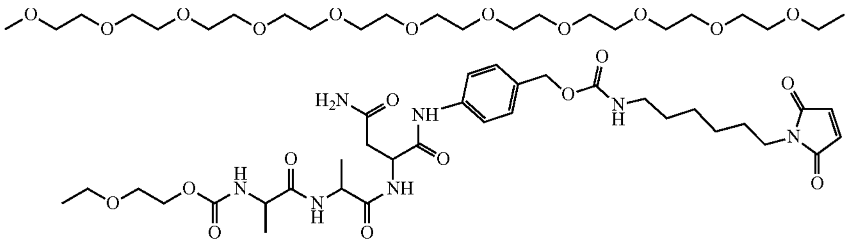 S9 |
| 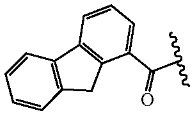 R1-3 | 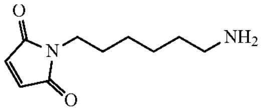 R4-7 | 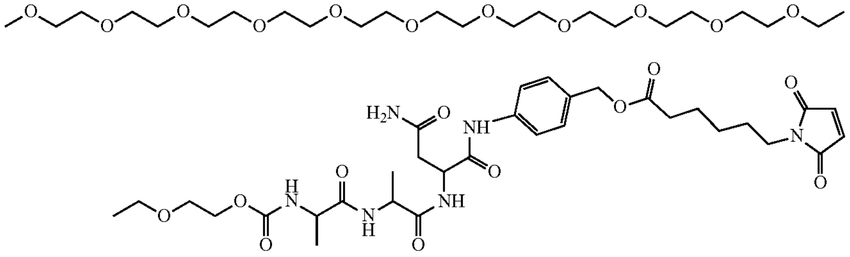 S7 |

TABLE 1-continued
| R1 | R4 | Compound |
|---|---|---|
| 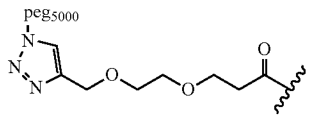<br>R1-4 | 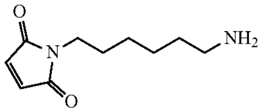<br>R4-7 | 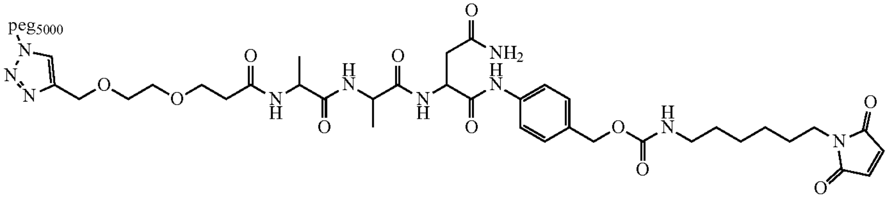<br>S13 |
| 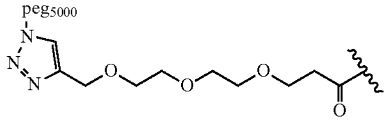<br>R1-5 | 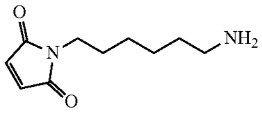<br>R4-7 | 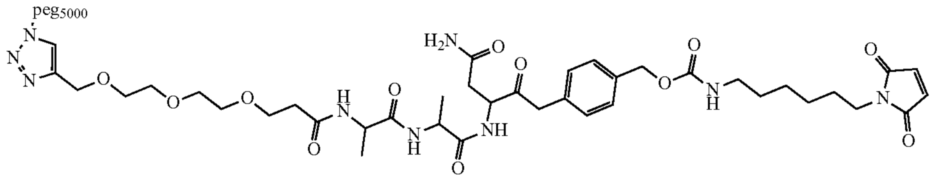<br>S15 |
| 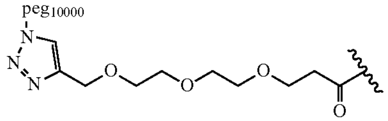<br>R1-6 | 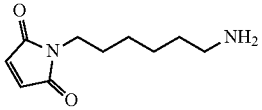<br>R4-7 | 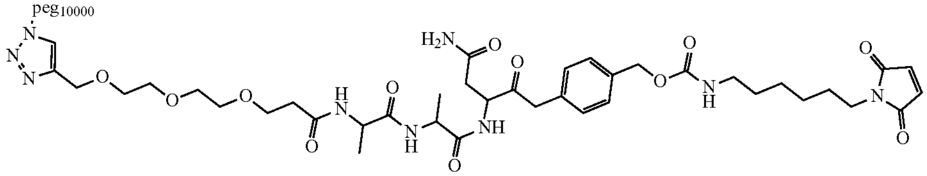<br>S17 |
| 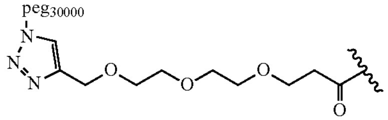<br>R1-7 | 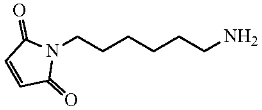<br>R4-7 | 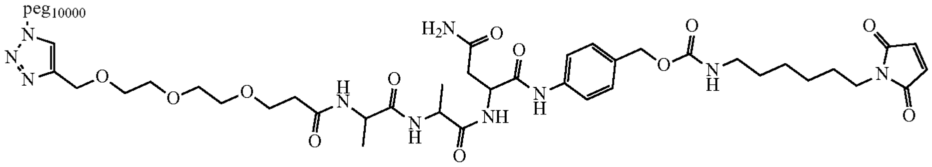<br>S25 |

TABLE 1-continued
| R1 | R4 | Compound |
|---|---|---|
| 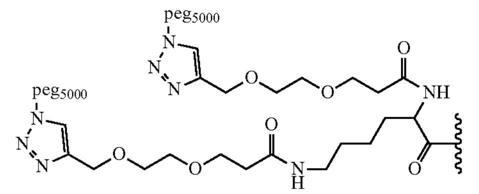<br>R1-18 | 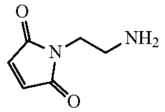<br>R4-5 | 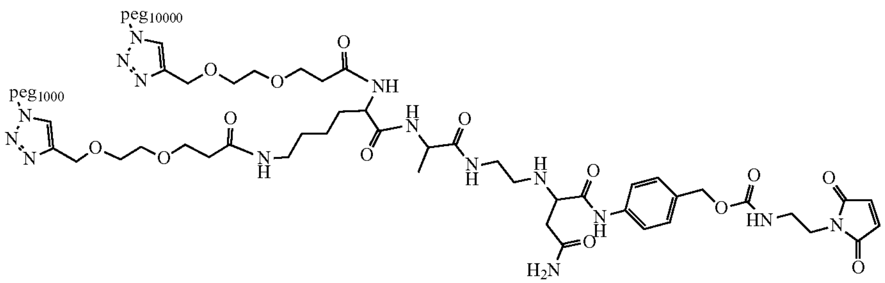<br>S29 |
| 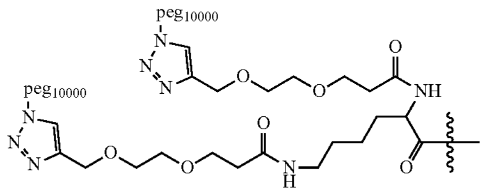<br>R1-19 | 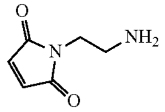<br>R4-5 | 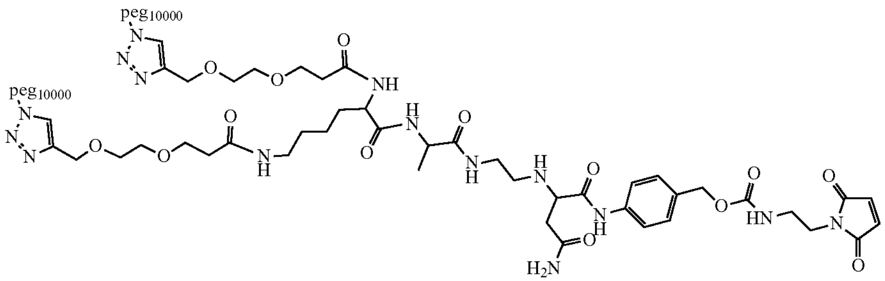<br>S31 |
| 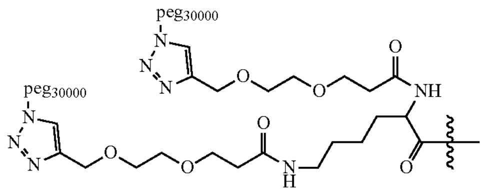<br>R1-19 | 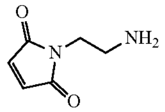<br>R4-5 | 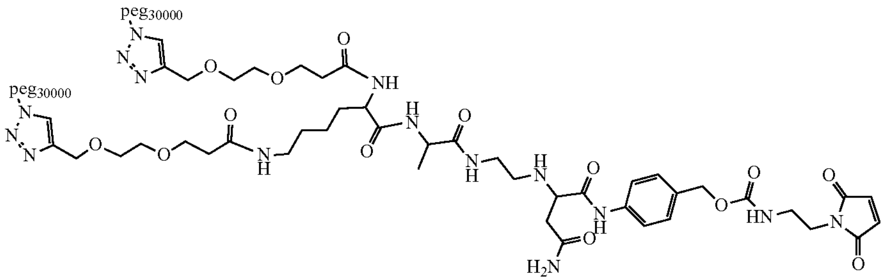<br>S33 |

TABLE 1-continued
| R1 | R4 | Compound |
|---|---|---|
| 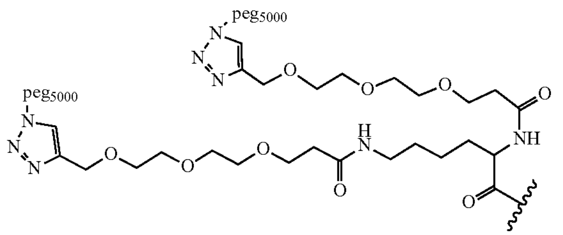 R1-21 | 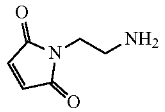 R4-5 | 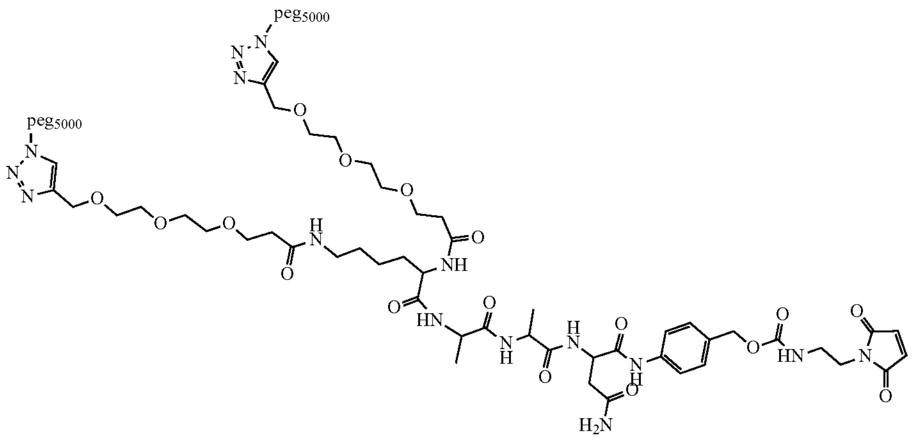 S35 |
| 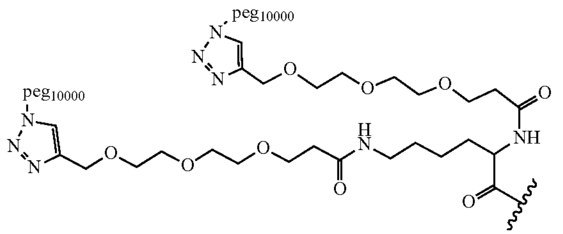 R1-22 | 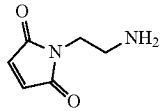 R4-5 | 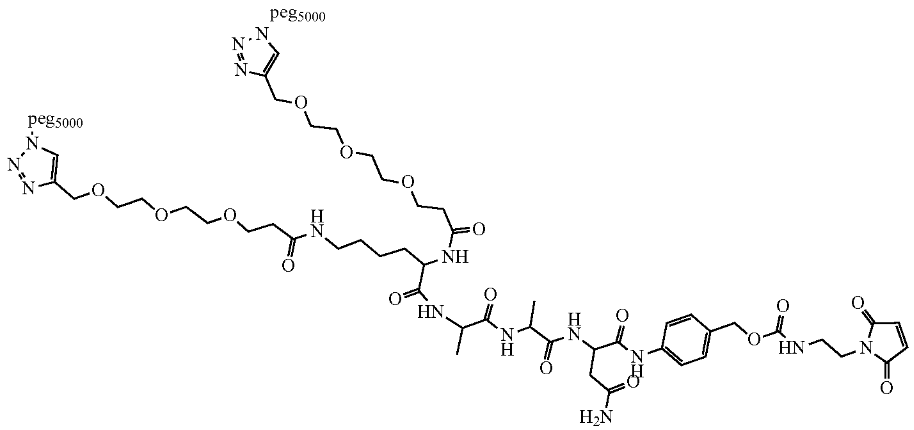 S37 |

TABLE 1-continued
| R1 | R4 | Compound |
|---|---|---|
| 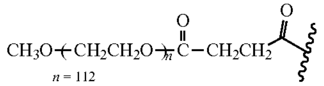 R1-12 | 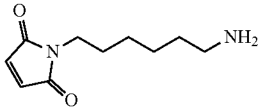 R4-7 | 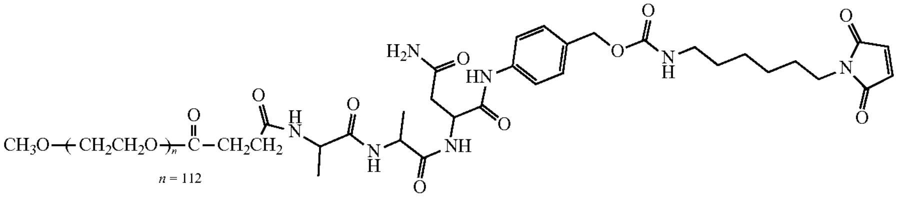 S39 |
| 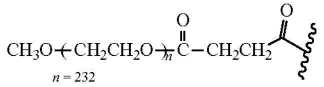 R1-13 | 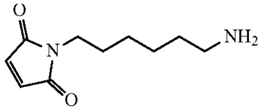 R4-7 | 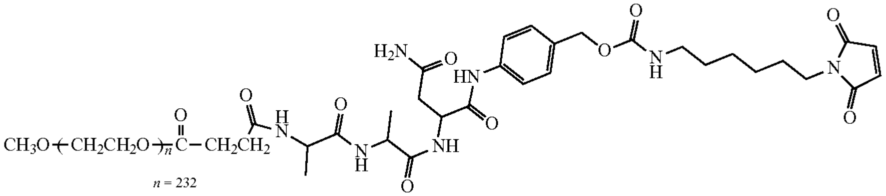 S41 |
| 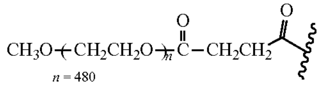 R1-15 | 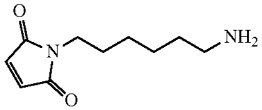 R4-7 | 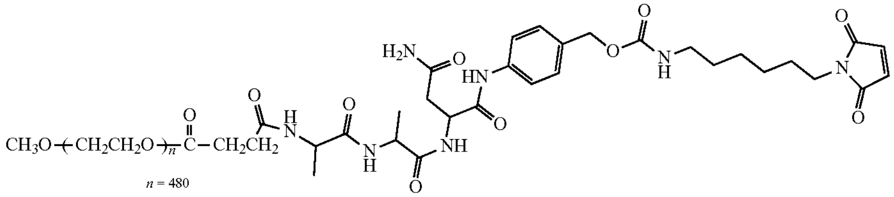 S43 |
| 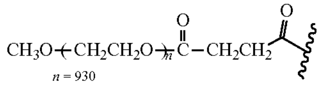 R1-16 | 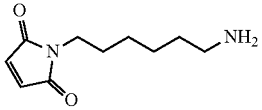 R4-7 | 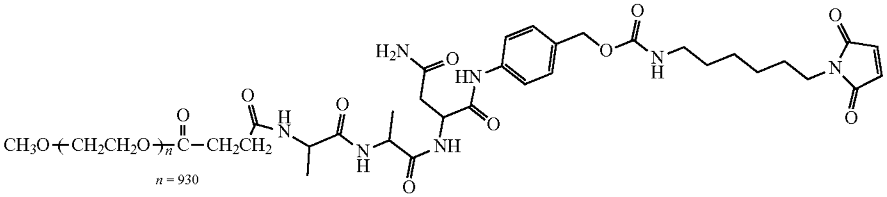 S45 |

TABLE 1-continued
| R1 | R4 | Compound |
|---|---|---|
| 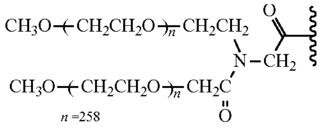 R1-17 | 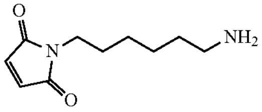 R4-7 | 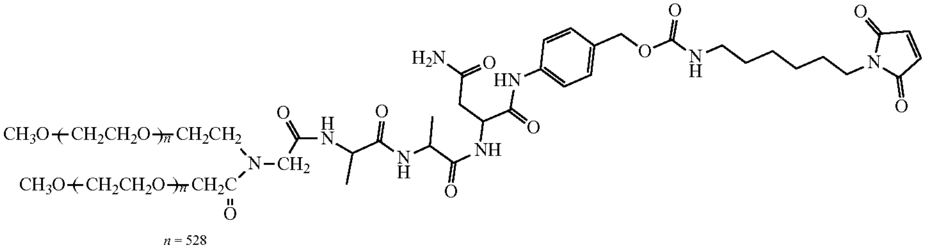 S47 |
| 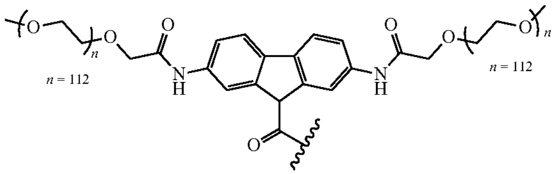 R1-28 | 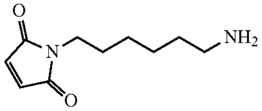 R4-7 | 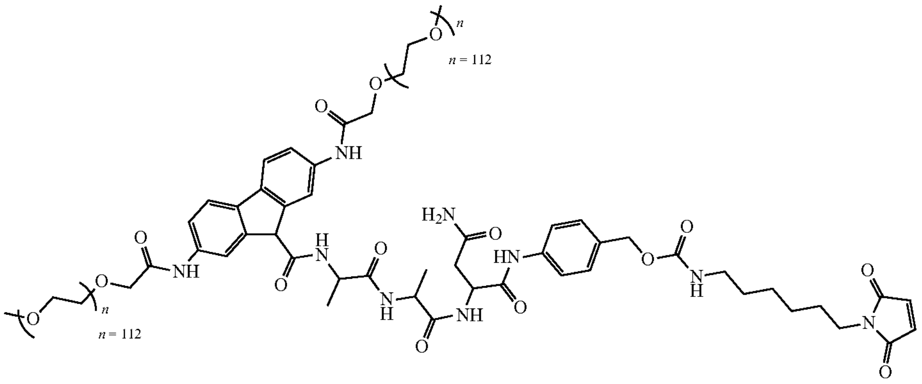 S57 |

TABLE 1-continued
| R1 | R4 | Compound |
|---|---|---|
| 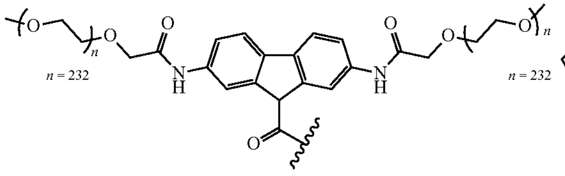 R1-29 | 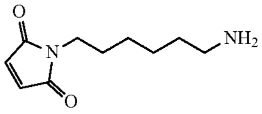 R4-7 | 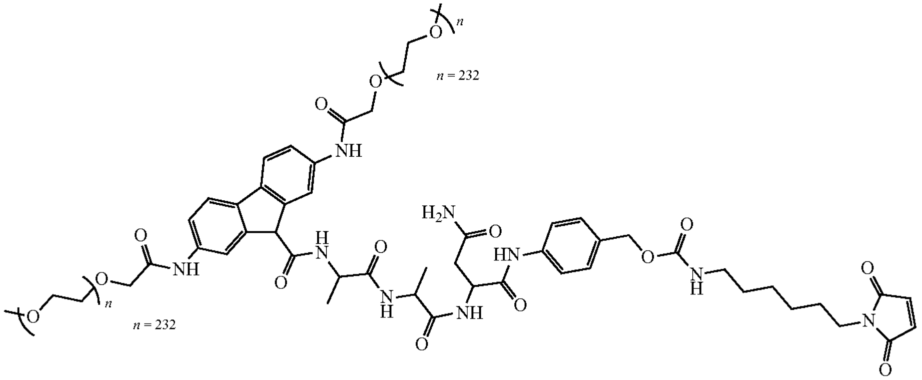 S59 |
| 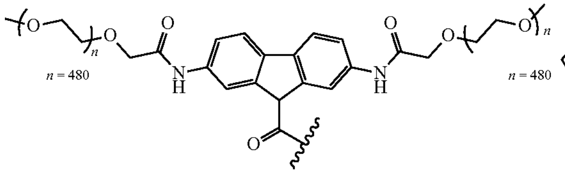 R1-30 | 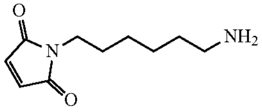 R4-7 | 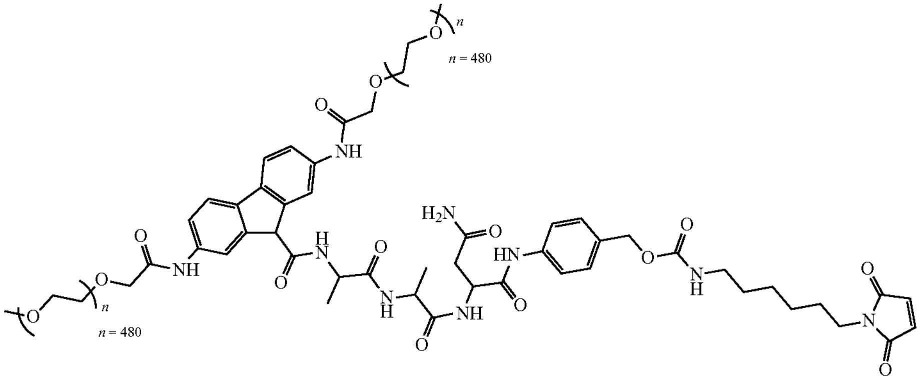 S61 |

TABLE 1-continued
| R1 | R4 | Compound |
|---|---|---|
| 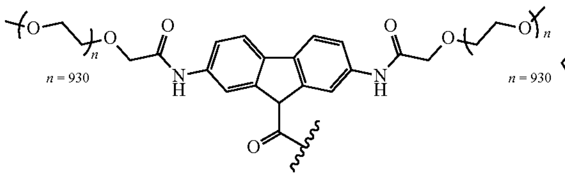 R1-31 | 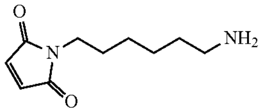 R4-7 | 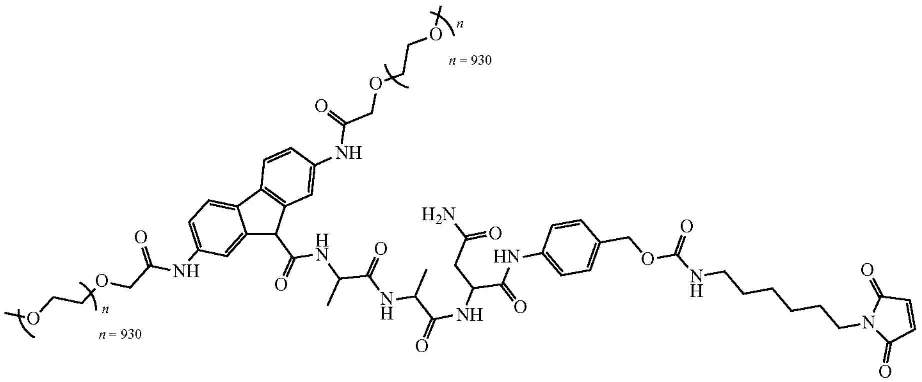 S63 |

As exemplified by S15, the specific synthesis process was shown below:
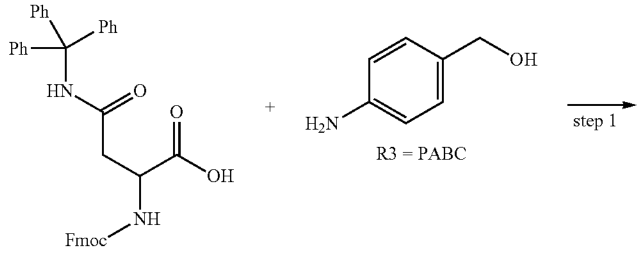
Fmoc-ASN(Trt)-OH
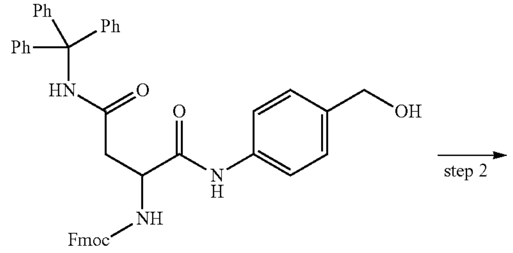
Fmoc-ASN(Trt)-PABC
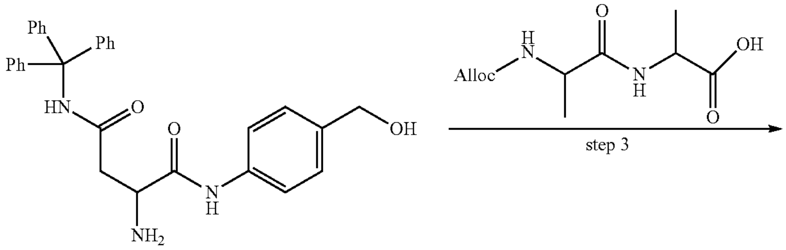
NH2-ASN(Trt)-PABC
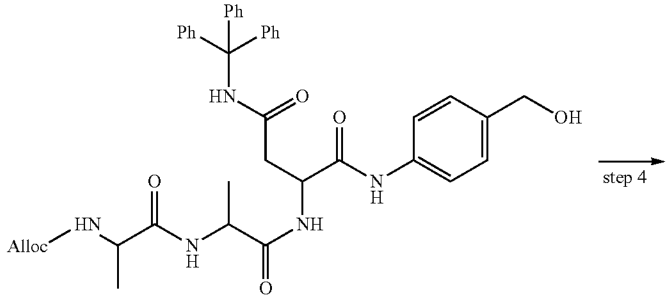
Alloc-AAN(Trt)-PABC
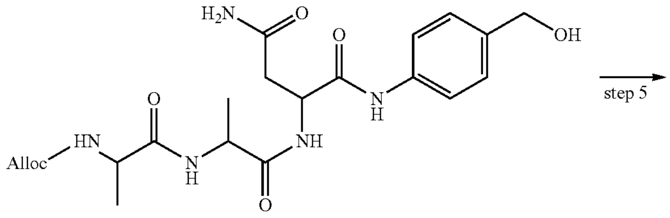
Alloc-AAN-PABC -continued

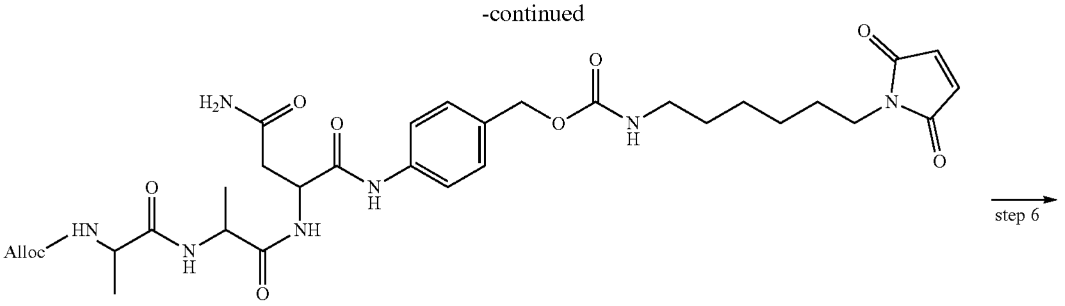

S15-1

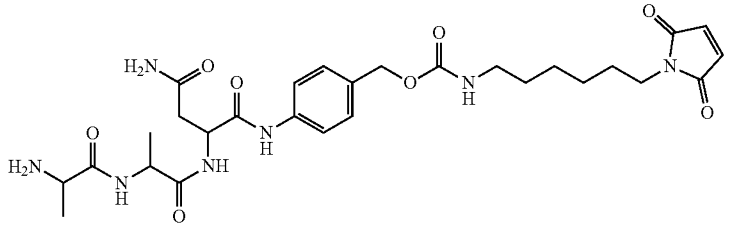

S15-2

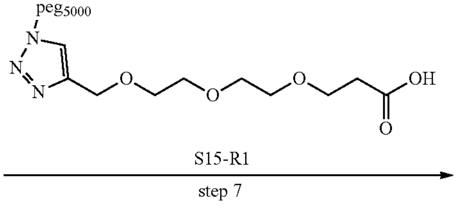

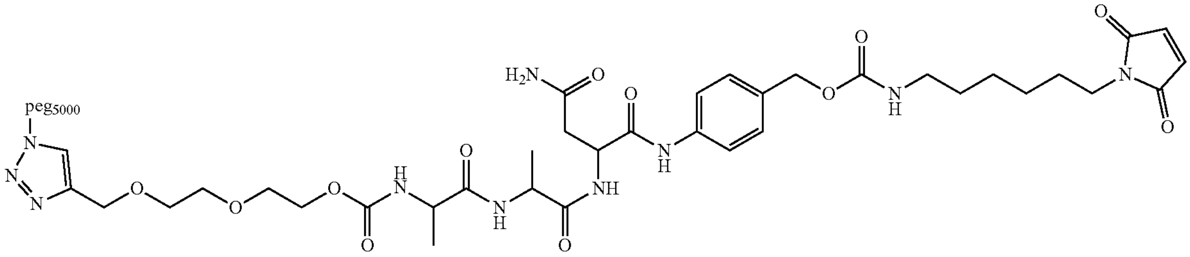

S15

1) Fmoc-Asn(Trt)-OH (20 g, 0.03 mol), 2-(7-azabenzotriazole)-N,N,N',N'-tetramethyluronium hexafluophosphate (HATU) (15 g, 0.04 mol), and DMF (200 mL) were added to a three-necked flask and stirred for 30 min. p-Aminobenzyl alcohol (4.1 g, 0.03 mol) and N,N-diisopropyl ethylamine (8.7 g, 0.06 mol) were added at 0° C., respectively and then stirred at room temperature for 3 hours. Most of DMF were removed by rotary evaporation. The residue was dissolved in acetic acetate (200 mL), washed with saturated ammonia chloride solution and saturated sodium chloride solution subsequently, dried over anhydrous sodium sulfate followed by filtration. The solvents were removed by evaporation. The crude product was beaten to obtain a white solid Fmoc-Asn(Trt)-PABC (21.3 g; Yield: 90%).

2) Fmoc-Asn(Trt)-PABC (16.0 g, 22 mmol) was dissolved in N,N-dimethyl formamide (80 mL). Piperidine (30 mL) were added and then stirred at room temperature for 2 hours. The solvents were removed by evaporation under reduced pressure. The residue was dried under high vacuum in a vacuum oven to remove a small amount of piperidine to produce 9.8 g pale yellow solid $NH_2$-Asn(Trt)-PABC which could be used in the next step without purification.

3) Alloc-Ala-Ala-OH (5.0 g, 20.4 mmol), benzotriazole-N,N,N',N'-tetramethyluronium hexafluophosphate (HBTU) (11.6 g, 30.6 mmol) and DMF (50 mL) were added into a three-necked flask and stirred for 30 min in an ice bath. $NH_2$-Asn(Trt)-PABC (9.8 g, 20.4 mmol) and N,N-diisopropyl ethylamine (7.89 g, 61.2 mmol) were added respectively at 0° C. and then stirred at room temperature overnight. The solvents were removed by evaporation under reduced pressure. The residue was dissolved in acetic acetate (200 mL), washed with saturated ammonia chloride solution and saturated sodium chloride solution subsequently, dried over anhydrous sodium sulfate followed by filtration. The solvents were removed by evaporation. The resulting crude product was subjected to recrystallization to obtain a white solid Alloc-AAN(Trt)-PABC (13.0 g; Yield: 90%).

4) Alloc-AAN(Trt)-PABC (10.0 g, 14.2 mmol) was dissolved in dichloromethane (100 mL). Trifluoroacetic acid (20 mL) were added and then stirred at room temperature for 4 hours. After washing with water and fraction, the organic phase was dried over anhydrous sodium sulfate. The solvents were removed by evaporation under reduced pressure and the residual trifluoroacetic acid was removed by evaporation under high vacuum. The crude product was isolated by column chromatography to obtain Alloc-AAN-PABC (5.9g; Yield: 89%).

5) Alloc-AAN-PABC (467 mg, 1.01 mmol) dissolved in dichloromethane (10 mL) were added to a three-necked flask. 4-Nitrophenyl chloroformate (406 mg, 2.02 mmol) in dichloromethane and pyridine (160 mg, 2.03 mmol) in dichloromethane were dropped into the flask, respectively, in an ice bath and under nitrogen gas protection and then stirred at room temperature overnight. 1-(6-Aminohexyl)-1H-pyrolo-2,5-dione (235 mg, 1.2 mmol) were added in batches into the above solution and was allowed to react at room temperature for 4 hours. The reaction solution was dried by rotary evaporation. The resulting crude product was purified by silica gel column chromatography to obtain a white solid S15-1 (540 mg; Yield: 80%).

6) DMF (10 ml), S15-1 (208 mg, 0.31 mmol), acetic acid (274 mg, 4.65 mmol), triphenylphosphine palladium (72 mg, 0.062 mmol) and tributyltin hydride (1.17 g, 4.03 mmol) were added successively into a one-neck flask. After replacing the air in the flask with nitrogen gas, the mixture was stirred at room temperature until S15-1 is reacted completely. After the reaction was completed, DMF was removed by evaporation under reduced pressure. The crude product was isolated and purified by silica gel column chromatography to obtain S15-2 (white solid, 116 mg, Yield: 62%).

7) S15-Ri (940 mg, 0.18 mmol), benzotriazole-N,N,N',N'-tetramethyluronium hexafluophosphate (HBTU) (95 mg, 0.25 mmol) and DMF (10 mL) were added to a three-necked flask, and then stirred in an ice bath for 30 min. Then compound S15-2 (110 mg, 0.18 mmol) and N,N-diisopropyl ethylamine (70 mg, 0.54 mmol) were added respectively at 0° C. and then stirred at room temperature overnight. The solvents were removed by evaporation under reduced pressure. The crude product was isolated and purified by silica gel column chromatography to obtain a white solid (418 mg; Yield: 40%), which was Compound S15.

When R2 has an amino acid sequence of Ala-Ala-Asp and R3 is PABC, the synthetic scheme is shown below:

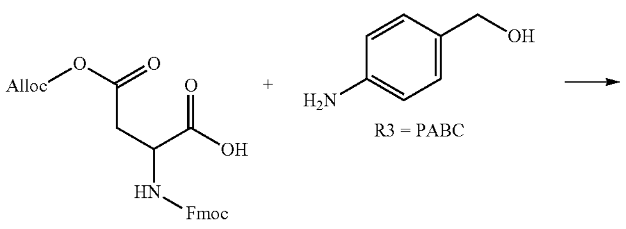

Fomc-Asp(Alloc)-OH

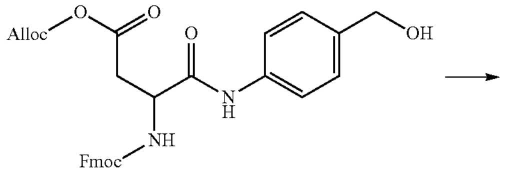

Fomc-Asp(Alloc)-PABC

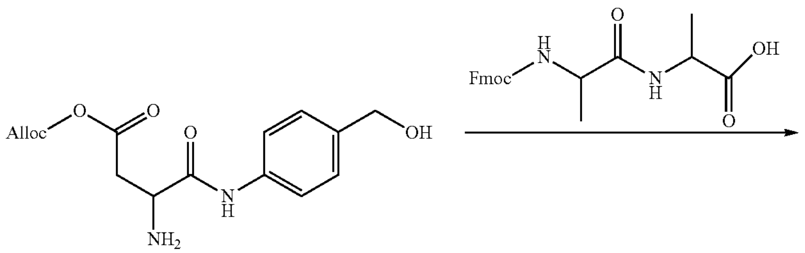

NH2-Asp(Alloc)-PABC

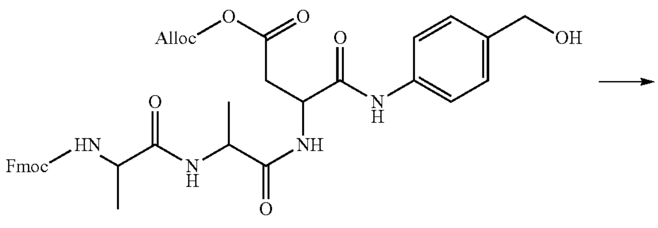

Fmoc-AAD(Alloc)-PABC

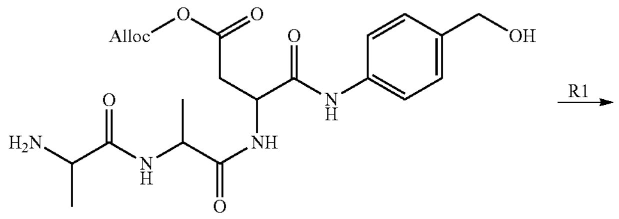

$NH_2$-AAD(Alloc)-PABC

-continued
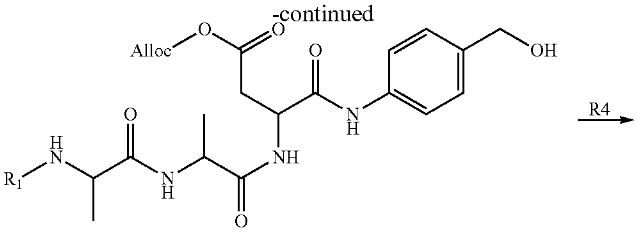
R1-AAD(Alloc)-PABC
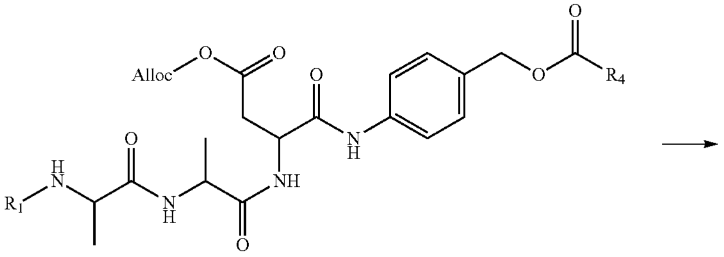
R1-AAD(Alloc)-PABC
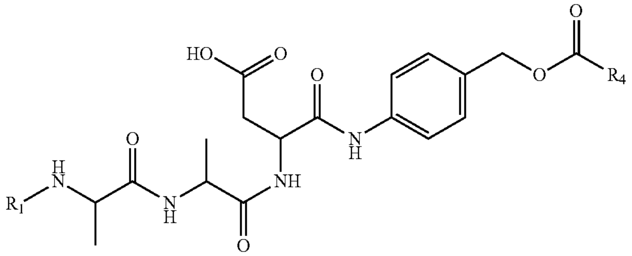
R1-AAD-PABC-R4
When R1 and R4 are different substituents, the following compounds in Table 2 were obtained.

TABLE 2
| R1 | R4 | Compound |
|---|---|---|
| 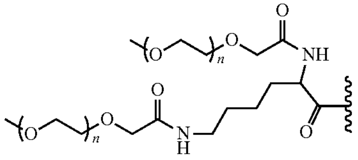<br>R1-1 | 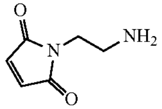<br>R4-5 | 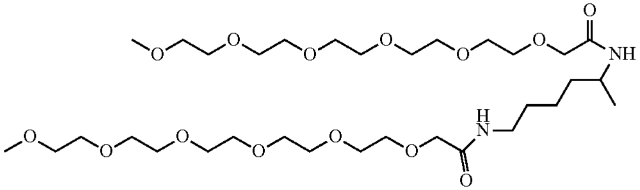<br>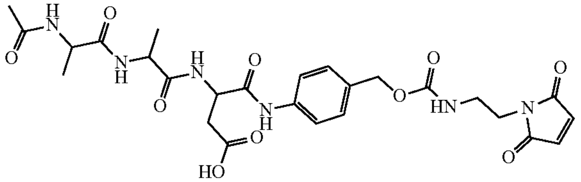<br>S2 |
| 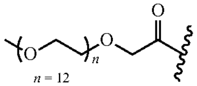<br>R1-2 | 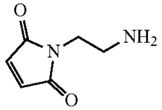<br>R4-5 | 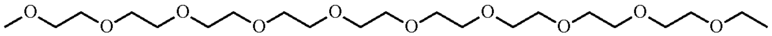<br>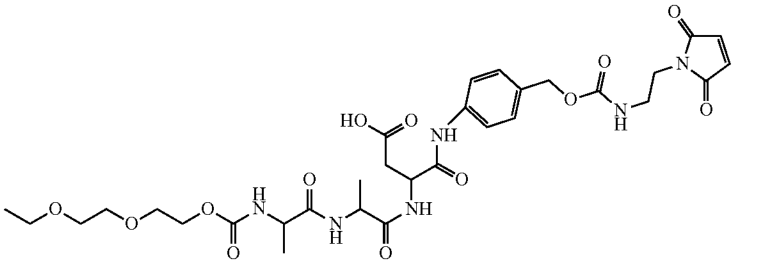<br>S4 |

TABLE 2-continued
| R1 | R4 | Compound |
|---|---|---|
| 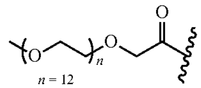 R1-2 | 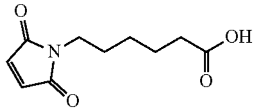 R4-13 | 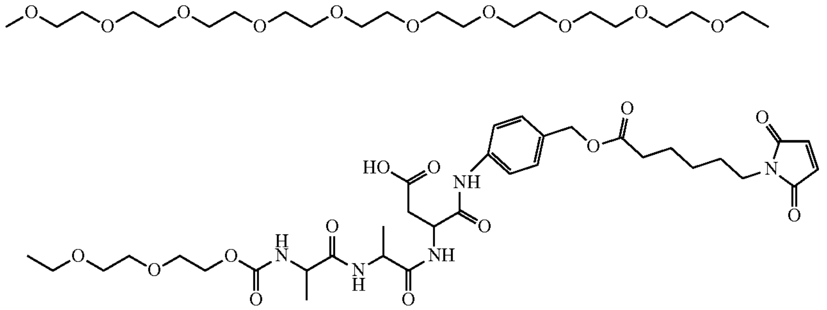 S8 |
| 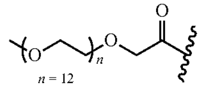 R1-2 | 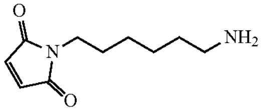 R4-7 | 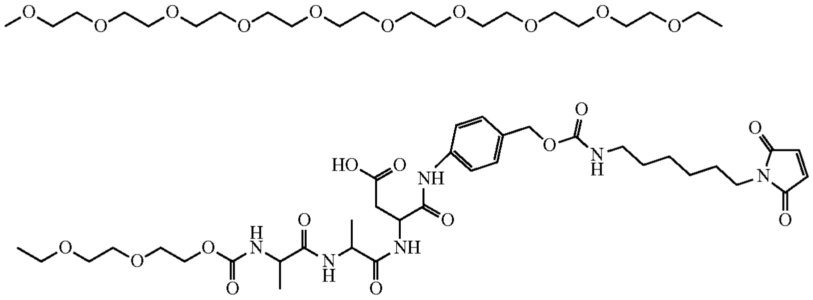 S10 |
| 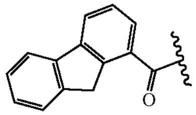 R1-3 | 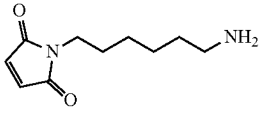 R4-7 | 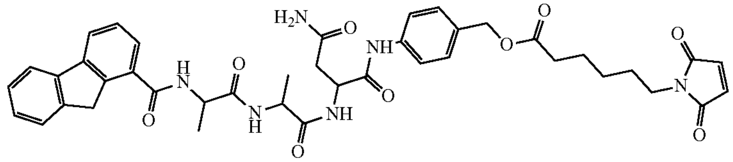 S12 |

TABLE 2-continued
| R1 | R4 | Compound |
|---|---|---|
| 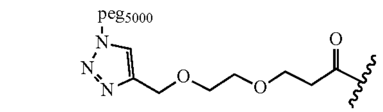 R1-4 | 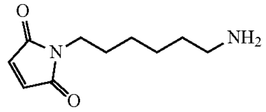 R4-7 | 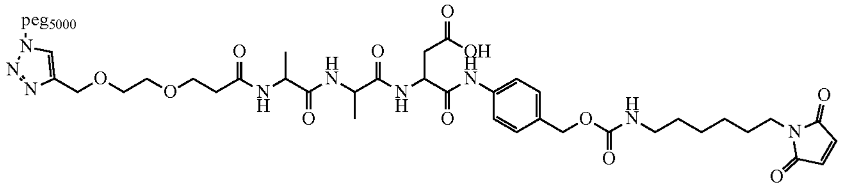 S14 |
| 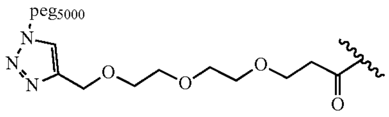 R1-5 | 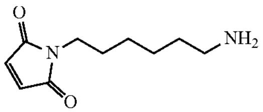 R4-7 | 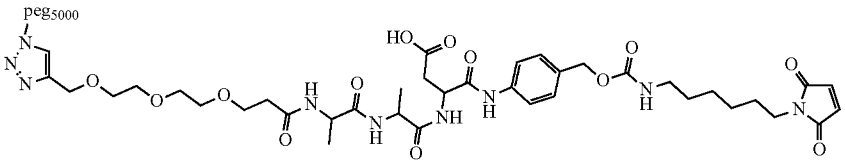 S16 |
| 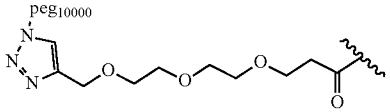 R1-6 | 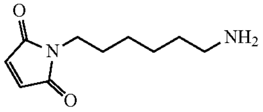 R4-7 | 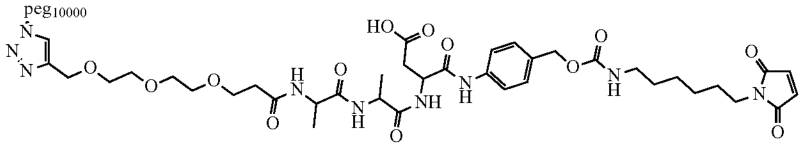 S18 |
| 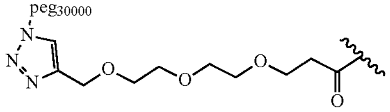 R1-7 | 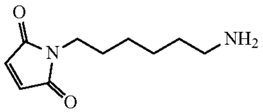 R4-7 | 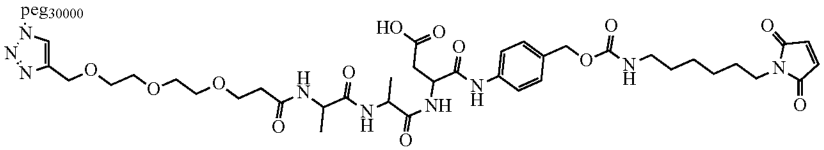 S26 |
| 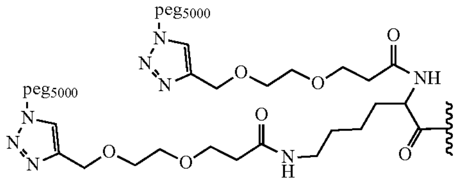 R1-18 | 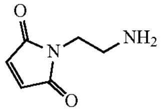 R4-5 | 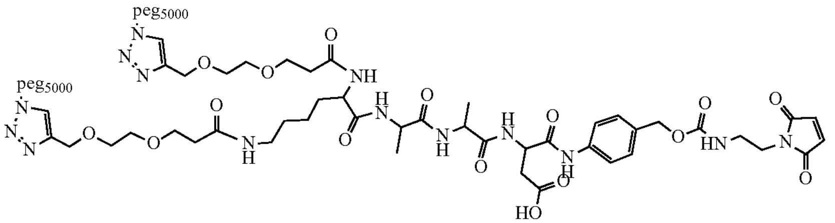 S30 |

TABLE 2-continued
| R1 | R4 | Compound |
| --- | --- | --- |
| 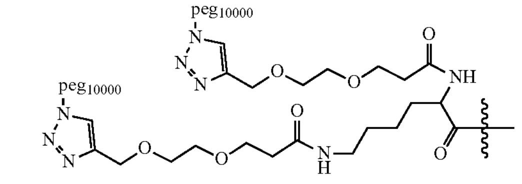 R1-19 | 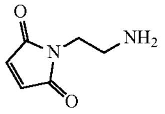 R4-5 | 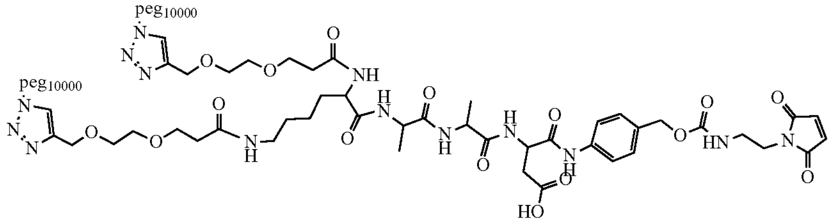 S32 |
| 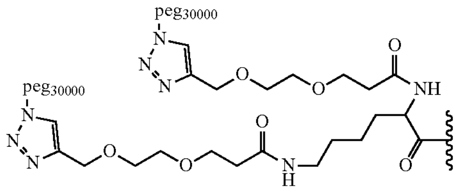 R1-20 | 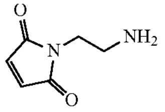 R4-5 | 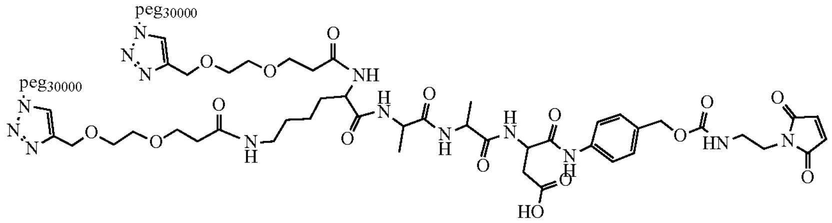 S34 |
| 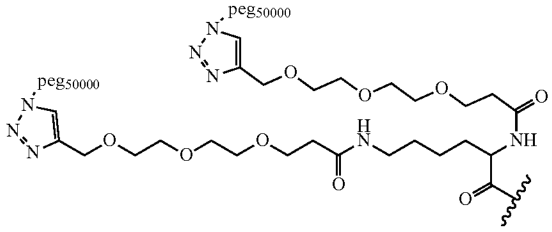 R1-21 | 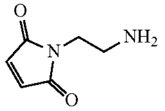 R4-5 | 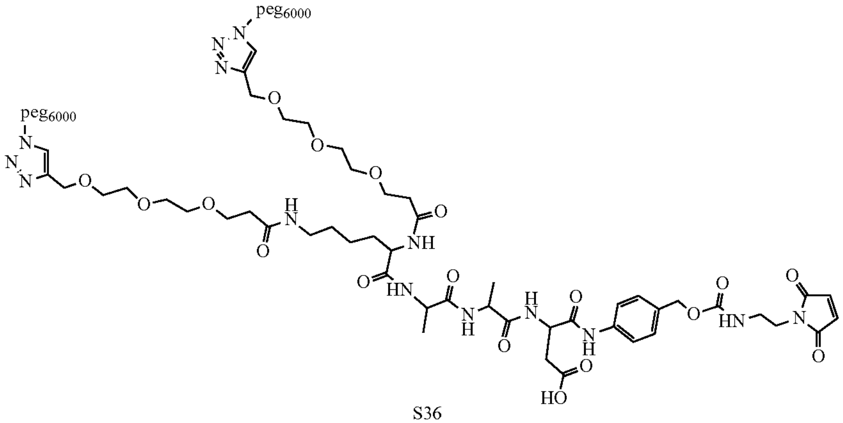 S36 |

TABLE 2-continued
| R1 | R4 | Compound |
|---|---|---|
| 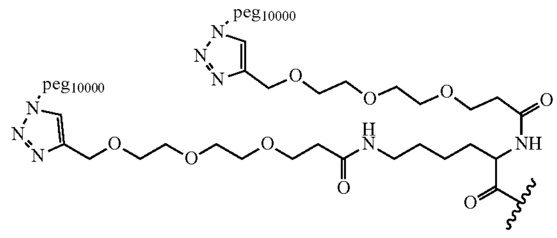 R1-22 | 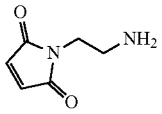 R4-5 | 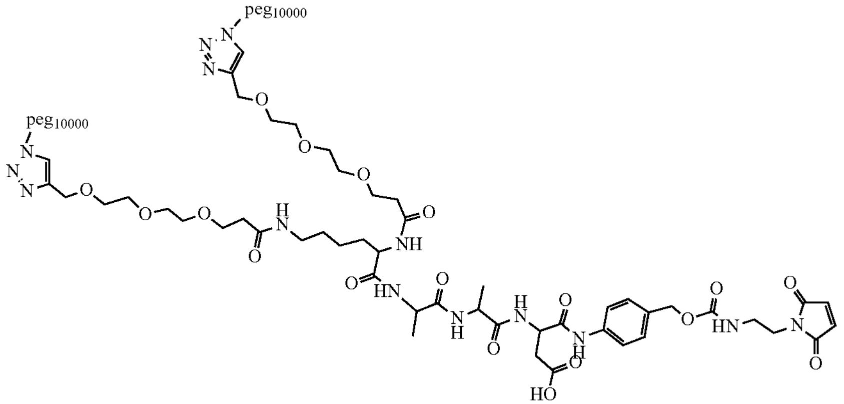 S38 |
| 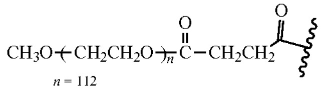 R1-12 | 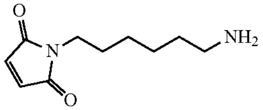 R4-7 | 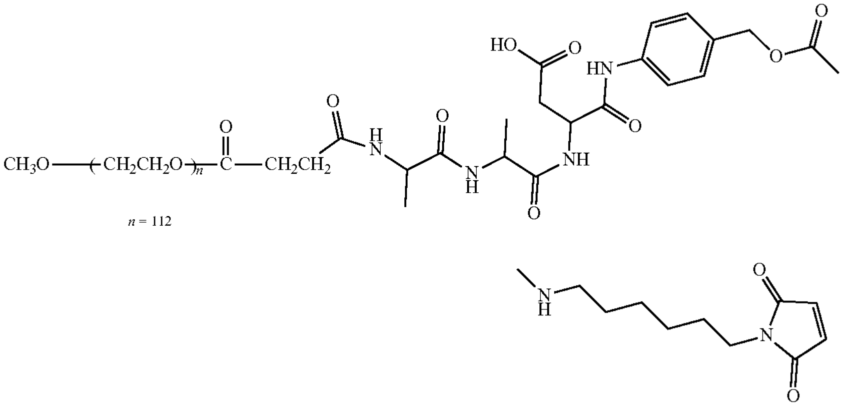 S40 |

TABLE 2-continued
| R1 | R4 | Compound |
|---|---|---|
| 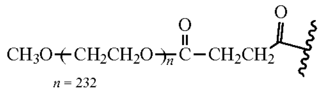 R1-13 | 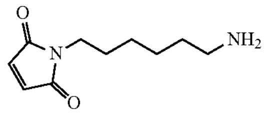 R4-7 | 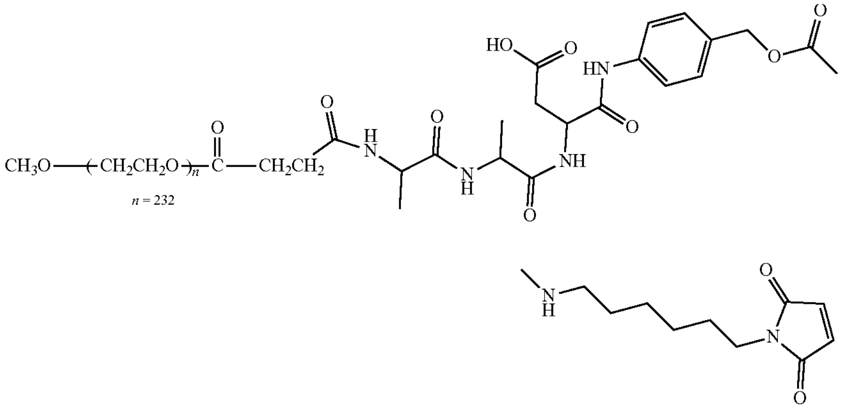 S42 |
| 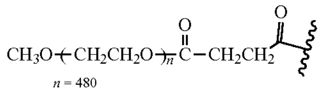 R1-15 | 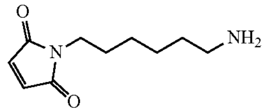 R4-7 | 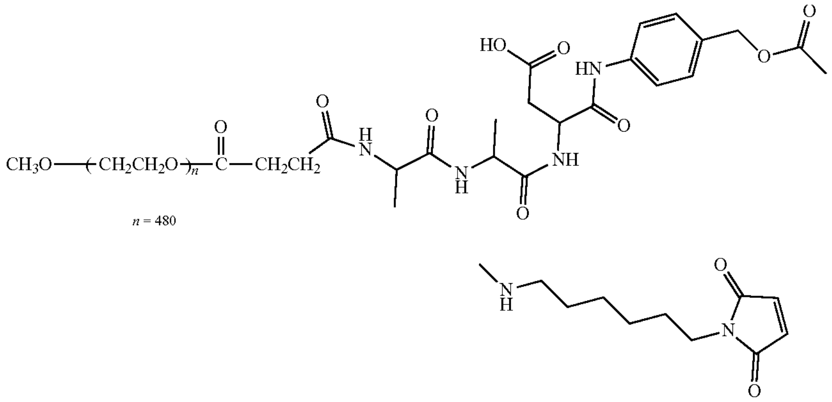 S44 |

TABLE 2-continued
| R1 | R4 | Compound |
|---|---|---|
| 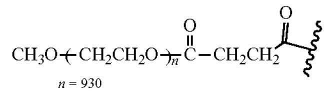 R1-16 | 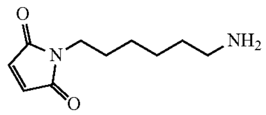 R4-7 | 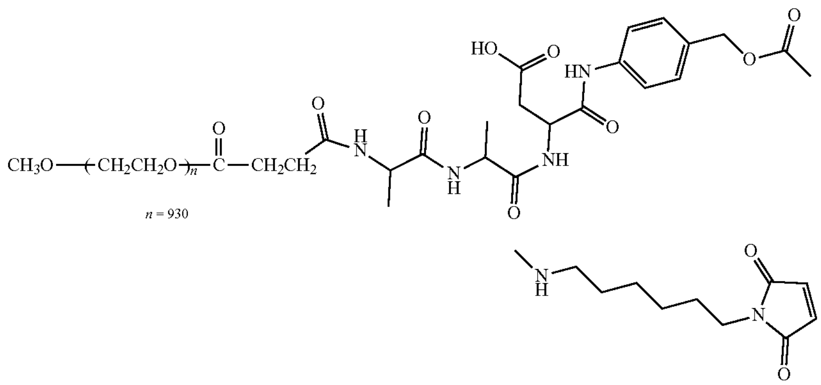 S46 |
| 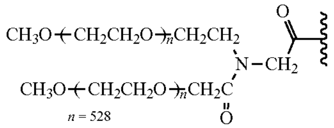 R1-17 | 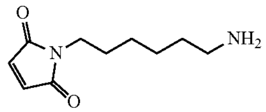 R4-7 | 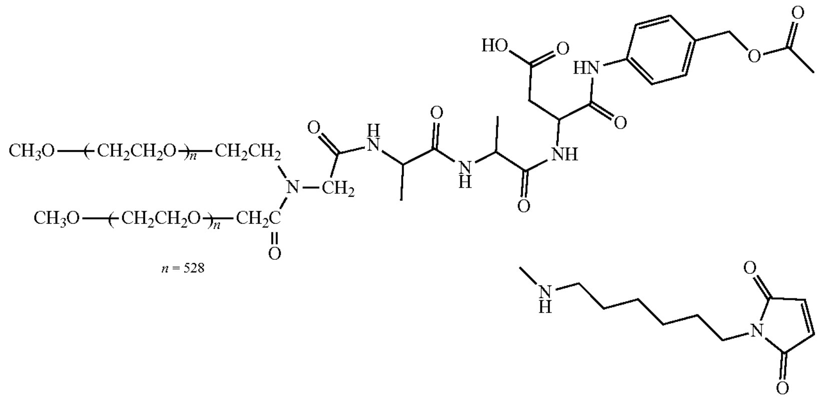 S48 |

TABLE 2-continued
| R1 | R4 | Compound |
|---|---|---|
| 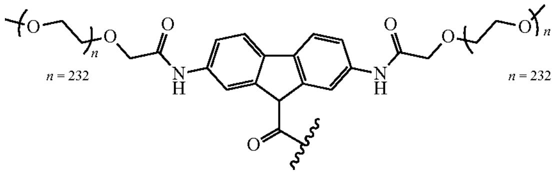<br>R1-28 | 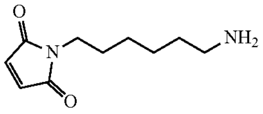<br>R4-7 | 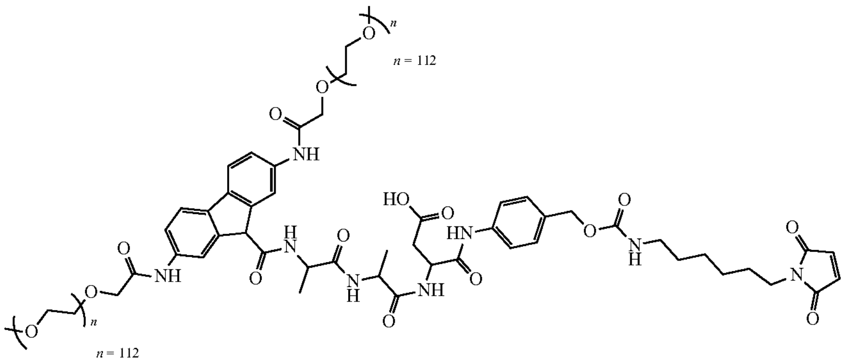<br>S58 |
| 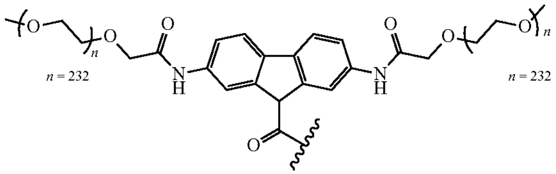<br>R1-29 | 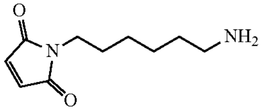<br>R4-7 | 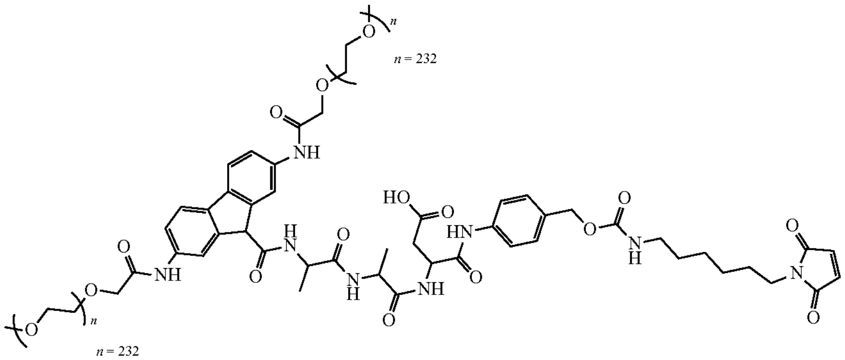<br>S60 |

TABLE 2-continued
| R1 | R4 | Compound |
| --- | --- | --- |
| 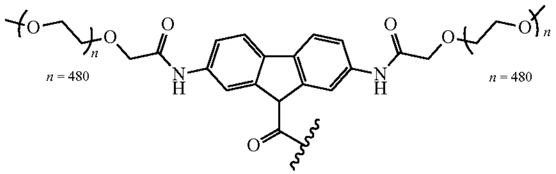 R1-30 | 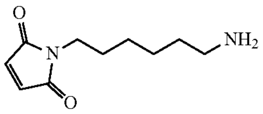 R4-7 | 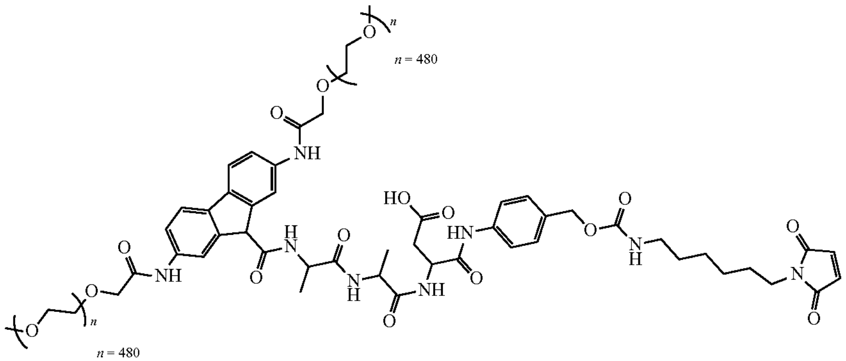 S62 |
| 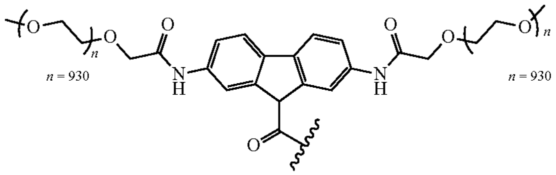 R1-31 | 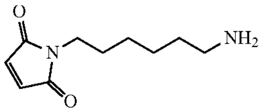 R4-7 | 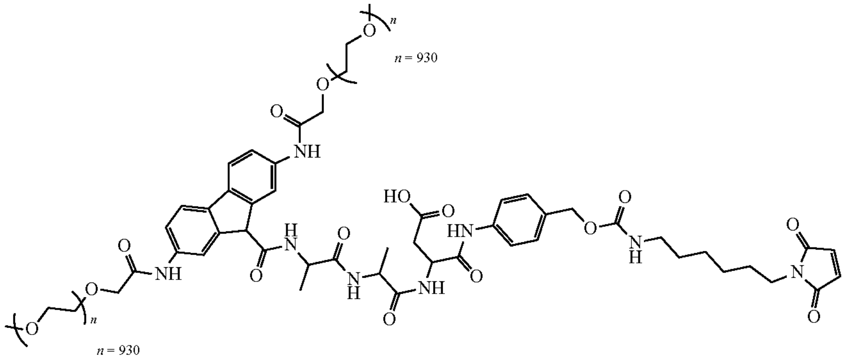 S64 |

As exemplified by S16, the specific synthesis process was shown below:
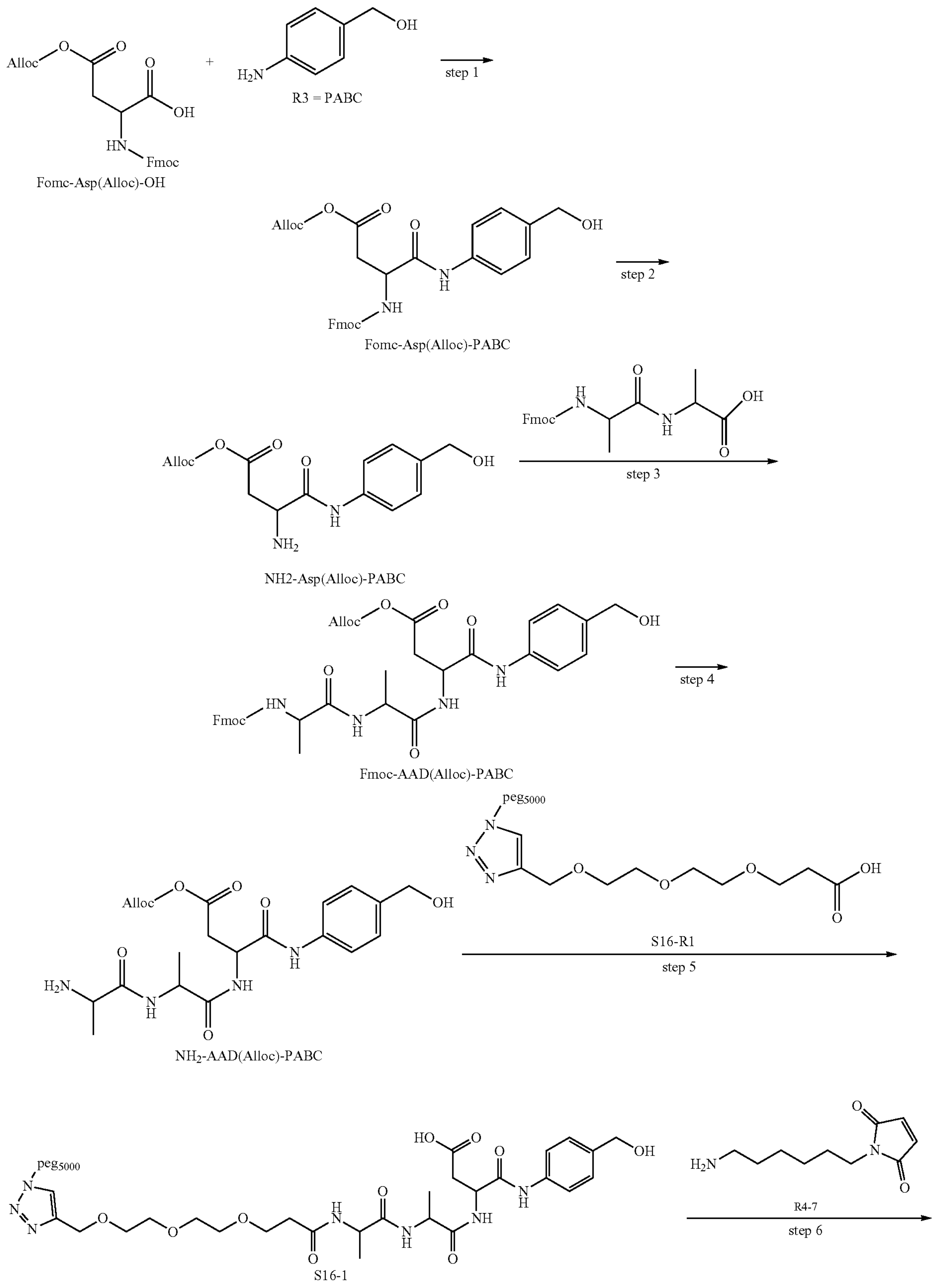

-continued

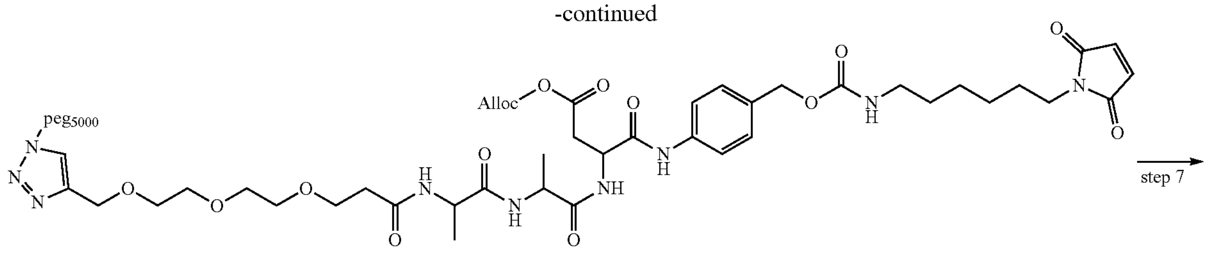

S16-2

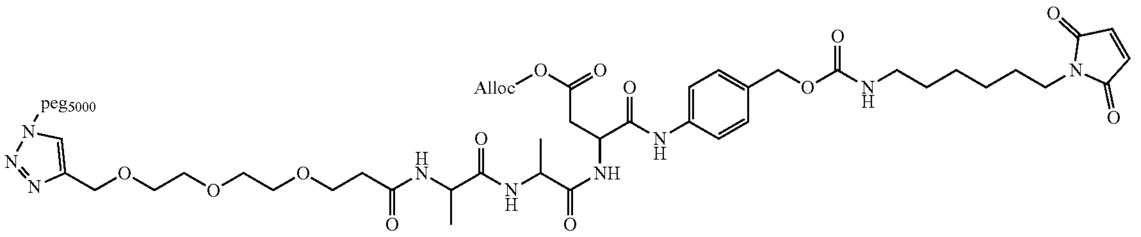

S16

1) Fmoc-Asp(Alloc)-OH (13.2 g, 0.03 mol), 2-(7-azabenzotriazole)-N,N,N',N'-tetramethyluronium hexafluophosphate (HATU) (15 g, 0.04 mol), and DMF (200 mL) were added to a three-necked flask and stirred for 30 min. p-Aminobenzyl alcohol (4.1 g, 0.03 mol) and N,N-diisopropyl ethylamine (8.7 g, 0.06 mol) were added at 0° C., respectively and then stirred at room temperature for 3 hours. DMF was removed by rotary evaporation. The residue was purified by column chromatography to obtain a white solid Fmoc-Asp(Alloc)-PABC (14.7g; Yield: 89%).

2) Fmoc-Asp(Alloc)-PABC (14.0 g, 25 mmol) was dissolved in N,N-dimethyl formamide (80 mL). Piperidine (30 mL) were added and then stirred at room temperature for 2 hours. The solvents were removed by evaporation under reduced pressure. The residue was dried under high vacuum in a vacuum oven to produce 8.0 g pale yellow solid $NH_2$-Asp(Alloc)-PABC which can be used in the next step without purification.

3) Fmoc-Ala-Ala-OH (7.8 g, 20.4 mmol), benzotriazole-N,N,N',N'-tetramethyluronium hexafluophosphate (HBTU) (11.6 g, 30.6 mmol) and DMF (50 mL) were added into a three-necked flask and stirred for 30 min in an ice bath. $NH_2$-Asp(Alloc)-PABC (6.6 g, 20.4 mmol) and N,N-diisopropyl ethylamine (7.89 g, 61.2 mmol) were added respectively at 0° C. and then stirred at room temperature overnight. The solvents were removed by evaporation under reduced pressure. The residue was purified by silica gel column chromatography to obtain a white solid Fmoc-AAD (Alloc)-PABC (12.6g; Yield: 90%).

4) Fmoc-AAD(Alloc)-PABC (12 g, 17.5 mmol) was dissolved in dichloromethane (80 mL). Piperidine (30 mL) were added and then stirred at room temperature for 2 hours. The solvents were removed by evaporation under reduced pressure. The residue was dried under high vacuum in a vacuum oven to obtain 7.0 g pale yellow solid, which was directly used in the next step.

5) Intermediate S16-R1 (522 mg, 0.1 mmol), 2-(7-azabenzotriazole)-N,N,N',N'-tetramethyluronium hexafluophosphate (46 mg, 0.12 mmol), and DMF (20 mL) were added into a three-necked flask and stirred for 30 min. $NH_2$-AAD (Alloc)-PABC (46 mg, 0.1 mmol) and N,N-diisopropyl ethylamine (38.7 mg, 0.3 mmol) were added, respectively, at 0° C. and then stirred at room temperature for 3 hours. DMF was removed by rotary evaporation. The residue was purified by column chromatography to obtain S16-1 (white solid, 251 mg, Yield: 45%).

6) S16-1 (240 mg, 0.046 mmol) dissolved in dichloromethane (10 mL) were added into a three-necked flask. 4-Nitrophenyl chloroformate (18 mg, 0.093 mmol) in dichloromethane and pyridine (7.3 mg, 0.093 mmol) in dichloromethane were dropped into the flask, respectively, in an ice bath and under nitrogen gas protection and then stirred at room temperature overnight. R4-7 (11 mg, 0.055 mmol) were added into the above solution and allowed to react at room temperature for 4 hours. The reaction solution was dried by rotary evaporation. The resultant crude product was purified by silica gel column chromatography to obtain a white solid S16-2 (96 mg; Yield: 38%).

7) DMF (10 ml), compound S16-2 (96 mg, 0.016 mmol), acetic acid (127 mg, 2.15 mmol), triphenylphosphine palladium (33 mg, 0.029 mmol) and tributyltin hydride (0.54 g, 1.86 mmol) were added successively into a one-necked flask. After replacing the air in the flask with nitrogen gas, the mixture was stirred at room temperature until compound S16-2 was reacted completely. After the reaction was completed, DMF was removed by evaporation under reduced pressure. The crude product was isolated and purified by silica gel column chromatography to obtain a white solid (54 mg; Yield: 62%), which was compound S16.

When an acidically activatable group was contained, the synthetic scheme was shown as follows:

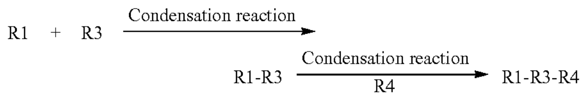

As exemplified by S20, the specific synthesis process was shown below:

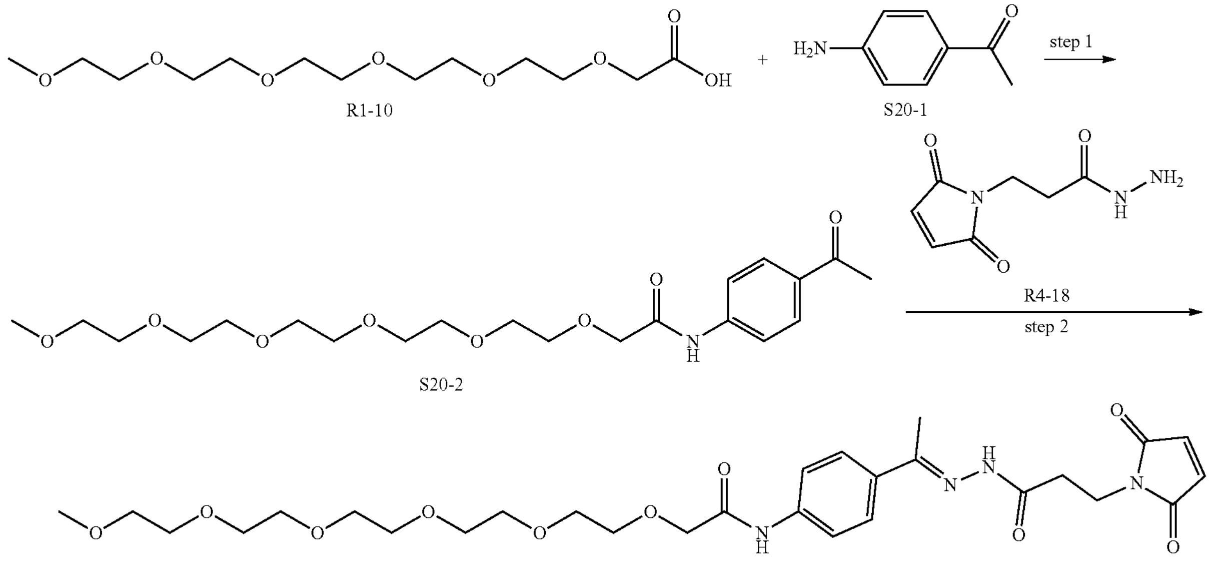

R1-10 + S20-1 → S20-2 → (R4-18) S20

1) R1-10 (3.1 g, 0.01 mol), 2-(7-azabenzotriazole)-N,N,N',N'-tetramethyluronium hexafluophosphate (HATU) (4.56 g, 0.012 mol), and DMF (20 mL) were added into a three-necked flask and stirred for 30 min. S20-1 (1.35 g, 0.01 mol) and N,N-diisopropyl ethylamine (3.87 g, 0.03 mol) were added respectively at 0° C. and then stirred at room temperature for 3 hours. DMF was removed by rotary evaporation. The residue was purified by silica gel column chromatography to obtain a pale yellow oily substance S20-2 (2.5g; Yield: 59%).

2) S20-2 (98 mg, 0.23 mmol) and R4-18 (42 mg, 0.23 mmol) were weighed and successively added into a 50 ml one-necked flask. Dichloromethane (5 mL) was added to dissolve S20-2 and R4-18 followed by addition of 4A molecular sieves (81 mg). After replacing the air in the flask with nitrogen gas, the mixture was allowed to react at room temperature overnight. The reaction solution was dried by rotary evaporation. The crude product was purified by silica gel column chromatography to obtain a white solid (81 mg; Yield: 60%), which was compound S20.

When R1, R3 and R4 were different substituents, the following compounds in Table 3 were obtained.

TABLE 3
| R1 | R3 | R4 | Compound |
|---|---|---|---|
| 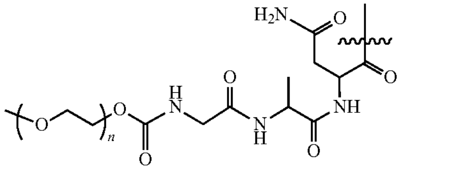 n = 12 | 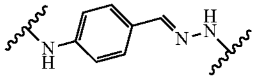 R3-1 | 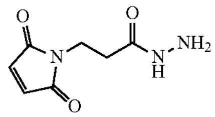 R4-18 | 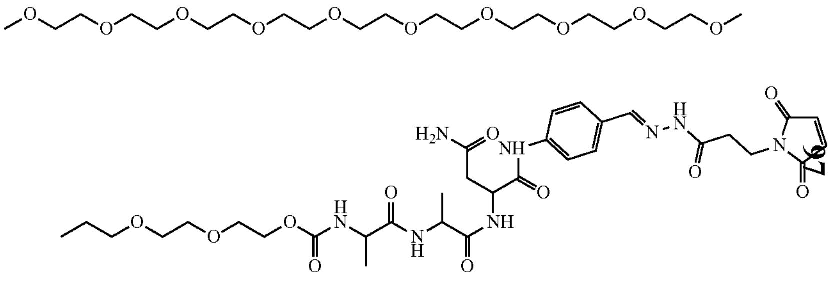 S5 |
| 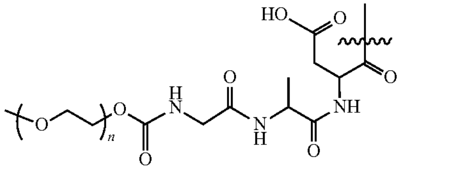 n = 12 | 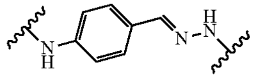 R3-1 | 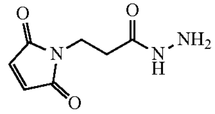 R4-18 | 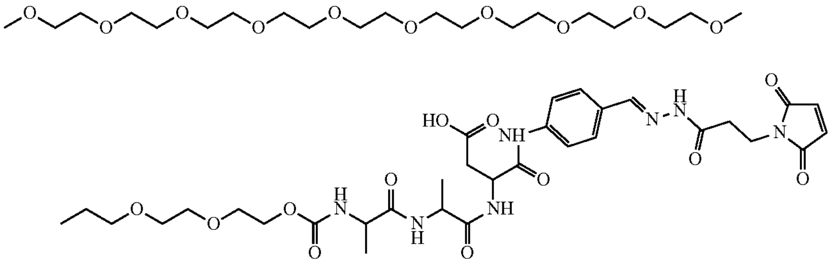 S6 |
| 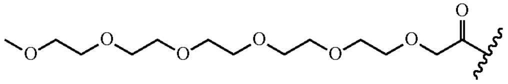 R1-10 | 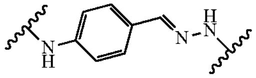 R3-1 | 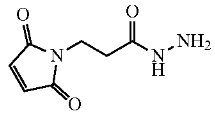 R4-18 | 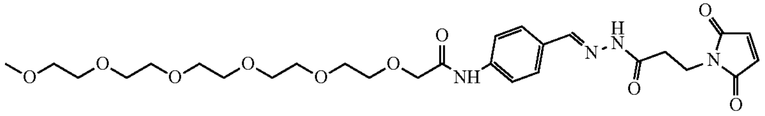 S19 |
| 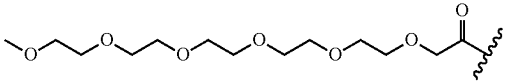 R1-10 | 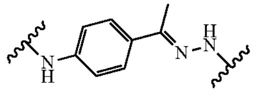 R3-2 | 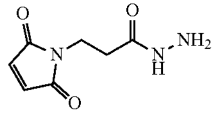 R4-18 | 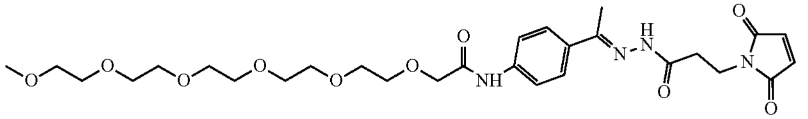 S20 |

TABLE 3-continued
| R1 | R3 | R4 | Compound |
|---|---|---|---|
| 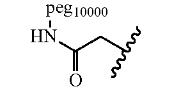 R1-11 | 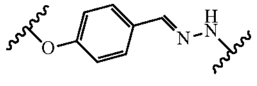 R3-3 | 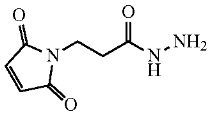 R4-18 | 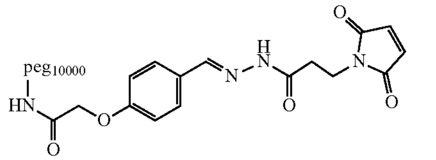 S21 |
| 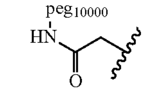 R1-11 | 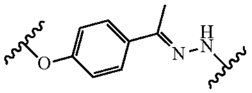 R3-4 | 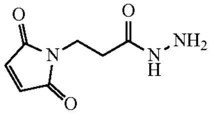 R4-18 | 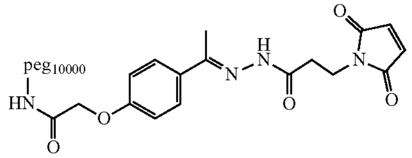 S22 |
| 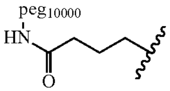 R1-14 | 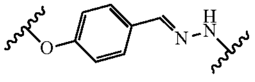 R3-3 | 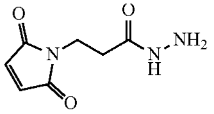 R4-18 | 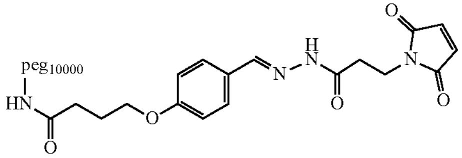 S23 |
| 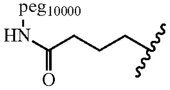 R1-14 | 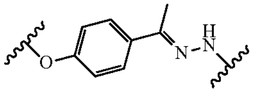 R3-4 | 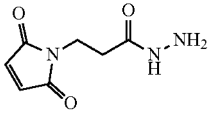 R4-18 | 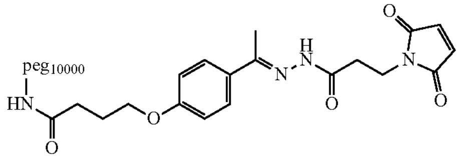 S24 |
| 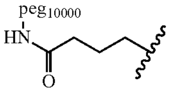 R1-27 | 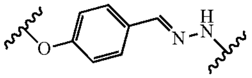 R3-3 | 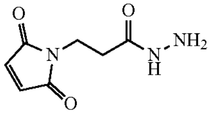 R4-18 | 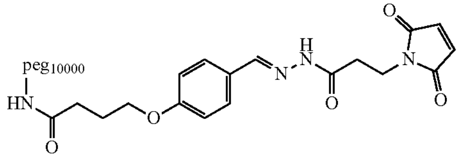 S27 |

TABLE 3-continued
| R1 | R3 | R4 | Compound |
|---|---|---|---|
| 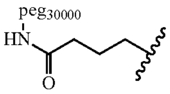 R1-27 | 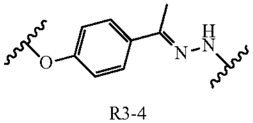 [SMILES: *N/N=C(\C)c1ccc(O*)cc1] R3-4 | 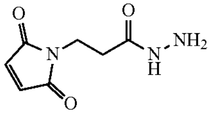 R4-18 | 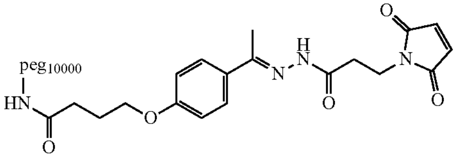 S28 |
| 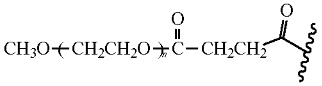 R1-12 | 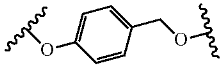 R3-6 | 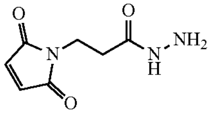 R4-18 | 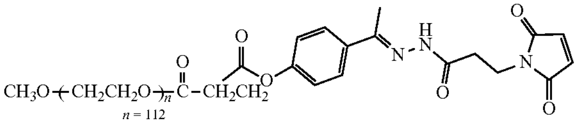 S49 |
| 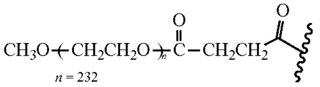 R1-13 | 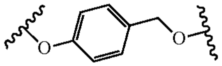 R3-6 | 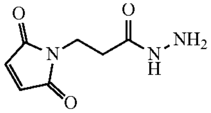 R4-18 | 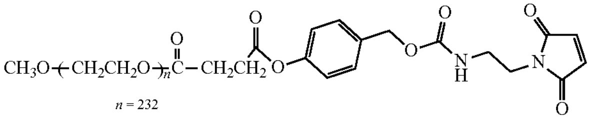 S50 |
| 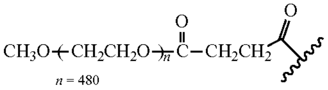 R1-15 | 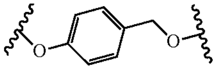 R3-6 | 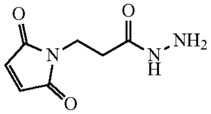 R4-18 | 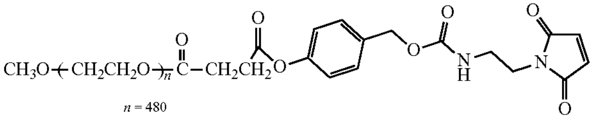 S51 |
| 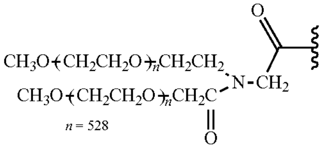 R1-17 | 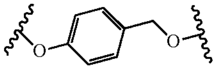 R3-6 | 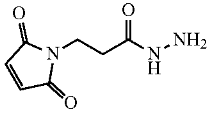 R4-18 | 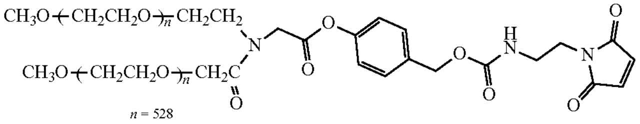 S52 |
| 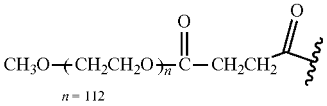 R1-12 | 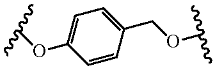 R3-6 | 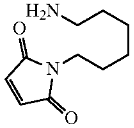 R4-7 | 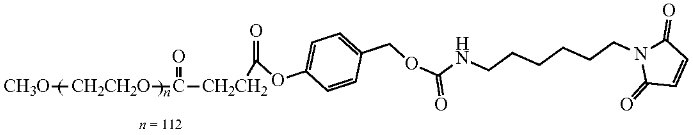 S53 |

TABLE 3-continued
| R1 | R3 | R4 | Compound |
| --- | --- | --- | --- |
| 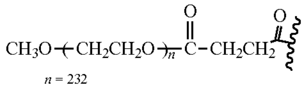 R1-13 | 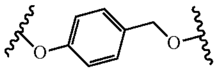 R3-6 | 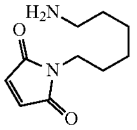 R4-7 | 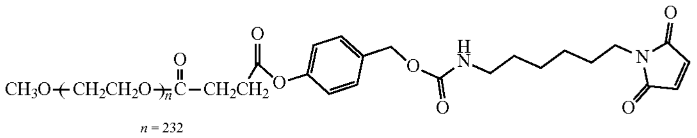 S54 |
| 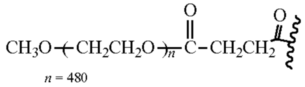 R1-15 | 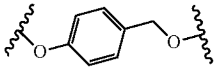 R3-6 | 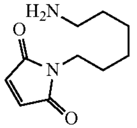 R4-7 | 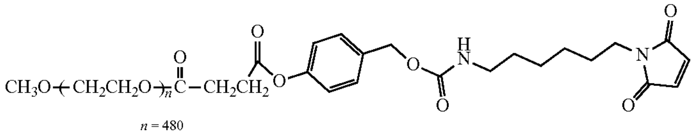 S55 |
| 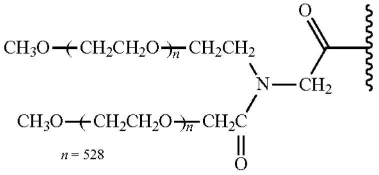 R1-17 | 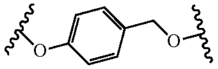 R3-6 | 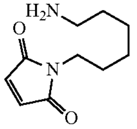 R4-7 | 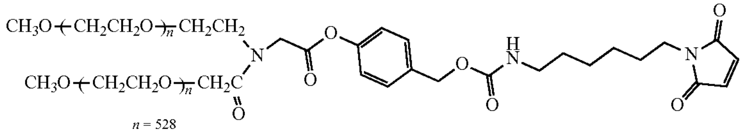 S56 |

Compounds S1-S64 were verified by mass spectrum (MS) and their molecular weights were shown in Table 4, which were consistent to the calculated molecular weights based on their structures.

TABLE 4

| No. | Detection by MS | Molecular Weight | Character | Yield |
|---|---|---|---|---|
| S1 | 1258 | 1258.37 | white solid | 71 mg |
| S2 | 1258 | 1258.37 | white solid | 49 mg |
| S3 | 1132 | 1132.21 | white solid | 236 mg |
| S4 | 1133 | 1133.20 | white solid | 93 mg |
| S5 | 1129 | 1129.21 | white solid | 37 mg |
| S6 | 1130 | 1130.20 | white solid | 46 mg |
| S7 | 1159 | 1159.28 | white solid | 158 mg |
| S8 | 1160 | 1160.26 | white solid | 102 mg |
| S9 | 1188 | 1188.32 | white solid | 34 mg |
| S10 | 1189 | 1189.30 | white solid | 28 mg |
| S11 | 765 | 764.82 | white solid | 18 mg |
| S12 | 766 | 765.81 | white solid | 31 mg |
| S13 | 5756 | 5755.81 | white solid | 364 mg |
| S14 | 5757 | 5756.80 | white solid | 270 mg |
| S15 | 5800 | 5799.87 | white solid | 418 mg |
| S16 | 5801 | 5800.85 | white solid | 54 mg |
| S17 | 10800 | 10799.87 | white solid | 189 mg |
| S18 | 10801 | 10800.85 | white solid | 167 mg |
| S19 | 579 | 578.61 | white solid | 102 mg |
| S20 | 593 | 592.64 | white solid | 81 mg |
| S21 | 10326 | 10326.32 | white solid | 106 mg |
| S22 | 10340 | 10340.35 | white solid | 97 mg |
| S23 | 10354 | 10354.38 | white solid | 139 mg |
| S24 | 10368 | 10368.40 | white solid | 76 mg |
| S25 | 30800 | 30799.87 | white solid | 143 mg |
| S26 | 30801 | 30800.85 | white solid | 125 mg |
| S27 | 30354 | 30354.38 | white solid | 136 mg |
| S28 | 30368 | 30368.40 | white solid | 121 mg |
| S29 | 10982 | 10982.37 | white solid | 223 mg |
| S30 | 10983 | 10982.46 | white solid | 184 mg |
| S31 | 20982 | 20982.28 | white solid | 274 mg |
| S32 | 20983 | 20982.32 | white solid | 231 mg |
| S33 | 60982 | 60982.19 | white solid | 362 mg |
| S34 | 60983 | 60983.26 | white solid | 284 mg |
| S35 | 11070 | 11070.34 | white solid | 164 mg |
| S36 | 11071 | 11071.41 | white solid | 182 mg |
| S37 | 21070 | 21070.18 | white solid | 155 mg |
| S38 | 21071 | 21071.27 | white solid | 169 mg |
| S39 | 5655 | 5655.37 | white solid | 156 mg |
| S40 | 5656 | 5656.22 | white solid | 231 mg |
| S41 | 10947 | 10947.42 | white solid | 143 mg |
| S42 | 10948 | 10948.36 | white solid | 157 mg |
| S43 | 21883 | 21883.84 | white solid | 241 mg |
| S44 | 21884 | 21884.72 | white solid | 185 mg |
| S45 | 41728 | 41728.86 | white solid | 174 mg |
| S46 | 41729 | 41729.73 | white solid | 169 mg |
| S47 | 47358 | 47358.46 | white solid | 248 mg |
| S48 | 47359 | 47359.39 | white solid | 312 mg |
| S49 | 5353 | 5343.61 | white solid | 254 mg |
| S50 | 10635 | 10635.68 | white solid | 216 mg |
| S51 | 21572 | 21572.47 | white solid | 198 mg |
| S52 | 47047 | 47047.18 | white solid | 183 mg |
| S53 | 5400 | 5399.76 | white solid | 175 mg |
| S54 | 10692 | 10691.74 | white solid | 168 mg |
| S55 | 21628 | 21628.51 | white solid | 156 mg |
| S56 | 47103 | 47103.24 | white solid | 141 mg |
| S57 | 10835 | 10835.22 | white solid | 139 mg |
| S58 | 10836 | 10836.09 | white solid | 145 mg |
| S59 | 21407 | 21407.28 | white solid | 182 mg |
| S60 | 21408 | 21408.17 | white solid | 163 mg |
| S61 | 43256 | 43256.02 | white solid | 196 mg |
| S62 | 43257 | 43257.10 | white solid | 175 mg |
| S63 | 81901 | 81901.07 | white solid | 154 mg |
| S64 | 81902 | 81902.14 | white solid | 139 mg |

Example 2: Analysis on the Binding Activity after Mutation in CDR of a Variable Region of an Antibody and Screening for R4

The amino acid sequence of anti-PD-1 antibody 1 was disclosed in WO200815712A1 and its DNA sequence was optimized for expression in a host and synthesized (GENEWIZ, Inc., Suzhou, China). The amino acid sequence of anti-PD-1 antibody 2 was disclosed in WO2006121168A2 and its DNA sequence was optimized for expression in a host and synthesized (GENEWIZ, Inc., Suzhou, China). The amino acid sequence of anti-CTLA-4 antibody was disclosed in US2015/0283234 and its DNA sequence was optimized and synthesized (GENEWIZ, Inc., Suzhou, China). The amino acid sequence of anti-TNFα antibody was disclosed in US009534046 and its DNA sequence was optimized for expression in a host and synthesized (GENEWIZ, Inc., Suzhou, China). The amino acid sequence of anti-CD28 antibody was disclosed in US007939638, and its DNA sequence was optimized for expression in a host and synthesized (GENEWIZ, Inc., Suzhou, China). The synthesized DNAs were digested and ligated to a modified pTT5 vector (Biovector) to produce pTT5-anti-PD-1-1, pTT5-anti-PD-1-2, pTT5-anti-CTLA-4, pTT5-anti-TNFα and pTT5-anti-CD28. Cysteine mutation was introduced by using pTT5-anti-PD-1-1, pTT5-anti-CTLA-4, pTT5-anti-TNFα and pTT5-anti-CD28 as templates, designing primer to replace the codon at the mutation position with that of cysteine, PCR and digesting and constructing the mutated fragment into the modified pTT5 vector.

The expression host was HEK293T cell (Life Technologies). Before transfection, HEK293T cells were cultured in a complete medium containing 10% FBS (Gibco) at 37° C. and 5% $CO_2$. One day before transfection, the cells were inoculated onto a 15 cm culture dish in an appropriate density and the culture medium was changed into FBS with low IgG (Gibco). 6 hours after transfection or on day 2, the culture medium was changed into Freestyle293 (Gibco).

On the day of transfection, when the cells reached a certain confluence, lipofectamine 2000 (Life Technologies) and PEI (sigma) were used to co-transfect the plasmids expressing the target protein to 293T cells. Antibody-expressing plasmids included heavy chain and light chain of the antibody. Culture supernatants were recovered on day 4 and day 6 after transfection, respectively. Expression and activity of the protein or antibody were detected, and the protein or antibody was purified.

The hypervariable regions of a variable region within heavy chain and light chain of an antibody (Ab) constitute an antigen (Ag) binding site of the antibody. Because the antigen binding site is complementary to a structure of an antigen epitope, the hypervariable region is also called as complementarity-determining region (CDR) of an antibody. The sequences of variable regions in light chain of anti-PD-1 antibody 1, anti-PD-1 antibody 2 and CTAL4 antibody were aligned and their CDRs were shown in FIG. 1.

In the present disclosure, the activity of each mutant having point mutation as compared to its initial antibody was detected by ELISA. Specifically, a 96-well plate was coated by an antigen of an antibody overnight and then blocked with 1% BSA blocker (ThermoFisher) for 2 hours at 37° C. and washed by PBST three times. Corresponding antibody or corresponding mutant was added and allowed to bind at 37° C. for 1 hour, then washed with PBST three times. HRP enzyme-conjugated anti-human IgG was added and allowed to bind at 37° C. for 1 hour and then washed with PBST three times. TMB substrate (Solarbio., Inc.) was used to detect absorbance at 450 nm. Effect on the binding strength of mutant was calculated by $OD_{after\ mutation}/OD_{wild\ type}$.

The binding activity of mutants of three antibodies, which had mutation at different positions as shown in Tables 5 and 6, were tested according to the above methods. In Tables 5 and 6, A represents a binding activity of 90-110%, B represents a binding activity of 70-90% and the symbol ↓ indicates a binding activity of less than 70a.

TABLE 5

Effect of mutation position in CDR of a variable region in a light chain of an antibody on binding activity

| CDR | Position | PD-1 Antibody 1 | Binding to PD-1 | anti-PD-1 antibody 2 | Binding to PD-1 | anti-CTLA-4 antibody | Binding to CTLA-4 |
|---|---|---|---|---|---|---|---|
| CDR1 | 25 | A | B | A | B | A | A |
| CDR1 | 26 | S | A | S | A | S | A |
| CDR1 | 27 | K | ↓ | | | | |
| CDR1 | 28 | G | A | S | A | S | A |
| CDR1 | 29 | | | | | | |
| CDR1 | 30 | S | A | S | A | G | A |
| CDR1 | 31 | T | B | S | A | S | A |
| CDR1 | 32 | S | A | Y | ↓ | S | A |
| CDR1 | 33 | G | A | L | ↓ | Y | ↓ |
| CDR1 | 34 | Y | ↓ | A | A | L | B |
| CDR1 | 35 | S | A | | | A | B |
| CDR1 | 36 | Y | ↓ | Y | ↓ | | |
| CDR1 | 37 | L | B | | | Y | ↓ |
| CDR2 | 51 | | | A | B | G | A |
| CDR2 | 52 | | | S | A | A | ↓ |
| CDR2 | 53 | Y | ↓ | | | | |
| CDR2 | 54 | L | B | S | A | S | A |
| CDR2 | 55 | A | B | A | B | | |
| CDR2 | 56 | S | A | T | A | A | B |
| CDR2 | 57 | | | G | A | T | A |
| CDR2 | 58 | | | I | B | G | A |
| CDR2 | 60 | S | A | A | B | | |
| CDR2 | 61 | G | A | | | | |
| CDR3 | 91 | | | S | A | | |
| CDR3 | 92 | | | S | A | Y | ↓ |
| CDR3 | 93 | | | | | G | A |
| CDR3 | 94 | | | | | S | A |
| CDR3 | 95 | S | A | | | S | A |
| CDR3 | 96 | | ↓ | | | | |
| CDR3 | 97 | D | ↓ | T | A | | |
| CDR3 | 98 | L | ↓ | F | ↓ | T | B |
| CDR3 | 99 | | ↓ | G | A | F | ↓ |
| CDR3 | 100 | L | ↓ | | | G | A |
| CDR3 | 101 | T | B | G | ↓ | | |
| CDR3 | 102 | F | ↓ | | | | |

TABLE 6

Effect of mutation position in CDR of a variable region in a heavy chain of an antibody on binding activity

| CDR | Position | PD-1 Antibody 1 | Binding to PD-1 | anti-PD-1 antibody 2 | Binding to PD-1 | anti-CTLA-4 antibody | Binding to CTLA-4 |
|---|---|---|---|---|---|---|---|
| CDR1 | 30 | T | A | S | A | S | A |
| CDR1 | 31 | | | | | S | A |
| CDR1 | 32 | Y | ↓ | S | A | Y | B |
| CDR1 | 33 | Y | ↓ | G | A | T | A |
| CDR1 | 35 | Y | B | | | | |
| CDR2 | 50 | G | A | | | | |
| CDR2 | 51 | I | B | I | B | I | B |
| CDR2 | 53 | | | Y | ↓ | Y | ↓ |
| CDR2 | 54 | S | A | D | B | D | B |
| CDR2 | 55 | | | G | A | G | A |
| CDR2 | 56 | G | A | S | A | S | A |
| CDR2 | 57 | G | A | K | ↓ | | |
| CDR2 | 58 | T | A | | | K | ↓ |
| CDR2 | 59 | | | Y | ↓ | Y | ↓ |
| CDR2 | 60 | | | Y | ↓ | Y | ↓ |
| CDR2 | 61 | | | A | B | A | A |
| CDR2 | 62 | | | D | ↓ | D | B |

TABLE 6-continued

| Effect of mutation position in CDR of a variable region in a heavy chain of an antibody on binding activity | | | | | | | |
|---|---|---|---|---|---|---|---|
| CDR | Position | PD-1 Antibody 1 | Binding to PD-1 | anti-PD-1 antibody 2 | Binding to PD-1 | anti-CTLA-4 antibody | Binding to CTLA-4 |
| CDR2 | 63 | K | B | S | A | S | A |
| CDR2 | 65 | K | ↓ | K | ↓ | K | ↓ |
| CDR2 | 66 | | | G | A | G | A |
| CDR3 | 100 | D | ↓ | D | ↓ | | |
| CDR3 | 101 | Y | ↓ | D | B | G | A |
| CDR3 | 102 | | | Y | ↓ | L | A |
| CDR3 | 104 | | | G | A | T | A |
| CDR3 | 105 | | | | | L | B |
| CDR3 | 106 | G | A | G | A | D | ↓ |
| CDR3 | 107 | | | T | A | Y | B |

The results showed that in variable region of different antibodies, mutating G, S and a portion of T to C had less effect on the binding activity as compared to the wild type antibody, which was 90% or more of the original binding activity. Mutating A, I and a portion of T to C produced a binding activity which was 70-90% of the binding activity of the wild type antibody.

Figure 2:
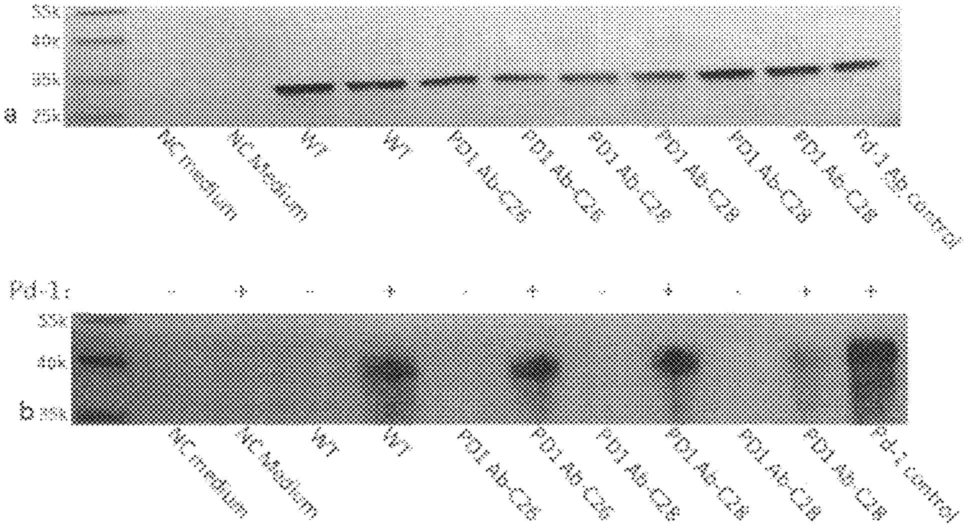
FIG. 2: Co-IP screening for point mutation in the light chain of anti-PD1 antibody.

Results obtained from Co-IP screening for point mutation on light chain of anti-PD1 antibody 1 are shown in FIG. 2, wherein panel a shows the effect of mutation of a wild-type antibody on expression detected by WB, and panel b shows the binding of the mutated antibody to PD1 detected by WB.

Analysis on the Binding Activity of Mutant of Antibody Having Mutation in CDR after Binding to R4

As shown in Tables 7-16, antibodies having mutation in CDR of a light chain or a heavy chain were conjugated to R4 in a library of small molecules for conjugation, and their binding activities were compared to wild type antibodies (binding activity of a conjugate to antibody/binding activity of wild type antibody*100%) to obtain a conjugation manner which would provide intermolecular force and enhance the binding activity.

TABLE 7

| Binding effect of mutants of anti-PD-1 antibody 1 having mutation in CDR of a light chain after conjugating to R4-1 or R4-5 | | | | |
|---|---|---|---|---|
| CDR | Position | anti-PD-1 antibody 1 | Conjugating to R4-1 | Conjugating to R4-5 |
| CDR 1 | 26 | S | 93.2% | |
| CDR 1 | 30 | S | 86.9% | |
| CDR 1 | 31 | T | 84.4% | |
| CDR 1 | 28 | G | 104.6% | 107.6% |
| CDR 1 | 35 | S | 88.3% | |
| CDR 1 | 36 | Y | 85.4% | |
| CDR 1 | 55 | A | 92.1% | |
| CDR 2 | 57 | Y | 87.7% | |
| CDR 2 | 60 | S | 89.4% | |
| CDR 3 | 104 | G | 83.6% | |

TABLE 8

| Binding effect of mutants of anti-PD-1 antibody 1 having mutation in CDR of a heavy chain after conjugating to R4 | | | | | |
|---|---|---|---|---|---|
| CDR | Position | anti-PD-1 antibody 1 | Conjugating to R4-1 | Conjugating to R4-4 | Conjugating to R4-7 |
| CDR 1 | 30 | T | 91.2% | | |
| CDR 1 | 32 | Y | | 89.5% | |

TABLE 8-continued

| Binding effect of mutants of anti-PD-1 antibody 1 having mutation in CDR of a heavy chain after conjugating to R4 | | | | | |
|---|---|---|---|---|---|
| CDR | Position | anti-PD-1 antibody 1 | Conjugating to R4-1 | Conjugating to R4-4 | Conjugating to R4-7 |
| CDR 2 | 50 | G | 84.4% | | |
| CDR 2 | 54 | S | 103.6% | | |
| CDR 2 | 58 | T | 93.9% | | |
| CDR 2 | 63 | K | | | 95.2% |
| CDR 3 | 101 | Y | | 86.1% | |
| CDR 3 | 106 | G | 95.1% | | |

According to Tables 7 and 8, after mutating A, G, S, Y, T or K in the CDRs of anti-PD-1 antibody 1 to C and binding to R4, the mutants could retain a binding efficiency of >80%.

TABLE 9

| Binding effect of mutants of anti-PD-1 antibody 2 having mutation in CDR of a light chain after conjugating to R4-1 or R4-5 | | | | |
|---|---|---|---|---|
| CDR | Position | anti-PD-1 antibody 2 | Conjugating to R4-1 | Conjugating to R4-5 |
| CDR 1 | 25 | A | 26.5% | 87.2% |
| CDR 1 | 26 | S | 86.8% | |
| CDR 1 | 28 | S | 88.9% | |
| CDR 1 | 30 | S | 34.4% | |
| CDR 1 | 31 | S | 95.7% | |
| CDR 1 | 32 | Y | 25.6% | |
| CDR 1 | 33 | L | 1.6% | |
| CDR 1 | 34 | A | 1.7% | 83.9% |
| CDR 2 | 51 | A | 95.6% | |
| CDR 2 | 52 | S | 34.6% | |
| CDR 2 | 55 | A | 99.5% | |
| CDR 2 | 56 | T | | 89.4% |
| CDR 3 | 57 | G | 89.8% | |
| CDR 3 | 91 | S | 93.5% | |
| CDR 3 | 92 | S | 45.5% | |
| CDR 3 | 97 | T | 93.7% | |

TABLE 10

| Binding effect of mutants of anti-PD-1 antibody 2 having mutation in CDR of a heavy chain after conjugating to R4 | | | | | | |
|---|---|---|---|---|---|---|
| CDR | Position | anti-PD-1 antibody 2 | Conjugating to R4-1 | Conjugating to R4-3 | Conjugating to R4-4 | Conjugating to R4-7 |
| CDR 1 | 30 | S | 107.2% | | | |
| CDR 1 | 32 | S | 86.8% | | | |
| CDR 1 | 33 | G | 88.9% | | | |
| CDR 2 | 53 | Y | | | 91.6% | |
| CDR 2 | 55 | G | 95.7% | | | |
| CDR 2 | 56 | S | 105.6% | | | |
| CDR 2 | 57 | K | | | | 89.7% |
| CDR 2 | 61 | A | 87.0% | | 83.9% | |
| CDR 2 | 63 | S | 95.6% | | | |
| CDR 2 | 65 | K | | | | 92.1% |
| CDR 2 | 66 | G | 99.5% | | | |
| CDR 3 | 104 | G | 89.4% | | | |
| CDR 3 | 106 | G | 91.8% | | | |
| CDR 3 | 107 | T | 95.7% | | | |
| CDR 3 | 108 | L | | 86.4% | | |

According to Tables 9 and 10, after mutating G, S, A, Y, K, L or T in the CDRs of anti-PD-1 antibody 2 to C and binding to R4, the mutants could retain a binding efficiency of >80%.

TABLE 11

| Binding effect of mutants of anti-CTLA-4 antibody having mutation in CDR of alight chain after conjugating to R4-1 | | | |
|---|---|---|---|
| CDR | Position | Anti-CTLA-4 Antibody | Conjugating to R4-1 |
| CDR 1 | 25 | A | 95.40% |
| CDR 1 | 26 | S | 91.00% |
| CDR 1 | 28 | S | 82.00% |
| CDR 1 | 30 | G | 95.30% |
| CDR 1 | 31 | S | 80.90% |
| CDR 1 | 32 | S | 99.00% |
| CDR 1 | 34 | L | 94.90% |

TABLE 11-continued

| Binding effect of mutants of anti-CTLA-4 antibody having mutation in CDR of alight chain after conjugating to R4-1 | | | |
|---|---|---|---|
| CDR | Position | Anti-CTLA-4 Antibody | Conjugating to R4-1 |
| CDR 1 | 35 | A | 91.50% |
| CDR 2 | 51 | G | 97.00% |
| CDR 2 | 52 | A | 92% |
| CDR 2 | 54 | S | 97.70% |
| CDR 2 | 56 | A | 102.30% |
| CDR 2 | 57 | T | 92.50% |
| CDR 2 | 58 | G | 88.10% |
| CDR 3 | 93 | G | 99.10% |
| CDR 3 | 94 | S | 92.40% |
| CDR 3 | 95 | S | 95.40% |
| CDR 3 | 98 | T | 91.00% |

TABLE 12

| Binding effect of mutants of anti-CTLA-4 antibody having mutation in CDR of a heavy chain after conjugating to R4 | | | | | | |
|---|---|---|---|---|---|---|
| CDR | Position | Anti-CTLA-4 Antibody | Conjugating to R4-1 | Conjugating to R4-3 | Conjugating to R4-4 | Conjugating to R4-7 |
| CDR 1 | 30 | S | 93.4% | | | |
| CDR 1 | 31 | S | 109.5% | | | |
| CDR 1 | 33 | T | 102.3% | | | |
| CDR 2 | 55 | G | 95.2% | | | |
| CDR 2 | 58 | K | | | | 87.6% |
| CDR 2 | 59 | Y | | | 89.1% | |
| CDR 2 | 60 | Y | | | 91.8% | |
| CDR 2 | 65 | K | | | | 96.2% |
| CDR 2 | 66 | G | 92.7% | | | |
| CDR 3 | 100 | G | 98.3% | | | |
| CDR 3 | 102 | L | | 83.9% | | |
| CDR 3 | 103 | G | 93.8% | | | |
| CDR 3 | 106 | D | | 87.6% | | |

According to Tables 11 and 12, after mutating A, G, S, L, T, K, Y or D in the CDRs of anti-CTLA-4 antibody to C and binding to R4, the mutants could retain a binding efficiency of >80%.

TABLE 13

Binding effect of mutants of anti-CD28 antibody having mutation in CDR of a light chain after conjugating to R4

| CDR | Position | anti-CD28 antibody | Conjugating to R4-1 | Conjugating to R4-3 | Conjugating to R4-4 | Conjugating to R4-7 |
|---|---|---|---|---|---|---|
| CDR 1 | 26 | S | 87.0% | | | |
| CDR 1 | 29 | I | | 88.5% | | |
| CDR 1 | 30 | Y | 19.5% | | 93.6% | |
| CDR 2 | 50 | K | 26.6% | | | 88.9% |
| CDR 2 | 51 | A | 97.7% | | | |
| CDR 2 | 52 | S | 84.0% | | | |
| CDR 3 | 91 | G | 88.3% | | | |
| CDR 3 | 93 | T | 87.0% | | | |
| CDR 3 | 94 | Y | 20.1% | | 83.7% | |
| CDR3 | 96 | Y | 14.9% | | 91.4% | |
| CDR 3 | 97 | T | 95.5% | | | |
| CDR 3 | 99 | G | 96.6% | | | |

TABLE 14

Binding effect of mutants of anti-CD28 antibody having mutation in CDR of a heavy chain after conjugating to R4

| CDR | Position | anti-CD28 antibody | Conjugating to R4-1 | Conjugating to R4-3 | Conjugating to R4-4 |
|---|---|---|---|---|---|
| CDR 1 | 25 | S | 87.0% | | |
| CDR 1 | 26 | G | 89.5% | | |
| CDR 1 | 27 | Y | | | 94.2% |
| CDR 1 | 28 | T | 108.6% | | |
| CDR 1 | 30 | T | 87.3% | | |
| CDR 1 | 31 | S | 97.5% | | |
| CDR 1 | 32 | Y | | | 81.8% |
| CDR 2 | 52 | Y | | | 91.6% |
| CDR 2 | 54 | G | 97.9% | | |
| CDR 2 | 58 | T | 89.3% | | |
| CDR 3 | 99 | S | 87.6% | | |
| CDR 3 | 101 | Y | | | 89.3% |
| CDR 3 | 102 | G | 80.1% | | |
| CDR 3 | 103 | L | 14.9% | 94.6% | |

According to Tables 13 and 14, by binding mutation position of G, S, A, I, L, K, Y or T in the CDRs of anti-CD28 antibody to R4, the mutants could retain a binding efficiency of >80%.

TABLE 15

Binding effect of mutants of anti-TNFα antibody having mutation in CDR of a light chain after conjugating to R4

| CDR | Position | anti-TNFα antibody | Conjugating to R4-1 | Conjugating to R4-3 | Conjugating to R4-4 |
|---|---|---|---|---|---|
| CDR 1 | 25 | A | 88.6% | | |
| CDR 1 | 26 | S | 97.1% | | |
| CDR 1 | 28 | G | 92.3% | | |
| CDR 1 | 29 | I | | 87.8% | |
| CDR 1 | 32 | Y | | | 89.1% |
| CDR 1 | 33 | L | | 89.4% | |
| CDR 1 | 34 | A | 85.7% | | |
| CDR 2 | 50 | A | 85.5% | | |
| CDR 2 | 51 | A | 95.1% | | |
| CDR 2 | 52 | S | 86.8% | | |
| CDR 2 | 53 | T | 89.4% | | |
| CDR 2 | 54 | L | | 82.2% | |
| CDR 2 | 56 | S | 95.4% | | |
| CDR 2 | 57 | G | 95.5% | | |
| CDR 3 | 91 | Y | 34.5% | | 90.1% |

TABLE 15-continued

Binding effect of mutants of anti-TNFα antibody having mutation in CDR of a light chain after conjugating to R4

| CDR | Position | anti-TNFα antibody | Conjugating to R4-1 | Conjugating to R4-3 | Conjugating to R4-4 |
|---|---|---|---|---|---|
| CDR 3 | 94 | A | 97.5% | | |
| CDR 3 | 97 | T | 82.5% | | |

TABLE 16

Binding effect of mutants of anti-TNFα antibody having mutation in CDR of a heavy chain after conjugating to R4

| CDR | Position | anti-TNFα antibody | Conjugating to R4-1 | Conjugating to R4-3 | Conjugating to R4-4 |
|---|---|---|---|---|---|
| CDR 1 | 32 | Y | | | 88.6% |
| CDR 1 | 33 | A | 95.1% | | |
| CDR 2 | 51 | I | | 102.6% | |
| CDR 2 | 52 | T | 82.8% | | |
| CDR 2 | 55 | S | 86.9% | | |
| CDR 2 | 56 | G | 88.7% | | |
| CDR 2 | 58 | I | | 86.7% | |
| CDR 2 | 60 | Y | | | 85.2% |
| CDR 2 | 61 | A | 95.7% | | |
| CDR 2 | 63 | S | 96.8% | | |
| CDR 2 | 66 | G | 99.4% | | |
| CDR 3 | 100 | S | 92.2% | | |
| CDR 3 | 101 | Y | | | 85.4% |
| CDR 3 | 102 | L | | 85.5% | |
| CDR 3 | 103 | S | 84.5% | | |
| CDR 3 | 104 | T | 97.3% | | |
| CDR 3 | 105 | A | 86.5% | | |
| CDR 3 | 106 | S | 98.3% | | |
| CDR 3 | 107 | S | 87.4% | | |
| CDR 3 | 108 | L | | 81.4% | |
| CDR 3 | 110 | Y | | | 82.5% |

According to Tables 13 and 14, after mutating A, G, S, L, I, Y or T in the CDRs of anti-TNFα antibody to C and binding to R4, the mutants could retain a binding efficiency of >80%.

Example 3: Analysis on the Binding Activity of Mutants Having a Mutation in a Sequence of High Homology in the Non-CDR of a Variable Region and Screening for R1

Figure 3:
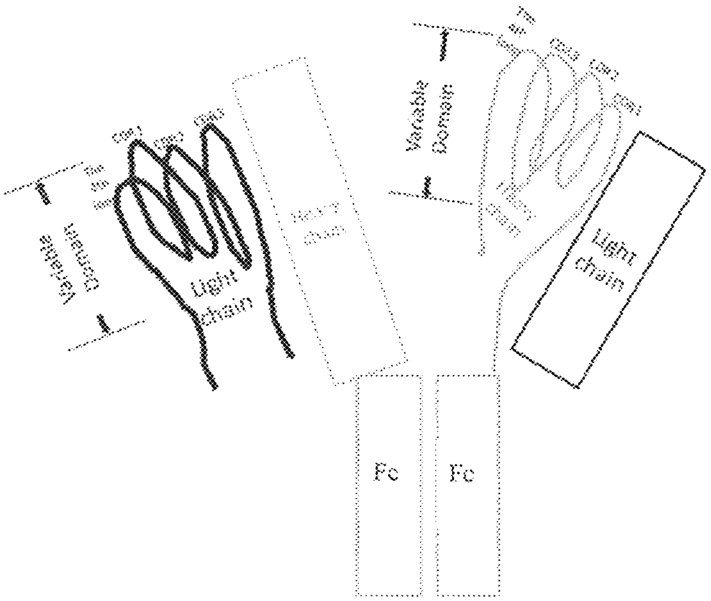
FIG. 3: Structure of antibody.

An antibody consists of 4 peptide chains, including two identical light chains (LC) and two identical heavy chains (HC). The chains form a monomer by disulfide bond(s) and non-covalent bonds. There are two types of light chains, i.e., κ and λ, and five types of heavy chains, i.e., μ, δ, γ, ε and α. An antibody, as a whole, is divided into a constant region and a variable region. The variable region is located at the terminus of the two arms of the Y-shaped structure. Humanized or human antibodies have a certain generality, that is, they all contain 4 loops in heavy chain or light chain at the terminus of the two arms of the Y-shaped structure (FIG. 3). Three loops are highly variable and directly anticipate in binding to an antigen. The regions in these loops are termed CDRs, wherein CDR1, CDR2 and CDR3 are present in these three loops, respectively. Another loop is also present at the same side where antibody binds to antigen from the four-dimensional space. Some loops not only have a conservative structure but also have a conservative sequence.

Figure 4:
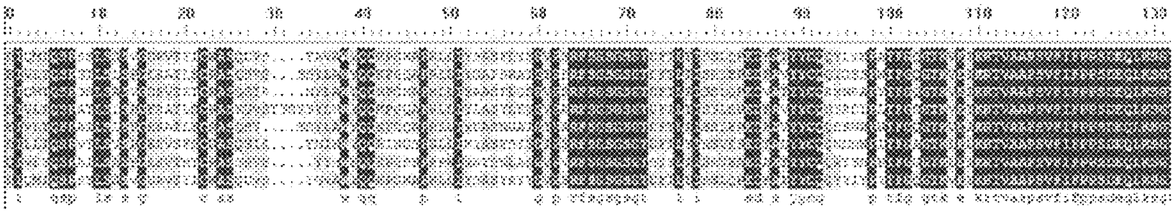
FIG. 4: The sequences of loop 4 in the variable region are conservative (From top to bottom: SEQ ID NO: 32, SEQ ID NO: 14, SEQ ID NO: 30, SEQ ID NO: 16, SEQ ID NO: 18, SEQ ID NO: 88, SEQ ID NO: 63 and SEQ ID NO: 89).

Light chains from 8 commercial antibodies (Tecentriq® (atezolizumab), Yervoy® (ipilimumab), Humira® (adalimumab), Keytruda® (pembrolizumab), Opdivo® (nivolumab), Erbitux® (cetuximab), Rituxan® (rituximab) and Perjeta® (pertuzumab), respectively, shown in the first to the last antibody of FIG. 4) were aligned and the results were shown in FIG. 4. The fourth loop in the variable region of each light chain (GSGSGST) was conservative.

There were 4 loops at the same side of the CDR of the light chain of anti-PD-1 antibody, wherein 3 loops were CDRs, including CDR1, CDR2 and CDR3. The remaining loop had a structure and a sequence which was conservative compared to many drugs approved by FDA. The sequence of this loop was RFSGSGSGT, located at positions 64-72 (FIG. 4). Each of the amino acid residues in loop 4 of anti-PD-1 antibody 1 was mutated to Cys and conjugated to S9 or S13. Effect of conjugation to R1-R4 of different length on binding activity of the mutant to PD-1 was detected by ELISA. Results were shown in Table 17. It could be found that 70% or more of an activity of the mutants may be inhibited by varying the steric structure or length of a conjugating arm.

TABLE 17

Binding activity of conjugates of anti-PD-1 antibody 1 having a mutation in loop 4 of a variable region of a light chain

| | Position | Residue | Binding Activity | Conjugating to S9 | Conjugating to S13 |
|---|---|---|---|---|---|
| Loop 4 | 67 | S | 87.8% | 27.2% | 17.8% |
| Loop 4 | 68 | G | 93.5% | 89.9% | 13.2% |
| Loop 4 | 69 | S | 96.1% | 90.6% | 16.2% |
| Loop 4 | 70 | G | 89.3% | 65.2% | 17.9% |
| Loop 4 | 71 | S | 99.5% | 89.0% | 16.0% |
| Loop 4 | 72 | G | 98.3% | 92.9% | 10.9% |
| Loop 4 | 73 | T | 93.5% | 90.2% | 10.6% |

Figure 5:
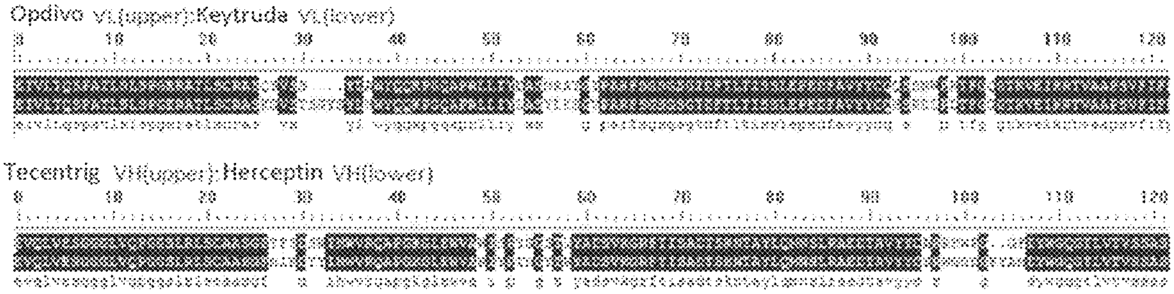
FIG. 5: Variable regions of two antibodies may come from the variable region framework of antibodies of same germline (From top to bottom: SEQ ID NO: 93, SEQ ID NO: 95, SEQ ID NO: 64 and SEQ ID NO: 80).

Antibody was produced by recombination of genes of immunoglobulin superfamily in vivo. Some framework regions of antibodies against different antigens may be derived from a gene or an amino acid sequence of a same germline antibody. For example, the heavy chain of an Her2 antibody, Herceptin® (trastuzumab) is different from that of Tecentriq® (atezolizumab), an anti-PD-1 antibody in the three CDRs. They have the same non-CDR framework sequence, which is derived from the same germline antibody (FIG. 5). Similar to the heavy chains of Herceptin® (trastuzumab) and Tecentriq, the light chains of Opdivo® (nivolumab) and Keytruda® (pembrolizumab), which are PD-1 antibodies, are different in the 3 CDRs in the variable region. Their non-CDR framework regions are derived from a same germline antibody (FIG. 5).

Figure 6:
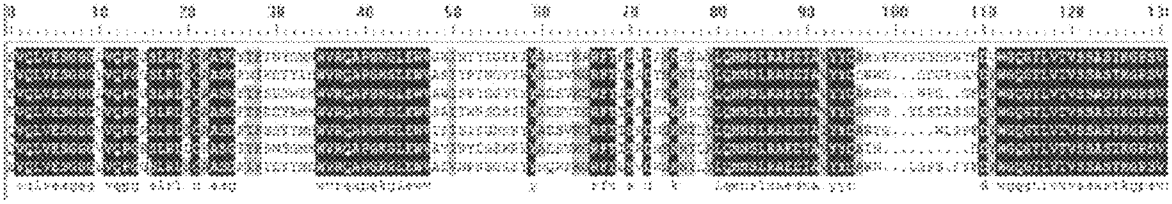
FIG. 6: Alignment of amino acid sequences of heavy chains of several antibodies (From top to bottom: SEQ ID NO: 60, SEQ ID NO: 27, SEQ ID NO: 31, SEQ ID NO: 29, SEQ ID NO: 13, SEQ ID NO: 17 and SEQ ID NO: 91).
Figure 7:
FIG. 7: Alignment of amino acid sequences of light chains of several antibodies (From top to bottom: SEQ ID NO: 93, SEQ ID NO: 95 and SEQ ID NO: 96).

Similar situation was found in many antibodies. As exemplified by reshaping antibodies (also called CDR-implanted antibodies) approved by FDA, to retain their specificity to an antigen and reduce heterology, the CDRs from murine derived antibody was directly replaced by CDRs from human derived antibody. As maturation of humanization technology and genetic engineering technology, the humanized antibodies later developed were mainly the humanized antibodies or human antibodies. However, even so, the heavy chains of many commercial antibodies still exhibit very high similarity. For example, FIG. 6 shows the comparison results for similarity of heavy chains of 7 commercial antibodies Avastin® (bevacizumab), Herceptin® (trastuzumab), Tecentriq® (atezolizumab), Humira® (adalimumab), Yervoy® (ipilimumab), Opdivo® (nivolumab) and Perjeta® (pertuzumab), shown in the first to the last antibody in FIG. 6), which is 85% or more. They are different from each other mainly in the CDRs and their framework regions in the variable regions have similar sequences. Even more, the framework structures of Tecentriq® (atezolizumab) and Herceptin® (trastuzumab) are identical (FIG. 5). After comparing the light chain variable regions of immune checkpoint antibodies, Opdivo® (nivolumab), Keytruda® (pembrolizumab) and Yervoy® (ipilimumab) (the first to the last antibody shown in FIG. 7, respectively), it could be found that their homology is 92%. The main difference is in the CDRs and the sequences in their framework regions are close to each other (FIG. 7).

Figure 8:
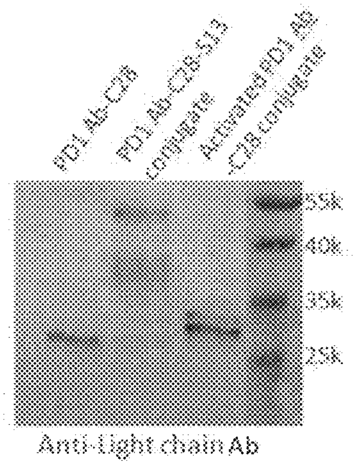
FIG. 8: Conjugation of PD1 Ab-C28.
Figure 9:
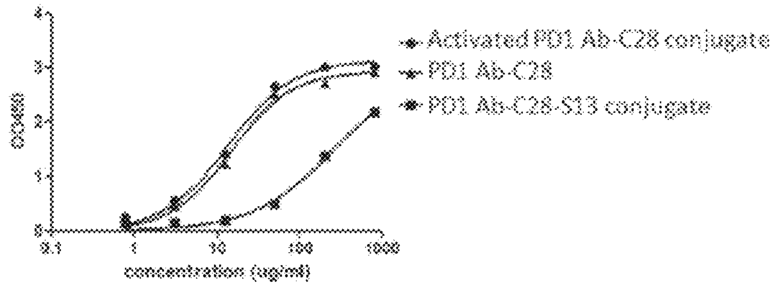
FIG. 9: Binding of the PD1 Ab-C28 conjugate to PD1 before and after activation.

For antibodies having a conservative framework region, activities of their mutants having a mutation in a framework region (non-CDR) of heavy or light chain variable region and conjugates thereof were tested. Each of the amino acid positions shown in tables 18 and 19 was mutated to cysteine and each of the resulted mutants was conjugated to S9 or S13. Effect of conjugation to a R1-R4 side chain having a different length on its binding activity to PD-1 was tested by ELISA. Results were shown in Tables 18 and 19. FIG. 8 shows conjugation of PD1 Ab-C28 (PD1-Ab-Gly28Cys) to 513, and FIG. 9 shows the binding of anti-PD1-Ab-C28 to PD1 before and after conjugating to S13.

TABLE 18

Binding activities of mutant of anti-PD-1 antibody 1 having a mutation in a framework region of a light chain variable region and conjugates thereof

| Position | Amino acid residue | Binding activity after mutation | Conjugating to S9 | Conjugating to S13 |
|---|---|---|---|---|
| 5 | T | 95.3% | 67.4% | 26.30% |
| 7 | S | 98.2% | 59.5% | 34.20% |
| 9 | A | 96.5% | 78.4% | 44.60% |
| 10 | T | 84.3% | 65.7% | 37.40% |
| 11 | L | 96.3% | 32.50% | |
| 12 | S | 85.5% | 13.50% | |
| 13 | L | 97.5% | 80.2% | 42.30% |
| 14 | S | 97.8% | 19.7% | |
| 16 | G | 89.4% | 75.3% | 21.70% |
| 19 | A | 86.4% | 49.9% | 25.00% |
| 20 | T | 89.7% | 69.7% | 32.10% |

TABLE 18-continued

Binding activities of mutant of anti-PD-1 antibody 1 having a mutation in a framework region of a light chain variable region and conjugates thereof

| Position | Amino acid residue | Binding activity after mutation | Conjugating to S9 | Conjugating to S13 |
|---|---|---|---|---|
| 25 | A | 83.3% | 70.3% | 37.20% |
| 41 | G | 88.5% | 17.4% | |
| 43 | A | 99.3% | 82.1% | 30.80% |
| 46 | L | 95.9% | 80.2% | 37.50% |
| 47 | L | 81.1% | 68.9% | 22.90% |
| 48 | I | 89.5% | 23.8% | |
| 51 | A | 92.1% | 82.1% | 31.2% |
| 55 | A | 87.3% | 72.3% | 29.4% |
| 69 | T | 83.4% | 67.9% | 20.5% |
| 76 | S | 90.2% | 68.7% | 21.9% |
| 77 | S | 83.8% | 69.3% | 32.1% |
| 106 | I | 98.3% | 76.7% | 26.8% |
| 107 | K | 87.1% | 70.1% | 35.6% |

TABLE 19

Binding activities of mutant of anti-PD-1 antibody 2 having a mutation in a framework region of a heavy chain variable region and conjugates thereof

| Position | Amino acid residue | Binding activity after mutation | Conjugating to S9 | Conjugating to S13 |
|---|---|---|---|---|
| 7 | S | 95.3% | 65.9% | 26.3% |
| 8 | G | 93.2% | 78.3% | 34.2% |
| 9 | G | 97.8% | 87.4% | 24.6% |
| 10 | G | 84.3% | 69.3% | 37.4% |
| 15 | G | 85.6% | 32.50% | 21.5% |
| 17 | S | 85.0% | 75.3% | 42.4% |
| 24 | A | 99.6% | 45.6% | 32.3% |
| 25 | S | 99.8% | 48.7% | 27.0% |
| 26 | G | 95.4% | 31.8% | 11.7% |
| 28 | T | 86.4% | 29.9% | 15.0% |
| 30 | S | 89.7% | 31.8% | 15.3% |
| 40 | A | 85.3% | 50.3% | 37.2% |
| 42 | G | 83.4% | 63.6% | 29.8% |
| 44 | G | 99.3% | 78.3% | 30.8% |
| 69 | T | 95.9% | 78.6% | 37.5% |
| 71 | S | 81.4% | 56.9% | 22.9% |
| 75 | S | 96.3% | 38.7% | 14.6% |
| 78 | T | 92.2% | 86.3% | 42.4% |
| 85 | S | 98.8% | 69.4% | 32.3% |
| 88 | A | 84.3% | 46.8% | 27.0% |
| 91 | T | 86% | 48.9% | 21.7% |
| 92 | A | 85.0% | 64.6% | 15.0% |
| 98 | T | 89.6% | 59.9% | 32.1% |
| 110 | T | 92.1% | 78.4% | 37.2% |
| 112 | S | 95.4% | 68.6% | 29.8% |
| 113 | S | 96.0% | 70.5% | 30.8% |
| 114 | A | 89.7% | 66.9% | 37.5% |
| 115 | S | 95.3% | 70.4% | 22.9% |
| 116 | T | 93.4% | 69.5% | 14.6% |
| 118 | G | 99.3% | 72.5% | 31.3% |
| 120 | S | 95.9% | 68.4% | 36.8% |

Analysis on the binding activities of mutants having a mutation in a non-CDR region of an antibody variable region showed that there was no significant effect on the binding activity when a mutation was introduced into a non-CDR and when the mutant was conjugated to a small conjugating molecule S9. However, when the mutant was conjugated to S13, the binding activity was reduced. These indicate that amino acid residue in a non-CDR could be mutated to cysteine and then the mutant could be conjugated to a R1-R2-R3-R4 having a large molecule weight or bearing a specific functional group to block the binding activity of the mutant. With this method, the activity of the mutant could be inhibited.

Anti-PD 1 antibodies having two or more mutations in light chain were prepared and conjugated to S13. The mutation sites were selected from the mutation sites of the aforementioned anti-PD1 antibody having one mutation and having 95% or more binding activity to PD1 antigen. The activity of such conjugates after activation was verified and the results were shown in Table 20.

TABLE 20

Binding activity of conjugates of anti-PDl antibody 1 with two or more mutations to PD1 before and after activation

| R1-R2-R3-R4 | R5 | Binding efficiency before activation | Binding efficiency after enzymatic or acidic activation |
|---|---|---|---|
| S13 | PD1 Ab-Ser7/Ser71 | 18.1% | 109.5% |
| S13 | PD1 Ab-Ser12/Gly72 | 19.6% | 95.3% |
| S13 | PD1 Ab-Ser14/Thr73 | 10.2% | 99.8% |
| S13 | PD1 Ab-Ser7/Ser14/Thr73 | 11.9% | 95.1% |

The above results demonstrate that conjugates of anti-PD1 antibody with two or more mutations could retain 95% or more binding activity to PD1 after activation.

Example 4: Screening for Biomolecule R5, Conjugation to R1, R2-R3-R4, and Activation after Conjugation During activation by a proteolytic enzyme in a pathological microenvironment, the site at which the activated linker arm binds to the biomolecule and its steric conformation has different effects on activation efficiency. Steric hindrance and structure-activity relationship determine an effect of cleavage by activation. To investigate an effect of the biomolecular conformation of conjugates of Example 3 in a pathological environment on activation by an enzyme or an acid in the pathological environment, the following in vitro activation investigations were performed.

In the activation test, 10 micrograms of a proteolytic enzyme for activation were added to 1 mg/ml Peg1000-R2-R3-R4-S-Cys-R5 conjugate for reaction for 1 hour at 37° C. The concentration of small compound Peg1000 produced after activation was detected by HPLC and activation or cleavage efficiency (%) in relative to a control group was calculated. Cleavage efficiency of each conjugate is shown in the following Table 21.

TABLE 21

| Mutant | R1 | R2 | R3 | R4 | Cleavage efficiency |
|---|---|---|---|---|---|
| PD-1-Ab-Gly28Cys | Peg1000 | -Ala-Ala-Asn- | | | Control, 100% |
| PD-1-Ab-Gly28Cys | Peg1000 | -Ala-Ala-Asn- | R3-1 | R4-3 | 99.5 |
| PD-1-Ab-Gly28Cys | Peg1000 | -Ala-Ala-Asn- | R3-2 | R4-3 | 99.8 |
| PD-1-Ab-Gly28Cys | Peg1000 | -Ala-Ala-Asn- | R3-3 | R4-3 | 98.6 |

As shown in Tables 22 and 23, the automatically shedding arm R3 substantially had no effect on the activation of Legumain due to its small molecular weight and linear structure, with R3-2 producing the lowest effect.

TABLE 22

| anti-PD-1 antibody 1 | | | | |
|---|---|---|---|---|
| R2 | R3 | R4 | R5 | Cleavage efficiency |
| -Ala-Ala-Asn- | R3-2 | | | Control, 100% |
| -Ala-Ala-Asn- | R3-2 | Paclitaxel (2-OH) | | 42.5 |
| -Ala-Ala-Asn- | R3-2 | R4-5 | PD-1-Ab1-Gly28Cys | 88.4 |
| -Ala-Ala-Asn- | R3-2 | R4-6 | PD-1-Ab1-Gly28Cys | 93.5 |
| -Ala-Ala-Asn- | R3-2 | R4-7 | PD-1-Ab1-Gly28Cys | 99.8 |
| -Ala-Ala-Asn- | R3-2 | R4-8 | PD-1-Ab1-Gly28Cys | 63.5 |
| -Ala-Ala-Asn- | R3-2 | R4-9 | PD-1-Ab1-Gly28Cys | 62.4 |
| -Ala-Ala-Asn- | R3-2 | R4-1 | PD-1-Ab1-Gly28Cys | 83.8 |
| -Ala-Ala-Asn- | R3-2 | R4-3 | PD-1-Ab1-Gly28Cys | 94.5 |
| -Ala-Ala-Asn- | R3-2 | R4-1 | PD-1-Ab1-Gly28Cys | 86.7 |
| -Ala-Ala-Asn- | R3-2 | R4-3 | PD-1-Ab1-Gly28Cys | 97.5 |

TABLE 23

| anti-CTLA-4 antibody | | | | |
|---|---|---|---|---|
| Acidic activation | R3 | R4 | R5 | Cleavage efficiency |
| Amide bond linkage | R3-2 | | | Control, 100% |
| Amide bond linkage | R3-2 | R4-2 | CTLA-4-Ser26Cys | 99.8 |
| Amide bond linkage | R3-2 | R4-15 | CTLA-4-Ser26Cys | 99.5 |
| Amide bond linkage | R3-2 | R4-16 | CTLA-4-Ser26Cys | 91.7 |
| Amide bond linkage | R3-2 | R4-17 | CTLA-4-Ser26Cys | 94.3 |
| Amide bond linkage | R3-2 | R4-18 | CTLA-4-Ser26Cys | 93.4 |
| Ester bond | R3-2 | | | Control, 100% |

TABLE 23-continued

| anti-CTLA-4 antibody | | | | |
|---|---|---|---|---|
| Acidic activation | R3 | R4 | R5 | Cleavage efficiency |
| Ester bond | R3-2 | R4-4 | CTLA-4-Ser26Cys | 92.8 |
| Ester bond | R3-2 | R4-19 | CTLA-4-Ser26Cys | 97.4 |
| Ester bond | R3-2 | R4-20 | CTLA-4-Ser26Cys | 93.8 |
| Ester bond | R3-2 | R4-21 | CTLA-4-Ser28Cys | 95.4 |
| Ester bond | R3-2 | R4-22 | CTLA-4-Ser28Cys | 96.4 |

In Tables 22 and 23, the activation efficiency produced by molecules without conjugating with the biomolecule was used as a positive control, while the activation efficiency produced by molecules with conjugation to a hydroxyl at position 2 of a heterocyclic compound Paclitaxel was used as a negative control. The length and side chain group of R4 affected the cleavage efficiency of the whole conjugate when conjugating to a mutation site in a variable region or a non-variable region of an antibody. A longer chain structure of R4 produced enhanced cleavage efficiency. As detected, after conjugating to Ala-Ala-Asn or Ala-Ala-Asp and then binding to antibody, R4-1 to R4-25 of the present disclosure all allowed the mutants to retain >60% of the activation efficiency, and >90% of the activation efficiency in an acid-sensitive activation.

Effect of R1 Selection and Test for Recovery of Binding Capacity

PBS (pH 7.2) was used to dilute ligand molecules PD1, TNFα, CTLA-4, CD28 to lug/ml, respectively. Then each of the diluted solutions was used to fix in a 96-well plate (Nunc) overnight. 1× block BSA (ThermoFisher) was used to block the plate for 2h. Corresponding conjugate of anti-PD-1 antibody, anti-TNFα antibody, anti-CTLA-4 antibody and anti-CD28 antibody was added, respectively, in an equal concentration, and allowed to bind at 37° C. for one hour. The plate was washed with PBST three times. HRP enzyme-conjugated human antibody used as secondary antibody was allowed to react at 37° C. for 1 hour and then washed with PBST three times. TMB substrate (Solarbio., Inc.) recognized by HRP enzyme was used for reaction at 37° C. for 15 minutes in dark. A ½ volume of stopping solution was used to stop the reaction. Absorbance strength (OD450) was read. The relative binding efficiency was calculated by a percentage ratio between the binding efficiency of the conjugate and the binding efficiency of the wild type antibody before or after activation. The results were shown in Tables 24-26.

TABLE 24

| Change of the binding activity of anti-PD-1 antibody after conjugating to R1 and after activating the conjugating arm | | | | | | |
|---|---|---|---|---|---|---|
| R1 | R2 | R3 | R4 | R5 | Binding efficiency before activation | Binding efficiency after activating by enzyme or acid |
| | -Ala-Ala-Asn- | R3-2 | R4-3 | PD-1-Ab1-Gly28Cys | 67.4% | 143.5% |
| R1 from S1 | -Ala-Ala-Asn- | R3-2 | R4-3 | PD-1-Ab1-Gly28Cys | 24.4% | 145.3% |
| R1 from S3 | -Ala-Ala-Asn- | R3-2 | R4-3 | PD-1-Ab1-Gly28Cys | 22.5% | 143.4% |
| R1 from S11 | -Ala-Ala-Asn- | R3-2 | R4-3 | PD-1-Ab1-Gly28Cys | 15.6% | 137.4% |
| R1 from S17 | -Ala-Ala-Asn- | R3-2 | R4-3 | PD-1-Ab1-Gly28Cys | 3.2% | 156.3% |

The results indicate that conjugating to R1 inhibits the activity of the anti-PD-1 antibody but does not affect the activation of the antibody. The binding efficiency of the conjugate without R1 to its antigen before activation was 67.4% of that of the wild type antibody to the antigen. However, after activation, the binding efficiency of the conjugate was improved to be 143% of that of the wild type antibody. After binding R1 to the same R2-R3-R4 and mutated antibody, it prevented the resultant conjugate from binding to its antigen. And the prevention of binding increased as the molecular weight of R1 increased. S17 could completely prevent the conjugate from binding to its antigen. However, the binding activity was recovered after cleaving by Legumain.

TABLE 25

Change of the binding activity of anti-TNFα antibody after conjugating to R1 and after activating the conjugating arm

| R1 | R2 | R3 | R4 | R5 | Binding efficiency before activation | Binding efficiency after activating by enzyme or acid |
|---|---|---|---|---|---|---|
| | -Ala-Ala-Asp- | R3-2 | R4-2 | TNFα-Ab-Ala50Cys | 57.9% | 125.6% |
| R1 from S2 | -Ala-Ala-Asp- | R3-2 | R4-2 | TNFα-Ab-Ala50Cys | 28.3% | 128.9% |
| R1 from S4 | -Ala-Ala-Asp- | R3-2 | R4-2 | TNFα-Ab-Ala50Cys | 21.9% | 127.5% |
| R1 from S12 | -Ala-Ala-Asp- | R3-2 | R4-2 | TNFα-Ab-Ala50Cys | 11.6% | 127.4% |
| R1 from S18 | -Ala-Ala-Asp- | R3-2 | R4-2 | TNFα-Ab-Ala50Cys | 0.9% | 125.3% |

The results indicate that conjugating to R1 inhibits the activity of the anti-TNFα antibody but does not affect the activation of the antibody. The binding efficiency of the conjugate without R1 to its antigen before activation was 57.9% of that of the wild type antibody to the antigen. However, after activation, the binding efficiency of the conjugate was 125.6% of that of the wild type antibody. After binding R1 to the same R2-R3-R4 and mutated antibody, it prevented the resultant conjugate from binding to its antigen. And the prevention of binding increased as the molecular weight of R1 increased. S18 could completely prevent the conjugate from binding to its antigen. However, the binding activity was recovered after cleaving by Legumain.

TABLE 26

Change of the binding activities of anti-CTLA-4 antibody and anti-CD28 antibody after conjugating to the conjugate and after activating the conjugating arm

| conjugating arm | R5 | Binding efficiency before activation | Binding efficiency after activating by enzyme or acid |
|---|---|---|---|
| S7 | CD28-Gly44Cys | 22.5% | 143.4% |
| S8 | CD28-Ala40Cys | 15.6% | 137.4% |
| S9 | CD28-Thr97Cys | 3.2% | 156.3% |
| S10 | CTLA-4-Ser26Cys | 67.4% | 143.5% |
| S13 | CTLA-4-Ser28Cys | 24.4% | 145.3% |
| S14 | CTLA-4-Tyr92Cys | 22.5% | 143.4% |
| S15 | CTLA-4-Leu34Cys | 15.6% | 137.4% |
| S16 | CTLA-4-Gly51Cys | 3.2% | 156.3% |

The results show that conjugating to R1 inhibits the activity of anti-CD28 antibody and anti-CTLA-4 antibody but does not affect the activation of the antibody.

Figure 10:
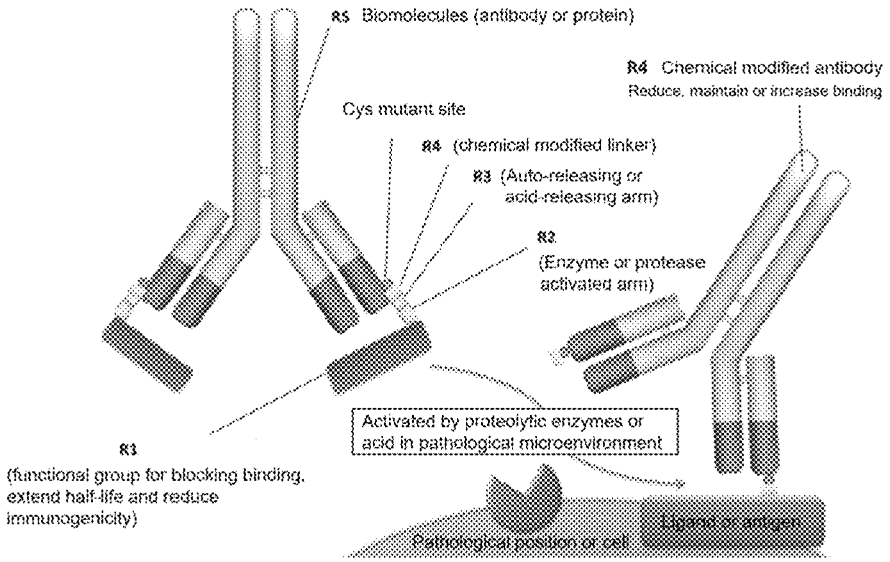
FIG. 10: Schematic drawing of conjugate of biomolecule which contains an activatable and binding arm and is activated in a pathologic microenvironment.

From Example 4, it could be found that the activation efficiency of a conjugate and its binding capacity to antigen after recovery were influenced by the mutation position in the antibody to some extent. However, with the use of R4 expected activation efficiency by enzymatic cleavage could be produced. As for the binding between a biomolecule and its ligand, the exposed group of R4 produced after cleavage by activation could regulate the binding capacity of an antibody mutant. Different exposed groups had different effects on different mutation positions. By screening for R1 and D4, it could be found that the hindering function of R1 led to complete loss of binding capacity of a conjugate to its antigen. However, the binding capacity was recovered or even enhanced after target cleavage by an enzyme. Such conjugate-type antibodies are only activated in a region that a target enzyme is highly expressed or secreted in a pathological microenvironment to release the antibody or protein. Thus, such microenvironment-activated antibodies are new target-activated antibodies as shown in FIG. 10.

Example 5: Promotion or Inhibition of Antibody on Immune Indexes

1. Anti-PD-1 Antibody Promoted T Cells to Secrete IFN-γ

Figure 11:
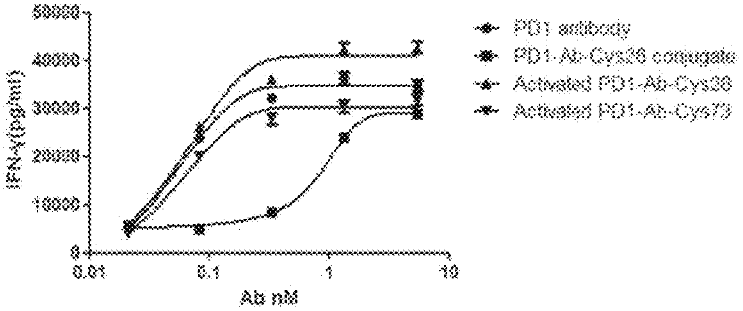
FIG. 11: Secretion of IFN-gamma.

Human whole blood (from Shang Ruijin Hospital) was diluted and uniformly mixed with PBS in an equal amount. The diluted solution was slowly transferred to another centrifugal tube containing lymphocyte separation solution along the wall of the centrifugal tube to allow the diluted solution to form a separated layer on the lymphocyte separation solution. The interface was kept clear. The tube was centrifuged at 2000 rpm for 20 minutes. After centrifugation, the centrifugal tube was taken out. The solution within the tube was layered. A mononuclear cell layer was extracted to a 50 ml centrifugal tube. Five-time volume of PBS was added and uniformly mixed and the mixture was centrifuged at 2000 rpm for 10 minutes. The supernatant was discarded and the precipitate was resuspended with PBS. Then the resultant mixture was centrifuged at 1500 rpm for 10 min and the resultant human peripheral blood mononuclear cells (PBMC) were resuspended with the RPMI1640 complete medium containing 5% heat-activated human serum. The human PBMC was inoculated in a 96-well plate in a concentration of $1\sim2\times10^5$ cells per well. The cells were stimulated with 0.1 ug/ml SEB for three days. The non-adherent cells (mainly mononuclear cells) were collected and uniformly inoculated to a new 96-well plate. Different concentrations of anti-PD-1 antibody without mutation or PD-1-Ab-Cys28-S-S13 conjugate were added and cultured at 37° C., 5% $CO_2$ for 4 days. Supernatant was collected and concentration of cytotoxic factor IFN-γ was detected by ELISA kit. Results showed that the activated anti-PD-1 antibody exhibited a close or even a significantly improved activity of secreting IFN-γ, as shown in FIG. 11.

The results indicate that after activation of the anti-PD-1 antibody conjugate in vitro, not only the stimulation of anti-PD-1 antibody to T cell could be recovered, but also the remaining group produced after cleavage could introduce one or several new functional groups for the antibody. As a result, after activation, PD-1-Ab-Cys28-S-S13 enhanced the activity of such activating T cells. Such kinds of conjugated-type antibodies are merely activated in a region highly expressing or secreting a target enzyme in a pathological microenvironment to release the antibody. Thus, such microenvironment-activated antibodies are new target-activated antibodies.

2. Conjugates of Anti-PD-1 Antibody and Anti-CD28 Antibody Reduce Body's Autoimmunity As is well known in the art, though anti-PD-1 antibody is a drug effective for treating tumor, it was found in the current clinic research that anti-PD-1 antibody exhibited two main issues. One of the issues is that a patient would exhibit a side effect of high fever and false progress after administration of the antibody, but the mechanism is unknown. We presume these side effects may be improved if the antibody is inhibited or blocked by a conjugate and is released after arriving at a local environment of tumor so as to reduce the exposed time or dose of active drug in a non-diseased environment. For this reason, experiments were conducted with mice suffered from type I diabetes mellitus (NOD). Diabetes mellitus of this kind of mice is an autoimmune disease, wherein self-activated T lymphocyte cells destroy pancreatic islet R cells, resulting in insufficient secretion of insulin. First, female NOD of 10 weeks old (Beijing Vital River Laboratory Animal Technology Co., Ltd.) were injected with control IgG, low (1 mpk), medium (5 mpk) or high (15 mpk) dose of antibody or conjugate of antibody, respectively at day 0. Indicators of diabetes mellitus, including glucose in urine and two blood sugar levels were observed every day for 12 days until no new indicator of urine glucose was observed.

Figure 12:
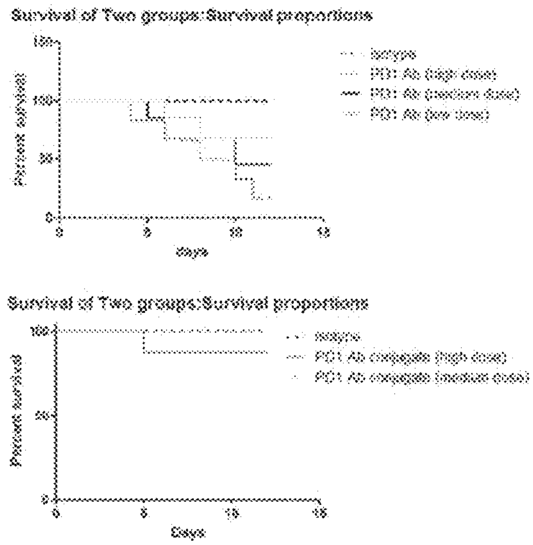
FIG. 12: Survival curve.
Figure 13:
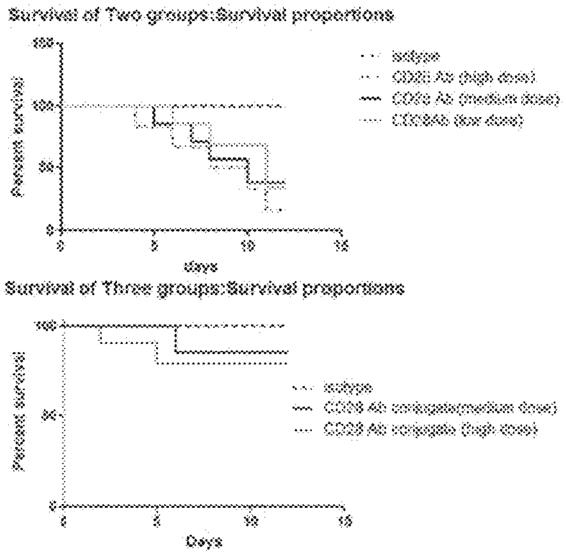
FIG. 13: Death curve.

Protection from autoimmunity by the PD-1-Ab-Cys28-S-S13 conjugate was shown in FIG. 12 and protection from autoimmunity by the CD28-Ab-Cys-S-S13 conjugate was shown in FIG. 13.

Results showed that protection of an immune system by a conjugate of anti-PD-1 antibody was increased by about 15 times as compared to anti-PD-1 antibody, and protection of an immune system by a conjugate of anti-CD28 antibody was increased by about 10 times as compared to anti-CD28 antibody. It can thus be seen that, when a linking moiety was used to hinder or reduce the activity of a protein or antibody, the binding of a conjugated protein or antibody to a related ligand in a normal tissue was reduced, because it was difficult to activate anti-PD-1 antibody and anti-CD28 antibody due to hydrolase and physiological environment outside a diseased microenvironment. As a result, the conjugate could reduce autoimmunity as compared to the primary antibody.

3. Conjugate of Anti-CD28 Antibody Specifically Activates CD4 or CD8 Cells.

CD8+ T cells and CD4+ T cells were isolated from human peripheral blood mononuclear cells with CD8 or CD4 magnetic beads (Dynabeads) according to the specific steps provided in the specification of a kit, counted and stained according to the CFSE specification. The cells were inoculated in a 96-well plate at a concentration of $1\sim2\times10^5$ cells per well. A suitable amount of control anti-CD3/anti-CD28 antibody, 0.3 ug/ml of anti-CD28 antibody or conjugate of anti-CD28 antibody were added, respectively.

Figure 14:
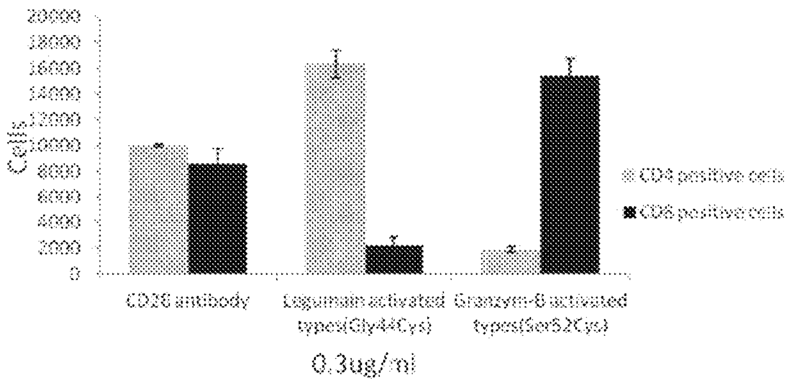
FIG. 14: Proliferation of T cells.

Results were shown in FIG. 14. According to the results, as compared to the original anti-CD28 antibody, the heavy chain conjugate CD28-Ab-Gly44Cys (CD28-Ab-Cys44-S-S13) could selectively activate CD4 T cells, and the light chain conjugate CD28-Ab-Ser52Cys (CD28-Ab-Cys52-S-S13) could selectively activated CD8 T cells. The results indicate that, when a linking moiety was used to hinder or reduce the activity of a protein or an antibody, the binding of the antibody conjugated to the linking moiety to a related antigen in a normal tissue was reduced before the antibody or protein arrives at a target tissue, because the hydrolase is expressed in a low level outside a diseased microenvironment and it is very difficult for the hydrolase to activate the linking moiety conjugated to the antibody or the protein. When the antibody conjugated to the linking moiety arrives at the diseased microenvironment, such as an inflammatory microenvironment, the conjugated linking moiety is activated by Legumain expressed on the surface of Treg, thereby stimulating proliferation of Treg and inhibiting inflammatory reaction. In a tumor region, the conjugated linking moiety is activated by Granzym-B expressed on the surface of CD8 cells, thereby stimulating proliferation of CD8 cells and inhibiting progress of tumor. The designed conjugates are regulated by hydrolase in a microenvironment and the activity of antibody is released only after the conjugated linking moiety is hydrolyzed. As a result, antibodies conjugated to a linking moiety could be greatly enriched in a microenvironment. Eventually, a whole effect, i.e., reduced side effects and improved efficacy could be achieved.

Figure 15:
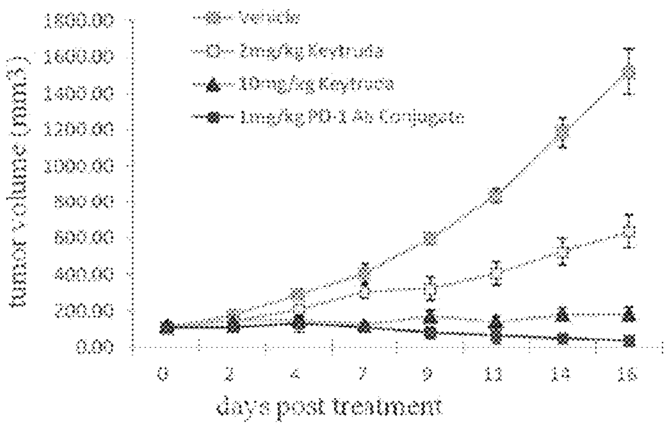
FIG. 15: Conjugate of anti-PD1 antibody inhibits growth of tumor on mice suffering from MC38 colon cancer.

Example 6: Anti-PD-1 Antibody Activated in a Microenvironment could Cure MC38 Tumor MC38 cells were subcutaneously inoculated to transgenic C57BL/6 mice (Shanghai Research Center for Model Organisms) transformed with human PD-1 fusion protein in a concentration of $2\times10^6$ cells per mouse. One week later, the mice implanted with MC38 tumor were randomly divided into 4 groups. Group 1 was injected with 10 mg/kg anti-PD-1 antibody Keytruda® (pembrolizumab), group 2 was injected with 2 mg/kg anti-PD-1 antibody Keytruda® (pembrolizumab), group 3 was injected with 1 mg/kg PD-1-Ab-G28C-S13 conjugate, and group 4 was injected with a solvent control, twice a week for 2 weeks. The tumors in mice were recorded 3 times each week. Results were shown in FIG. 15.

Mouse transformed with human PD-1 fusion protein is a transgenic mouse. Its endogenous PDCD1 gene is replaced with human PDCD1, thereby expressing human PDCD1 protein. Such mouse could respond to human anti-PD-1 antibody and stimulate downstream immunity. The results show that 10 mg/kg anti-PD-1 antibody could effectively inhibit growth of MC38 tumor, with one mouse being cured and five mice having a significant inhibitory effect, which was 80% or more. 1 mg/kg PD-1-Ab-G47C-S13 conjugate produced better inhibitory effect than 10 mg/kg anti-PD-1 antibody Keytruda® (pembrolizumab). The results demonstrate that the conjugate of anti-PD-1 antibody could enhance the activity of effector T cells and enrichment of the antibody in a tumor microenvironment, as proved in Example 5. Thus, the conjugate exhibits an improved efficacy than the original antibody.

Example 7a: IL2 Protein Activated in a Microenvironment

The amino acid sequence of IL2 is a native human IL2 protein. Its DNA sequence was optimized for expression in a host and synthesized (GENEWIZ, Inc., Suzhou, China). The synthesized DNA was digested and ligated to a modified pTT5 vector (Biovector) to produce pTT5-IL2. The mutated vector was constructed by using pTT5-IL2 as template, designing primer to replace the codon at the mutation position with that of cysteine, PCR and digesting and constructing the mutated fragment to the modified pTT5 vector. Synthesis, mutation and transfection of IL2 gene were performed according to the methods described in Example 2. Its binding activity to ligand IL2Rα or IL2Rb was analyzed by IP and ELISA in accordance with the mutation position.

To verify that activation of macromolecule in a microenvironment is not limited to antibody but is applicable to various proteins, cytokine IL2 was used as an example herein. Its mutation position, activity, linker arm, and activity and function after activation were screened. Results are shown in the following Tables 27-29.

TABLE 27

| Activity of mutated IL2 and screening for linker arm | | | | | | |
|---|---|---|---|---|---|---|
| Amino acid | Position | Type of inhibitory ligand | Binding activity to IL2Ra after mutation | Binding activity to IL2Rb after mutation | Conjugating to S3 | Conjugating to S13 |
| Lys | 32 | α | 86.5% | 100% | 26.1% | |
| Lys | 35 | α | 87.1% | 100% | | 32.4% |
| Thr | 37 | α | 98.1% | 100% | | |
| Thr | 41 | α | 99.2% | 100% | 18.7% | |
| Lys | 43 | α | 89.9% | 100% | | 31.3% |
| Lys | 48 | α | 88.4% | 100% | | |
| Lys | 49 | α | 79.8% | 100% | | 39.4% |
| Leu | 72 | α | 98.8% | 100% | | 25.5% |
| Ala | 73 | α | 84.3% | 100% | 27.9% | |
| Ser | 75 | α | 86.2% | 100% | | |
| Lys | 76 | α | 85.0% | 100% | | 32.2% |
| Leu | 94 | α | 99.6% | 100% | | 27.2% |
| Thr | 101 | α | 99.8% | 100% | | 32.0% |
| Thr | 102 | α | 95.3% | 100% | | 29.6% |
| Ala | 108 | α | 93.9% | 100% | | 16.9% |
| Thr | 111 | α | 94.9% | 100% | | 35.3% |
| Ala | 112 | α | 97.3% | 100% | | 41.9% |
| Leu | 19 | β | 100% | 97.5% | 39.5% | |
| Gly | 27 | β | 100% | 42.3% | | |
| Ser | 75 | β | 100% | 93.3% | | 31.1% |
| Leu | 80 | β | 100% | 27.0% | | |
| Ser | 87 | β | 100% | 31.6% | | |
| Leu | 94 | β | 100% | 47.6% | | |
| Gly | 98 | β | 100% | 79.5% | | 16.9% |
| Ser | 99 | β | 100% | 99.2% | | 18.9% |
| Thr | 101 | β | 100% | 21.7% | | |
| Thr | 133 | β | 100% | 96.9% | | 27.8% |
| Thr | 51 | γ | 100% | 100% | 89.70% | 91.60% |

It could be found from the results that, for the mutants retaining 80% or more of binding activity to its corresponding receptor as compared to the native IL2, their activity of binding receptor could be inhibited or hindered by regulating the length of a linker arm. For example, after mutating Lys32, Thr41, Ala73 or Leu19 to Cys, conjugating each of the resulted mutants to S3 may inhibit 60% of binding activity to their corresponding receptor; whereas after mutating Lys35, Lys43, Leu72, Lys76, Leu94, Thr101, Thr102, Ala108, Thr111, Ala112, Gly98, Ser99, Thr133, or the like to Cys, conjugating each of the resulted mutants to S13 may inhibit 60% or more of binding activity to their corresponding receptor.

TABLE 28

| Cleavage efficiency of conjugated IL2 | | | | |
|---|---|---|---|---|
| R2 | R3 | R4 | R5 | Cleavage efficiency |
| -Ala-Ala-Asp- | R3-2 | | | Control, 100% |
| -Ala-Ala-Asp- | R3-2 | Paclitaxel (2-OH) | | 45.5% |
| -Ala-Ala-Asp- | R3-2 | R4-10 | IL2-Thr37 | 86.5% |
| -Ala-Ala-Asp- | R3-2 | R4-11 | IL2-Thr37 | 92.7% |
| -Ala-Ala-Asp- | R3-2 | R4-12 | IL2-Thr37 | 96.7% |
| -Ala-Ala-Asp- | R3-2 | R4-13 | IL2-Thr37 | 73.9% |
| -Ala-Ala-Asp- | R3-2 | R4-14 | IL2-Thr37 | 62.4% |
| -Ala-Ala-Asp- | R3-2 | R4-1 | IL2-Thr37 | 73.8% |
| -Ala-Ala-Asn- | R3-2 | R4-3 | IL2-Thr37 | 84.7% |
| -Ala-Ala-Asp- | R3-2 | R4-1 | IL2-Thr41 | 86.7% |
| -Ala-Ala-Asp- | R3-2 | R4-3 | IL2-Thr41 | 95.5% |

Results indicate that activation by Legumain is not influenced due to the small molecular linear structure of the automatically shedding arm R3.

TABLE 29

| Change of binding efficiency to its receptor after conjugating IL2 to R1 an after activation of a linking arm | | | |
|---|---|---|---|
| R1 | R5 | Binding efficiency before activation | Binding efficiency after enzymatic or acidic activation |
| S3 | IL2-Thr37 | 28.1% | 143.5% |
| S5 | IL2-Ser87 | 31.6% | 145.3% |
| S6 | IL2-Thr-41 | 99.2% | 124.8% |
| S13 | IL2-Leu-19 | 97.5% | 118.7% |

It can thus be seen that the activation efficiency of a conjugate and its binding capacity to receptor after activation were influenced by the mutation position in a protein to some extent. However, with the use of R4, activation efficiency by target enzymatic cleavage could be produced. As for the binding between a biomolecule and its ligand, the exposed group of R4 produced after cleavage by activation could regulate the binding capacity of a mutated antibody. Different exposed groups had different effects on different mutation positions. By screening for R1 and D4, it could be found that the hindering function of R1 led to complete loss of binding capacity of the conjugate to its antigen. However, the binding capacity was recovered or even enhanced after cleavage by a target enzyme. Such conjugated-type proteins are merely activated or released their activity in a region highly expressing or secreting a target enzyme in a pathological microenvironment. Thus, such proteins are new target-activated proteins.

IL2 mutants having two or more mutations were prepared and conjugated to S13. The mutation sites were selected from the mutation sites of the aforementioned IL2 mutants having one mutation and having 95% or more binding activity to its receptor. The activity of such conjugates after activation was verified and the results were shown in Table 30.

TABLE 30

Binding activity of conjugates of IL2 mutants with two or more mutations to its receptor before and after activation

| R1-R2-R3-R4 | R5 | Binding efficiency before activation | Binding efficiency after enzymatic or acidic activation |
|---|---|---|---|
| S13 | IL2-Thr37/Leu19 | 12.1% | 113.5% |
| S13 | IL2-Ser37/Thr41 | 11.6% | 98.3% |
| S13 | IL2-Thr-41/Ser87 | 19.2% | 102.8% |
| S13 | IL2-Leu-19/Ser87 | 17.5% | 96.7% |
| S13 | IL2-Leu19/Ser37/Ser87 | 10.9% | 95.9% |

The above results demonstrate that conjugates of IL2 mutants with two or more mutations could retain 95% or more binding activity to corresponding receptor after activation.

Conjugate of IL2 Protein Specifically Activates CD4 or CD8 Cells.

Figure 16:
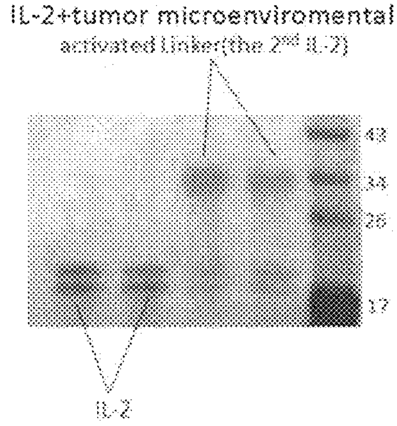
FIG. 16: Conjugation of IL2-C41 mutant.
Figure 17:
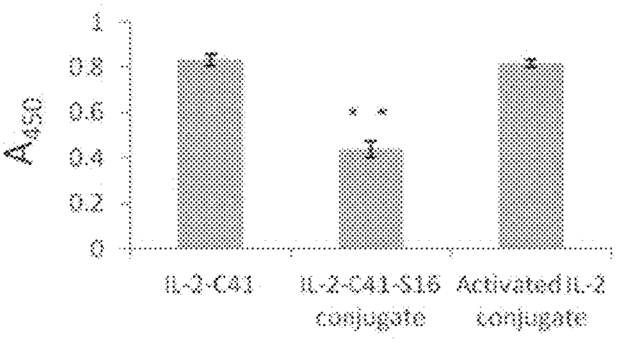
FIG. 17: Binding of the IL2-C41 conjugate to IL2 receptor alpha before and after activation.
Figure 18:
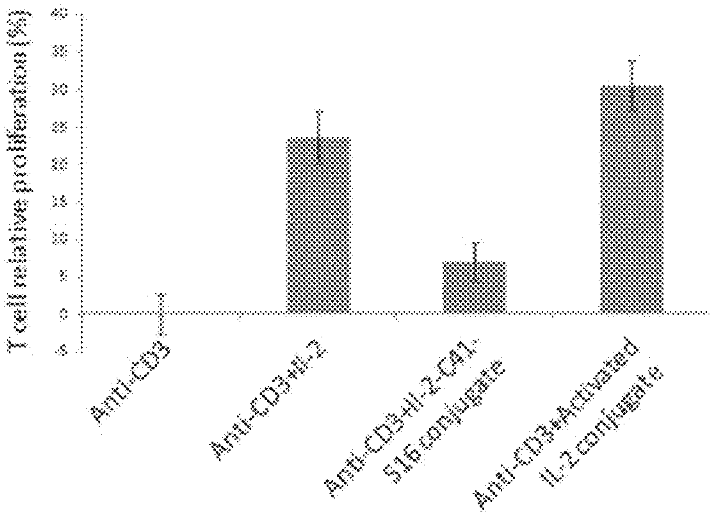
FIG. 18: Effect of IL2 mutant conjugation (IL2-Thr41Cys, i.e., IL2-C41) on proliferation of T cells.

CD8+ T cells and CD4+ T cells were isolated from human peripheral blood mononuclear cells with CD8 or CD4 magnetic beads (Dynabeads) according to the specific steps provided in the specification of a kit, counted and stained according to the CFSE specification. The cells were inoculated in a 96-well plate at a concentration of 1~2×$10^5$ cells per well. A suitable amount of control anti-CD3 antibody, 0.05 ug/ml of IL2 protein or conjugate IL2-T41C-S16 conjugated to S16 were added, respectively. FIG. 16 shows conjugation of IL2-T41C (IL2-Thr41Cys) to S16. FIG. 17 shows the binding to IL2 receptor alpha before and after conjugation. FIG. 18 shows effect of the IL2-C41-S16 conjugation on proliferation of T cells before and after activation.

Figure 19:
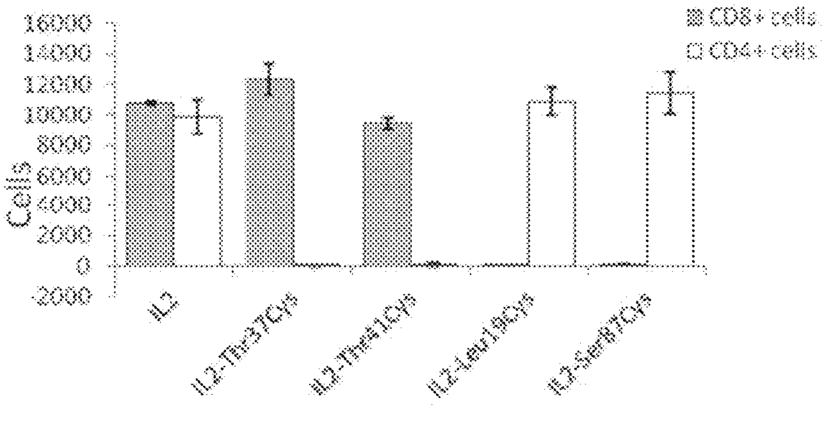
FIG. 19: Effect of IL2 conjugate on CD4/CD8 proliferation.

Native IL2 exhibited similar stimulation on CD8 and CD4. However, after conjugating to a functional moiety activated in a microenvironment, IL2-Thr37Cys and IL2-Thr41Cys could specifically activate proliferation of CD8 T cells and reduce proliferation of CD4 cells. The ratio of cell number between CD8 cells and CD4 cells increased from the original 1:1 to 410:1 and 157:1, respectively. IL2-Leu19Cys and IL2-Ser87Cys could specifically activate proliferation of CD4 T cells, with the cell ratio of CD4/CD8 being increased to 435:1 and 126:1, respectively. Results are shown in FIG. 19. The results demonstrate that CD8 or CD4 could be selectively activated by conjugating IL2 to a functional moiety to control its binding activity to each of receptors and to allow it to be activated in a specific microenvironment.

Conjugates of IL2 Protein Effectively Inhibit Growth of Melanoma B16F10 and Colon Cancer MC38.

0.5×$10^6$ B16F10 cells per mouse were subcutaneously inoculated to C57BL/6 mice. One week later, when the tumor's volume reached 100 $mm^3$, the mice implanted with melanoma were randomly divided into 4 groups, with 6 mice per group. Group 1 was injected with 2.5 mg/kg of IL2-T37C-S14 protein conjugate weekly. Group 2 was injected with 0.5 mg/kg of IL2-Thr37Cys protein conjugate weekly. Group 3 was injected with 3 mg/kg of aldesleukin (control) twice a week. Group 4 was injected with solvent (control) twice a week. All groups were continuously administered for 3 weeks. Mice tumors were measured twice a week and mice were weighed twice a week.

MC38 cells were subcutaneously inoculated to transgenic C57BL/6 mice transformed with human PD-1 fusion protein in a concentration of 0.5×$10^6$ cells per mouse. One week later, the mice implanted with MC38 tumor were randomly divided into 4 groups. Group 1 was injected with 2 mg/kg of IL2-T37C-S14 protein conjugate. Group 2 was injected with 0.5 mg/kg of IL2-Thr37Cys conjugate and 100 μg per time of anti-PD-1 antibody twice a week. Group 3 was injected with 3 mg/kg of aldesleukin (control) twice a week. Group 4 was injected with solvent (control) twice a week. All groups were continuously administered for 3 weeks. Mice tumors were measured twice a week and mice were weighed twice a week.

Figure 20:
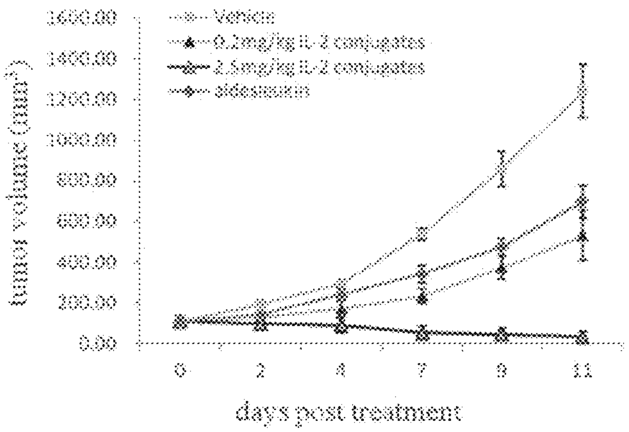
FIG. 20: Conjugate of IL2 inhibits growth of B16F10 tumor.
Figure 21:
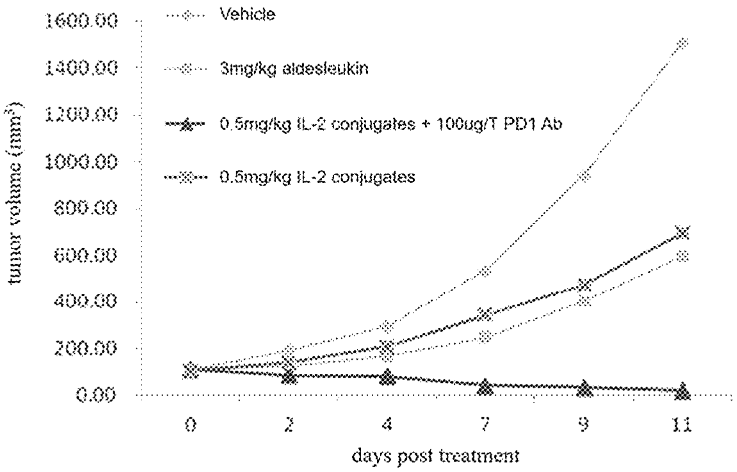
FIG. 21: Conjugate of IL2 in combination with anti-PD-1 antibody inhibits growth of MC38 tumor.

Results are shown in FIGS. 20 and 21, which demonstrate that the IL2-Thr37Cys conjugate could not only be used in a reduced use dose, but also significantly enhance the effect of treating B16F10 tumor, as compared to the existing IL2 product, aldeslekin. And in the combination treatment group with anti-PD-1 antibody, there were MC38 mice being cured.

From the above results, it could be found that, when using a functional moiety to hinder or reduce the activity of a protein or antibody, the binding of a protein to its receptor or ligand in a normal tissue could be reduced before it arrives at a target tissue because it is very difficult to activate the functional moiety conjugated to the protein by a hydrolase and a physiological environment outside a diseased microenvironment. However, in a diseased microenvironment, IL2-Thr37Cys and IL2-Thr41Cys and the like were influenced by the hydrolase in the diseased microenvironment and activated on the surface of Granzym-B highly expressing CD8 cells, thereby binding to a receptor on the surface of CD8 cells and activating CD8 cells. As a result, the protein conjugated with a functional moiety could reduce immune toxicity while enhancing targeted efficacy.

For the same reasons, IL2-Leu19Cys and IL2-Ser87Cys were activated on the surface of Legumain highly expressing Treg cells, allowing the activated IL2 to bind to a receptor on the surface of Treg cells to activate proliferation of Treg cells.

Example 7b: Tumor Microenvironment Activated IL2 Cytokine (IL2 TMEAkine)

1. Expression and Purification of the Mutant IL2 Cytokine

The mutant IL2 DNA sequence ligated to a modified pTT5 vector (Biovector) was optimized for expression in 293T cells and synthesized (GENEWIZ Inc., Suzhou, China). Transfection of the mutant IL2 DNA was performed. After incubation for 4-7 days, the supernatant containing mutant IL2 was collected.

In eukaryotic expression, the expression vector pPICZα A containing the mutant IL2 genes was optimized and prepared (GENEWIZ Inc., Suzhou, China). The amino acid sequence of wild type IL2 was described is shown below:

```
                                        (SEQ ID NO: 11)
APASSTKKTQLQLEHLLLDLQMILNGINNYKNPKLTRMLTFKFYMPKKA
TELKHLQCLEEELKPLEEVLNLAQSKNFHLRPRDLISNINVIVLELKGS
ETTFMCEYADETATIVEFLNRWITFSQSIISTLT.
```

The expression vector pPICZα A was transformed in *E. coli* (DH5u) for plasmid purification. Then pPICZα A was transformed into GS 115 by electroporation. The transformed colony was selected by obtaining the growing colonies after growing on the 100, 300, 500, 1000, 1500, 2000 μg/mL Zeocin™ containing YPD plates. After finally selecting the transformant, the recombinant GS115 strain was grown in BMGY medium at 30° C., with vigorous shaking in baffled flasks to an OD600 of 2-6. The cells were then pelleted by centrifugation and suspended in BMMY to an OD600 of 1, to which was added 0.5% methanol daily in order to induce the heterologous protein expression. After a four-day induction, supernatant containing the secreted mutant IL2 protein was collected by centrifugation. The total protein in the supernatant was concentrated by ultrafiltration using a 10-kDa molecular mass cutoff membrane. The concentrated protein was dialyzed with buffer A (50 mM HAc/NaAc, pH4.5) for more than 24 h, then loaded onto a cation-exchange column equilibrated with buffer A. Mutant IL2 was eluted from the column with gradient concentration of NaCl and the eluent was collected and concentrated. The condensed sample was further purified on Sephacryl S-100 HR gel filtration column using 20 mM Tris-HCl, 20 mM NaCl, pH7.4, as the elution buffer.

In prokaryotic expression, the expression vector pET22b (+) containing the mutant IL2 genes was optimized and prepared (GENEWIZ Inc., Suzhou, China). The amino acid sequences of wild type IL2 were described in SEQ ID NO: 12. The positive clone was selected and transformed into the *E. coli* cells (BL21DE3). Standard procedure for induction of the target protein using isopropyl thiogalactoside (IPTG) was followed. The induced *E. coli* cells were centrifuged and the cell pellet was resuspended in 100 mM Tris-HCl buffer (pH 8.0) containing 5 mM EDTA and 1 mM PMSF. Cells were lysed by sonication and centrifuged to isolate IL2 protein inclusion bodies (IBs). The IB pellet was then washed with 100 mM Tris-HCl buffer (pH 8.0) containing 5 mM EDTA and 2% deoxycholate, and distilled water, respectively. The IBs were solubilized in 6 M guanidine hydrochloride (GuHCl) solution (prepared in 0.1 M Tris buffer, pH 8.0) and incubated for 30 min at room temperature with gentle vortexing, followed by centrifugation. The supernatant was diluted with refolding buffer (0.1 M Tris buffer, pH 8.0 containing 10 mM reduced and 1 mM oxidized glutathione in a ratio of 10:1) so as to obtain a protein concentration and GuHCl of 0.1 mg/mL and 2 M, respectively. Subsequently, the solution was kept for 16 h at room temperature for slow refolding of IL2. The insoluble protein was removed by centrifugation. The supernatant was concentrated and loaded on a gel filtration column Sephacryl 5-100 HR, equilibrated with 0.1 M Tris buffer containing 2 M GuHCl.

Wild type IL2 amino acid sequence produced by the transformant is shown below:

```
                                        (SEQ ID NO: 12)
PTSSTKKTQLQLEHLLLDLQMILNGINNYKNPKLTRMLTFKFYMPKKAT
ELKHLQCLEEELKPLEEVLNLAQSKNFHLRPRDLISNINVIVLELKGSE
TTFMCEYADETATIVEFLNRWITFSQSIISTLT.
```

2. Screening the Mutants of their Binding Activity to IL2Rα or IL2Rβ after Mutation Various IL2 mutants were expressed by 293T cells and secreted to the medium. Supernatant containing IL2 mutants was obtained through centrifugation as described in section 1. Then 1 ug His-tagged IL2Rα or IL2Rβ was added to 1 mL supernatant mentioned above and incubate for 1h at 4° C. with gentle agitation. 50 uL pre-washed Ni-NTA resin was transferred to the mixed solution of the supernatant and IL2Rα or IL2Rβ, and incubated for 1 h at 4° C. with gentle agitation. The mixture was subjected to centrifugation and the supernatant was discarded. The resultant pellet was washed with 500 μL PBS containing 25 mM imidazole for three times. The amount of IL2 mutants and IL2Rα/Rβ was visualized by western blotting using IL2 antibody and anti His-tag monoclonal antibody.

3. Conjugating S47 to the Mutant IL2

Figure 22:
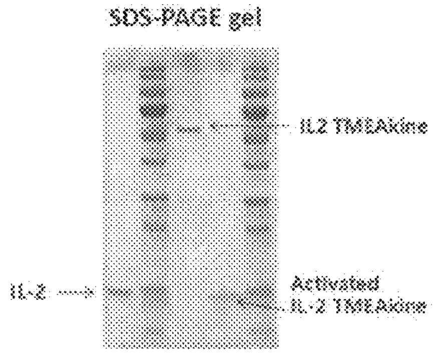
FIG. 22: The SDS-PAGE results of mutant IL2, IL2 TMEAkine and the recovery active IL2 after enzyme cleavage in vitro.

Mutant IL2 protein was generated and purified as described above in section 1. Purified mutant IL2 was incubated as the concentration of 0.3 mg/mL in 50 mM phosphate buffer (pH 7.4) containing 5 mM EDTA. TCEP solution was added to mutant IL2 in a molar ratio of 100:1 and the resultant mixture was incubated for 4 h at 4° C. with gentle agitation. Then the mixture was dialyzed with 50 mM phosphate buffer (pH 7.4) containing 150 mM NaCl for 2 h at 4° C. Afterwards, S47 was immediately added to the mixture in a molar ratio of 20:1 and the resultant mixture was incubated for 16 h at 25° C. with gentle agitation. The reaction was stopped and residual S47 was removed. Before enzyme cleavage, the buffer used for the conjugate of IL2-S47 (IL2 TMEAkine, Tumor Microenvironment Activated IL2 cytokine) was changed to a buffer used for enzyme through dialysis. Then enzyme was added to the IL2 TMEAkine solution and the mixture was incubated at 37° C. for 16h. FIG. 22 shows the SDS-PAGE results, with a colloidal blue stain for mutant IL2, IL2 TMEAkine and the recovery active IL2 after enzyme cleavage in vitro.

Figure 23:
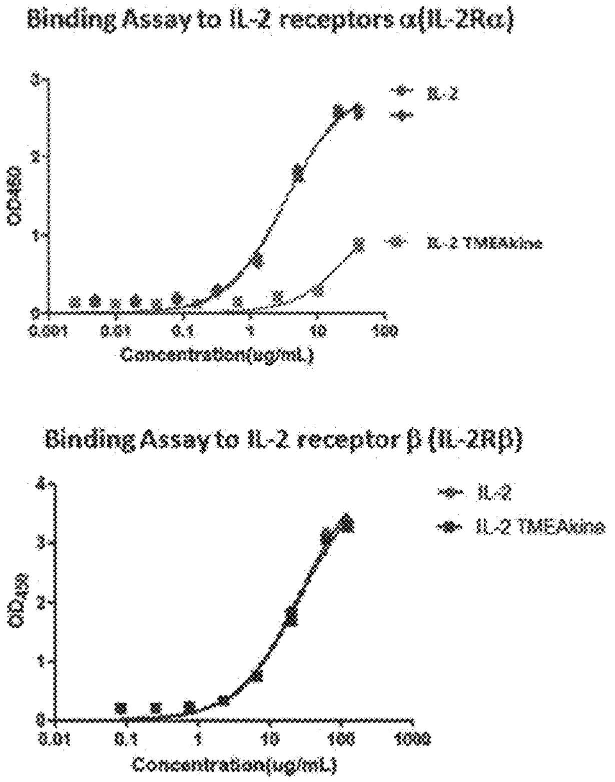
FIG. 23: ELISA results indicating the binding activity of IL2 TMEAkine to IL2Rα or Rβ before and after enzyme cleavage in vitro.

4. Screening IL2 TMEAkine that Blocks the Binding to IL2Rα or IL2Rβ and Recovers the Binding Activity after Enzyme Cleavage In Vitro 60 μl PBS buffer containing 1 ug IL2Rα-Fc/IL2Rβ-Fc solution were dispensed into wells. Sealing tape was applied to the top of the plate and then the plate was incubated at 4° C. overnight. After incubation, the tape was removed to aspirate each well. After washing with PBST for three times, the plate was blocked by dispensing 200 μl of PBS buffer containing 2% BSA into each well and then the plate was incubated at room temperature for 2 h. The plate was washed three times and 60 μl of serial diluted samples were added to the appropriate wells. The plate was incubated at room temperature for 1.5h. After washing with PBST for three times, 60 μl of 1 μg/mL IL2 biotinylated antibody solution was dispensed to each well and the resultant mixture was incubated at room temperature for 1 hour. The plate was washed three times and then 60 μl of streptavidin solution was dispensed to each well. Then the plate was incubated at room temperature for 30 minutes. After washing three times, 100 μl of the HRP substrate solution was dispensed into each well and the plate was incubated at 37° C. for 15 minutes. After color development, 50 μl of stop solution was dispensed into each well and the absorbance of each well was immediately measured at a wavelength of 450 nm. ELISA results were shown in FIG. 23, indicating the binding activity of IL2 TMEAkine to IL2Rα or Rβ before and after enzyme cleavage in vitro. Compared with binding activity of wild type IL2 to IL2Rα and IL2Rβ, IL2 TMEAkine binds to IL2Rα with much lower binding affinity but binds to IL2Rβ with almost the same binding affinity. After activation by enzyme, the binding affinity of IL2 TMEAkine to IL2Ru equals to that of wild type IL2 to IL2Rα.

5. Summary of Various IL2 Mutation Sites

IL2 receptors may associate on the cell surface to form the following heteromers: intermediate-affinity receptor: IL2Rβγ to IL2 (Kd=1 nM) and low-affinity receptor: IL2Rα to IL2 (Kd=10 nM). Because it is a low-affinity binding (Kd=10 nM), it is easier than CDR region of antibody to screen a position for linking to R4 group for recovering the binding affinity. Because we did not want to increase the binding affinity between R4-S-IL2 and IL2Rα, we selected the conjugated IL2 with the special R4, which can recover the native binding affinity. In some cases, there are some R4 groups which can enhance the binding affinity, but we did not select them as drug candidates. We prefer R-1, R4-7, R4-5, R4-8 and R4-12 for the large scale synthesis in our CMC development. S47 is cleaved by Legumain. After cleaving, its R4-7 chemical group remained. To select drug candidates, we also performed the screening expression and S47 conjugation reaction with all amino acids of IL2 in the domain that binds IL2Rα and IL2Rβ. We acquired the possible drug candidates and results are shown in the following Tables 31-33.

TABLE 31

Activity of mutated IL2 and screening for linker arm

| Position | Amino acid | Type of inhibitory ligand | R4 | Binding recovery (>60%) | Decreased fold of binding to ligand after Conjugating with S47 (>3 fold) |
|---|---|---|---|---|---|
| 32 | K | α | R4-7 | 100.2% | 3-fold |
| 35 | K | α | R4-7 | 85.4% | 89-fold |
| 37 | T | α | R4-7 | 98.9% | 51-fold |
| 38 | R | α | R4-18 | 81.2% | 145-fold |
| 41 | T | α | R4-7 | 99.2% | 135-fold |
| 42 | F | α | R4-8 | 82.3% | 120-fold |
| 43 | K | α | R4-7 | 89.3% | 110-fold |
| 43 | K | α | R4-18 | 109.7% | |
| 44 | F | α | R4-8 | 96.7% | 60-fold |
| 45 | Y | α | R4-7 | 96.8% | 125-fold |
| 45 | Y | α | R4-8 | 143.6% | |
| 48 | K | α | R4-7 | 100.2% | 12-fold |
| 49 | K | α | R4-18 | 100.7% | |
| 60 | E | α | R4-12 | 97.1% | 5-fold |
| 61 | E | α | R4-12 | 83.4% | 134-fold |
| 62 | E | α | R4-12 | 86.6% | 120-fold |
| 63 | L | α | R4-5 | 99.3% | 13-fold |
| 64 | K | α | R4-7 | 97.1% | |

TABLE 31-continued

Activity of mutated IL2 and screening for linker arm

| Position | Amino acid | Type of inhibitory ligand | R4 | Binding recovery (>60%) | Decreased fold of binding to ligand after Conjugating with S47 (>3 fold) |
|---|---|---|---|---|---|
| 67 | E | α | R4-12 | 99.6% | 9-fold |
| 68 | E | α | R4-12 | 95.4% | 89-fold |
| 71 | N | α | R4-18 | 98.6% | 5-fold |
| 72 | L | α | R4-5 | 90.1% | 110-fold |
| 74 | Q | α | R4-19 | 100.0% | 3-fold |
| 75 | S | α | R4-7 | 100.0% | 4-fold |
| 76 | K | α | R4-7 | 100.0% | 3-fold |
| 101 | T | α | R4-7 | 100.0% | 5-fold |
| 102 | T | α | R4-7 | 100.0% | 4-fold |
| 102 | T | α | R4-3 | 122.5% | |
| 107 | Y | α | R4-4 | 97.7% | 78-fold |
| 108 | A | α | R4-5 | 100.0% | 10-fold |
| 111 | T | α | R4-7 | 98.9% | 20-fold |
| 112 | A | α | R4-5 | 100.0% | 5-fold |
| 5 | S | β | R4-7 | 99.8% | 3-fold |
| 5 | S | β | R4-2 | 109.5% | |
| 8 | K | β | R4-7 | 66.7% | 6-fold |
| 9 | K | β | R4-6 | 97.0% | 9-fold |
| 9 | K | β | R4-7 | 124.6% | |
| 12 | L | β | R4-5 | 93.4% | 13-fold |
| 13 | Q | β | R4-19 | 85.1% | 28-fold |
| 15 | E | β | R4-12 | 81.4% | 25-fold |
| 19 | L | β | R4-5 | 92.3% | 27-fold |
| 20 | D | β | R4-11 | 87.3% | 31-fold |
| 27 | G | β | R4-1 | 100.0% | 3-fold |
| 76 | K | β | R4-6 | 100.0% | 3-fold |
| 76 | K | β | R4-7 | 130.4% | |
| 80 | L | β | R4-2 | 100.0% | 5-fold |
| 81 | R | β | R4-18 | 95.2% | 12-fold |
| 84 | D | β | R4-11 | 80.1% | 36-fold |
| 85 | L | β | R4-7 | 98.4% | 9-fold |
| 85 | L | β | R4-5 | 113.6% | |
| 87 | S | β | R4-7 | 99.5% | 30-fold |
| 88 | N | β | R4-18 | 82.3% | 46-fold |
| 91 | V | β | R4-5 | 94.5% | 25-fold |
| 92 | I | β | R4-5 | 89.3% | 19-fold |
| 94 | L | β | R4-5 | 99.5% | 30-fold |
| 95 | E | β | R4-12 | 60.1% | 8-fold |
| 98 | G | β | R4-1 | 98.6% | 4-fold |
| 99 | S | β | R4-7 | 100.0% | 3-fold |
| 101 | T | β | R4-7 | 100.0% | 3-fold |
| 133 | T | β | R4-7 | 100.0% | 3-fold |

TABLE 32

Binding activity of conjugates of IL2 mutants with two or more mutation sites to its receptors before and after activation

| TMEAkine | Mutation position (Rα binding) | Mutation position (Rβ binding) | Decreased fold of binding to α ligand after Conjugating with S47 | Decreased fold of binding to β ligand after Conjugating with S47 | Binding recovery (>60%) |
|---|---|---|---|---|---|
| IL2-Thr37/Thr3 | IL2-Thr37, IL-Thr | | 51-fold | N.D. | 98.9% |
| IL2-Thr3/Thr41 | IL2-Thr, IL2-Thr41 | | 135-fold | N.D. | 101.8% |
| IL2-Thr-41/Ser87 | IL2-Thr-41 | IL2-Ser87 | 135-fold | 30-fold | 96.8% |
| IL2-Thr37/Ser87 | IL2-Thr37 | IL2-Ser87 | 51-fold | 30-fold | 98.4% |
| IL2-Thr/Ser87 | IL2-Thr3 | IL2-Ser87 | N.D. | 30-fold | 99.3% |

The results demonstrate that conjugates of IL2 mutants with two or more mutation sites could retain 95% or more binding activity to corresponding receptor after activation.

After screening expression, binding activity, conjugation, cleavage, recovery and functional assay, we acquired the drug candidates with one or more stable mutations on the binding domain with Rα and one conjugation on the binding domain with Rβ, as shown in Table 33. Particularly, stable mutation sites on the domain binding with Rα were Arg38 and Glu61, in which Arg38 was mutated to Asp and Glu61 was mutated to Arg, affecting binding activity of IL2 and IL2Rα. Therefore, these conjugations are releasing stable mutants on the binding domain with Rα after cleaving in tumor microenvironment.

TABLE 33

Binding activity of candidates with one or more stable mutations and one conjugation to its receptors before and after activation

| TMEAkine | Stable mutation for blocking Rα binding | Mutation position (Rβ binding) for conjugation with S47 | Decreased fold of binding to α ligand after conjugating with S47 | Decreased fold of binding to β ligand after conjugating with S47 | Binding recovery of β ligand (>60%) |
|---|---|---|---|---|---|
| IL2-Arg38/Ser87 | Arg38AsP | Ser87 | 200-fold | 32-fold | 99.5% |
| IL2-Glu61/Ser87 | Glu61Arg | Ser87 | 110-fold | 30-fold | 99.5% |
| IL2-Arg38/Glu61/Ser87 | Arg38 Asp/ Glu61Arg | Ser87 | >200-fold | 32-fold | 96.4% |

TABLE 34

Binding activity of candidates with two stable mutants and one conjugation to its receptors before and after activation

| Mutation for adjusting Rα binding | Mutant of Rβ binding for conjugation | Decreased fold of binding to Rα | Binding recovery to Rβ |
|---|---|---|---|
| Arg38Asp/Glu61Arg | with R4-7 | >200-fold | |
| | Lys9 | | 124.6% |
| | Lys76 | | 130.4% |
| Arg38Asp/ Glu61Arg | Lys9, Lys76 | >200-fold | 165.7% |

The results demonstrated that, with conjugation of R4 library screening and mutation, we got a new chemically modified IL2 with decreasing 200 folds of binding to Rα and increasing 1.35 folds of binding to Rβ.

6. Stability in Human Serum

Figure 24:
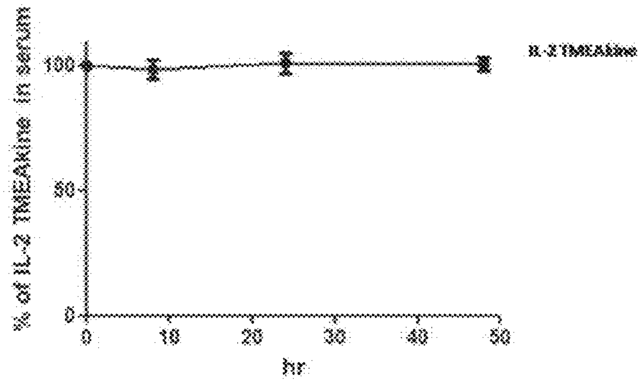
FIG. 24: The amount of IL2-T41C-S47 detected by western blot and the corresponding results.

IL2-T41C-S47 solution and human serum were mixed in a ratio of 1:19 (v/v) and the mixture was incubated at 37° C. for Oh, 8 h, 24 and 48h, respectively. Then the amount of IL2-T41C-S47 was detected by western blot and the corresponding results were shown in FIG. 24. IL2-T41C-S47 was stable in human serum after 48 hours, indicating that IL2-T41C-S47 may be much more stable than IL2 in human serum in vitro. The stability in human serum of other conjugates of IL2 mutants was shown in Table 35.

TABLE 35

The stability of other conjugates of IL2 mutants in human serum

| R1-R2-R3-R4 | R5 | Stability in Human Serum |
|---|---|---|
| S47 | IL2-Thr37 | 100% |
| S47 | IL2-Thr41 | 99.8% |
| S47 | IL2-Ser87 | 99.2% |

TABLE 35-continued

The stability of other conjugates of IL2 mutants in human serum

| R1-R2-R3-R4 | R5 | Stability in Human Serum |
|---|---|---|
| S47 | IL2-Thr41/Ser87 | 99.5% |
| S47 | IL2-Ser37/Ser87 | 99.5% |

7. Pharmacokinetics in Mice

Figure 25:
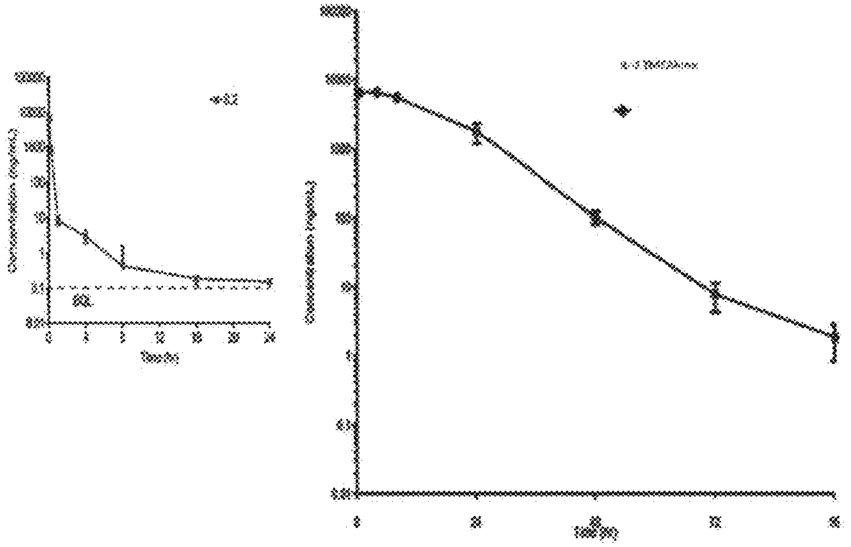
FIG. 25: The pharmacokinetic study in vivo indicating that IL2 TMEAkine has a long half-life and a high exposure in plasma when compared with IL2.

Mice received a single intravenous injection of IL2-T41C-S47 (0.8 mg/kg), n=3 mice per sampling time. Approximately 200 μL blood was collected into K2EDTA-coated tubes. Plasma was separated after centrifugation and frozen at −80° C. until analysis. The IL2-T41C-S47 concentration was then measured using a quantified ELISA. Results were shown in FIG. 25. The pharmacokinetic study in vivo indicates that IL2 TMEAkine has a long half-life and a high exposure in plasma when compared with IL2.

8. Toxicity

Figure 26:
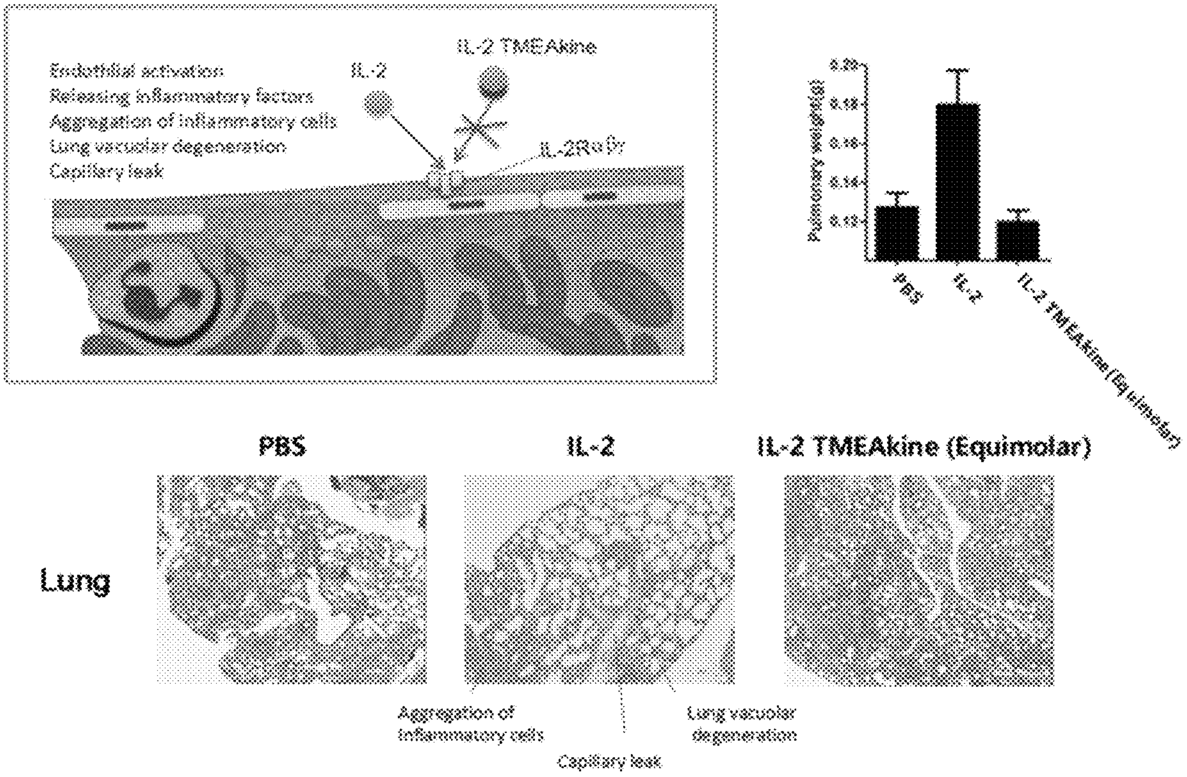
FIG. 26: The measurement of pulmonary (wet weight) and the sections stained with hematoxylin and eosin indicating that IL2 TMEAkine induces less toxicity to lung than wild-type IL2.

C57BL/6 mice received daily i.p. injection of PBS or 25 ug IL2 for 5 days or i.p. injection of equimolar IL2-T41C-S47 every 5 days for 5 doses, respectively. Mice were sacrificed and lungs were fixed in 10% formalin solution and paraffin-embedded sections were stained with hematoxylin and eosin. The results were shown in FIG. 26. The measurement of pulmonary (wet weight) and the sections stained with hematoxylin and eosin indicate that IL2 TMEAkine induces less toxicity to lung than wild-type IL2.

Figure 27:
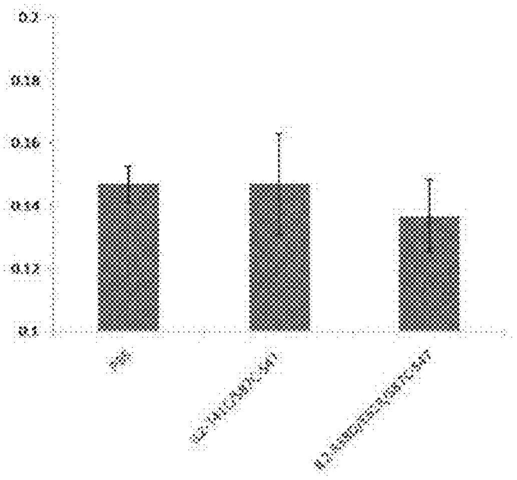
FIG. 27: The measurement of pulmonary indicating that IL2-T41C/S87C-S47 and IL2-R38D/E61R/S87C-S47 induce almost no toxicity to lung.

C57BL/6 mice received i.p. injection of PBS, 25 ug IL2-T41C/S87C-S47 and equimolar IL2-R38D/E61R/S87C-S47 every 5 days for 5 doses, respectively. Mice were sacrificed. The wet weight of lungs was measured and lungs were fixed in 10% formalin solution and paraffin-embedded sections were stained with hematoxylin and eosin. Results were shown in FIG. 27. The measurement of pulmonary indicates that IL2-T41C/S87C-S47 and IL2-R38D/E61R/S87C-S47 induce almost no toxicity to lung.

9. Study on Efficacy of IL2-T41C-S47 and IL2-T41C-S47 in Combination with Anti-PD-1 Antibody on the CT26 Tumor Model in BALB/C Mice Model Test purpose: to investigate the anti-tumor efficacy of IL2-T41C-S47 and IL2-T41C-S47 in combination with anti-PD-1 antibody in BALB/C mice for treatment of the CT26 tumor model.

Test drug: IL2-T41C-S47, anti-PD-1 antibody and IL2 injection, diluted to corresponding concentrations by PBS when testing.

Method and Results

1. Animal: BALB/C Mice of 5 Weeks Old, all Female.
2. Production of Tumor Model

1) CT26 cells were purchased from American type culture collection (ATCC) and identified according to the specification provided by ATCC. Cells were cultivated in RPMI 1640 culture solution containing 10% fetal bovine serum at 37° C. and 5% $CO_2$. The cells were passaged for every three days and cells within the 9th passage were used.

2) Production of tumor model. CT26 cells were subcutaneously injected to the back of the BALB/C mice. Mice were randomly grouped after the tumor grew to about 100-200 $mm^3$ and drug treatment began. Mice were killed after anesthesia on day 31.

3) Course of treatment

There were 5 groups with 6 animals in each group. Included were a control group treated on day 0, 5 and 11, and three single agent groups (treated by anti-PD-1 antibody on day 2, 4, 7, 9, 13 and 15, or by IL2 on day 0, 5, 11, or by IL2-T41C-S47 on day 0, 5 and 11) and one combined immunotherapy group in which IL2-T41C-S47 (given on day 0, 5 and 11) treatment was initiated prior to anti-PD-1 antibody treatment (given on day 2, 4, 7, 9, 13 and 15).

4) Grouping and test results are shown in Table 36.

TABLE 36

Effects of IL2-T41C-S47and IL2-T41C-S47 in combination with anti-PD-1 antibody on the CT26 tumor model in BALB/C mice model

| Group | Complete Regression |
|---|---|
| Control Group | 0 |
| Anti-PD-1 antibody | 16.79% |
| IL2 | 16.79% |
| IL2-T41C-S47 | 33% |
| IL2-T41C-S47 in combination with Anti-PD-1 antibody | 100% |

Figure 28:
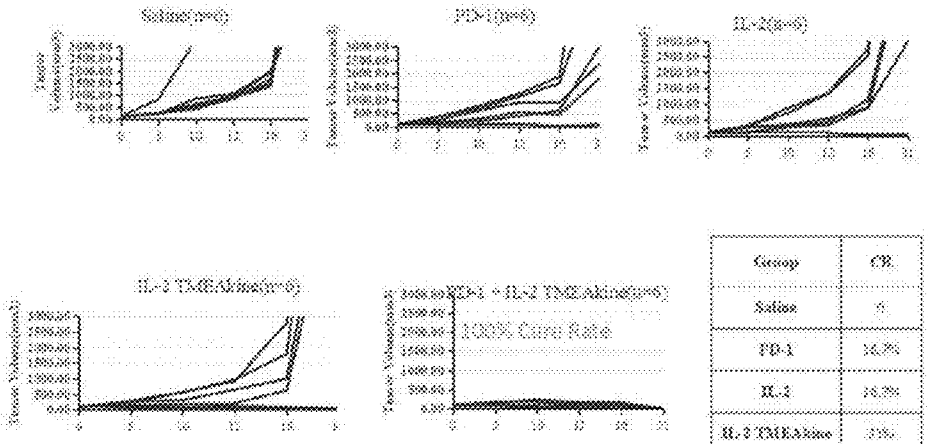
FIG. 28: Tumor volumes after treatment.

Tumor volumes were monitored 2-3 times a week and were presented in FIG. 28.

5) Results and discussion. As shown in Table 36, the regression on the CT26 tumor of BALB/C mice was greatly improved after injection of IL2-T41C-S47 in combination with anti-PD-1 antibody, indicating that IL2-T41C-S47 in combination with anti-PD-1 antibody exhibits an excellent anti-tumor efficacy on the CT26 tumor model.

10. Biodistribution of Active IL2 from IL2-T41C-S47 in Tumor, Lung and Heart

Figure 29:
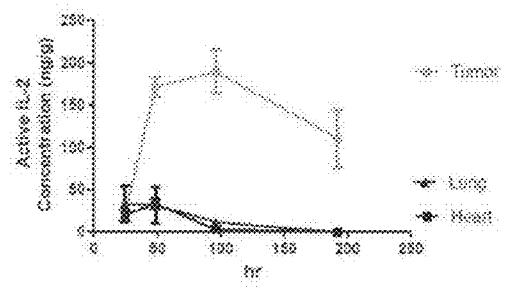
FIG. 29: High exposure of active IL2 in tumor, which is consistent with high efficacy of anti-tumor effect, and low exposure of active IL2 in lung and heart, which is consistent with low toxicity of pulmonary edema.

BALB/C mice were implanted subcutaneously into the right flank with CT26 cells. Seven days after implantation, when tumors measured 200 $mm^3$, animals were administered with IL2-T41C-S47 (2 mg/kg×1). After 24 h, 48h, 96h and 192h, tumor, lung and heart were harvested (n=2 per observation time), homogenized in ice-cold PBS containing protease inhibitor and 0.25% acetic acid, and centrifuged to obtain supernatant. To quantify IL2-T41C-S47 level, ELISA was performed in which PEG antibody was used as capture antibody and IL2 biotinylated antibody was used as detection antibody. To quantify IL2-T41C-S47 and active IL2 levels, ELISA was performed in which IL2 monoclonal antibody was used as capture antibody and IL2 biotinylated antibody was used as detection antibody. The results were shown in FIG. 29, indicating high exposure of active IL2 in tumor, which is consistent with high efficacy of anti-tumor effect, and low exposure of active IL2 in lung and heart, which is consistent with low toxicity of pulmonary edema.

Example 8: Section of Chemical Modified Linker to Acquire High Activation Efficiency R2-R3 is a chemical modified linker showing high activation efficiency as compared to the native peptide sequence linker. The activation of different R2-R3 linkers in which R1 was a 5 kDa PEG and R4 was R4-2 and control linker (C1-C4 shown in the Tables) was evaluated in activation assay. The R1-R2-R3-R4 conjugates were dissolved and diluted ten times to a final concentration of 0.1 mM/ml. At 37° C., test compounds were added into 100 μg acidized human breast cancer (MDA-MB435) tumor tissue homogenates (pH6.0) in a concentration of 1 mg/ml. The enzyme in tumor tissue homogenates could release R1. The released R1 was detected by HPLC, thereby comparing the activation efficiency of the linkers. Results were shown in Tables 37-39.

TABLE 37

Activation efficiency (%) of different linkers

| R2-R3 | Activation efficiency (%) |
|---|---|
| C1: AANL | 68.4 |
| C2: AANP | 45.9 |
| C3: SDNP | 22.7 |
| C4: SANP | 32.6 |
| C5: SDNH | 23.9 |
| AAN-R3-5 | 99.6 |
| AAN-R3-6 | 97.5 |
| AAN-R3-7 | 73.3 |
| AAN-R3-8 | 93.3 |
| AAN-R3-9 | 63.3 |
| AAN-R3-10 | 55.1 |
| AAN-R3-11 | 76.3 |
| AAN-R3-12 | 64.5 |
| AAN-R3-1 | 99.7 |
| AAN-R3-2 | 99.5 |
| AAN-R3-3 | 99.1 |
| AAN-R3-4 | 98.9 |

TABLE 38

Activation efficiency (%) of different linkers

| R2-R3 | Activation efficiency (%) |
|---|---|
| C1: AADL | 41.7 |
| C2: AADP | 37.8 |
| C3: SDDP | 46.8 |
| C4: SADP | 31.3 |
| C5: SDNH | 10.7 |
| AAD-R3-5 | 92.3 |
| AAD-R3-6 | 90.5 |
| AAD-R3-7 | 84.6 |
| AAD-R3-8 | 86.7 |
| AAD-R3-9 | 73.4 |
| AAD-R3-10 | 53.6 |
| AAD-R3-11 | 49.6 |
| AAD-R3-12 | 57.7 |
| AAD-R3-1 | 93.7 |
| AAD-R3-2 | 96..5 |
| AAD-R3-3 | 90.1 |
| AAD-R3-4 | 97.9 |

TABLE 39

| Activation efficiency (%) of different linkers | |
|---|---|
| R2-R3 (R2 is absent) | Activation Efficiency (%, pH 6.0) |
| R3-1 | 43.3 |
| R3-2 | 65.1 |
| R3-3 | 46.3 |
| R3-4 | 60.1 |
| R3-5 | 8.8 |
| R3-6 | 79.5 |

MDA-MB435 tumor tissue exhibits high activity of Legumain, Grazym B and MMP2 or other protease. In the assay, it was proved that AAN-R3-5, AAN-R3-6, AAD-R3-5, AAD-R3-6, AAD-3-7 and AAD-R3-8 had relatively higher activation efficiency (>80%). When R2 is absent, R3-5 is stable at pH6.0, and R3-2, R3-4 and R3-6 are an acidically (pH6.0) activated linkers with relatively higher activation efficiency (>60%).

Example 9: Activation Efficiency of Different Activatable Linker for Targeted Activation in Different Tumor Microenvironment Six R1-R2-R3-R4 conjugates were detected in different human tumor tissue, wherein R1 was a 5 kDa PEG and R4 was R4-2. The R1-R2-R3-R4 conjugates were each dissolved and diluted ten times to a concentration of 0.1 mM/ml. At 37° C., test compounds were added into 100 μg different acidized human tumor tissue homogenates (pH6.0) in a concentration of 1 mg/ml. The enzyme in tumor tissue homogenates could release R1. The released R1 was detected by HPLC, thereby comparing the activation efficiency of the linkers. Results were shown in Table 40.

TABLE 40

Activation efficiency (%) of R3-3, R3-5, R3-6, AAN-R3-5, AAN-R3-6, and AAD-R3-5 in homogenates from different tumor tissues

| Tumor tissues | Cells producing tumor | Activation efficiency (%) R3-2 | R3-4 | R3-6 | AAN-R3-5 | AAN-R3-6 | AAD-R3-5 |
|---|---|---|---|---|---|---|---|
| Human fibrosarcoma | HT-1080 | 63.7 | 64.7 | 78.9 | 87.2 | 84.5 | 89.5 |
| Human breast cancer | MDA-MB231 | 66.3 | 53.7 | 89.6 | 97.8 | 84.7 | 92.6 |
| Human ovarian cancer | SK-OV-3 | 56.6 | 35.7 | 78.4 | 99.4 | 85.8 | 95.8 |
| Human colon cancer | HT-29 | 63.8 | 56.7 | 58.8 | 93.6 | 83.7 | 91.5 |
| Human chronic leukemia | K562 | 64.8 | 53.8 | 58.3 | 88.2 | 84.6 | 84.8 |
| Human pancreatic cancer | Panc-1 | 46.8 | 73.8 | 74.8 | 96.1 | 94.8 | 79.8 |
| Human non-small cell lung cancer | A549 | 57.8 | 62.7 | 74.7 | 86.2 | 85.8 | 96.4 |
| Human prostate cancer | PC-3 | 37.8 | 64.8 | 89.6 | 96.5 | 94.7 | 89.6 |
| Human liver cancer | Hepg2 | 46.8 | 64.5 | 45.8 | 87.0 | 83.6 | 85.7 |
| Human renal cancer | OS-RC-2 | 35.7 | 54.6 | 75.7 | 95.7 | 90.4 | 88.4 |
| Human heart | | 8.6 | 3.7 | 7.4 | 0.1 | 0.1 | 6.8 |
| Human Lung | | 6.7 | 6.5 | 4.9 | 0.1 | 0.1 | 1.8 |

Example 10: Chemical Modified Linker Shows No Steric Hindrance to Different Biomolecules when Activated by Tumor Tissue Protease R4-1 is the shortest chemical group in the exemplified R4 groups. Different biomolecules were conjugated to R1-R2-R3-R4, in which R1 was a 5 kDa PEG, R2-R3 were shown in the following table and R4 was R4-1. The conjugates were dissolved and diluted ten times to a concentration of 0.1 mM/ml. At 37° C., the conjugates were added into 100 g different acidized human tumor tissue homogenates (pH6.0) in a concentration of 1 mg/ml or were added into a legumain solution (0.1 ug/ml) or a Granzyme B solution (0.1 ug/ml), respectively. The enzyme in tumor tissue homogenates could release R1. The released R1 was detected by HPLC, thereby comparing the activation efficiency of the linkers. Results were shown in Table 41.

TABLE 41

Activation efficiency (%) of linker of different antibody

| Biomolecule | Activation efficiency (%) AAN-R3-5 | AAN-R3-6 | AAD-R3-5 | R3-6 | Legumain AAN-R3-5 | Granzyme B AAD-R3-5 |
|---|---|---|---|---|---|---|
| Human IL2 (SEQ ID NO: 11) | 95.6 | 94.4 | 93.4 | 67.8 | 99.5 | 102.8 |
| PD-1 (SEQ ID NO: 19) | 91.4 | 88.6 | 82.8 | 76.4 | 101.6 | 94.7 |

TABLE 41-continued

| Activation efficiency (%) of linker of different antibody | | | | | | |
|---|---|---|---|---|---|---|
| | Activation efficiency (%) | | | | Legumain | Granzyme B |
| Biomolecule | AAN-R3-5 | AAN-R3-6 | AAD-R3-5 | R3-6 | AAN-R3-5 | AAD-R3-5 |
| Nivolumab (SEQ ID NO: 18) | 82.4 | 92.9 | 94.6 | 63.6 | 103.6 | 99.5 |
| Pembrolizumab (SEQ ID NO: 15) | 87.7 | 76.3 | 73.2 | 67.2 | 100.6 | 97.7 |
| Ip1(CTLA-4 Ab) (SEQ ID NO: 13) | 97.8 | 93.8 | 94.5 | 66.1 | 99.4 | 102.7 |
| Anti-human 4-1BB (SEQ ID NO: 25) | 89.5 | 92.4 | 84.4 | 66.2 | 96.8 | 104.4 |
| Adalimumab (SEQ ID NO: 29) | 100.3 | 101.4 | 79.3 | 76.5 | 99.1 | 93.7 |
| Niv-se001 (SEQ ID NO: 41) | 88.7 | 87.6 | 76.5 | 77.0 | 103.7 | 95.7 |

The results demonstrate that the cleaving site in R2 is distant to the biomolecule (R5). Even with the shortest R4-1, cleavage of R2 is not affected by the biomolecule and the activation efficiency is not affected.

Example 11: Stability of Chemical Modified Linker in Human Serum

The stability of the chemical modified linker R2-R3 was tested in human serum. R1-R2-R3-R4 conjugates, in which R1 was a 5 kDa PEG (PEG500), R2-R3 was shown in the following Tables and R4 was R4-1, were prepared. The conjugates were dissolved and diluted for ten times to a concentration of 0.1 mM/ml. Conjugates were each added into 100 µg human serum in a concentration of 1 mg/ml at 37° C. for 48 hr. The intact conjugate can be detected by ELISA Assay. By comparing the concentration of remaining conjugates, stability could be calculated. Results were shown in Tables 42 and 43.

TABLE 42

| Stability (% of control) of different linkers | |
|---|---|
| R2-R3 | stability (% of control) |
| C1: AANL | 97.4 |
| C2: AANP | 55.9 |
| C3: SDNP | 72.7 |
| C4: SANP | 62.6 |
| C5: SDNH | 73.9 |
| AAN-R3-5 | 99.9 |
| AAN-R3-6 | 99.5 |
| AAN-R3-7 | 99.3 |
| AAN-R3-8 | 98.3 |
| AAN-R3-9 | 97.2 |
| AAN-R3-10 | 98.7 |
| AAN-R3-11 | 96.3 |
| AAN-R3-12 | 97.5 |
| AAN-R3-1 | 89.7 |
| AAN-R3-2 | 89.5 |
| AAN-R3-3 | 79.1 |
| AAN-R3-4 | 88.9 |

TABLE 43

| Stability (% of control) of different linkers | |
|---|---|
| R2-R3 (R2 is absent) | Stability (%) |
| R3-1 | 88.8 |
| R3-2 | 83.7 |
| R3-3 | 94.6 |
| R3-4 | 91.8 |
| R3-5 | 85.8 |
| R3-6 | 86.4 |

Example 12: Increased Conjugation Efficiency with Increased Antibody/S13 Linker For small scale conjugation, 5~10 mg IgG for different variants were buffer exchanged with ultrafiltration tubes (Merck Millipore) into 50 mM Tris-HCl, pH7.5 containing 2 mM EDTA by repeated centrifugation. Then the antibodies were mildly reduced by DTT in a 1:20~1:200 molar ratio at room temperature for 4~16 h. Then the reduced antibodies were dialyzed into 50 mM Tris-HCl, 150 mM NaCl, pH7.5 and re-oxidated by $Cu_2SO_4$ or Dehydroascorbic acid (DHAA, Sigma) in a 1:50-1:200 molar ratio for 1~3h at room temperature. Then the re-oxidated antibodies with free sulfydryl were conjugated by S13 chemical linker in a ratio of 1:10, 1:20, 1:50 or 1:100 at room temperature for 4 h. The conjugation efficiency was shown by reduced SDS-PAGE. As shown in Table 44, different conjugation efficiency was obtained.

TABLE 44

| Increased conjugation efficiency with increased antibody (Ipilimumab, SEQ ID NO: 13)/S13 linker ratio | |
|---|---|
| Antibody/S13 linker molecular ratio | Conjugation efficiency |
| 1:10 | 60% |
| 1:20 | 72% |
| 1:50 | 89% |
| 1:100 | 95% |

Figure 30:
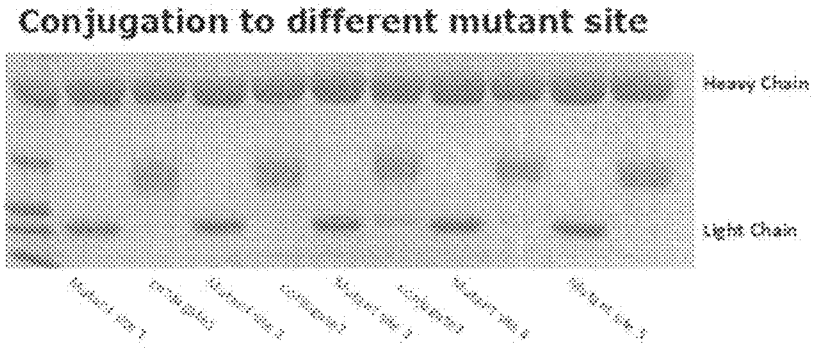
FIG. 30: Reduced SDS-PAGE gel results showing that all five positions are conjugated with S13 linker in a high efficiency.

In a conjugation reaction of CTLA4-antibody (Ipilimumab, SEQ ID NO: 14): S13 linker=1:100 condition with Cys mutation in different position of CTLA4-antibody, the mutant sites were shown in Table 45. In the CTLA4-antibody:S13=1:100 condition, all five positions are conjugated with S13 linker in a high efficiency, as shown in reduced SDS-PAGE gel in FIG. 30.

TABLE 45

| Different mutation sites for 1:100 molecular ratio conjugation | |
|---|---|
| Mutation ID | Conjugation efficiency (%) |
| 1# (FR1, L22S) | 96 |
| 2# (FR2, L49Y) | 99 |
| 3# (FR2, L72T) | 95 |
| 4# (CDR1, L24R) | 97 |
| 5# (CDR3, L13G) | 99 |

Example 13: Conjugation Efficiency and Affinity Change of Framework (Non-CDR) of Variable Region of Human CTLA-Antibody We mutated every non-Cysteine amino acid to Cysteine in framework region (FR) of CTLA-4 antibody to make cystine mutant for experiments. Some mutation sites showed nearly 100% conjugation efficiency. The conjugation efficiency for different mutants was high in a CTLA4-antibody: S13=1:100 condition, which was summarized in Table 46 and Table 47. Some mutations show very low conjugation, indicating that Cys may be buried in the interior of antibody.

TABLE 46

Conjugation efficiency for Ipilimumab light chain framework region

| Region (Kabat) | Kabat No. | Ipilimumab VL | Conjugation efficiency of S13 (%) |
|---|---|---|---|
| FR1 | L1 | E | 35 |
| | L2 | I | 58 |
| | L3 | V | 99 |
| | L4 | L | 29 |
| | L5 | T | 96 |
| | L6 | Q | 95 |
| | L7 | S | 87 |
| | L8 | P | 98 |
| | L9 | G | 96 |
| | L10 | T | 95 |
| | L11 | L | 62 |
| | L12 | S | 88 |
| | L13 | L | 16 |
| | L14 | S | 88 |
| | L15 | P | 95 |
| | L16 | G | 64 |
| | L17 | E | 69 |
| | L18 | R | 72 |
| | L19 | A | 10 |
| | L20 | T | 28 |
| | L21 | L | 13 |
| | L22 | S | 96 |
| | L23 | C | n/d |
| FR2 | L35 | W | 13 |
| | L36 | Y | 88 |
| | L37 | Q | 16 |
| | L38 | Q | 86 |
| | L39 | K | 89 |
| | L40 | P | 19 |
| | L41 | G | 92 |
| | L42 | Q | 85 |
| | L43 | A | 46 |
| | L44 | P | 63 |
| | L45 | R | 25 |
| | L46 | L | 16 |

TABLE 46-continued

Conjugation efficiency for Ipilimumab light chain framework region

| Region (Kabat) | Kabat No. | Ipilimumab VL | Conjugation efficiency of S13 (%) |
|---|---|---|---|
| | L47 | L | 18 |
| | L48 | I | 85 |
| | L49 | Y | 99 |
| FR3 | L57 | G | 86 |
| | L58 | I | 95 |
| | L59 | P | 94 |
| | L60 | D | 96 |
| | L61 | R | 86 |
| | L62 | F | 75 |
| | L63 | S | 95 |
| | L64 | G | 95 |
| | L65 | S | 94 |
| | L66 | G | 68 |
| | L67 | S | 88 |
| | L68 | G | 88 |
| | L69 | T | 87 |
| | L70 | D | 94 |
| | L71 | F | 28 |
| | L72 | T | 95 |
| | L73 | L | 26 |
| | L74 | T | 95 |
| | L75 | I | 16 |
| | L76 | S | 94 |
| | L77 | R | 96 |
| | L78 | L | 13 |
| | L79 | E | 88 |
| | L80 | P | 96 |
| | L81 | E | 85 |
| | L82 | D | 13 |
| | L83 | F | 18 |
| | L84 | A | 10 |
| | L85 | V | 85 |
| | L86 | Y | 12 |
| | L87 | Y | 19 |
| | L88 | C | n/d |
| FR4 | L98 | F | 87 |
| | L99 | G | 88 |
| | L100 | Q | 19 |
| | L101 | G | 86 |
| | L102 | T | 12 |
| | L103 | K | 95 |
| | L104 | V | 8 |
| | L105 | E | 95 |
| | L106 | I | 75 |
| | L107 | K | 92 |

TABLE 47

Conjugation efficiency for Ipilimumab heavy chain framework region

| Region (Kabat) | Kabat No. | Ipilimumab VH | Conjugation efficiency of S13 (%) |
|---|---|---|---|
| FR1 | H1 | Q | 68 |
| | H2 | V | 95 |
| | H3 | Q | 86 |
| | H4 | L | 86 |
| | H5 | V | 88 |
| | H6 | E | 18 |
| | H7 | S | 68 |
| | H8 | G | 89 |
| | H9 | G | 85 |
| | H10 | G | 84 |
| | H11 | V | 68 |
| | H12 | V | 18 |
| | H13 | Q | 86 |

TABLE 47-continued

| Conjugation efficiency for Ipilimumab heavy chain framework region | | | |
|---|---|---|---|
| Region (Kabat) | Kabat No. | Ipilimumab VH | Conjugation efficiency of S13 (%) |
| | H14 | P | 85 |
| | H15 | G | 85 |
| | H16 | R | 86 |
| | H17 | S | 78 |
| | H18 | L | 18 |
| | H19 | R | 78 |
| | H20 | L | 8 |
| | H21 | S | 79 |
| | H22 | C | n/d |
| | H23 | A | 89 |
| | H24 | A | 12 |
| | H25 | S | 86 |
| | H26 | G | 89 |
| | H27 | F | 88 |
| | H28 | T | n/d |
| | H29 | F | 89 |
| | H30 | S | 89 |
| FR2 | H36 | W | 13 |
| | H37 | V | 18 |
| | H38 | R | 19 |
| | H39 | Q | 89 |
| | H40 | A | 82 |
| | H41 | P | 98 |
| | H42 | G | 96 |
| | H43 | K | 12 |
| | H44 | G | 96 |
| | H45 | L | 93 |
| | H46 | E | 88 |
| | H47 | W | 18 |
| | H48 | V | 15 |
| | H49 | T | 23 |
| FR3 | H66 | R | 26 |
| | H67 | F | 29 |
| | H68 | T | 95 |
| | H69 | I | 18 |
| | H70 | S | 86 |
| | H71 | R | 28 |
| | H72 | D | 83 |
| | H73 | N | 82 |
| | H74 | S | 85 |
| | H75 | K | 92 |
| | H76 | N | 98 |
| | H77 | T | 25 |
| | H78 | L | 26 |
| | H79 | Y | 95 |
| | H80 | L | 15 |
| | H81 | Q | 95 |
| | H82 | M | 17 |
| FR4 | H103 | W | 68 |
| | H104 | G | 29 |
| | H105 | Q | 92 |
| | H106 | G | 29 |
| | H107 | T | 28 |
| | H108 | L | 95 |
| | H109 | V | 88 |
| | H110 | T | 87 |
| | H111 | V | 27 |
| | H112 | S | 90 |
| | H113 | S | 85 |

The mutant sites with high conjugation efficiency of S13 (>80%) were conjugated with R4-7 and tested for relative binding activity in an ELISA based assay according to EC50 ratio (EC50 of WT antibody: EC50 of mutant antibody-R4-7*100%0). Specifically, a 96-well ELISA plate (NUNC) was coated by 1 g g/ml His-CTLA-4 protein (Sino Biological) overnight and then blocked with 1% BSA blocker (ThermoFisher) for 2 hours at 37° C. and washed by PBST three times. Corresponding antibody or corresponding mutant with R4-7 conjugation was added and allowed to bind at 37° C. for 1 hour, then washed with PBST three times. HRP enzyme-conjugated anti-human IgG was added and allowed to bind at 37° C. for 1 hour and then washed with PBST three times. TMB substrate (Solarbio., Inc.) was used to detect absorbance at 450 nm. Data analysis was carried out with GraphPad software and EC50 for each antibody or conjugate was calculated.

After comparing the binding affinity R4-7-s-cys-CTLA-4 in FR region and WT antibody of CTLA-4, we found most of position achieved a good effect to maintain the binding affinity (Group A, >60% comparing with WT antibody) while some positions (Group B, <60% comparing with WT antibody) exhibited a lower binding affinity, as shown in Table 48 and Table 49.

TABLE 48

| Binding activity of light chain framework mutants after conjugation with R4-7 | | | | |
|---|---|---|---|---|
| Region (Kabat) | Kabat No. | Ipilimumab VL | Conjugation efficiency of S13 (%) | Binding activity after conjugation with R4-7 |
| | L3 | V | 99 | A |
| | L5 | T | 96 | A |
| | L6 | Q | 95 | A |
| | L7 | S | 87 | A |
| | L8 | P | 98 | B |
| | L9 | G | 96 | A |
| | L10 | T | 95 | A |
| | L12 | S | 88 | A |
| | L14 | S | 88 | A |
| | L15 | P | 95 | B |
| | L16 | G | 64 | A |
| | L22 | S | 96 | A |
| | L36 | Y | 88 | A |
| | L38 | Q | 86 | A |
| | L39 | K | 89 | A |
| | L41 | G | 92 | A |
| | L42 | Q | 85 | A |
| | L48 | I | 85 | B |
| | L49 | Y | 99 | A |
| FR3 | L57 | G | 86 | B |
| | L58 | I | 95 | A |
| | L59 | P | 94 | B |
| | L60 | D | 96 | A |
| | L61 | R | 86 | A |
| | L63 | S | 95 | A |
| | L64 | G | 95 | A |
| | L65 | S | 94 | A |
| | L67 | S | 88 | A |
| | L68 | G | 88 | B |
| | L69 | T | 87 | B |
| | L70 | D | 94 | B |
| | L72 | T | 95 | A |
| | L74 | T | 95 | A |
| | L76 | S | 94 | A |
| | L77 | R | 96 | A |
| | L79 | E | 88 | A |
| | L80 | P | 96 | B |
| | L81 | E | 85 | A |
| | L85 | V | 85 | A |

TABLE 48-continued

Binding activity of light chain framework mutants after conjugation with R4-7

| Region (Kabat) | Kabat No. | Ipilimumab VL | Conjugation efficiency of S13 (%) | Binding activity after conjugation with R4-7 |
|---|---|---|---|---|
| FR4 | L98 | F | 87 | A |
| | L99 | G | 88 | A |
| | L101 | G | 86 | A |
| | L103 | K | 95 | A |
| | L105 | E | 95 | A |
| | L107 | K | 92 | A |

TABLE 49

Binding activity of heavy chain framework mutants after conjugation with R4-7

| Region (Kabat) | Kabat No. | Ipilimumab VH | Conjugation efficiency of S13 (%) | R4-7 |
|---|---|---|---|---|
| | H2 | V | 95 | A |
| | H3 | Q | 86 | A |
| | H4 | L | 86 | A |
| | H5 | V | 88 | A |
| | H8 | G | 89 | A |
| | H9 | G | 85 | A |
| | H10 | G | 84 | A |
| | H13 | Q | 86 | A |
| | H14 | P | 85 | B |
| | H15 | G | 85 | A |
| | H16 | R | 86 | A |
| | H23 | A | 89 | A |
| | H25 | S | 86 | A |
| | H26 | G | 89 | A |
| | H27 | F | 88 | A |
| | H29 | F | 89 | A |

TABLE 49-continued

Binding activity of heavy chain framework mutants after conjugation with R4-7

| Region (Kabat) | Kabat No. | Ipilimumab VH | Conjugation efficiency of S13 (%) | R4-7 |
|---|---|---|---|---|
| | H30 | S | 89 | B |
| | H39 | Q | 89 | A |
| | H40 | A | 82 | A |
| | H41 | P | 98 | B |
| | H42 | G | 96 | A |
| | H44 | G | 96 | A |
| | H45 | L | 93 | A |
| | H46 | E | 88 | A |
| | H68 | T | 95 | A |
| | H70 | S | 86 | A |
| | H72 | D | 83 | B |
| | H73 | N | 82 | B |
| | H74 | S | 85 | B |
| | H75 | K | 92 | A |
| | H76 | N | 98 | A |
| | H79 | Y | 95 | A |
| | H81 | Q | 95 | A |
| | H105 | Q | 92 | A |
| | H108 | L | 95 | A |
| | H109 | V | 88 | A |
| | H110 | T | 87 | A |
| | H112 | S | 90 | A |
| | H113 | S | 85 | A |

For these sites with binding activity<60% (class B in the above tables), we conjugated them with different chemical linkers to rescue the binding activity. As shown in Table 50, for some of them, the binding activity can be restored with specific chemical modification of R4. These results indicate that the side chain of these sites might contribute to the antibody/antigen interaction and specific chemical linker can mimic the light chain structure and provide molecular interaction against antigen like the native WT amino acid.

TABLE 50

R4 screening to restore the activity of sites with low activity when conjugated with R4-7

| Kabat | Original | | R4 screening | | | | | | |
|---|---|---|---|---|---|---|---|---|---|
| No. | amino acid | R4-7 | R4-1 | R4-3 | R4-4 | R4-5 | R4-8 | R4-11 | R4-27 |
| L8 | P | B | B | B | B | B | B | A | B |
| L15 | P | B | B | B | B | B | B | B | B |
| L48 | I | B | B | B | B | A | B | B | B |
| L57 | G | B | A | B | B | B | B | B | B |
| L59 | P | B | B | B | B | B | B | B | B |
| L68 | G | B | A | B | B | B | B | B | B |
| L69 | T | B | A | A | B | B | B | B | B |
| L70 | D | B | B | B | B | B | B | A | B |
| L80 | P | B | B | B | B | B | B | B | B |
| H14 | P | B | B | B | B | B | B | B | B |
| H30 | S | B | A | A | B | B | B | B | B |
| H41 | P | B | B | B | B | B | B | B | B |
| H72 | D | B | B | B | B | B | B | A | B |
| H73 | N | B | B | B | B | B | B | A | B |
| H74 | S | B | A | B | B | B | B | B | B |

Blocking Effect of Selected Sites when Conjugated with S13 (5 kD Functional Group) or S47 (40 kD Functional Group) Chemical Linker We selected the above sites whose activity can be restored after conjugating with R4-7 or other R4 linkers as candidate sites for tumor microenvironment activated antibody (TMEAbody) screening, because after protease cleavage, the conjugated antibody will remain the identical structure with antibody mutant-s-R4 form. Blocking effect after conjugated with S13 (5 kD functional group) was first evaluated with the ELISA assay like Example 1. As shown in Table 51, after conjugation with S13 linker, some of them showed significant blocking effect of the binding activity against the antigen protein. We also categorize these sites with <30% activity as class A and other sites as class B, as shown in the Table 51.

TABLE 51

Blocking efficiency of selected sites when conjugated with S13 (5 kD) linker

| Kabat No. | Original amino acid | Conjugation efficiency of S13 (%) | Binding Activity after S13 (5 kD) blocking |
|---|---|---|---|
| L3 | V | 99 | A |
| L5 | T | 96 | B |
| L6 | Q | 95 | B |
| L7 | S | 87 | B |
| L9 | G | 96 | B |
| L10 | T | 95 | B |
| L12 | S | 88 | B |
| L14 | S | 88 | B |
| L22 | S | 96 | A |
| L36 | Y | 88 | A |
| L38 | Q | 86 | B |
| L39 | K | 89 | B |
| L41 | G | 92 | B |
| L42 | Q | 85 | B |
| L49 | Y | 99 | A |
| L58 | I | 95 | A |
| L60 | D | 96 | A |
| L61 | R | 86 | B |
| L63 | S | 95 | B |
| L64 | G | 95 | B |
| L65 | S | 94 | A |
| L67 | S | 88 | A |
| L69 | T | 87 | A |
| L70 | D | 94 | A |
| L72 | T | 95 | B |
| L74 | T | 95 | B |
| L76 | S | 94 | B |
| L77 | R | 96 | B |
| L79 | E | 88 | B |
| L81 | E | 85 | B |
| L85 | V | 85 | B |
| L98 | F | 87 | B |
| L99 | G | 88 | B |

TABLE 51-continued

Blocking efficiency of selected sites when conjugated with S13 (5 kD) linker

| Kabat No. | Original amino acid | Conjugation efficiency of S13 (%) | Binding Activity after S13 (5 kD) blocking |
|---|---|---|---|
| L101 | G | 86 | B |
| L103 | K | 95 | B |
| L105 | E | 95 | B |
| L107 | K | 92 | B |
| H2 | V | 95 | A |
| H3 | Q | 86 | A |
| H4 | L | 86 | A |
| H5 | V | 88 | A |
| H8 | G | 89 | B |
| H9 | G | 85 | B |
| H10 | G | 84 | B |
| H13 | Q | 86 | B |
| H14 | P | 85 | B |
| H15 | G | 85 | B |
| H16 | R | 86 | B |
| H23 | A | 89 | A |
| H25 | S | 86 | A |
| H26 | G | 89 | A |
| H27 | F | 88 | A |
| H29 | F | 89 | A |
| H30 | S | 89 | A |
| H39 | Q | 89 | B |
| H40 | A | 82 | B |
| H42 | G | 96 | B |
| H44 | G | 96 | B |
| H45 | L | 93 | B |
| H46 | E | 88 | B |
| H68 | T | 95 | A |
| H70 | S | 86 | A |
| H72 | D | 83 | A |
| H73 | N | 82 | A |
| H74 | S | 85 | A |
| H75 | K | 92 | A |
| H76 | N | 98 | A |
| H79 | Y | 95 | A |
| H81 | Q | 95 | B |
| H105 | Q | 92 | B |
| H108 | L | 95 | B |
| H109 | V | 88 | B |
| H110 | T | 87 | B |
| H112 | S | 90 | B |
| H113 | S | 85 | B |

We further investigated if blocking efficiency could be improved with higher molecular weight functional group. S47 (with 40 kD functional group) and S64 (with 80 kD functional group) were used for conjugation and blocking efficiency was measured with the above method in a binding ELISA assay. The results were summarized in Table 52, which showed that the increased molecular weight can significantly improve the blocking efficiency of binding activity. All of the sites showed <30% activity when conjugated with S64 (80 kD) functional group.

TABLE 52

Blocking efficiency of selected sites when conjugated with S13 (5 kD), S37 (20 kD), S47 (40 kD) or S64 (80 kD) linkers

| Kabat No. | Original amino acid | Conjugation efficiency of S13 (%) | Binding Activity after S13 (5 kD) blocking | Binding Activity after S37 (20 kD) blocking | Binding Activity after S47 (40 kD) blocking | Binding Activity after S64 (80 kD) blocking |
|---|---|---|---|---|---|---|
| L3 | V | 99 | A | A | A | A |
| L5 | T | 96 | B | A | A | A |
| L6 | Q | 95 | B | A | A | A |
| L7 | S | 87 | B | A | A | A |
| L9 | G | 96 | B | B | A | A |

TABLE 52-continued

Blocking efficiency of selected sites when conjugated with S13 (5 kD), S37 (20 kD), S47 (40 kD) or S64 (80 kD) linkers

| Kabat No. | Original amino acid | Conjugation efficiency of S13 (%) | Binding Activity after S13 (5 kD) blocking | Binding Activity after S37 (20 kD) blocking | Binding Activity after S47 (40 kD) blocking | Binding Activity after S64 (80 kD) blocking |
|---|---|---|---|---|---|---|
| L10 | T | 95 | B | B | B | A |
| L12 | S | 88 | B | A | A | A |
| L14 | S | 88 | B | A | A | A |
| L22 | S | 96 | A | A | A | A |
| L36 | Y | 88 | A | A | A | A |
| L38 | Q | 86 | B | A | A | A |
| L39 | K | 89 | B | B | A | A |
| L41 | G | 92 | B | B | B | A |
| L42 | Q | 85 | B | A | A | A |
| L49 | Y | 99 | A | A | A | A |
| L58 | I | 95 | A | A | A | A |
| L60 | D | 96 | A | A | A | A |
| L61 | R | 86 | B | A | A | A |
| L63 | S | 95 | B | B | B | A |
| L64 | G | 95 | B | B | B | A |
| L65 | S | 94 | A | A | A | A |
| L67 | S | 88 | A | A | A | A |
| L69 | T | 87 | A | A | A | A |
| L70 | D | 94 | A | A | A | A |
| L72 | T | 95 | B | A | A | A |
| L74 | T | 95 | B | A | A | A |
| L76 | S | 94 | B | B | A | A |
| L77 | R | 96 | B | B | B | A |
| L79 | E | 88 | B | B | B | A |
| L81 | E | 85 | B | B | B | A |
| L85 | V | 85 | B | B | B | A |
| L98 | F | 87 | B | B | B | A |
| L99 | G | 88 | B | B | A | A |
| L101 | G | 86 | B | B | A | A |
| L103 | K | 95 | B | A | A | A |
| L105 | E | 95 | B | A | A | A |
| L107 | K | 92 | B | A | A | A |
| H2 | V | 95 | A | A | A | A |
| H3 | Q | 86 | A | A | A | A |
| H4 | L | 86 | A | A | A | A |
| H5 | V | 88 | A | A | A | A |
| H8 | G | 89 | B | A | A | A |
| H9 | G | 85 | B | A | A | A |
| H10 | G | 84 | B | A | A | A |
| H13 | Q | 86 | B | B | B | A |
| H14 | P | 85 | B | B | B | A |
| H15 | G | 85 | B | A | A | A |
| H16 | R | 86 | B | A | A | A |
| H23 | A | 89 | A | A | A | A |
| H25 | S | 86 | A | A | A | A |
| H26 | G | 89 | A | A | A | A |
| H27 | F | 88 | A | A | A | A |
| H29 | F | 89 | A | A | A | A |
| H30 | S | 89 | A | A | A | A |
| H39 | Q | 89 | B | A | A | A |
| H40 | A | 82 | B | A | A | A |
| H42 | G | 96 | B | B | A | A |
| H44 | G | 96 | B | B | B | A |
| H45 | L | 93 | B | A | A | A |
| H46 | E | 88 | B | A | A | A |
| H68 | T | 95 | A | A | A | A |
| H70 | S | 86 | A | A | A | A |
| H72 | D | 83 | A | A | A | A |
| H73 | N | 82 | A | A | A | A |
| H74 | S | 85 | A | A | A | A |
| H75 | K | 92 | A | A | A | A |
| H76 | N | 98 | A | A | A | A |
| H79 | Y | 95 | A | A | A | A |
| H81 | Q | 95 | B | A | A | A |
| H105 | Q | 92 | B | A | A | A |
| H108 | L | 95 | B | B | A | A |
| H109 | V | 88 | B | B | A | A |
| H110 | T | 87 | B | B | B | A |
| H112 | S | 90 | B | B | B | A |
| H113 | S | 85 | B | B | B | A |

Improving Binding Affinity of R4 Modified Antibody by R4 Library in Framework (Non-CDR) of a Variable Region of Human CTLA-4 Antibody and PD-1 Antibody Framework (non-CDR) region is a conservative sequence and has been used to link the CDR region to form different antibody. As shown in Table 51 and Table 52, when the side chain of some amino acid changes, the binding are reduced (class B), indicating that side chain of amino acid may provide an interaction or a space to help antigen binding with CDR. Normally, the interaction between framework and antigen is weaker than that between CDR region and antigen. By conjugation of the different R4 to the selected mutant position of PD-1 antibody (Nivolumab), we have the chance to obtain a higher affinity or to maintain the affinity of the chemical modified antibody, as compared to the wild type antibody.

TABLE 53

Binding activity of R4 conjugated with mutation biomolecular library in conservative FR sites (% of WT antibody) for PD-1 antibody (Nivolumab)

| PD-1 | R4-1 | R4-2 | R4-3 | R4-4 | R4-5 | R4-6 | R4-7 | R4-8 | R4-9 |
|---|---|---|---|---|---|---|---|---|---|
| Gly41 | 62.6 | 45.6 | 1.6 | 33.6 | 24.6 | 34.4 | 32.7 | 31.7 | 58.7 |
| Glu46 | 26.4 | 48.9 | 67.8 | 45.1 | 49.6 | 29.7 | 86.4 | 78.4 | 10.4 |
| Tyr49 | 67.8 | 48.6 | 33.4 | 14.5 | 18.4 | 105.4 | 97.4 | 62.4 | 59.8 |
| Arg61 | 67.4 | 108.4 | 48.6 | 78.4 | 64.1 | 89.1 | 91.5 | 57.9 | 48.5 |
| Ser63 | 89.5 | 98.4 | 108.9 | 84.5 | 89.4 | 85.5 | 84.5 | 88.9 | 116.9 |
| Thr72 | 48.9 | 47.6 | 115.9 | 67.4 | 48.5 | 75.8 | 68.7 | 12.4 | 34.9 |

The results showed that in FR region of different antibodies, conjugating different R4 to the conservative site can adjust the binding activity. In a representative Gly41, it also has a chance to recover 62.6% binding affinity by conjugation with R4-1. In conservative Gln3, Ser7, Ser26, Glu46, Thr68, Asp72 in VH, and Thr5, Tyr49, Arg61, Ser63, Ser65, Ser67, Thr72, Thr74, Ser76, Asp82 in framework, it can be screened out higher affinity binding conjugation. Because framework sequences (FR1, FR2 and FR3) are conservative in all kinds of human antibody, by conjugating different R4 to these conservative sites in FR region, any antibody has the chance to maintain or increase the binding affinity.

Analysis on the Binding Activity of Mutants in a Sequence of High Homology in the Framework (Non-CDR) of a Variable Region of Human Germline Antibody Human antibody consists of 4 peptide chains, including two identical light chains (LC) and two identical heavy chains (HC). The chains form a monomer by disulfide bond(s) and non-covalent bonds. There are two types of light chains, κ and λ, and five types of heavy chains, i.e., μ, δ, γ, ε and α. An antibody, as a whole, is divided into a constant region and a variable region. The variable region is located at the terminus of the two arms of the Y-shaped structure. Humanized or human antibodies have a certain generality, that is, they all contain 4 loops in heavy chain or light chain at the terminus of the two arms of the Y-shaped structure. Three loops are highly variable and directly anticipate in binding to an antigen. The regions in these loops are termed CDRs, wherein CDR1, CDR2 and CDR3 are present in these three loops, respectively.

Figure 31:
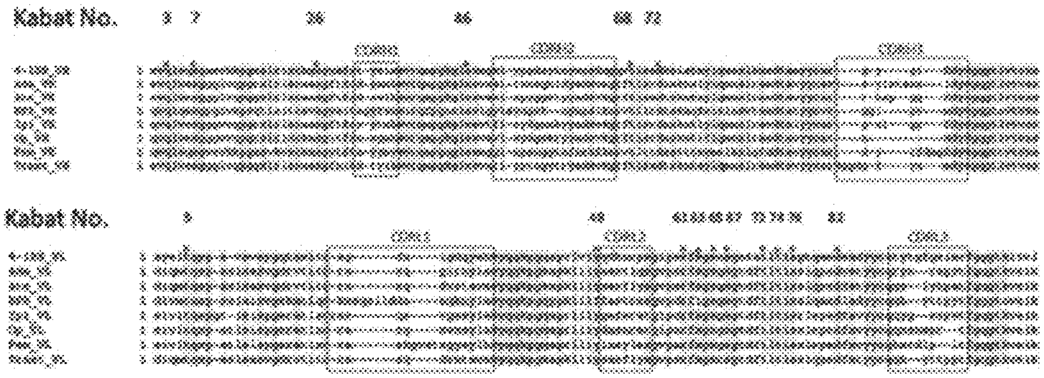
FIG. 31: The 8 selected antibodies sequences (Upper from top to bottom: SEQ ID NO: 99, SEQ ID NO: 101, SEQ ID NO: 64, SEQ ID NO: 19, SEQ ID NO: 97, SEQ ID NO: 92, SEQ ID NO: 102 and SEQ ID NO: 105; lower from top to bottom: SEQ ID NO: 98, SEQ ID NO: 100, SEQ ID NO: 65, SEQ ID NO: 20, SEQ ID NO: 96, SEQ ID NO: 93, SEQ ID NO: 103 and SEQ ID NO: 106).

Antibody was produced by recombination of genes of immunoglobulin superfamily in vivo. Some framework regions of antibodies against different antigens may be derived from a gene or an amino acid sequence of a same germline antibody. Between the CDR, there are framework sequences (FR1, FR2, and FR3), which are conservative in all kinds of human antibody. All kinds of human antibody for variable region is shown in full from the start codon to the last nucleotide before the variable region gene exon in the case of the leader sequence, from the beginning of the V gene exon (Residue 1 in FR1) to the last nucleotide/amino acid before the heptamer recombination signal sequence in the case of VH, VK and VL. The 8 selected antibodies sequences are shown in FIG. 31.

We mutated other antibodies' heavy chain and light chain DNA sequences corresponding to the same conserved position for expression to compare the binding affinity with other sites in FR region and WT antibody. In the 5 antibody sequences, the conservative sites of Gln3, Ser7, Ser26, Glu46, Thr68 and Asp72 in VH, and Thr5, Tyr49, Arg61, Ser63, Ser65, Ser67, Thr72, Thr74, Ser76 and Asp82 in VL (the position of the amino acid is numbered according to Kabat numbering) were selected to conjugate with R4-7.

TABLE 54

Binding activity of R4-7 conjugated with mutation biomolecular library in conservative FR sites (% of WT antibody)

| sites | 41BB | Ada | PD-1-k | Ip1 | Trast |
|---|---|---|---|---|---|
| Gln3 | 68.3 | 78.4 | 73.8 | 98.3 | 94.5 |
| Ser7 | 94.5 | 87.4 | 105.6 | 110.4 | 110.6 |
| Ser26 | 87.1 | 68.4 | 97.1 | 74.8 | 104.6 |
| Glu46 | 97.4 | 78.4 | 69.4 | 67.8 | 78.4 |
| Thr68 | 68.7 | 97.8 | 74.7 | 79.8 | 87.7 |
| Thr5 | 86.4 | 97.4 | 84.1 | 67.4 | 69.7 |
| Gly41 | 24.8 | 16.4 | 8.9 | 8.4 | 8.9 |
| Tyr49 | 79.7 | 97.8 | 99.7 | 112.4 | 107.8 |
| Arg61 | 87.9 | 78.9 | 67.8 | 79.8 | 94.1 |
| Ser63 | 89.7 | 69.5 | 69.1 | 78.9 | 97.4 |
| Ser65 | 69.4 | 78.9 | 70.8 | 69.7 | 97.8 |
| Ser67 | 79.7 | 68.7 | 69.2 | 79.0 | 64.9 |
| Thr72 | 68.5 | 66.4 | 72.8 | 70.9 | 79.8 |
| Thr74 | 107.5 | 97.4 | 89.4 | 99.8 | 95.8 |
| Ser76 | 69.4 | 78.9 | 69.1 | 78.4 | 78.4 |
| Asp82 | 98.5 | 74.8 | 68.7 | 79.4 | 67.8 |

The results showed that in FR region of different antibodies, conjugating R4-7 to the conservative sites of Gln3, Ser7, Ser26, Glu46, Thr68 or Asp72 in VH, and Thr5, Tyr49, Arg61, Ser63, Ser65, Ser67, Thr72, Thr74, Ser76 or Asp82 in VL can maintain the binding activity as compared to the wild type antibody or other positions, which was 60% or more of the original binding activity. In a representative negative control Gly41, it lost binding affinity in all antibody (<60% of WT antibody).

Example 14 Mutated Amino Acid in CDR Region of CTLA-4 Antibody to Screen Different R4 Group for Maintaining or Increasing the Binding Affinity CTLA-4 is on the T cell surface in tumor microenvironment. We mutated every amino acid in CDR region of its antibody to screen by different R4 group for maintaining or increasing the binding affinity. In some case, there are some R4 groups which could enhance the binding affinity, but we did not select them as drug candidates in our development. We prefer R-1, R4-7, R4-5, R4-8 and R4-12 for the large scale synthesis and stability in our drug development. The conjugated CTLA-4 antibody with R4 can recover the binding >60% in some positions by chemical modified maturation of R4 library screening.

TABLE 55

Binding effect of mutants of anti-CTLA-4 antibody having mutation in CDR regions after conjugating to different R4 molecules

| Region (Kabat) | Kabat No. | Original amino acid | R4 | Binding activity |
|---|---|---|---|---|
| CDRL1 | L24 | R | R4-26 | 89% |
| | L25 | A | R4-1 | 95% |
| | L26 | S | R4-1 | 91% |
| | L27 | Q | R4-11 | 88% |
| | L28 | V | R4-7 | 78% |
| | L29 | G | R4-1 | 95% |
| | L30 | S | R4-1 | 81% |
| | L30 | S | R4-2 | 104% |
| | L30 | S | R4-3 | 96% |
| | L31 | S | R4-1 | 99% |
| | L32 | Y | R4-7 | 98% |
| | L32 | Y | R4-8 | 107% |
| | L33 | L | R4-1 | 95% |
| | L34 | A | R4-1 | 92% |
| CDRL2 | L50 | G | R4-1 | 97% |
| | L50 | G | R4-3 | 107% |
| | L51 | A | R4-1 | 92% |
| | L52 | F | R4-1 | 72% |
| | L53 | S | R4-1 | 98% |
| | L54 | R | R4-26 | 163% |
| | L55 | A | R4-1 | 102% |
| | L55 | A | R4-3 | 106% |
| | L56 | T | R4-1 | 93% |
| CDRL3 | L89 | Q | R4-7 | 96% |
| | L90 | Q | R4-7 | 75% |
| | L91 | Y | R4-5 | 95% |
| | L91 | Y | R4-7 | 105% |
| | L92 | G | R4-1 | 99% |
| | L92 | G | R4-3 | 104% |
| | L93 | S | R4-1 | 92% |
| | L94 | S | R4-1 | 95% |
| | L94 | S | R4-11 | 142% |
| | L95 | P | R4-1 | 62% |
| | L96 | W | R4-4 | 72% |
| | L97 | T | R4-1 | 91% |
| CDRH1 | H31 | S | R4-1 | 110% |
| | H32 | Y | R4-7 | 92% |
| | H32 | Y | R4-18 | 208% |
| | H33 | T | R4-1 | 102% |
| | H34 | M | R4-1 | 65% |
| | H35 | H | R4-5 | 72% |
| CDRH2 | H50 | F | R4-4 | 73% |
| | H51 | I | R4-4 | 72% |
| | H52 | S | R4-1 | 95% |
| | H52 | S | R4-3 | 107% |
| | H52A | Y | R4-7 | 93% |
| | H53 | D | R4-11 | 91% |
| | H54 | G | R4-1 | 95% |
| | H55 | N | R4-11 | 96% |
| | H56 | N | R4-11 | 91% |
| | H57 | K | R4-7 | 88% |
| | H58 | Y | R4-7 | 89% |
| | H59 | Y | R4-4 | 92% |
| | H59 | Y | R4-10 | 105% |
| | H60 | A | R4-4 | 65% |
| | H61 | D | R4-11 | 92% |
| | H62 | S | R4-3 | 91% |
| | H63 | V | R4-1 | 68% |
| | H64 | K | R4-7 | 96% |
| | H64 | K | R4-18 | 137% |
| | H65 | G | R4-1 | 93% |
| CDRH3 | H95 | T | R4-3 | 92% |
| | H95 | T | R4-1 | 152% |
| | H96 | G | R4-1 | 65% |
| | H96 | G | R4-2 | 85% |
| | H97 | W | R4-8 | 92% |
| | H98 | L | R4-3 | 84% |
| | H99 | G | R4-1 | 94% |

TABLE 55-continued

Binding effect of mutants of anti-CTLA-4 antibody having mutation in CDR regions after conjugating to different R4 molecules

| Region (Kabat) | Kabat No. | Original amino acid | R4 | Binding activity |
|---|---|---|---|---|
| | H100 | P | R4-1 | 69% |
| | H100A | F | R4-4 | 84% |
| | H101 | D | R4-3 | 88% |
| | H102 | Y | R4-7 | 95% |
| | H102 | Y | R4-5 | 242% |

According to the results, after mutating G, A, S, L, T, I, F, E, K, D, N, Q, R or Y in the CDRs of anti-CTLA-4 antibody to C and binding to different R4, the mutants could retain a binding efficiency of >60%.

In some cases, there are some R4 groups which could enhance the binding affinity. We selected the binding affinity between 60~100% of R4-s-R5 as drug candidates in our drug development. We prefer R-1, R4-7, R4-5, R4-8 and R4-12 for the large scale synthesis and stability in our drug development. S47 is cleaved by Legumain, and after cleaving the R4-7 chemical group is retained. After S47 conjugating to the amino acid of CDR, all these conjugates can block CTLA-4 binding with decreased affinity (activity<30% than WT CTLA-4). So the positions in CDR regions or mutant can become a primary drug candidate for tumor microenvironment activated antibody.

TABLE 56

Blocking efficiency of CDR regions conjugated with S47 (40 kD) linkers

| Region (Kabat) | Kabat No. | Original amino acid | R4 | Binding activity | Activity after S47 (40 kD) blocking |
|---|---|---|---|---|---|
| CDRL1 | L24 | R | R4-26 | 89% | 28% |
| | L25 | A | R4-1 | 95% | 29% |
| | L26 | S | R4-1 | 91% | 18% |
| | L27 | Q | R4-11 | 88% | 8% |
| | L27A | S | R4-1 | 82% | 24% |
| | L28 | V | R4-7 | 78% | 25% |
| | L29 | G | R4-1 | 95% | 19% |
| | L30 | S | R4-1 | 81% | 19% |
| | L31 | S | R4-1 | 99% | 12% |
| | L32 | Y | R4-7 | 95% | 13% |
| | L33 | L | R4-1 | 95% | 6% |
| | L34 | A | R4-1 | 92% | 11% |
| CDRL2 | L50 | G | R4-1 | 97% | 19% |
| | L51 | A | R4-1 | 92% | 25% |
| | L52 | F | R4-1 | 72% | 16% |
| | L53 | S | R4-1 | 98% | 5% |
| | L54 | R | R4-26 | 113% | 17% |
| | L55 | A | R4-1 | 102% | 20% |
| | L56 | T | R4-1 | 93% | 5% |
| CDRL3 | L89 | Q | R4-7 | 96% | 15% |
| | L90 | Q | R4-7 | 75% | 7% |
| | L91 | Y | R4-7 | 95% | 8% |
| | L92 | G | R4-1 | 99% | 16% |
| | L93 | S | R4-1 | 92% | 9% |
| | L94 | S | R4-1 | 95% | 12% |
| | L95 | P | R4-1 | 62% | 13% |
| | L96 | W | R4-4 | 72% | 12% |
| | L97 | T | R4-1 | 91% | 16% |
| CDRH1 | H31 | S | R4-1 | 110% | 25% |
| | H32 | Y | R4-7 | 92% | 23% |
| | H33 | T | R4-1 | 102% | 26% |
| | H34 | M | R4-1 | 65% | 29% |
| | H35 | H | R4-5 | 72% | 28% |

TABLE 56-continued

Blocking efficiency of CDR regions conjugated with S47 (40 kD) linkers

| Region (Kabat) | Kabat No. | Original amino acid | R4 | Binding activity | Activity after S47 (40 kD) blocking |
|---|---|---|---|---|---|
| CDRH2 | H50 | F | R4-4 | 73% | 25% |
| | H51 | I | R4-4 | 72% | 27% |
| | H52 | S | R4-1 | 95% | 5% |
| | H52A | Y | R4-7 | 93% | 18% |
| | H53 | D | R4-11 | 91% | 11% |
| | H54 | G | R4-1 | 95% | 15% |
| | H55 | N | R4-11 | 96% | 22% |
| | H56 | N | R4-11 | 91% | 8% |
| | H57 | K | R4-7 | 88% | 11% |
| | H58 | Y | R4-7 | 89% | 7% |
| | H59 | Y | R4-4 | 92% | 15% |
| | H60 | A | R4-4 | 65% | 22% |
| | H61 | D | R4-11 | 92% | 19% |
| | H62 | S | R4-3 | 91% | 23% |
| | H63 | V | R4-1 | 68% | 22% |
| | H64 | K | R4-7 | 96% | 26% |
| | H65 | G | R4-1 | 93% | 28% |
| CDRH3 | H95 | T | R4-3 | 92% | 18% |
| | H96 | G | R4-1 | 65% | 11% |
| | H97 | W | R4-8 | 92% | 9% |
| | H98 | L | R4-3 | 84% | 6% |
| | H99 | G | R4-1 | 94% | 12% |
| | H100 | P | R4-1 | 69% | 3% |
| | H100A | F | R4-4 | 84% | 16% |
| | H101 | D | R4-3 | 88% | 23% |
| | H102 | Y | R4-7 | 95% | 16% |

According to the results, after mutating native amino acid in the CDRs of anti-CTLA-4 antibody to cystine and chemically conjugating to different R4 (R4 library screening), the mutants could retain a binding efficiency of >60%. After S47 conjugation reaction with amino acid of CDR, all these positions can block CTLA-4 binding with decrease affinity (<30% comparing with WT CTLA-4). Therefore, all S47 conjugates can become primary drug candidates for tumor microenvironment activated antibody.

Figure 32:
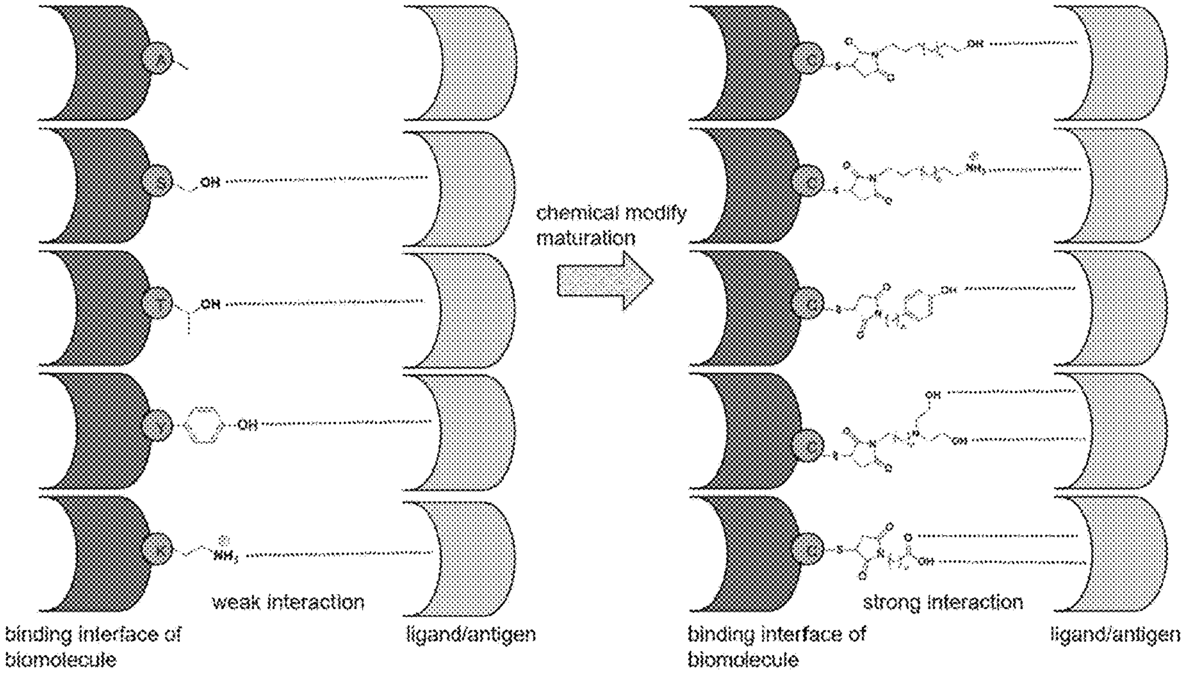
FIG. 32: By site-specially conjugating different R4 groups to the selected mutant site of antibody, the R4 group could be selectively changed for screening.

To improve affinity of antibody, amino acid on CDR loop was mutated during affinity maturation. In fact, optimization of antibody affinity also can be achieved by conjugating to a suitable R4 (termed herein as chemical maturation of antibody). As shown in FIG. 32, by site-specially conjugating different R4 groups to the selected mutant site of antibody, we can selectively change the R4 group for screening. (1) Native amino acid has no H-bond or charge interaction with ligand. Chemical maturation can induce new interaction. (2) Native amino acid has weak H-bond or charge interaction with ligand for the distance. Chemical maturation can adjust distance (by $R_{4\text{-}b}$) to screen the best distance. (3) Native amino acid has weak H-bond or charge interaction. Chemical maturation can change interaction group to screen the best $R_{4\text{-}c}$ group. (4) Chemical maturation also can increase charge by increasing $NH_2^+$ or $O^-$. As a result, there are chances to increase the interaction of H-bond or charge interaction as a kind of new affinity maturation.

We performed chemical maturation of antibody by conjugating R4 to three mutants having one or two mutations at a same CTLA-4 antibody. The results were shown in Table 57.

TABLE 57

Binding activity of conjugating R4 to three mutants

| | Mutant 1 | Mutant 2 | Binding activity |
|---|---|---|---|
| R4-18 | H32 | | 208% |
| R4-18 | | H64 | 137% |
| R4-18 | H32 | H64 | 356% |

Optimization of antibody affinity can also be achieved by chemical maturation in CDR loop of an antibody by conjugating to a suitable R4 group.

Example 15

Binding ELISA Characterization of Constructed CTLA-4 TMEAbodies

In drug development, we collected the sites with best blocking efficiency and restored activity for further development. After conjugation with S47, the human antibody become a tumor microenvironment activated antibody, and is named as TMEAbody.

To assess the recovery capability of TMEAbodies in binding against human CTLA-4 protein in a tumor microenvironment, the conjugated TMEAbodies were in vitro digested by Legumain and the digested product was used for evaluating recovered binding activity to human CTLA-4. To characterize the binding property of the constructed TMEAbodies to the human CTLA-4, 0.5 μg/ml CTLA-4 Fc fusion protein (R&D systems) was coated on the Maxisorp ELISA plate (Nunc) by incubation at 4° C. overnight. Then the plate was washed three times with PBST and blocked by 2% BSA at room temperature for 2 h. After washing by PBST for three times, the plate was incubated with serial concentration of conjugated TMEAbodies, TMEAbodies before conjugation (Cysteine mutant form), and control wild type (WT) Ipilimumab antibody at room temperature for 1h. The plate was then washed three times by PBST and incubated by goat anti-human IgG Fab fragment conjugated with HRP (Sigma) with 1:5000 dilution at room temperature for 1h. After washing by PBST three times, the plates were developed with tetramethylbenzidine (TMB, Solarbio) and ELISA stop buffer (Solarbio). Absorbance at 450 nm was then measured by ELISA plate reader (Biotek™). Data was then analyzed by GraphPad Prism 5 software.

As shown in table 58, conjugation of chemical linker to different mutant sites can give rise to different degrees of blocking efficiency. Blocking efficiency can be calculated by the fold change the $EC_{50}$ value of binding curve. The conjugated TMEAbodies with blocking efficiency bigger than 10 fold and Restored ($EC_{50}$ value<2 fold of WT) were considered as good candidates for further development.

TABLE 58

Ipilimumab TMEAbody candidates selected by blocking efficiency and restored activity after protease cleavage

| Selected Mutation ID | Heavy or chain | Mutation Site | Position | Kabat No. | R4 | Conjugation efficiency of S47 | Blocking efficiency after conjugation with S47 | Restored activity after protease cleavage |
|---|---|---|---|---|---|---|---|---|
| Ipi-se001 | HC | Y | 53 | H52A | R4-7 | 95% | 20 fold | Restored |
| Ipi-se002 | HC | D | 54 | H53 | R4-11 | 95% | 9 fold | Restored |
| Ipi-se003 | HC | Y | 59 | H58 | R4-4 | 94% | 15 fold | Restored |
| Ipi-se004 | HC | D | 73 | H72 | R4-11 | 94% | 6 fold | Restored |
| Ipi-se005 | HC | K | 76 | H75 | R4-7 | 94% | 8 fold | Restored |
| Ipi-se006 | HC | P | 104 | H100 | R4-1 | 96% | 30 fold | Restored |
| Ipi-se007 | LC | Q | 27 | L27 | R4-11 | 95% | 13 fold | Resorted |
| Ipi-se009 | LC | S | 54 | L53 | R4-1 | 95% | 22 fold | Restored |
| Ipi-se053 | LC | Y | 50 | L49 | R4-7 | 98% | 163 fold | Resorted |
| Ipi-se066 | LC | S | 68 | L67 | R4-7 | 97% | 3 fold | Resorted |

Figure 33:
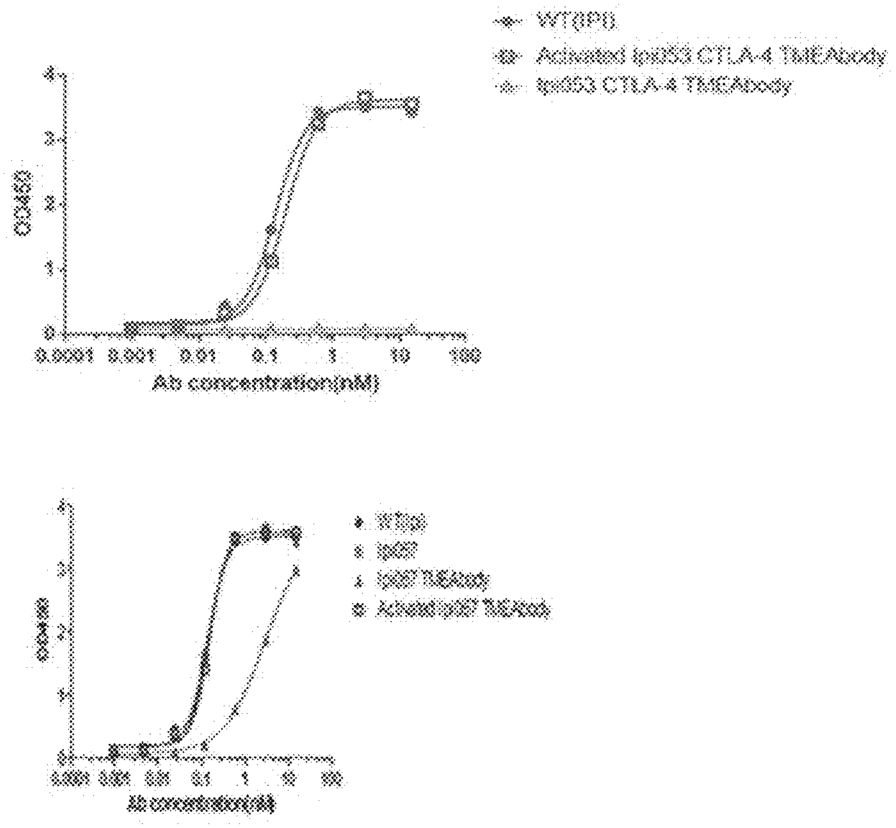
FIG. 33: Conjugating to different sites shows different degrees of binding activity recovery.

The same ELISA method was performed as described above. As shown in FIG. 33, conjugating to different sites showed different degree of binding activity recovery. Some mutant sites showed comparable binding activity to the WT Ipilimumab after digestion ($EC_{50}$ change fold<2, or in other words, the activity>50% of WT).

Blocking of Antigen Binding of TMEAbodies Resulted in Decreased Receptor Blocking Activity of Ipilimumab Receptor blocking activity (RBA) assay was then employed to prove that the decreased binding of TMEAbodies to the CTLA-4 protein would also decrease the blocking efficacy of Ipilimumab for B7-1 CTLA-4 interaction. 0.5 μg/ml human CTLA-4 Fc fusion protein (R&D systems) was absorbed on the Maxisorp ELISA plate (Nunc) and then the plate was blocked by 2% BSA. 0.02 μg/ml biotinylated human B7-1 or B7-2 protein with different concentration of TMEAbodies or WT Ipilimumab were completely incubated with the plate and then the receptor blocking activity was measured with Streptavidin-HRP (ThermoFisher Scientific) incubation followed by TMB reaction like the procedure of standard ELISA.

Figure 34:
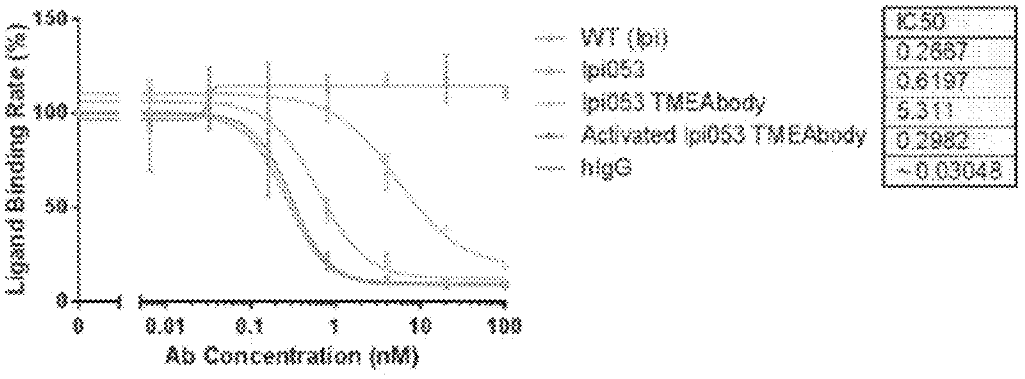
FIG. 34: The TMEAbodies with significant decreased binding activity to human CTLA-4 protein also show dramatic decrease of receptor blocking activity.

As shown in FIG. 34, the TMEAbodies with significant decreased binding activity to human CTLA-4 protein also showed dramatic decrease of receptor blocking activity. The fold change of $IC_{50}$ could be used as quantitative parameter for evaluating the decrease of receptor blocking activity.

Data of other candidates on RBA assay was summarized in Table 59.

TABLE 59

RBA assay data summary of Ipilimumab TMEAbody candidates

| Selected Mutation ID | Blocking efficiency (RBA) | Restored RBA activity after protease cleavage |
|---|---|---|
| Ipi-se001 | 15 fold | Restored |
| Ipi-se002 | 5 fold | Restored |
| Ipi-se003 | 8 fold | Resorted |
| Ipi-se004 | 7 fold | Resorted |
| Ipi-se005 | 10 fold | Resorted |
| Ipi-se006 | 25 fold | 2.5 fold decreased |
| Ipi-se007 | 16 fold | Resorted |
| Ipi-se053 | 20 fold | Resorted |
| Ipi-se009 | 18 fold | Resorted |
| Ipi-se066 | 9 fold | 3.5 fold decreased |

Blocking of Antigen Binding of TMEAbodies Resulted in Decreased Functional Efficacy in SEB Induced T Cell Activation Assay Next, to evaluate whether the decreased antigen binding activity and receptor blocking activity observed in TMEAbodies can contribute to decrease of functional efficacy of Ipilimumab, staphylococcal enterotoxin (SEB) induced T cell activation assay was performed. SEB is a superantigen which can strongly activate T lymphocyte and induce cytokine secretion. Whole PBMC cell from healthy donors (Allcells) were cultured as 1E5 cells per well in 1640 medium (GIBCO) with 10% FBS (GIBCO), 100 ng/ml SEB (Toxin Technology) and different concentration of TMEAbodies, WT Ipilimumab, or isotype control human IgG, respectively. After 96 h of activation, supernatant were collected by centrifugation and IL2 release was measured by IL2 detection kit with ELISA method (R&D systems).

Figure 35:
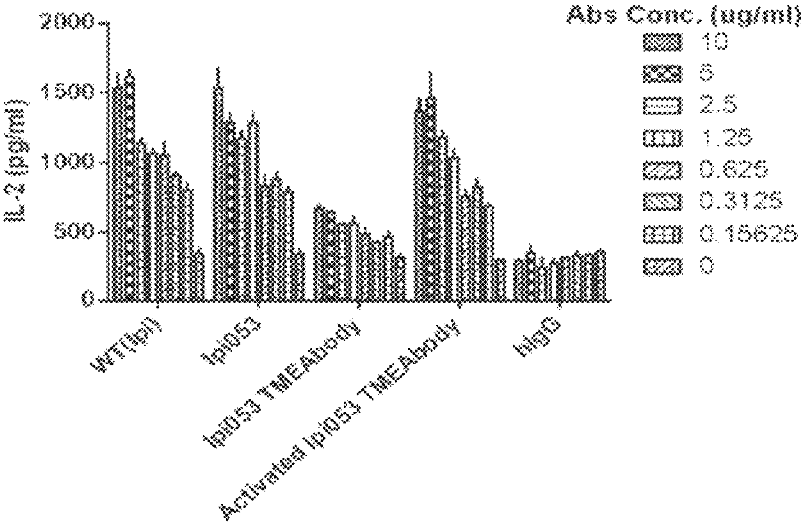
FIG. 35: TMEAbody with decreased binding activity against CTLA-4 shows impairment of functional efficacy of T cell activation, and protease mediated activation can restore the activity of TMEAbody.

As shown in FIG. 35, TMEAbody with decreased binding activity against CTLA-4 showed impairment of functional efficacy of T cell activation, and protease mediated activation can restore the activity of TMEAbody.

This assay was also carried out for other TMEAbody at single concentration (10 μg/ml) and blocking efficiency was calculated ((WT−TMEAbody)/(WT−hIgG)*100%)). Results were shown in Table 60.

TABLE 60

TMEAbody blocking efficiency SEB induced T cell activation

| Selected Mutation ID | Blocking efficiency (SEB) | Restored RBA activity after protease cleavage |
|---|---|---|
| Ipi-se001 | 63% | Restored |
| Ipi-se002 | 45% | Restored |
| Ipi-se003 | 40% | Restored |
| Ipi-se004 | 43% | Restored |
| Ipi-se005 | 64% | Restored |
| Ipi-se006 | 90% | 3 fold decreased |
| Ipi-se007 | 68% | Restored |
| Ipi-se053 | 70% | Restored |
| Ipi-se009 | 72% | Restored |
| Ipi-se066 | 56% | 4 fold decreased |

Ipilimumab TMEAbodies Regulated Treg in Tumor but not in Periphery

Figure 36:
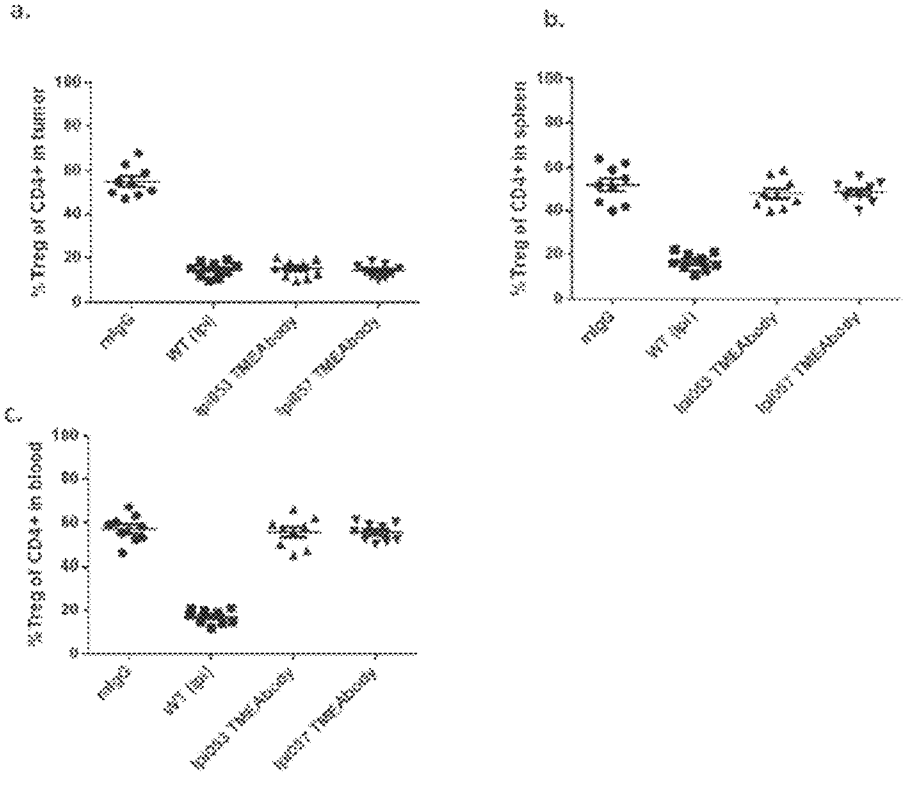
FIG. 36: Ipilimumab TMEAbodies significantly down regulate Treg population in the tumor, with the similar efficacy as WT Ipilimumab.

Mechanism study was performed to see whether TMEAbodies were specifically activated in tumor microenvironment but not in the periphery lymph organs. One of the proposed mechanisms for ipilimumab therapy is that it can down-regulate the population of Treg cells through antibody dependent cell mediated cytotoxicity (ADCC) effect, thus to activate the immune response against tumors. Treg population was analyzed with flow cytometry with CD4, CD25, and Foxp3 markers, respectively. As shown in FIG. 36, Ipilimumab TMEAbodies significantly down regulated Treg population in the tumor, with the similar efficacy as WT Ipilimumab. Nevertheless, in the spleen or periphery blood, Ipilimumab TMEAbodies showed very weak or no modulation of Treg population. These results demonstrated that the Ipilimumab TMEAbodies showed specific activity in the tumor microenvironment but not in periphery lymph organs or blood.

TMEAbody are Stable in Human Plasma

Figure 37:
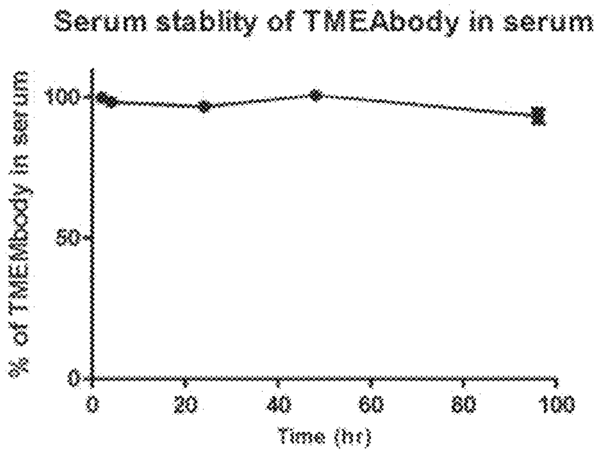
FIG. 37: TMEAbody shows high stability in mouse serum, without significant degradation after 96 h at 37° C.

To evaluate the stability of TMEAbody in serum, 1 ug CTLA-4 TEMAbody (Ipi053 with conjugation of S13) was put into 20 ul mouse serum and kept in 37° C. for 2 h, 4h, 24 h, 48h, and 96h, respectively. Then the sample was prepared for Western blot with anti-human Fab HRP antibody (Sigma). Gel intensity was analyzed with ImageJ software and the relative intensity was analyzed by GraphPad. As shown in the following FIG. 37, TMEAbody showed high stability in mouse serum, without significant degradation after 96 h at 37° C.

Figure 38:
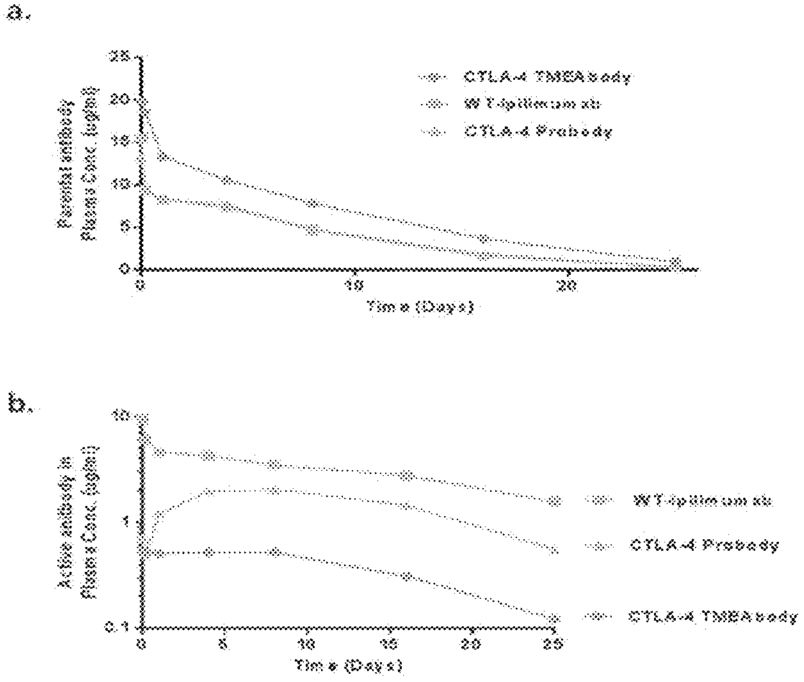
FIG. 38: CTLA-4 TMEAbodies show increased half-life and exposure by conjugation with S47 functional group comparing with WT-Ipilimumab and CTLA-4 probody.

CTLA-4 TMEAbodies Showed Increased Half-Life and Exposure by Conjugation with S47 Functional Group Comparing with WT-Ipilimumab and CTLA-4 Probody To evaluate the potential effect of chemical conjugation in modulating the pharmacokinetics property of TMEAbody, single IV dose of 1 mg/kg WT Ipilimumab or ipilimumab TMEAbody was injected into Balb/c mice. After 0.5 h, 2 h, 4 h, 8 h, 1 d, 2 d, 5 d, 10 d, 15 d, 20 d, plasma was collected for ELISA test of total antibody and active antibody concentration determination. For total antibody concentration determination, anti-human Fc antibody (Invitrogen) was coated on the ELISA plate (NUNC) and injected antibody was detected by anti-human Fab HRP secondary antibody (Invitrogen). For active antibody concentration determination, human CTLA-4 protein (Sino Biological) was coated on the ELISA plate. Active antibody was then detected by anti-human Fc HRP secondary antibody (Invitrogen). Standard curve was drawn by serial dilution of WT Ipilimumab or Ipilimumab TEMAbody and the standard binding curve was established through four-parameter fitting. The concentration of total antibody or active antibody was calculated through interpolating the Y value to the standard curve. As shown in FIG. 38(*a*), the half-life of TMEAbody was increased after conjugation with 40 kd functional group, comparing with the WT Ipilimumab antibody or Ipilimumab probody (WO 2018/085555 A1 with MY11 as masking peptide and 2011 as cleavage moiety). Moreover, CTLA-4TMEAbody showed less activation in plasma than Ipilimumab probody with the time, as shown in FIG. 38(*b*).

In Vivo Characterization of TMEAbodies in Mouse Tumor Model

Figure 39:
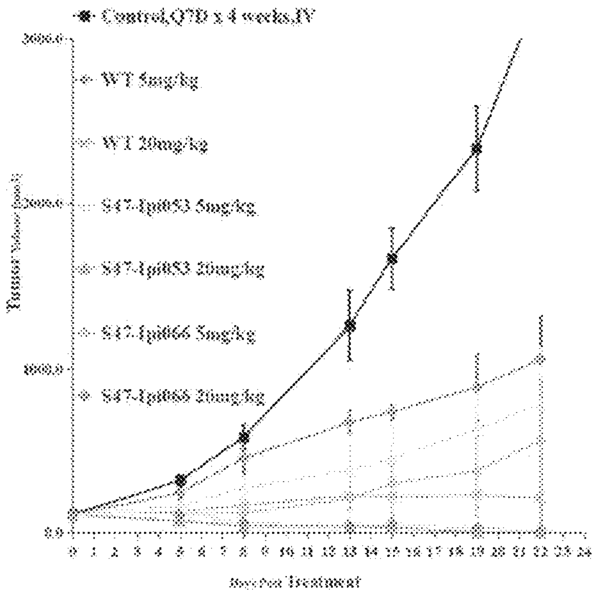
FIG. 39: Ipilimumab TMEAbodies control the tumor size with comparable efficacy as WT Ipilimumab, whereas control human IgG fails to show any efficacy.

To further characterize the in vivo efficacy of TMEAbodies in treating tumor in animal model, ipilimumab TMEAbodies, as well as WT ipilimumab and control human IgG were administrated into MC38 colon adenocarcinoma tumor model in human CTLA-4 knock-in C57BL/6 mice. Human CTLA-4 knock-in C57BL/6 mice were subcutaneously injected with 2E6 MC38 cells into their left lower abdominal quadrant. After 7 days for tumor growth, animals were grouped to have similar mean tumor volume. Animals were administrated with indicated single dose of control human IgG, WT Ipilimumab or equimolar TMEAbodies (the concentration of antibody, n=6), respectively, and tumor volumes were monitored for each animal. As shown in FIG. 39, ipilimumab TMEAbodies control the tumor size with comparable efficacy as WT Ipilimumab, whereas control human IgG failed to show any efficacy. The tumor volume inhibition rate was summarized in Table 61. This result implied that Ipilimumab TMEAbodies could be activated in the tumor microenvironment and inspired anti-tumor immune response.

TABLE 61

Tumor growth inhibition rate at day 17 after administration

| Mutation ID | Dose | Cure rate | Dead |
|---|---|---|---|
| human IgG | 5 mg/kg | 0 | 2 |
| WT (Ipi) | 5 mg/kg | 0 | 0 |
| WT (Ipi) | 20 mg/kg | 33.3 | 1 |
| S47-Ipi-se053 | 5 mg/kg | 16.6% | 0 |
| S47-Ipi-se053 | 20 mg/kg | 83.3% | 0 |
| S47-Ipi-se066 | 5 mg/kg | 33.3% | 0 |
| S47-Ipi-se066 | 20 mg/kg | 83.3% | 0 |

As shown in Table 61, inhibition on tumor growth and cure rate by S47-Ipi053 and S47-Ipi066 were greatly improved as compared with the groups treated by WT (Ipi) using the same molar concentration.

CTLA-4 TMEAbodies Showed Low Immunogenicity in Animals

Figure 40:
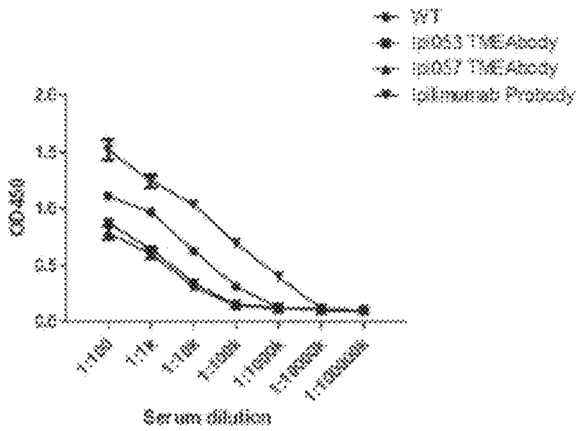
FIG. 40: TMEAbody causes very low immune response in the animals, with comparable or lower antibody titer than WT Ipilimumab.

To evaluate the immunogenicity of TMEAbody, three groups of Balb/c mice (each n=5) were immunized with 50 μg Ipilimumab TMEAbody, WT Ipilimumab, or Ipilimumab Probody (WO 2018/085555 A1 with MY11 as masking peptide and 2011 as cleavage moiety) with complete Freund's adjuvant (CFA). After 14 days of primary immunization, animals were boosted with 25 μg Ipilimumab TMEAbody, WT Ipilimumab, or Ipilimumab Probody with incomplete Freund's adjuvant (IFA). Serum was obtained on the 7$^{th}$ day after boosting, and tested for antibody titer against Ipilimumab TMEAbody, WT Ipilimumab, or Ipilimumab Probody, respectively. 1% human serum was used in the serum dilution buffer to block any antibodies against constant region of human IgG. As shown in FIG. 40, TMEAbody caused very low immune response in the animals, with comparable or lower antibody titer than WT Ipilimumab. Nevertheless, Ipilimumab Probody caused dramatic increase of immunogenicity, which might be due to the foreign sequences included in the N terminal of light chain.

CTLA-4 TMEAbodies Showed Low Toxicity In Vivo

It is well known in the art, though combination of anti-PD-1 and anti-CTLA-4 antibody are effective_(ORR) for treating melanoma, it was found in the current clinic research that combination exhibited 55% TRAEs grade 3-4 and 30% patient have to discontinue the therapy. We presume these TRAEs may be improved if the antibody is inhibited or blocked by a conjugate and is released after arriving at a local environment of tumor so as to reduce the exposed time or dose of active drug in a non-diseased environment. For this reason, experiments were conducted with mice suffering from type I diabetes mellitus (NOD). Diabetes mellitus of this kind of mice is an autoimmune disease, wherein self-activated T lymphocyte cells destroy pancreatic islet p cells, resulting in insufficient secretion of insulin. First, female NOD of 10 weeks old (Beijing Vital River Laboratory Animal Technology Co., Ltd.) were injected with control IgG, high (15 mpk) dose of anti-PD-1 and anti-CTLA-4 antibody or 15 mpk dose of anti-PD-1 and anti-CTLA-4 TMEAbody, respectively at day 0. Indicators of diabetes mellitus, including glucose in urine and two blood sugar levels were observed every day for 12 days until no new indicator of urine glucose was observed.

Figure 41:
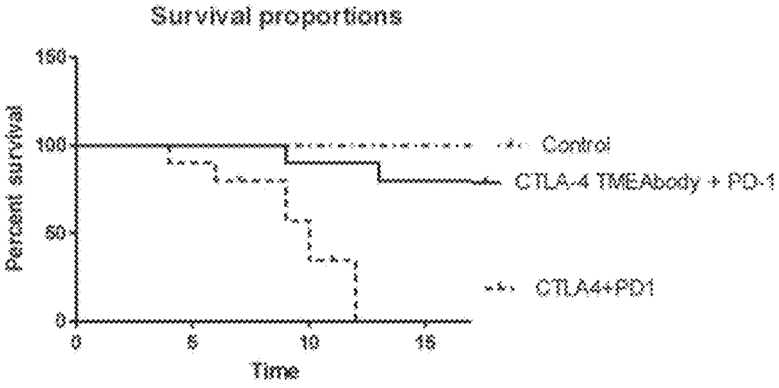
FIG. 41: Protection of an immune system by a conjugate of anti-CTLA4 TMEAbody in combination therapy conjugate could reduce autoimmunity as compared to the primary antibody.

Protection from autoimmunity by the conjugate was shown in FIG. 41. Results showed that protection of an immune system by a conjugate of anti-CTLA4 TMEAbody in combination therapy conjugate could reduce autoimmunity as compared to the primary antibody.

Example 16: Generation and Characterization of PD-1 TMEAbody (Pembrolizumab)

As shown in example of Ipilimumab TMEAbody screening above, multiple sites of anti-PD-1 antibody (pembrolizumab) were mutated into Cysteine for site specific conjugation. The mutation position in a heavy chain of the anti-PD-1 antibody (pembrolizumab) is selected from the group consisting of (Numbered sequentially from N terminal to C terminal without using the Kabat or other antibody numbering systems): Ser7, Gly8, Gly15, Ala16, Ser17, Ala24, Ser25, Gly26, Tyr27, Thr28, Thr30, Asn31, Tyr32, Tyr33, Tyr35, Ala40, Gly42, Gly44, Leu45, Gly49, Gly50, Ile51, Asn52, Ser54, Asn55, Gly56, Gly57, Thr58, Asn59, Lys63, Lys65, Thr69, Leu70, Thr71, Thr72, Asp73, Ser74, Ser75, Thr76, Thr77, Thr78, Ala79, Leu83, Ser85, Leu86, Thr91, Ala92, Arg99, Asp100, Tyr101, Arg102, Asp104, Gly106, Gly111, Gly113, Thr114, 115Thr, 117Thr, Ser119, Ser120, Ala121, Ser122, Thr123, Lys124, Gly125 and Ser127; the mutation position in a light chain is selected from the group consisting of: Ile2, Thr5, Ser7, Ala9, Thr10, Leu11, Ser12, Leu13, Ser14, Gly16, Ala19, Thr20, Ala25, Ser26, Lys27, Gly28, Ser30, Thr31, Ser32, Gly33, Tyr34, Ser35, Tyr36, Leu37, Gly45, Ala47, Leu5, Leu51, Leu52, Tyr53, Leu54, Ala55, Ser56, Tyr57, Leu58, Ser60, Gly61, Ala64, Ser67, Gly68, Ser69, Gly70, Ser71, Gly72, Thr73, Ala76, Thr78, Ser80, Ser81, Ser95, Arg96, Asp97, Leu98, Leu100, Thr101, Phe102, Gly104, Ile110, Lys111 and K130. ELISA characterization with human Fc tagged PD-1 protein (Sino Biological) was carried out to identify the candidate sites with good blocking efficiency and recovery efficiency. Sites with blocking efficiency>5 (in other words, the activity<20%) fold and restored activity after enzyme digestion (EC50 change<2 fold, or in other words, the activity>50%) were selected for further development, as shown in Table 62.

TABLE 62

Selected anti-PD-1 TMEAbody (Pembrolizumab) candidates based on blocking and recovery efficiency

| Selected Mutation ID | Heavy or light chain | Mutation site | R4 | Conjugation efficiency | Blocking efficiency of S47 | Restored activity after R4 conjugation |
|---|---|---|---|---|---|---|
| Pem-se001 | HC | Tyr27 | R4-7 | 89% | 5 fold | Restored |
| Pem-se002 | HC | Tyr32 | R4-7 | 91% | 6 fold | Restored |
| Pem-se003 | HC | Asn55 | R4-11 | 92% | 5 fold | Restored |
| Pem-se004 | HC | Lys65 | R4-7 | 88% | 7 fold | Restored |
| Pem-se005 | HC | Arg102 | R4-26 | 87% | 6 fold | Restored |
| Pem-se006 | LC | Lys27 | R4-7 | 91% | 6 fold | Restored |
| Pem-se007 | LC | Gly28 | R4-1 | 94% | 8 fold | Restored |
| Pem-se008 | LC | Tyr34 | R4-7 | 90% | 10 fold | Restored |
| Pem-se009 | LC | Tyr36 | R4-7 | 93% | 18 fold | Restored |
| Pem-se010 | LC | Tyr57 | R4-7 | 95% | 25 fold | Restored |
| Pem-se011 | LC | Arg96 | R4-26 | 90% | 7 fold | Restored |

Example 17: Functional Characterization of Anti-PD-1 TMEAbody (Pembrolizumab)

The human PBMC (Allcells) was inoculated in a 96-well plate in a concentration of $1\times10^5$ cells per well. The cells were stimulated with 0.1 ug/ml SEB for three days. Different concentrations of WT anti-PD-1 antibody, TMEAbody, or activated TMEAbody were added and cultured at 37° C., 5% C32 for 4 days. Supernatant was collected and concentration of cytotoxic factor IFN-γ was detected by ELISA kit (R&D). The functional blocking efficiency and recovery rate was summarized in Table 63.

TABLE 63

Functional characterization of anti-PD-1 TMEAbody (Pembrolizumab) candidates

| Selected Mutation ID | Heavy or light chain | Mutation site | Blocking efficiency of S47 in IFN-γ assay | Restored activity after R4 conjugation |
|---|---|---|---|---|
| Pem-se001 | HC | Tyr27 | 3 fold | Restored |
| Pem-se002 | HC | Tyr32 | 4 fold | Restored |
| Pem-se003 | HC | Asn55 | 6 fold | Restored |
| Pem-se004 | HC | Lys65 | 7 fold | Restored |
| Pem-se005 | HC | Arg102 | 5 fold | Restored |
| Pem-se006 | LC | Lys27 | 7 fold | Restored |
| Pem-se007 | LC | Gly28 | 10 fold | Restored |

TABLE 63-continued

| Functional characterization of anti-PD-1 TMEAbody (Pembrolizumab) candidates | | | | |
|---|---|---|---|---|
| Selected Mutation ID | Heavy or light chain | Mutation site | Blocking efficiency of S47 in IFN-γ assay | Restored activity after R4 conjugation |
| Pem-se008 | LC | Tyr34 | 9 fold | Restored |
| Pem-se009 | LC | Tyr36 | 19 fold | Restored |
| Pem-se010 | LC | Tyr57 | 24 fold | Restored |
| Pem-se011 | LC | Arg96 | 10 fold | Restored |

Example 18: Generation and Characterization of PD-1 TMEAbody (Nivolumab)

As shown in example of Ipilimumab and Pembrolizumab TMEAbody screening above, multiple sites of anti-PD-i antibody (nivolumab) were mutated into Cysteine for site specific conjugation. the mutation position in a heavy chain of the anti-PD-i antibody (nivolumab) is selected from the group consisting of: Gln3, Ser7, Gly8, Gly9, Gly10, Gly15, Ser17, Lys23, Ala24, Ser25, Gly26, Ile27, Asn31, Thr28, Ser30, Ser32, Gly33, Ala40, Gly42, Gly44, Leu45, Ala49, Ile51, Tyr53, Asp54, Gly55, Ser56, Lys57, Tyr59, Tyr60, Ala61, Asp62, Ser63, Lys65, Gly66, Thr69, Ile70, Ser71, Arg72, Asp73, Asn74, Ser75, Lys76, Asn77, Thr78, Leu79, Leu81, Ser85, Leu86, Ala88, Thr91, Ala92, Thr98, Asn99, Asp100, Asp101, Tyr102, Gly104, Gly106, Thr107, Leu108, Thr110, Ser112, Ser113, Ala114, Ser115, Thr116, Lys117, Gly118 and Ser120; the mutation position in a light chain is selected from the group consisting of: Ile2, Leu4, Thr5, Ser7, Ala9, Thr10, Leu11, Ser12, Leu13, Ser14, Gly16, Ala19, Thr20, Leu21, Ala25, Ser26, Ser28, Ser30, Ser31, Tyr32, Leu33, Ala34, Tyr36, Gly41, Ala43, Leu46, Leu47, Ile48, Tyr49, Asp50, Ala51, Ser52, Asn53, Arg54, Ala55, Thr56, Gly57, Ile58, Ala60, Arg61, Ser63, Gly64, Ser65, Gly66, Ser67, Gly68, Thr69, Thr72, Leu73, Thr74, Ile75, Ser76, Ser77, Leu78, Ala84, Ser91, Ser92, Asn93, Arg96, Thr97, Phe98, Gly99, Gly101, Thr102, Ile106, Lys107, Thr109, Ala11, Alal 12, Ser114, Ile117 and Ser121 Sites with blocking efficiency>5 fold and restored activity after enzyme digestion (EC50 change<2 fold) were selected for further development, as shown in Table 64.

TABLE 64

| Selected anti-PD-1 TMEAbody (Nivolumab) candidates based on blocking and recovery efficiency | | | | | | |
|---|---|---|---|---|---|---|
| ID of selected Mutation | Heavy or light chain | Mutation site | R4 | Conjugation efficiency | Blocking efficiency of S47 | Restored activity after R4 conjugation |
| Niv-se001 | HC | Lys23 | R4-7 | 95% | 15 fold | Increased, 432% of WT |
| Niv-se002 | HC | Tyr53 | R4-7 | 89% | 5 fold | Restored |
| Niv-se003 | HC | Lys57 | R4-7 | 88% | 6 fold | Restored |
| Niv-se004 | LC | Tyr32 | R4-7 | 92% | 8 fold | Restored |
| Niv-se005 | LC | Tyr49 | R4-7 | 94% | 85 fold | Increased, 125% of WT |
| Niv-se006 | LC | Arg54 | R4-26 | 93% | 7 fold | Restored |
| Niv-se007 | LC | Ser91 | R4-1 | 95% | 25 fold | Restored |
| Niv-se008 | LC | Arg96 | R4-26 | 93% | 23 fold | Restored |

Figure 42:
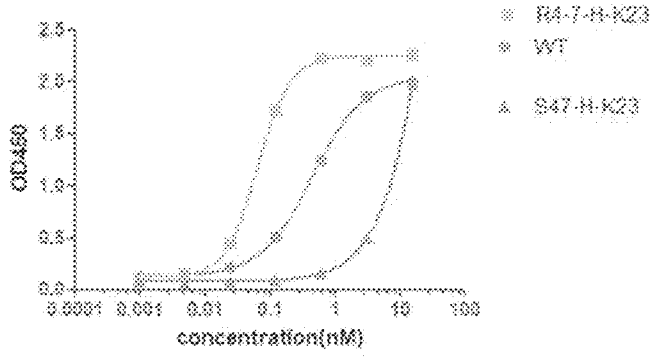
FIG. 42: Niv-se001 shows increased activity after R4-7 conjugation or protease cleavage of 40 kD conjugated TMEAbody, which is 432% of WT Nivolumab.

As shown in FIG. 42, Niv-se001 showed increased activity after R4-7 conjugation or protease cleavage of 40 kD conjugated TMEAbody, which is 432% of WT Nivolumab. This might be due to the R4-7 provided increased the binding activity than native Lysine residue.

Figure 43:
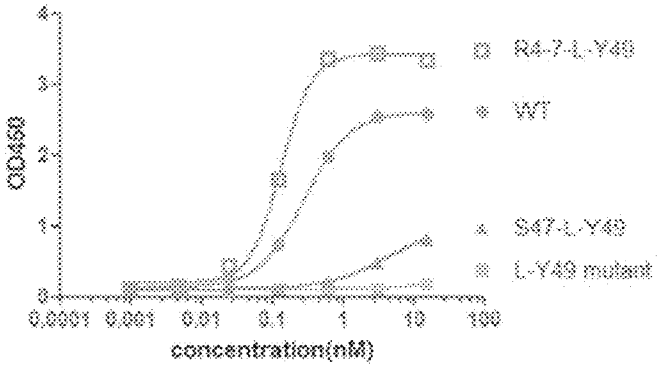
FIG. 43: After conjugation with R4-7, or after protease cleavage of Niv-se005 conjugated with 40 kD functional group, the binding activity of Niv-se005 is restored with comparable level than WT Nivolumab (125% of WT).

Niv-se005 showed lost binding activity when the Try49 is mutated into Cysteine. However, after conjugation with R4-7, or after protease cleavage of Niv-se005 conjugated with 40 kD functional group, the binding activity is restored with comparable level than WT Nivolumab (125% of WT), as shown in FIG. 43.

Example 19: Functional Characterization of Anti-PD-1 TMEAbody (Nivolumab)

The human PBMC (Allcells) was inoculated in a 96-well plate in a concentration of $1\times10^5$ cells per well. The cells were stimulated with 0.1 ug/ml SEB for three days. Different concentrations of WT anti-PD-1 antibody (nivolumab), TMEAbody (nivolumab), or activated TMEAbody (nivolumab) were added and cultured at 37° C., 5% $CO_2$ for 4 days. Supernatant was collected and concentration of cytotoxic factor IFN-γ was detected by ELISA kit (R&D). The functional blocking efficiency and recovery rate was summarized in Table 65.

TABLE 65

| Functional characterization of anti-PD-1 TMEAbody (Nivolumab) candidates | | | | |
|---|---|---|---|---|
| Selected Mutation ID | Heavy chain or light chain | Mutation site | Blocking efficiency of S47 in IFN-γ assay | Restored activity after R4 conjugation |
| Niv-se001 | HC | Lys23 | 18 fold | Increased, 332% of WT |
| Niv-se002 | HC | Tyr53 | 3 fold | Restored |
| Niv-se003 | HC | Lys57 | 7 fold | Restored |
| Niv-se004 | LC | Tyr32 | 8 fold | Restored |
| Niv-se005 | LC | Tyr49 | 25 fold | Restored 122% of WT |
| Niv-se006 | LC | Arg54 | 9 fold | Restored |
| Niv-se007 | LC | Ser91 | 24 fold | Restored |
| Niv-se008 | LC | Arg96 | 21 fold | Restored |

Example 20: In Vivo Characterization of Anti-PD-1 TMEAbody (Pembrolizumab and Nivolumab) in Treating Mouse Tumor To further characterize the in vivo efficacy of anti-PD-1 TMEAbodies in treating tumor in animal model, anti-PD-1 TMEAbodies (Pem-se010 TMEAbody based on pembrolizumab and Niv-se007 TMEAbody based on Nivolumab), as well as WT PD-1 antibodies (pembrolizumab and nivolumab) and control human IgG were administrated into MC38 colon adenocarcinoma tumor model in human PD-1 knock-in C57BL/6 mice. Human PD-1 knock-in C57BL/6 mice were subcutaneously injected with 2E6 MC38 cells into their left lower abdominal quadrant. After 7 days for tumor growth, animals were grouped to have similar mean tumor volume. Animals were administrated 10 mg/kg single dose of PD-1 TMEAbodies (the concentration of antibody without PEG linker), WT PD-1 antibodies, or control human IgG and tumor volumes were monitored for each animal.

Figure 44:
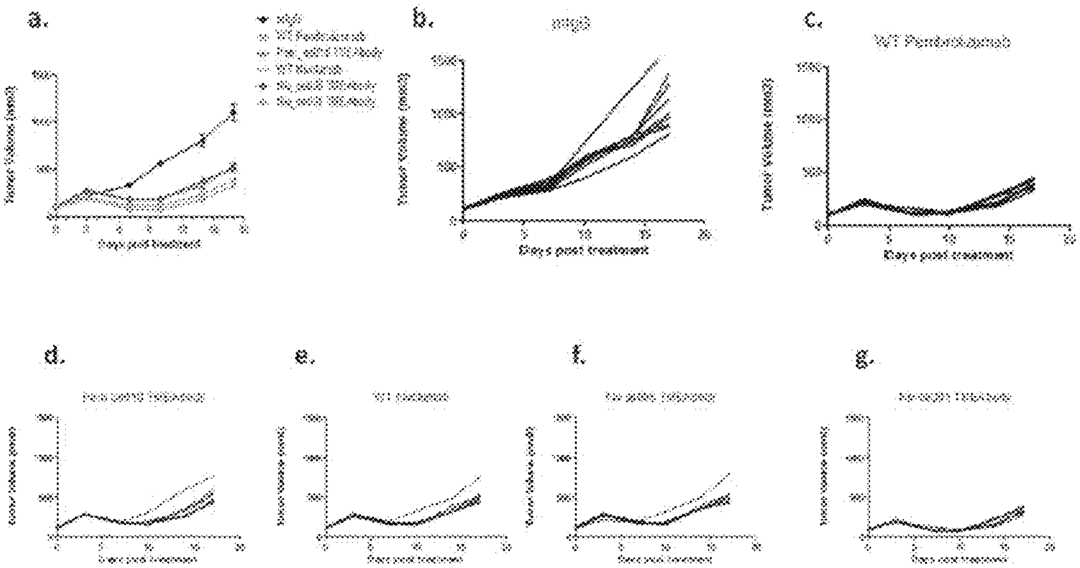
FIG. 44: Pembrolizumab and Nivolumab TMEAbodies control the tumor size with comparable efficacy as WT Pembrolizumab or Nivolumab antibodies, whereas control human IgG failed to show any efficacy.

As shown in FIG. 44, pembrolizumab and nivolumab TMEAbodies control the tumor size with comparable efficacy as WT pembrolizumab or nivolumab antibodies, whereas control human IgG failed to show any efficacy. Interestingly, Niv-se001 TMEAbody showed improved efficacy than WT nivolumab in treating tumor, which might be due to its enhanced binding activity after protease cleavage. The results implied that these anti-PD-1 TMEAbodies could be activated in the tumor microenvironment and inspire anti-tumor immune response.

Example 21: Generation of Mouse Anti-PD-1 Antibody (J43v2) for Efficacy Study in Mouse Tumor Model Hamster anti-mouse PD-1 antibody sequences were disclosed in US 20170044259A1. This heavy chain of this antibody was re-formatted into mouse IgG2a to reduce the immunogenicity in mouse. As the screening method above, multiple sites were designed for screening of TMEAbody with high blocking efficiency. Finally Ser95 on LC was selected for TMEAbody generation due to its high efficiency blocking (35 fold in ELISA assay with mouse PD-1 protein). MC38 mouse tumor model was carried out with 10 mg/kg single dose of WT J43v2 antibody or J43v2 TMEAbody (for each group n=8). At the days of 17 after administration, J43v2 TMEAbody showed 75% tumor inhibition, with comparable inhibition efficacy than WT J43v2 antibody (83%). This result indicated that the PD-1 antibody can be activated and played its anti-tumor activity in vivo.

Example 22: Generation of Anti-Mouse CTLA-4 Antibody (9D9) for Efficacy Study in Mouse Tumor Model To generate mouse CTLA-4 surrogate TMEAbody for further functional and toxicity studies, we produced and purified anti-mouse CTLA-4 antibody and its mutant variants (9D9 clone, mIgG2b isotype, sequences shown in WO 2007/123737 A2). As the screening method above, multiple sites were designed for screening of TMEAbody with high blocking efficiency. Finally Tyr54 on LC was selected for TMEAbody generation due to its high efficiency blocking (26 fold in ELISA assay with mouse CTLA-4 protein). CT26 mouse tumor model was carried out with 10 mg/kg single dose of WT 9D9 antibody or 9D9 TMEAbody (for each group n=8). At the days of 17 after administration, 9D9 TMEAbody showed 69% tumor inhibition, with comparable inhibition efficacy than WT 9D9 antibody (74%). This result indicated that the 9D9 TMEAbody can be activated and played its anti-tumor activity in vivo.

Example 23: Mouse PD-1 and CTLA-4 TMEAbody Showed Decreased Toxicity than WT Antibodies It is well known in the art, though combination of anti-PD-1 and anti-CTLA-4 antibody are effective (ORR) for treating melanoma, it was found in the current clinic research that combination exhibited 55% TRAEs grade 3-4 and 30% patient have to discontinue the therapy.

We presume these TRAEs may be improved if the antibody is inhibited or blocked by a conjugate and is released after arriving at a local environment of tumor so as to reduce the exposed time or dose of active drug in a non-diseased environment. For this reason, experiments were conducted with mice suffering from type I diabetes mellitus (NOD). Diabetes mellitus of this kind of mice is an autoimmune disease, wherein self-activated T lymphocyte cells destroy pancreatic islet β cells, resulting in insufficient secretion of insulin. First, female NOD of 10 weeks old (Beijing Vital River Laboratory Animal Technology Co., Ltd.) were injected with control IgG, high (15 mpk) dose of anti-mouse PD-1 (J43v2) and anti-mouse CTLA-4 antibody (9D9), or one or both of these two antibodies were replaced with its TMEAbody form at day 0. Indicators of diabetes mellitus, including glucose in urine and two blood sugar levels were observed every day for 12 days until no new indicator of urine glucose was observed.

Figure 45:
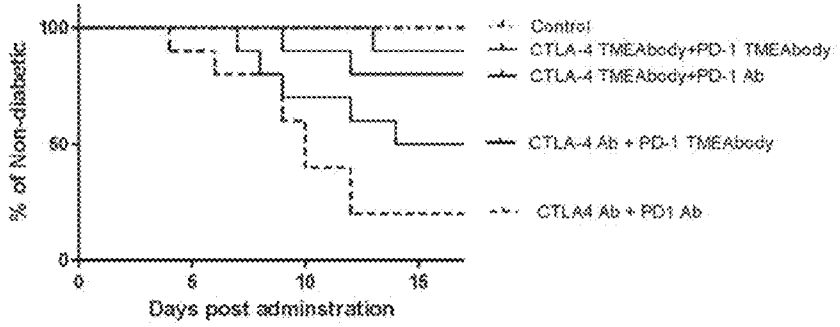
FIG. 45: Anti-CTLA4 or anti-PD1 TMEAbody in combination therapy could reduce autoimmunity as compared to the primary antibody.

Protection from autoimmunity by the conjugate shown in FIG. 45. Results showed that anti-CTLA4 or anti-PD1

TMEAbody in combination therapy could reduce autoimmunity as compared to the primary antibody. Moreover, combination of these two TMEAbodies resulted in very low toxicity with comparable level than control group.

Example 24: Generation and Characterization of Anti-PD-1 TMEAbody (Patent WO 2017/124050 A1)

As the method above, anti-PD-1 antibody sequence was downloaded from patent WO 2017/124050 A1 and sites screening was performed to identify TMEAbody with good blocking efficiency. The mutation position in a heavy chain of the anti-PD-1 antibody is selected from the group consisting of: Ser28, Ser31, tyr33, Asn36, Gly50, Tyr51, Ser53, Tyr54, Asp55, Ser57, Lys58, Asn59, Tyr60, Asn61, Lys65, Asn66, Thr69, Thr74, Gly100, Asp105, Tyr106; the mutation position in a light chain is selected from the group consisting of Lys24, Gln27, Ser28, Asp31, Asp32, Asn33, Asn34, Gln35, Lys36, Asn37, Tyr38, Ser58, Arg60, Glu61, Ser62, Gly63, Gly70, Ser73, Thr75, Gln95, Gln96, Tyr98, Thr100, Tyr102. Binding ELISA was performed with Fc tagged human PD-1 protein (Sino Biological) and selected sites with good blocking efficiency (EC50 change>5 fold) and recovery (EC50 change<2 fold) was summarized in Table 66.

TABLE 66

Selected anti-PD-1 TMEAbody (WO 2017/124050 A1) candidates based on blocking and recovery efficiency

| ID of selected Mutation | Heavy chain or light chain | Mutation site | R4 | Conjugation efficiency | Blocking efficiency of S47 | Restored activity after R4 conjugation |
|---|---|---|---|---|---|---|
| PD1-se001 | HC | Tyr33 | R4-7 | 99% | 198 fold | Restored |
| PD1-se002 | HC | Ser53 | R4-1 | 95% | 9 fold | Restored |
| PD1-se003 | HC | Tyr60 | R4-7 | 88% | 6 fold | Restored |
| PD1-se004 | LC | Tyr38 | R4-7 | 94% | 15 fold | Restored |
| PD1-se005 | LC | Ser58 | R4-1 | 93% | 16 fold | Restored |
| PD1-se006 | LC | Thr100 | R4-3 | 91% | 6 fold | Restored |

Example 25: Generation and Characterization of Anti-4-1BB TMEAbody 4-1BB antibody sequence was downloaded from US 2018/0194851 A1 (clone MOR 7480.1). The mutation position in a heavy chain of the anti-4-1BB antibody is selected from the group consisting of: Thr31, Tyr32, Ser35, Lys50, Tyr52, Asp55, Ser56, Tyr57, Thr58, Asn59, Tyr60, Ser61, Gln65, Gly66, Gly99, Tyr100, Gly101, Asp104, Tyr105; the mutation position in a light chain is selected from the group consisting of: Ser23, Gly24, Asp25, Asn26, Gly28, Asp29, Gln30, Tyr31, Gln49, Asp50, Lys51, Asn52, Arg53, Ser55, Gly56, Thr89, Tyr90, Thr91, Gly92, Gly94, Ser95.Human 4-1BB protein was used for ELISA characterization to identify mutant sites with good blocking efficiency (EC50 change>5 fold) as well as good recovery (EC50 change<2 fold) after protease digestion. The selected sites were summarized in Tables 67 and 68.

TABLE 67

Selected anti-4-1BB TMEAbody candidates based on blocking and recovery efficiency

| ID of selected Mutation | Heavy chain or light chain | Mutation site | R4 | Conjugation efficiency | Blocking efficiency of S47 | Restored activity after R4 conjugation |
|---|---|---|---|---|---|---|
| 4-1BB-se001 | HC | Tyr32 | R4-7 | 95% | 23 fold | Restored |
| 4-1BB -se002 | HC | Lys50 | R4-7 | 93% | 16 fold | Restored |
| 4-1BB -se003 | HC | Tyr105 | R4-7 | 94% | 9 fold | Restored |
| 4-1BB -se004 | LC | Tyr31 | R4-7 | 94% | 18 fold | Restored |
| 4-1BB -se005 | LC | Lys51 | R4-7 | 96% | 6 fold | Restored |
| 4-1BB -se006 | LC | Tyr90 | R4-7 | 95% | 7 fold | Restored |
| 4-1BB -se007 | LC | Thr91 | R4-1 | 91% | 11 fold | Restored |

TABLE 68

| Selected anti-4-1BB TMEAbody candidates based on blocking and recovery efficiency | | | | | | | |
|---|---|---|---|---|---|---|---|
| ID of selected Mutation | Heavy chain or light chain | Mutation site | R4 | Blocking efficiency of S27 | Blocking efficiency of S48 | S48 Restored activity by Granzyme B | S27 Restored activity by pH 6.0 |
| 4-1BB-se001 | HC | Tyr32 | R4-7 | 23 fold | 20 fold | Restored | Restored |
| 4-1BB -se002 | HC | Lys50 | R4-7 | 16 fold | 12 fold | Restored | Restored |
| 4-1BB -se003 | HC | Tyr105 | R4-7 | 9 fold | 7 fold | Restored | Restored |
| 4-1BB -se004 | LC | Tyr31 | R4-7 | 18 fold | 18 fold | Restored | Restored |
| 4-1BB -se005 | LC | Lys51 | R4-7 | 6 fold | 5 fold | Restored | Restored |
| 4-1BB -se006 | LC | Tyr90 | R4-7 | 7 fold | 6 fold | Restored | Restored |
| 4-1BB -se007 | LC | Thr91 | R4-1 | 11 fold | 10 fold | Restored | Restored |

Example 26: Generation and Characterization of Anti-Her2 TMEAbody (Trastuzumab)

The heavy chain and light chain sequences of Trastuzumab was downloaded from Drug Bank (www-.drugbank.ca/drugs/DB00072) and sites screening was performed to identify anti-Her2 TMEAbody with good blocking efficiency. The mutation position in a heavy chain of the anti-Her2 antibody (trastuzumab) is selected from the group consisting of: Arg19, Lys30, Asp31, Tyr33, Arg50, Tyr62, Asn55, Tyr57, Arg59, Tyr60, Asp62, Lys65, Asp102, Tyr105; the mutation position in a light chain is selected from the group consisting of: Asp1, Gln3, Gln27, Asp28, Asn30, Tyr49, Tyr55, Arg66, Asp70, Tyr92. His tagged Her2 protein (Sino Biological) was used for ELISA. The selected sites with good blocking efficiency and good recovery were summarized in Table 69.

TABLE 69

| Selected anti-Her2 TMEAbody candidates based on blocking and recovery efficiency | | | | | | |
|---|---|---|---|---|---|---|
| ID of selected Mutation | Heavy chain or light chain | Mutation site | R4 | Conjugation efficiency | Blocking efficiency of S47 | Restored activity after R4 conjugation |
| Trast-se001 | HC | Tyr33 | R4-7 | 97% | 13 fold | Restored |
| Trast-se002 | HC | Lys65 | R4-7 | 95% | 8 fold | Restored |
| Trast-se003 | HC | Tyr105 | R4-7 | 90% | 25 fold | Restored |
| Trast -se004 | LC | Gln30 | R4-11 | 89% | 16 fold | Restored |
| Trast -se005 | LC | Tyr49 | R4-7 | 91% | 20 fold | Restored |
| Trast -se006 | LC | Asp70 | R4-11 | 96% | 7 fold | Restored |

Example 27: Generation and Characterization of Anti-TNFα TMEAbody (Adalimumab)

The heavy chain and light chain sequences of Adalimumab was downloaded from Drug Bank (www.drugbank.ca/drugs/DB00051) and sites screening was performed to identify anti-TNFα TMEAbody with good blocking efficiency. The mutation position in a heavy chain of the anti-TNFα antibody is selected from the group consisting of Ser7, Gly8, Gly9, Gly10, Leu11, Gly15, Ser17, Leu18, Leu20, Ala24, Ser25, Gly26, Thr28, Asp30, Asp31, Tyr32, Ala33, Ala40, Gly42, Gly44, Leu45, Ser49, Ala50, Ile51, Thr52, Asn54, Ser55, Gly56, Ile58, Asp59, Tyr60, Ala61, Asp62, Ser63, Glu65, Gly66, Phe68, Thr69, Ile70, Ser71, Asp73, Asn74, Ala75, Lys76, Ser78, Leu79, Tyr80, Leu81, Ser85, Leu86, Ala88, Thr91, Ala92, Lys98, Ser100, Tyr101, Leu102, Ser103, Thr104, Ala105, Ser106, Ser107, Leu108, Asp109, Tyr110, Gly112, Gly114, Thr115, Leu116, thr118, Ser120, Ser121, Ala122, Ser123 and Thr124; the mutation position in a light chain is selected from the group consisting of: Asp1, Thr5, Ser7, Ser9, Ser10, Leu11, Ser12, Ala13, Ser14, Gly16, Thr20, Ile21, Ala25, Ser26, Gln27, Gly28, Ile29, Arg30, Asn31, Tyr32, Leu33, Ala34, Tyr36, Lys39, Gly41, Lys42, Ala43, Leu48, Leu47, Ile48, Tyr49, Ala50, Ala51, Ser52, Thr53, Leu54, Gln55, Ser56, Gly57, Ser60, Ser63, Gly64, Ser65, Gly66, Ser67, Gly68, Thr69, Asp70, Thr72, Leu73, Thr74, Ile75, Ser76, Ser77, Leu78, Ala84, Thr85, Tyr91, Asn92, Arg93, Ala94, Tyr96, Thr97, Phe98, Gly99, Gly101, Thr102, Ile106, Lys107, Thr109 and Ala111. TNFα protein (Sino Biological) was used for ELISA characterization and selected sites with good blocking efficiency (EC50 change>5 fold) and good recovery (EC50 change<2 fold) were summarized in the Table 70.

TABLE 70

| Selected anti-TNFa TMEAbody candidates based on blocking and recovery efficiency | | | | | | |
|---|---|---|---|---|---|---|
| ID of selected Mutation | Heavy chain or light chain | Mutation site | R4 | Conjugation efficiency | Blocking efficiency of S47 | Restored activity after R4 conjugation |
| Ada-se001 | HC | Tyr32 | R4-7 | 95% | 11 fold | Restored |
| Ada-se002 | HC | Asp59 | R4-11 | 92% | 7 fold | Restored |

TABLE 70-continued

| Selected anti-TNFa TMEAbody candidates based on blocking and recovery efficiency | | | | | | |
|---|---|---|---|---|---|---|
| ID of selected Mutation | Heavy chain or light chain | Mutation site | R4 | Conjugation efficiency | Blocking efficiency of S47 | Restored activity after R4 conjugation |
| Ada-se003 | HC | Tyr101 | R4-7 | 93% | 6 fold | Restored |
| Ada-se004 | LC | Arg30 | R4-26 | 96% | 25 fold | Restored |
| Ada-se005 | LC | Tyr32 | R4-7 | 94% | 28 fold | Restored |
| Ada-se006 | LC | Gln55 | R4-11 | 91% | 32 fold | Restored |
| Ada-se007 | LC | Tyr96 | R4-7 | 92% | 9 fold | Restored |

Example 28: Generation and Characterization of Anti-PD-L1 TMEAbody (Atezolizumab)

The heavy chain and light chain sequences of anti-PD-L1 antibody (Atezolizumab) was downloaded from Drug Bank (www.drugbank.ca/drugs/DB11595) and sites screening was performed to identify anti-TNFα TMEAbody with good blocking efficiency. The mutation position in a heavy chain of the anti-PD-Li antibody (atezolizumab) is selected from the group consisting of: Gln3, Asp31, Tyr54, Tyr59, Tyr60, Asp62, Lys65, Asp73, Lys76, Asn77, Arg99; the mutation position in a light chain is selected from the group consisting of: Arg24, Gln27, Asp28, Tyr49, Tyr55, Asp70, Gln89, Gln90, Tyr91, Tyr93. Fc tagged human PD-L1 protein (Sino Biological) was used for ELISA characterization and selected sites with good blocking efficiency (EC50 change>5 fold) and good recovery (EC50 change<2 fold) were summarized in Table 71.

TABLE 71

| Selected anti-PD-L1 TMEAbody candidates based on blocking and recovery efficiency | | | | | | |
|---|---|---|---|---|---|---|
| ID of selected Mutation | Heavy chain or light chain | Mutation site | R4 | Conjugation efficiency | Blocking efficiency of S47 | Restored activity after R4 conjugation |
| Ate-se001 | HC | Tyr54 | R4-7 | 98% | 15 fold | Restored |
| Ate-se002 | HC | Lys76 | R4-7 | 93% | 7 fold | Restored |
| Ate-se003 | LC | Asp28 | R4-11 | 91% | 10 fold | Restored |
| Ate-se004 | LC | Tyr49 | R4-7 | 96% | 13 fold | Restored |
| Ate-se005 | LC | Tyr91 | R4-7 | 92% | 23 fold | Restored |

Example 29: Generation and Characterization of Anti-CD28 TMEAbody

Anti-human CD28 antibody heavy chain and light chain sequences were downloaded from patent US008709414B2 and sites screening was performed to identify anti-CD28 TMEAbody with good blocking efficiency. The mutation position in a heavy chain of the anti-CD28 antibody is selected from the group consisting of: Ser7, Gly8, Gly15, Ala16, Ser17, Ser21, Ala24, Ser25, Gly26, Tyr27, Thr28, Thr30, Ser31, Tyr32, Ala40, Gly42, Gly44, Gly49, Tyr52, Gly54, Thr58, Ala68, Thr69, Thr71, Thr74, Ser75, Ser77, Thr78, Ala79, Ser84, Leu86, Ser88, Thr91, Ala92, Thr97, Ser99, Tyr101, Gly102, Leu103, Gly113, Thr114, Thr115, Thr117, Ser 19, Ser120, Ala121, Ser122 and Thr123; the mutation position in a light chain is selected from the group consisting of: Thr5, Ser7, Ser9, Ser10, Ser11, Ser12, Ala13, Ser14, Gly16, Thr20, Thr22, Ala25, Ser26, Ser27, Ile29, Tyr30, Ala43, Leu46, Leu47, Tyr49, Lys50, Ala51, Ser52, Leu54, Thr56, Gly57, Ser60, Ser63, Gly64, Ser65, Gly66, Ser67, Gly68, Thr69, Asp70, Thr72, Thr74, Ser76, Ser77, Ala84, Thr85, Gly91, Thr93, Tyr94, Tyr96, Thr97, Phe98, Gly99, Gly100, Gly101, Thr102, Thr109 and Ala111. Fc tagged human CD28 protein (Sino Biological) was used for ELISA characterization and selected sites with good blocking efficiency (EC50 change>5 fold) and good recovery (EC50 change<2 fold) were summarized in the Table 72.

TABLE 72

| Selected anti-CD28 TMEAbody candidates based on blocking and recovery efficiency | | | | | | |
|---|---|---|---|---|---|---|
| ID of selected Mutation | Heavy chain or light chain | Mutation site | R4 | Conjugation efficiency | Blocking efficiency of S47 | Restored activity after R4 conjugation |
| CD28-se001 | HC | Tyr27 | R4-7 | 95% | 6 fold | Restored |
| CD28-se002 | HC | Thr58 | R4-1 | 93% | 7 fold | Restored |
| CD28-se003 | HC | Tyr101 | R4-7 | 91% | 6 fold | Restored |
| CD28-se004 | LC | Tyr30 | R4-7 | 91% | 16 fold | Restored |
| CD28-se005 | LC | Tyr49 | R4-7 | 98% | 32 fold | Restored |

TABLE 72-continued

| Selected anti-CD28 TMEAbody candidates based on blocking and recovery efficiency | | | | | | |
|---|---|---|---|---|---|---|
| ID of selected Mutation | Heavy chain or light chain | Mutation site | R4 | Conjugation efficiency | Blocking efficiency of S47 | Restored activity after R4 conjugation |
| CD28-se006 | LC | Lys50 | R4-7 | 92% | 27 fold | Restored |
| CD28-se007 | LC | Tyr96 | R4-7 | 90% | 13 fold | Restored |

Example 30: Tumor Microenvironment Activated IL-10 Cytokine (IL-10 TMEAkine)

1. Expression and Purification of the Mutant IL-10 Cytokine

The mutant IL-10 DNA sequence ligated to a modified pTT5 vector (Biovector) was optimized for expression in 293T cells and synthesized (GENEWIZ, Inc., Suzhou, China). Transfection of the mutant IL-10 DNA was performed and after incubation for 4-7 days, the supernatant containing mutant IL-10 was collected.

In *Pichia Pastoris* expression, the expression vector pPICZαA containing the mutant IL-10 genes was optimized and prepared (GENEWIZ, Inc., Suzhou, China). The amino acid sequence of the mutant IL-10 was described in SEQ ID NO. 1. The expression vector pPICZα A was transformed in *E. coli* (DH5a) for plasmid purification. Then pPICZα A was transformed into GS115 by electroporation. The transformed colony was selected by obtaining the growing colonies after growing on the 100, 300, 500, 1000, 1500, 2000 μg/mL Zeocin™ containing YPD plates. After finally selecting the transformant, the recombinant GS 115 strain was grown in BMGY medium at 30° C., with vigorous shaking in baffled flasks to an OD600 of 2-6. The cells were then pelleted by centrifugation and suspended in BMMY to an OD600 of 1, to which was added 0.5% methanol daily in order to induce the heterologous protein expression. After a four-day induction, supernatant containing the secreted mutant IL-10 protein was collected by centrifugation. The total protein in the supernatant was concentrated by ultrafiltration using a 10-kDa molecular mass cutoff membrane. The concentrated protein was dialyzed with buffer A (20 mMBIS-TRIS, 0.065M NaCl, pH 6.5) for more than 24 h, then loaded onto a cation-exchange column equilibrated with buffer A. Mutant IL-10 was eluted from the column with gradient concentration of NaCl in the range of 0.065-0.4M and the eluent was collected and concentrated. The condensed sample was further purified on Sephacryl 5-100 HRgel filtration column using 10 mMTris-HCl, pH7.4, as the elution buffer.

2. Conjugate S48 to the Mutant IL-10 and it was Called as the Name of IL-10 TMEAkine (Tumor Microenvironment Activated IL-1-Cytokine).

Mutant IL-10 protein was generated and purified as described above. Purified mutant IL-10 was performed as the concentration of 0.5 mg/mL in 20 mMTris buffer (pH 7.4) containing 2 mM EDTA. Add TCEP solution to mutant IL-10 as a ratio of 100:1 and incubate for 4 h at 4° C. with gentle agitation. Then the mutant IL-10 solution was dialyzed with 20 mMTris buffer (pH 7.4) containing 150 mM NaCl for 4 h at 4° C. Afterwards, immediately add the S48 to mutant IL-10 solution as a ratio of 20:1 and incubate for 16 h at 25° C. with gentle agitation. Terminate the reaction by removal of residual S48. Before the enzyme cleavage, change the IL-10 TMEAkine buffer to enzyme buffer through dialysis. For activation, enzyme was added to IL-10 TMEAkine solution and incubated for 16 h at 37° C.

3. Screening IL-10 TMEAkine that Blocks the Binding to IL-10R1 or R2, and Recovers the Binding Activity after Enzyme Cleavage In Vitro.

Dispense 60 μl PBS buffer containing 1 ug IL-10R1-Fc/IL-10R2-Fc/His solution into the wells. Apply sealing tape to the top of the plate and incubate the plate overnight at 4° C. After incubation, remove the tape and aspirate each well. After three-time wash with PBST, block the plate by dispensing 200 μl of PBS buffer containing 2% BSA into each well and incubate the plate for 2 h at room temperature. Wash the plate three times and add 60 μl of serial diluted samples to the appropriate wells. Incubate the plate for 1.5h at room temperature. After three-time wash with PBST, dispense 60 μl of 2 ug/mL IL-10 biotinylated antibody solution to each well and incubate for 1 hour at room temperature. Wash the plate three times and dispense 60 μl of streptavidin solution to each well. Incubate for 30 minutes at room temperature. After washing three times, dispense 100 μl of the HRP substrate solution into each well and incubate for 15 minutes at 37° C. After color development, dispense 50 μl of stop solution into each well and immediately measure the absorbance of each well at a wavelength of 450 nm.

4. Summary of Various IL-10 Mutation Sites

IL-10 receptors on the cell surface have two different forms: high-affinity receptor: IL-10R1 to IL-10 (Kd=50-200 pM) and low-affinity receptor: IL-10R2 to IL10. The conjugated IL-10 with R4 can recover the binding >80% in some positions by chemical modified maturation of R4 library screening. To select drug candidates, we also performed the screening expression and S48 conjugation reaction with all amino acids of IL-10 in the domain of binding IL-10R1 and IL-10R2. We acquired the possible drug candidates and results are shown in the following Table 73.

TABLE 73

Activity of mutated IL-10 and screening for linker arm

| Position | Amino acid | Amino acid | Type of inhibitory ligand | R4 | Binding recovery (>60%) | Decreased fold of binding to ligand after Conjugating with S48 (>3fold) |
|---|---|---|---|---|---|---|
| 6 | T | Thr | 1 | R4-7 | 101.2% | 3-fold |
| 8 | S | Ser | 1 | R4-5 | 100.0% | 3-fold |
| 11 | S | Ser | 1 | R4-7 | 132.9% | 9-fold |
| 13 | T | Thr | 1 | R4-6 | 99.1% | 7-fold |
| 17 | G | Gly | 1 | R4-1 | 90.2% | 15-fold |
| 18 | N | Asn | 1 | R4-18 | 92.3% | 12-fold |
| 19 | L | Leu | 1 | R4-7 | 95.3% | 8-fold |
| 21 | N | Asn | 1 | R4-18 | 99.7% | 7-fold |
| 22 | M | Met | 1 | R4-1 | 96.8% | 5-fold |
| 23 | L | Leu | 1 | R4-6 | 101.2% | 12-fold |
| 24 | R | Arg | 1 | R4-20 | 90.0% | 33-fold |
| 25 | D | Asp | 1 | R4-12 | 97.1% | 3-fold |
| 26 | L | Leu | 1 | R4-6 | 93.4% | 3-fold |
| 27 | R | Arg | 1 | R4-20 | 86.6% | 12-fold |
| 28 | D | Asp | 1 | R4-11 | 92.3% | 30-fold |
| 30 | F | Phe | 1 | R4-8 | 97.1% | 6-fold |
| 31 | S | Ser | 1 | R4-2 | 124.6% | 39-fold |
| 32 | R | Arg | 1 | R4-7 | 90.4% | 13-fold |
| 34 | K | Lys | 1 | R4-7 | 99.6% | 50-fold |
| 35 | T | Thr | 1 | R4-6 | 90.1% | 36-fold |
| 38 | Q | Gln | 1 | R4-19 | 87.0% | 52-fold |
| 39 | M | Met | 1 | R4-1 | 88.0% | 62-fold |
| 41 | D | Asp | 1 | R4-11 | 95.2% | 13-fold |
| 42 | Q | Gln | 1 | R4-19 | 90.0% | 18-fold |
| 44 | D | Asp | 1 | R4-11 | 92.1% | 43-fold |
| 45 | N | Asn | 1 | R4-18 | 97.7% | 7-fold |
| 46 | L | Leu | 1 | R4-6 | 89.6% | 22-fold |
| 48 | L | Leu | 1 | R4-7 | 98.9% | 3-fold |
| 49 | K | Lys | 1 | R4-5 | 114.0% | 7-fold |
| 50 | E | Glu | 1 | R4-12 | 99.8% | 4-fold |
| 51 | S | Ser | 1 | R4-7 | 96.7% | 3-fold |
| 53 | L | Leu | 1 | R4-6 | 99.4% | 3-fold |
| 54 | L | Leu | 1 | R4-6 | 98.4% | 3-fold |
| 56 | Q | Gln | 1 | R4-19 | 95.1% | 3-fold |
| 57 | E | Glu | 1 | R4-12 | 95.4% | 10-fold |
| 65 | L | Leu | 1 | R4-6 | 92.3% | 3-fold |
| 69 | I | Ile | 1 | R4-6 | 97.3% | 3-fold |
| 72 | Y | Tyr | 1 | R4-4 | 109.0% | 3-fold |
| 75 | V | Val | 1 | R4-5 | 98.6% | 4-fold |
| 90 | H | His | 1 | R4-19 | 86.5% | 8-fold |
| 91 | V | Val | 1 | R4-5 | 97.2% | 3-fold |
| 93 | S | Asp | 1 | R4-2 | 100.1% | 3-fold |
| 94 | L | Leu | 1 | R4-6 | 88.4% | 5-fold |
| 97 | N | Asn | 1 | R4-18 | 94.5% | 5-fold |
| 100 | T | Thr | 1 | R4-7 | 99.3% | 4-fold |
| 104 | R | Arg | 1 | R4-20 | 98.5% | 3-fold |
| 105 | L | Leu | 1 | R4-6 | 92.3% | 5-fold |
| 107 | R | Arg | 1 | R4-20 | 99.5% | 3-fold |
| 111 | F | Phe | 1 | R4-8 | 90.1% | 12-fold |
| 117 | K | Lys | 1 | R4-7 | 116.6% | 3-fold |
| 118 | S | Ser | 1 | R4-5 | 100.0% | 3-fold |
| 119 | K | Lys | 1 | R4-7 | 99.0% | 3-fold |
| 130 | K | Lys | 1 | R4-7 | 100.0% | 3-fold |
| 131 | L | Leu | 1 | R4-6 | 98.5% | 5-fold |
| 134 | K | Lys | 1 | R4-7 | 128.3% | 5-fold |
| 135 | G | Gly | 1 | R4-1 | 99.5% | 3-fold |
| 137 | Y | Tyr | 1 | R4-4 | 99.1% | 5-fold |
| 138 | K | Lys | 1 | R4-7 | 97.6% | 23-fold |
| 140 | M | Met | 1 | R4-1 | 89.0% | 3-fold |
| 141 | S | Ser | 1 | R4-7 | 112.5% | 19-fold |
| 142 | E | Glu | 1 | R4-12 | 78.0% | 13-fold |
| 143 | F | Phe | 1 | R4-8 | 69.0% | 7-fold |
| 144 | D | Asp | 1 | R4-11 | 90.5% | 15-fold |
| 148 | N | Asn | 1 | R418 | 84.3% | 10-fold |
| 149 | Y | Tyr | 1 | R4-4 | 115.3% | 5-fold |
| 151 | E | Glu | 1 | R4-12 | 82.5% | 13-fold |
| 155 | T | Thr | 1 | R4-7 | 98.1% | 3-fold |
| 157 | K | Lys | 1 | R4-7 | 98.6% | 3-fold |
| 158 | I | Ile | 1 | R4-6 | 81.7% | 9-fold |
| 159 | R | Arg | 1 | R4-20 | 99.0% | 3-fold |
| 15 | F | Phe | 2 | R4-8 | 90.0% | 3-fold |
| 18 | N | Asn | 2 | R4-18 | 99.8% | 4-fold |
| 21 | N | Asn | 2 | R4-18 | 85.3% | 6-fold |
| 22 | M | Met | 2 | R4-1 | 80.0% | 6-fold |

TABLE 73-continued

Activity of mutated IL-10 and screening for linker arm

| Position | Amino acid | Amino acid | Type of inhibitory ligand | R4 | Binding recovery (>60%) | Decreased fold of binding to ligand after Conjugating with S48 (>3fold) |
|---|---|---|---|---|---|---|
| 24 | R | Arg | 2 | R4-20 | 98.1% | 9-fold |
| 25 | D | Asp | 2 | R4-11 | 91.5% | 5-fold |
| 28 | R | Arg | 2 | R4-20 | 99.0% | 6-fold |
| 29 | A | Ala | 2 | R4-5 | 78.0% | 3-fold |
| 31 | S | Ser | 2 | R4-2 | 87.4% | 7-fold |
| 32 | R | Arg | 2 | R4-7 | 89.6% | 9-fold |
| 33 | V | Val | 2 | R4-7 | 91.4% | 3-fold |
| 34 | K | Lys | 2 | R4-7 | 97.3% | 5-fold |
| 35 | T | Thr | 2 | R4-5 | 123.0% | 6-fold |
| 36 | F | Phe | 2 | R4-8 | 79.6% | 3-fold |
| 81 | E | Glu | 2 | R4-12 | 93.6% | 3-fold |
| 86 | D | Asp | 2 | R4-11 | 81.0% | 3-fold |
| 87 | I | Ile | 2 | R4-6 | 95.7% | 4-fold |
| 88 | K | Lys | 2 | R4-7 | 99.0% | 3-fold |
| 89 | A | Ala | 2 | R4-1 | 78.7% | 5-fold |
| 90 | H | His | 2 | R4-19 | 79.0% | 7-fold |
| 92 | N | Asn | 2 | R4-18 | 86.4% | 3-fold |
| 96 | E | Glu | 2 | R4-12 | 98.0% | 3-fold |
| 97 | N | Asn | 2 | R4-18 | 80.7% | 4-fold |
| 99 | K | Lys | 2 | R4-7 | 116.6% | 3-fold |
| 100 | T | Thr | 2 | R4-7 | 90.7% | 8-fold |
| 101 | L | Leu | 2 | R4-6 | 91.0% | 3-fold |
| 102 | R | Arg | 2 | R4-20 | 99.0% | 3-fold |
| 103 | L | Leu | 2 | R4-6 | 89.4% | 3-fold |
| 104 | R | Arg | 2 | R4-20 | 96.6% | 6-fold |
| 106 | R | Arg | 2 | R4-7 | 99.6% | 3-fold |
| 107 | R | Arg | 2 | R4-20 | 84.0% | 5-fold |
| 119 | K | Lys | 2 | R4-7 | 105.9% | 4-fold |
| 122 | E | Glu | 2 | R4-12 | 99.8% | 3-fold |
| 123 | Q | Gln | 2 | R4-19 | 96.5% | 3-fold |
| 126 | N | Asn | 2 | R4-18 | 99.0% | 3-fold |
| 130 | K | Lys | 2 | R4-7 | 99.7% | 3-fold |

5. Study on Efficacy of ILIO-K34C-S48 on the 4T1 Tumor Model in BALB/C Mice Model.

Test purpose: to investigate the anti-tumor efficacy of IL10-K34C-S48 in BALB/C mice for treatment of the 4T1 tumor model. Test drug: IL10-K34C-S48 and IL-10 injection, diluted to corresponding concentrations by physiological PBS when testing.

Method and Results

1. Animal: BALB/C Mice of 5 Weeks Old, all Female.
2. Production of Tumor Model 1) 4T1 cells were purchased from American type culture collection (ATCC) and identified according the specification provided by ATCC. Cells were cultivated in RPMI 1640 culture solution containing 10% fetal bovine serum at 37° C. and 5% $CO_2$. The cells were passaged every three days and cells within the 13th passage were used.

2) Production of tumor model. 4T1 cells were subcutaneously injected to the back of the BALB/C mice. Mice were randomly grouped after the tumor grew to about 100 $mm^3$ and drug treatment began. Mice were killed after anesthesia on day 28.

3) Course of treatment. There were 3 groups with 6 animals in each group. Included were a control group treated daily, and two single agent groups (1 mg/kg IL-10 treated daily or IL-10-K34C-S48 daily (1 mg/kg IL-10 equivalents dose).

4) Grouping and test results are shown in Table 74.

5) Results and discussion. As shown in Table 74, comparing with IL-10, the complete regression on the 4T1 tumor of BALB/C mice was greatly improved after injection of IL10-K34C-S48, indicating that IL10-K34C-S48 exhibits a good anti-tumor efficacy on the 4T1 tumor model.

TABLE 74

Effects of IL10-K34C-S48 on the 4T1 tumor model in BALB/C mice model

| Group | Number of animals | Complete Regression |
|---|---|---|
| Control Group | 6 | 0 |
| IL10-K34C-S48 | 6 | 33.33% |
| IL-10 | 6 | 0 |

Figure 46:
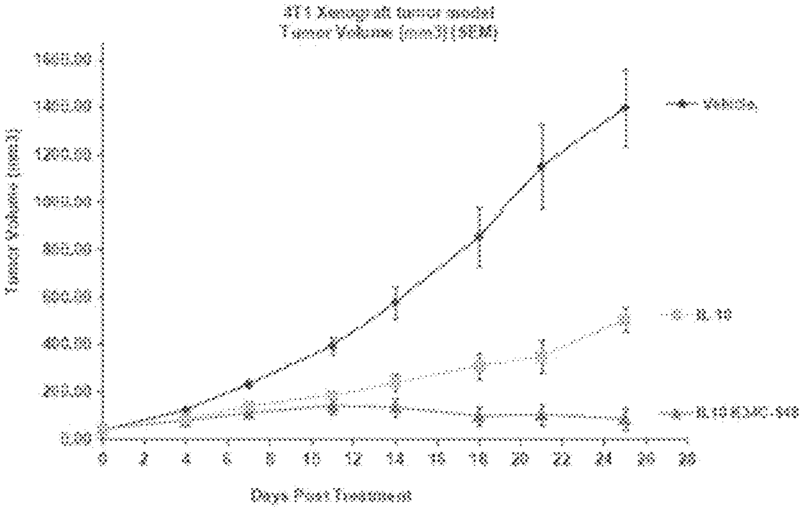
FIG. 46: Tumor volumes after treatment.

Tumor volumes were monitored 2-3 times a week and are presented in FIG. 46.

Example 31: Activation Efficiency of Different R2 for Targeted Activation in Different Tissue Cleaving effect of conjugates in which R1 was S13, R3 was R3-5, R4 was R4-7 and R2 was each of the groups shown in Table 75 were evaluated in different tissues. The conjugates were each dissolved and diluted ten times to a concentration of 0.1 mM/ml. At 37° C., conjugates were each added into 100 μg different acidized human tumor tissue homogenates (pH6.0) in a concentration of 0.2 mg/ml. The enzyme in tumor tissue homogenates could release R1. The released R1 was detected by HPLC, thereby comparing the activation efficiency of the linker. Results were shown in Table 75

TABLE 75

| Activation ratio (%) of different R2 peptide in homogenates from different tumor tissues | | | | | |
|---|---|---|---|---|---|
| Human tissues | Cells producing tumor | R2 = LTPRLGPAAN | R2 = GPAAN | R2 = LSGRSDN | R2 = AAN |
| Fibrosarcoma | HT-1080 | 66.4 | 47.8 | 19.8 | 45.9 |
| Breast cancer | MDA-MB231 | 71.8 | 76.7 | 25.4 | 68.4 |
| Liver cancer | Hepg2 | 68.9 | 58.4 | 21.8 | 55.7 |
| Heart | | 1.6 | 1.1 | 4.3 | 0 |
| Lung | | 1.7 | 1.5 | 5.9 | 0 |

According to the results, extended R2, which is activated by multiple enzymes, exhibits a higher activation than AAN. But activation with multiple enzymes may cause stability problems as shown in heart and lung tissue.

Example 32: Generation and Characterization of Anti-VEGF TMEAbody (Bevacizumab)

The heavy chain and light chain sequences of Bevacizumab were downloaded from Drug Bank (www-.drugbank.ca/drugs/DB00112) and site screening was performed to identify anti-VEGF TMEAbody with good blocking efficiency. The mutation position in a heavy chain of the anti-VEGF antibody (bevacizumab) was selected from the group consisting of: Tyr32, Asn35, Tyr54, Tyr60, Lys65, Arg66, Tyr102, Tyr103 and Tyr109; and the mutation position in a light chain was selected from the group consisting of: Ser24, Ser26, Asp28, Tyr32, Tyr49, Thr51, Tyr91, Ser92, and Thr93. His tagged VEGF protein was used for ELISA. The selected sites with good blocking efficiency and good recovery were summarized in Table 76.

TABLE 76

| Selected anti-VEGF TMEAbody candidates based on blocking and recovery efficiency | | | | | | |
|---|---|---|---|---|---|---|
| ID of selected Mutation | Heavy or light chain | Mutation site | R4 | Conjugation efficiency | Blocking efficiency of S47 | Restored activity after R4 conjugation |
| Beva-se001 | HC | Lys65 | R4-7 | 95% | 9 fold | Restored |
| Beva-se002 | LC | Ser26 | R4-1 | 91% | 16 fold | Restored |
| Beva-se003 | LC | Tyr49 | R4-7 | 95% | 26 fold | Restored |
| Beva -se004 | LC | Thr51 | R4-1 | 87% | 13 fold | Restored |

Example 33: Generation and Characterization of Anti-CD20 TMEAbody (Rituximab)

The heavy chain and light chain sequence of Bevacizumab was downloaded from Drug Bank (www-.drugbank.ca/drugs/DB00073) and site screening was performed to identify anti-CD20 TMEAbody with good blocking efficiency. The mutation position in a heavy chain of the anti-CD20 antibody (rituximab) was selected from the group consisting of Tyr32, Asn33, Tyr52, Asn55, Lys63, Lys65, Tyr101, Tyr102 and Tyr107; and the mutation position in a light chain was selected from the group consisting of Ser26, Ser28, Tyr31, Tyr48, Thr50, Asn52, Thr91 and Thr96. His tagged CD20 protein was used for ELISA. The selected sites with good blocking efficiency and good recovery were summarized in Table 77.

TABLE 77

| Selected anti-VEGF TMEAbody candidates based on blocking and recovery efficiency | | | | | | |
|---|---|---|---|---|---|---|
| ID of selected Mutation | Heavy or light chain | Mutation site | R4 | Conjugation efficiency | Blocking efficiency of S47 | Restored activity after R4 conjugation |
| Ritu-se001 | HC | Tyr32 | R4-7 | 92% | 16 fold | Restored |
| Ritu-se002 | HC | Lys63 | R4-7 | 98% | 8 fold | Restored |
| Ritu-se003 | LC | Tyr31 | R4-7 | 91% | 13 fold | Restored |
| Ritu-se004 | LC | Tyr48 | R4-7 | 92% | 15 fold | Restored |
| Ritu-se005 | LC | Thr50 | R4-1 | 89% | 21 fold | Restored |

Example 34: Blocking and Cleaving Screening of Different R4 and R5 for Drug Candidates Blocking and cleaving effect of conjugates in indicated conjugation were evaluated. The conjugates were each dissolved and diluted for ten times to a concentration of 0.1 mM/ml. At 37° C., conjugates were each added into 100 μg MDA-MB231 human tumor tissue homogenates (pH7) in a concentration of 1 mg/ml for 8 hr. The conjugated and released biomolecule was detected binding by ELISA, thereby comparing the activation efficiency of the linker. Results were shown in Table 78.

TABLE 78

Blocking and cleaving effect of S48 to different biomolecules

| R1-R2-R3-R4 | R5 | Binding decrease by conjugation | Recovery binding after activation (%) |
|---|---|---|---|
| S48 | SEQ ID: 13 | 34-fold | 96 |
| S48 | SEQ ID: 14 | 25-fold | 95 |
| S48 | SEQ ID: 15 | 18-fold | 105 |
| S48 | SEQ ID: 16 | 42-fold | 96 |
| S48 | SEQ ID: 17 | 67-fold | 95 |
| S48 | SEQ ID: 18 | 32-fold | 96 |
| S48 | SEQ ID: 19 | 67-fold | 85 |
| S48 | SEQ ID: 26 | 24-fold | 94 |
| S48 | SEQ ID: 27 | 54-fold | 94 |
| S48 | SEQ ID: 28 | 14-fold | 107 |
| S48 | SEQ ID: 29 | 18-fold | 106 |
| S48 | SEQ ID: 30 | 9-fold | 91 |
| S48 | SEQ ID: 31 | 13-fold | 89 |
| S48 | SEQ ID: 32 | 14-fold | 93 |
| S48 | SEQ ID: 44 | 75-fold | 99 |
| S48 | SEQ ID: 54 | 24-fold | 96 |
| S48 | SEQ ID: 60 | 16-fold | 96 |
| S48 | SEQ ID: 61 | 19-fold | 107 |
| S48 | SEQ ID: 62 | 74-fold | 96 |
| S48 | SEQ ID: 63 | 34-fold | 93 |

Blocking and cleaving effect of conjugates in indicated conjugation in Table 79 were evaluated. The conjugates were each dissolved and diluted ten times to a concentration of 0.1 mM/ml. At 37° C., conjugates were each added into MMP2 (pH6) in a concentration of 1 mg/ml for 16 hr. The conjugated and released biomolecule was detected binding by ELISA, thereby comparing the activation efficiency of the linker. Results were shown in Table 79.

TABLE 79

Blocking and cleaving effect of conjugations of S65 to different biomolecules

| R1-R2-R3-R4 | R5 | Binding decrease by conjugation | Recovery binding after activation (%) |
|---|---|---|---|
| S65 | SEQ ID: 13 | 19-fold | 96 |
| S65 | SEQ ID: 14 | 21-fold | 99 |
| S65 | SEQ ID: 15 | 58-fold | 95 |
| S65 | SEQ ID: 16 | 124-fold | 97 |
| S65 | SEQ ID: 17 | 164-fold | 99 |
| S65 | SEQ ID: 18 | 26-fold | 95 |
| S65 | SEQ ID: 19 | 35-fold | 89 |
| S65 | SEQ ID: 26 | 43-fold | 94 |
| S65 | SEQ ID: 27 | 17-fold | 95 |
| S65 | SEQ ID: 28 | 12-fold | 99 |
| S65 | SEQ ID: 29 | 25-fold | 105 |
| S65 | SEQ ID: 30 | 48-fold | 101 |
| S65 | SEQ ID: 31 | 75-fold | 97 |
| S65 | SEQ ID: 32 | 34-fold | 93 |
| S65 | SEQ ID: 44 | 19-fold | 96 |
| S65 | SEQ ID: 54 | 25-fold | 94 |
| S65 | SEQ ID: 60 | 75-fold | 97 |
| S65 | SEQ ID: 61 | 34-fold | 93 |

TABLE 79-continued

Blocking and cleaving effect of conjugations of S65 to different biomolecules

| R1-R2-R3-R4 | R5 | Binding decrease by conjugation | Recovery binding after activation (%) |
|---|---|---|---|
| S65 | SEQ ID: 62 | 19-fold | 96 |
| S65 | SEQ ID: 63 | 25-fold | 94 |

Blocking and Cleaving effect of conjugates in indicated conjugation were evaluated. The conjugates were each dissolved and diluted ten times to a concentration of 0.1 mM/ml. At 37° C., conjugates were each added into 100 μg MDA-MB231 acidized human tumor tissue homogenates (pH6.5). The conjugated and released biomolecule was detected binding by ELISA, thereby comparing the activation efficiency of the linker. Results were shown in Table 80.

TABLE 80

Blocking and cleaving effect of conjugations of S27 to different biomolecules

| R1-R2-R3-R4 | R5 | Binding decrease by conjugation | Recovery binding after activation (%) |
|---|---|---|---|
| S27 | SEQ ID: 13 | 43-fold | 91 |
| S27 | SEQ ID: 14 | 11-fold | 95 |
| S27 | SEQ ID: 15 | 8-fold | 98 |
| S27 | SEQ ID: 16 | 14-fold | 95 |
| S27 | SEQ ID: 17 | 19-fold | 98 |
| S27 | SEQ ID: 18 | 33-fold | 95 |
| S27 | SEQ ID: 19 | 45-fold | 96 |
| S27 | SEQ ID: 26 | 28-fold | 99 |
| S27 | SEQ ID: 27 | 37-fold | 95 |
| S27 | SEQ ID: 28 | 36-fold | 97 |
| S27 | SEQ ID: 29 | 106-fold | 106 |
| S27 | SEQ ID: 30 | 135-fold | 102 |
| S27 | SEQ ID: 31 | 75-fold | 107 |
| S27 | SEQ ID: 32 | 58-fold | 97 |
| S27 | SEQ ID: 44 | 74-fold | 99 |
| S27 | SEQ ID: 54 | 35-fold | 97 |

According to the results, these drug candidates exhibited blocking effect and activation effect in the indicated activation conditions.

Example 35: Study on Efficacy of Indicated S27, S39, S40, S47, S48 and S65 Conjugated with Mouse CTLA-4 Antibody in CT26 Tumor Immune Model Test purpose: to investigate the anti-tumor efficacy of S27, S39, S40, S47, S48, S65 conjugated with mouse CTLA-4 antibody for immune treatment.

Test drug: S27, S39, S40, S47, S48, S65 conjugated with mouse CTLA-4 antibody (9D9), all used in 20 mg/kg (equimolar of CTLA-4 antibody).

Production of Tumor Model:

1) CT26 tumor cells were purposed from ATCC. Cells were cultivated in DMEM culture solution containing 10% fetal bovine serum at 37° C. and 5% $CO_2$. The cells were passaged every three days and cells within the 15th passage were used.

2) Tumor immunization. $5\times10^5$ CT26 cancer cells (purchased from ATCC) which were killed by irradiation were intraperitoneally injected to mice. The mice were injected 3 times, once every two weeks. After immunization, mice were injected with tumor cells and the drugs were administered weekly for 4 weeks.

3) Production of tumor. At day 32, $10^6$ live lung tumor cells were subcutaneously injected to the back of the C57 mice immunized by tumor. Treatment began when the tumor grew to 0.3-0.4 cm.

4) Analysis on tumor CD8+ T cells. The tumor tissue was homogenated and individual cells in the tumor were filtered, separated and washed by buffer twice, then cultivated with the leucocyte common antigen CD45-PE and CD8-FITC marked antibodies for 1 hour at ambient temperature. The cells were washed by phosphate buffer containing 100 fetal bovine serum twice and then analyzed for the ratio of the T lymphocyte antigen (CD8) positive cells in the leucocyte common antigen (CD45) positive cells by flow cytometry. Increasement of the ratio indicates increased T lymphocyte cells and thus the animal immunity against the tumor was improved.

5) Grouping and test results are shown in Table 81.

TABLE 81

Effect on inhibition of tumor and immune activation of S27, S39, S40, S47, S48 and S65 conjugated with mouse CTLA-4 antibody and control

| Group | Number of animal | Size of tumor ($mm^3$) Day 28 | Cure number of mouse Day 28 | CD8:CD45 (%) |
|---|---|---|---|---|
| PBS | 8 | 1887.56 ± 323.4 | 0 | 5.2 |
| Mouse CTLA-4 antibody (WT) | 8 | 74.46 ± 467.34 | 2 (Dead 2) | 13.1 |
| S27-Mouse CTLA-4 Antibody (9D9) | 8 | 37.60 ± 358.57 | 6 | 28.4 |
| S39-Mouse CTLA-4 Antibody (9D9) | 8 | 31.57 ± 124.45 | 5 | 29.7 |
| S40-Mouse CTLA-4 Antibody (9D9) | 8 | 57.63 ± 157.32 | 6 | 26.3 |
| S47-Mouse CTLA-4 Antibody (9D9) | 8 | 53 ± 216.47 | 7 | 38.4 |
| S48-Mouse CTLA-4 Antibody (9D9) | 8 | 75.78 ± 32.74 | 4 | 23.6 |
| S65-Mouse CTLA-4 Antibody (9D9) | 8 | 74.28 ± 38.45 | 6 | 26.7 |

6) Results and discussion. Treatment effects of S27, S39, S40, S47, S48 and S65 conjugated with mouse CTLA-4 antibody were greatly improved as compared to the control group and the WT CTLA-4 antibody treatment groups. WT CTLA-4 antibody Causing 1 death in WT CTLA-4 antibody treatment may be caused by toxicity in high dose treatment. Treatment effects of S27, S39, 540, S47, S48 and S65 conjugated with mouse CTLA-4 antibody show an excellent effect and promote CD8/CD45 T cell ratio in tumor tissue.

Example 36: Study on Efficacy of Adalimumab (SEQ ID NO:29) Conjugated with S27, S47, S48 or S65 in RA Mouse Model The TgTC mice were generated using a human TNF/β-globin (TNFglobin) recombinant gene construct, which contained a 2.8 kb fragment with the entire coding region and promoter of the hTNFα gene, fused to a 0.77 kb fragment with the 3' untranslated region (UTR) and polyadenylation site of human β-globin replacing that of the hTNFα gene. The fragment was then microinjected into pronuclei of FVB/J inbred strain fertilized eggs. Finally, the injected fertilized eggs were implanted into the oviduct of 8-week-old female pseudo-pregnant ICR mice. Transgenic lineages were established by back-crossing the transgenic founder individuals to the FVB/J inbred strain. The genotyping was performed by PCR to screen for transgenic animals as well as routine tail genotyping. The transgene specific PCR primers were:

```
            (forward primer, SEQ ID NO: 87)
5'-GAACTCCCTCGATGTTAACCA-3';
and

            (reverse primer, SEQ ID NO: 88)
5'-TTCAATCCCCAAATCCTAGCC-3'.
```

The PCR reactions were performed as follows: 94° C. for 4 min; 35 cycles at 95° C. for 30 s, 57° C. for 40 s, and 72° C. for 40 s; 72° C. for 10 min.

Different anti-hTNFα antibody (Adalimumab 2 mg/kg) and conjugated antibody (2 mg/kg equimolar of Adalimumab) dissolved in saline were intraperitoneally administered (2 mg/kg) to TgTC mice weekly from three to ten weeks, with saline-treated TgTC mice serving as control. Clinical assessment Weekly body weight and arthritis scores in all four limbs were recorded after weaning. Clinical severity of arthritis for each paw (fingers, tarsus, and ankle) was quantified by attributing a score ranging from 0 to 3: 0, normal; 1, slight redness and/or swelling; 2, pronounced edematous swelling; 3, joint deformity and rigidity. The arthritis score per mouse was an average of the four limbs. Grouping and test results are shown in Table 82.

TABLE 82

Effect on inhibition of arthritis by S27, S47, S48 and S65 conjugated with Adalimumab antibody

| Group | Number of animal | The arthritis score Day 5 | The arthritis score Day 10 |
|---|---|---|---|
| PBS | 4 | 3 | 3 |
| Adalimumab | 4 | 3 | 2 |
| S27-Adalimumab | 4 | 1 | 1 |
| S47-Adalimumab | 4 | 2 | 1 |
| S48-Adalimumab | 4 | 1 | 1 |
| S65-Adalimumab | 4 | 1 | 1 |

Results showed that Adalimumab conjugated with S27, S47, S48 and S65 greatly reduced the arthritis scores.

Example 37: Generation and Characterization of Anti-Her2/Anti-CD3 Bispecific TMEAbody The heavy chain and light chain sequences of Trastuzumab was downloaded from Drug Bank (www- .drugbank.ca/drugs/DB00072) and sites screening was performed to identify scFv form of anti-Her2 with good blocking efficiency. The mutation position in a light chain is selected from the group consisting of: Asp1, Gln3, Gln27, Asp28, Asn30, Tyr49, Tyr55, Arg66, Asp70, and Tyr92. The mutation position in a light chain is selected from the group consisting of Arg19, Lys30, Asp31, Tyr33, Arg50, Tyr62, Asn55, Tyr57, Arg59, Tyr60, Asp62, Lys65, Asp102, and Tyr105. The scFv forms of above selected mutants were expressed in HEK293 with C Terminal 6His tag, purified with Ni-NTA column, and conjugated with corresponding chemical linkers. Binding ELISA was carried out with His-tagged human Her2 protein as antigen and anti-human kappa chain as secondary antibody. The blocking efficiency was summarized in Table 84.

TABLE 83

Selected scFv form of anti-Her2 candidates based on blocking and recovery efficiency

| ID of selected Mutation for scFv form | Single Heavy/ Light chain | Mutation site | R4 | Conjugation efficiency | Blocking efficiency of S47 | Activity after R4 conjugation |
|---|---|---|---|---|---|---|
| Trast-se001scFv | Heavy chain | Tyr33 | R4-7 | 95% | 15 fold | Restored |
| Trast-se002scFv | Heavy chain | Lys65 | R4-7 | 93% | 6 fold | Restored |
| Trast-se003scFv | Heavy chain | Tyr105 | R4-7 | 92% | 32 fold | Restored |
| Trast -se004scFv | Light chain | Gln30 | R4-11 | 83% | 15 fold | Restored |
| Trast -se005scFv | Light chain | Tyr49 | R4-7 | 93% | 43 fold | Restored |
| Trast -se006scFv | Light chain | Asp70 | R4-11 | 91% | 13 fold | Restored |

We fused anti-Her2 scFv with selected Cysteine mutation (Tyr49 in light chain) to anti-human CD3 scFv containing C terminal 6His tag to form bispecific antibody targeting to tumor and T cells. These Her2/CD3 bispecific antibodies were produced in HEK293 cells and purified with Ni-NTA column. These Her2/CD3 bispecific antibodies with mutant was further conjugated with S47 and a 38 fold decreased binding activity to human Her2 protein was obtained. After digestion with legumain, both binding activities were restored.

The single chain of Her2/CD3 TMEAbody were produced by conjugating 527, S47 or S48 to a fusion protein anti-Her2 scFV with anti-CD3 or its scFv, as shown in Table 84.

TABLE 84

Selected scFv form of anti-Her2 candidates based on blocking and recovery efficiency

| Bispecific TMEAbody | anti-Her2 | anti-CD3 | SEQ ID NO: | R1-R2-R3-R4 |
|---|---|---|---|---|
| Her2/CD3 TMEAbody1 | anti-Her2 scFv | anti-CD3 scFv | 70 | S27 |
| Her2/CD3 TMEAbody2 | anti-Her2 scFv | anti-CD3 scFv | 70 | S47 |
| Her2/CD3 TMEAbody3 | anti-Her2 scFv | anti-CD3 scFv | 70 | S48 |

TABLE 84-continued

Selected scFv form of anti-Her2 candidates based on blocking and recovery efficiency

| Bispecific TMEAbody | anti-Her2 | anti-CD3 | SEQ ID NO: | R1-R2-R3-R4 |
|---|---|---|---|---|
| Her2/CD3 TMEAbody4 | anti-Her2 scFv | anti-CD3 scFv | 82 | S27 |
| Her2/CD3 TMEAbody5 | anti-Her2 scFv | anti-CD3 scFv | 82 | S47 |
| Her2/CD3 TMEAbody6 | anti-Her2 scFv | anti-CD3 scFv | 82 | S48 |
| Her2/CD3 TMEAbody7 | anti-Her2 | anti-CD3 | Anti-Her2:71 and 72 Anti-CD3:75 | S27 |
| Her2/CD3 TMEAbody8 | anti-Her2 | anti-CD3 | Anti-Her2:71 and 72 Anti-CD3:75 | S47 |
| Her2/CD3 TMEAbody9 | anti-Her2 | anti-CD3 | Anti-Her2:71 and 72 Anti-CD3:75 | S48 |

We fused PD-1 antibody or PD-L1 antibody with mutant IL-2 (IL2-S87C) to form targeting tumor associated antigen PD-L1/IL-2 TMEAkines or PD-1/IL-2 TMEAkines.

These TMEAkines with IL2-T41C mutant was further conjugated with S47. A >135 fold decreased binding activity to human IL-2Rβ was obtained. After digestion with legumain, both binding activity to IL-2Rβ were restored. The fused PD-L1 or PD-1 antibody with mutant IL-2 (mutant at binding IL-2Rα S87C) were further conjugated with S47 to get legumain activation fusion TMEAkine as shown in Table 85.

TABLE 85

Fusion protein candidates based on blocking and recovery efficiency

| Fusion TMEAkine | Fusion protein sequence | R1-R2-R3-R4 |
|---|---|---|
| 1 | N-teminal-IL2(S87C)-GSGS-PD-1(SEQ ID NO:15) | S47 |
| 2 | N-teminal-IL2(S87C)-GSGS-PD-1(SEQ ID NO:17) | S47 |
| 3 | N-teminal-IL2(S87C)-GSGS-PD-L1(SEQ ID NO:27) | S47 |

TABLE 85-continued

Fusion protein candidates based on blocking and recovery efficiency

| Fusion TMEAkine | Fusion protein sequence | R1-R2-R3-R4 |
|---|---|---|
| 4 | N-terminal-PD-1(SEQ ID NO:15)-GSGS-IL2(S87C) | S47 |
| 5 | N-terminal-PD-1(SEQ ID NO:17)-GSGS-IL2(S87C) | S47 |
| 6 | N-terminal-PD-L1(SEQ ID NO:27)-GSGS-IL2(S87C) | S47 |
| 7 | N-terminal-EGFR(SEQ ID NO:78&79)-GSGS-IL2(S87C) | S47 |
| 8 | N-terminal-VEGFR (SEQ ID NO:80&81)-GSGS-IL2(S87C) | S47 |
| 9 | N-terminal-Her2 (SEQ ID NO:82&83)-GSGS-IL2(S87C) | S47 |
| 10 | PD-1/IL-2 fusion protein(SEQ ID NO:73) | S47 |
| 11 | PD-L1/IL-2 fusion protein(SEQ ID NO:74) | S47 |

In Vivo Characterization of Toxicity in Human PBMC-Transferred Mouse Model

Test purpose: to investigate the acute toxicity of the fusion TMEAbody via intravenous injection.

Animal: the first class SCID mouse, weighing 19-21 g and all mice being female.

Method and results: SCID mouse were randomly divided into 21 groups according to their body weights, with 10 mice in each group. As shown in Table 86, the mice were intravenously injected with D1, D7 and D14 for just one time in a dose of 30 mg/kg (equimolar of antibody). Control tests were performed by injecting 30 mg/kg human IgG. Animals were observed for 21 continuous days for presence or absence of the following behaviors on each day: pilo-erection, hair tousle and lackluster, lethargy, stoop and irritable reaction, and body weight and death were recorded as shown in Table 86.

TABLE 86

Comparison of mortality rates of test mice receiving different fusion TMEAbody injections

| Group | injections | Number of animal | Number of dead animal (day21) | Mortality rate (%) |
|---|---|---|---|---|
| 1 | human IgG | 10 | 0 | 0 |
| 2 | Her2/CD3 scFv | 10 | 4 | 40 |
| 3 | Her2/CD3 antibody | 10 | 3 | 30 |
| 4 | Her2/CD3 TMEAbody 1 | 10 | 0 | 0 |
| 5 | Her2/CD3 TMEAbody 2 | 10 | 0 | 0 |
| 6 | Her2/CD3 TMEAbody 3 | 10 | 0 | 0 |
| 7 | Her2/CD3 TMEAbody 4 | 10 | 0 | 0 |
| 8 | Her2/CD3 TMEAbody 5 | 10 | 0 | 0 |
| 9 | Her2/CD3 TMEAbody 6 | 10 | 0 | 0 |

Results and discussions: no pilo-erection, hair tousle and lackluster, lethargy, stoop, irritable reaction and death were observed in mice receiving 30 mg/kg of group 2, 3, 10, and 14. As shown in Table 86, The MTD of the fusion protein is less than 30 mg/kg, which can be observed toxicity and deaths.

In Vivo Characterization of Toxicity in Human PBMC-Transferred Mouse Model

Test purpose: to investigate the acute toxicity of the fusion TMEAbody via intravenous injection.

Animal: the first class SCID mouse, weighing 19-21 g and all mice being female.

Method and results: SCID mouse were randomly divided into 21 groups according to their body weights, with 5 mice in each group. As shown in Table 88, the mice were intravenously injected with fusion protein and fusion protein conjugation with S47 at D1, D7 and D14 for just one time in a dose of 30 mg/kg (equimolar of antibody). Control tests were performed by injecting 30 mg/kg saline. Animals were observed for 21 continuous days for presence or absence of the following behaviors on each day: pilo-erection, hair tousle and lackluster, lethargy, stoop and irritable reaction, and body weight and death were recorded as shown in Table 87.

TABLE 87

Comparison of mortality rates of test mice receiving different fusion TMEAkine injections

| Fusion protein sequence | Death number | Death number after conjugating to S47 |
|---|---|---|
| saline | 0 | 0 |
| N-teminal-IL2(S87C)-GSGS-PD-1(SEQ ID NO:15) | 5 | 0 |
| N-teminal-IL2(S87C)-GSGS-PD-1(SEQ ID NO:17) | 3 | 0 |
| N-terminal-IL2(S87C)-GSGS-PD-L1(SEQ ID NO:27) | 5 | 0 |
| N-terminal-PD-1(SEQ ID NO:15)-GSGS-IL2(S87C) | 2 | 0 |
| N-terminal-PD-1(SEQ ID NO:17)-GSGS-IL2(S87C) | 1 | 0 |
| N-terminal-PD-L1(SEQ ID NO:27)-GSGS-IL2(S87C) | 4 | 0 |
| N-terminal-EGFR(SEQ ID NO:77&79)-GSGS-IL2(S87C) | 3 | 0 |
| N-terminal-VEGFR (SEQ ID NO:80&81)-GSGS-IL2(S87C) | 4 | 0 |
| N-terminal-Her2 (SEQ ID NO:82&83)-GSGS-IL2(S87C) | 5 | 1 |
| PD-1/IL-2 fusion protein(SEQ ID NO:73) | 4 | 0 |
| PD-L1/IL-2 fusion protein(SEQ ID NO:74) | 5 | 1 |

Results and discussions: no pilo-erection, hair tousle and lackluster, lethargy, stoop, irritable reaction and death were observed in mice receiving 30 mg/kg of all group of fusion TMEAkine. But the toxicity was reduced after fusion with S47.

In Vivo Characterization of Single Chain of CD3-Her2 TMEAbody in Mouse Tumor Model To further characterize the in vivo efficacy of single chain of CD3-Her2 TMEAbody in treating tumor in animal model, single chain of CD3-Her2 TMEAbody, as well as single chain CD3-Her2 antibody were administrated into Tumor xenografts. To initiate tumor xenografts, $3\times10^6$ KPL-4 cells were implanted orthotopically into the right penultimate inguinal mammary fat pad of female severe combined immunodeficient (SCID) beige mice. Tumors were allowed to growth (20 d for KPL4) after implantation before initiation of treatment. Mice with KPL-4 tumors (100 $mm^3$) were treated with indicated drug (10 mg/kg weekly for 5 weeks) for the duration of the study. Tumor volumes and body weights were measured twice weekly. The tumor volume inhibition rate was summarized in Table 88. Results implied that single chain of CD3-Her2 TMEAbody could be activated in the tumor microenvironment and enhance the efficacy of single chain of CD3-Her2 antibody.

TABLE 88

| Tumor growth inhibition rate at day 20 after administration | | | |
|---|---|---|---|
| Group | Dose | Cure rate (%) | Dead |
| human IgG | 10 mg/kg | 0 | 0 |
| Her2/CD3 scFv | 10 mg/kg | 16.7 | 0 |
| Her2/CD3 antibody | 10 mg/kg | 33.3 | 2 |
| Her2/CD3 TMEAbody1 | 10 mg/kg | 66.7% | 0 |
| Her2/CD3 TMEAbody2 | 10 mg/kg | 83.3% | 0 |
| Her2/CD3 TMEAbody3 | 10 mg/kg | 100% | 0 |
| Her2/CD3 TMEAbody4 | 10 mg/kg | 100% | 0 |
| Her2/CD3 TMEAbody5 | 10 mg/kg | 100% | 0 |
| CD3-Her2 TMEAbody6 | 10 mg/kg | 100% | 0 |
| PD-1/IL-2 fusion | 10 mg/kg | 100% | 2 |
| Fusion TMEAkine1 | 10 mg/kg | 83.3% | 0 |
| Fusion TMEAkine 2 | 10 mg/kg | 100% | 0 |
| TMEAkine4 | 10 mg/kg | 100% | 0 |
| Fusion TMEAkine5 | 10 mg/kg | 100% | 0 |
| Fusion TMEAkine10 | 10 mg/kg | 100% | 0 |
| PD-L1/IL-2 fusion | 10 mg/kg | 100% | 2 |
| FusionTMEAkine3 | 10 mg/kg | 83.3% | 0 |
| Fusion TMEAkine6 | 10 mg/kg | 100% | 0 |
| Fusion TMEAkine11 | 10 mg/kg | 83.3% | 0 |

As shown in Table 88, inhibition on tumor growth and cure rate by Her2/CD3 TMEAbody were greatly improved as compared with the groups treating by Her2/CD3 scFv or Her2/CD3 antibody by using the same molar concentration. Inhibition on tumor growth and cure rate by PD-L1/IL-2 TMEAkine or antibody show efficacy and cure the mice. But in the PD-L1/IL-2 fusion antibody group, the toxicity caused some mice death.

The invention claimed is:

1. A conjugate of a biomolecule having the following structure:

R1-R2-R3-R4-S-cys-R5 wherein,

R5 represents a biomolecule, wherein the biomolecule is a fusion protein with one or more cysteine residues introduced by mutation;

cys represents the cysteine residue(s) contained in R5;

S represents sulfur atom(s) of the cysteine residue(s);

R1 is a group that prevents R5 from binding to its antigen, ligand or receptor;

R2 is a cleavable linker arm capable of being activated by one or more proteolytic enzymes or a chemical bond capable of being acidically activated in a pathologic microenvironment;

R3 is a linker arm capable of automatically shedding after R2 is cleaved or a chemical bond capable of being acidically activated in a pathologic microenvironment; with the proviso that when R2 is absent, R3 is the chemical bond capable of being acidically activated in a pathologic microenvironment; and R4 is a group covalently linked to R5 via the sulfur atom(s) of the cysteine residue(s) contained in R5 that recovers, maintains or promotes the binding capacity of R5 to its antigen, ligand or receptor after the moiety R1-R2-R3 is cleaved, wherein the fusion protein containing an antigen binding domain of an antibody selected from the group consisting of SEQ ID NO: 73, SEQ ID NO: 74, SEQ ID NO: 83 and SEQ ID NO: 82.

2. The conjugate of the biomolecule of claim 1, wherein R1 is selected from the group consisting of polyethylene glycol-$C_{1-5}$ alkylcarbonyl,

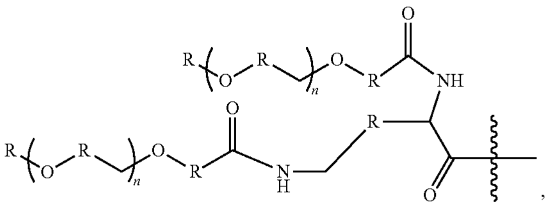
,
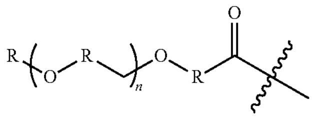
,
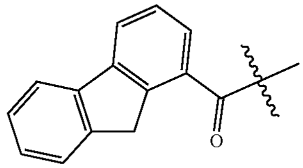
,
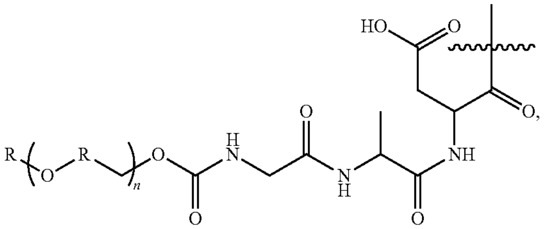
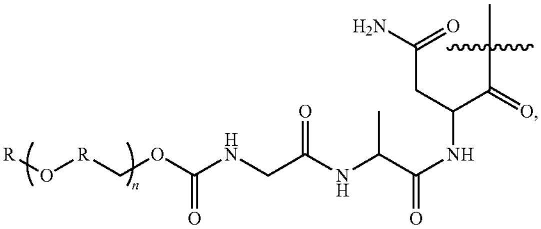
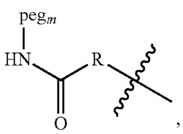
,
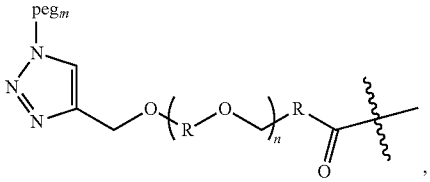
, -continued

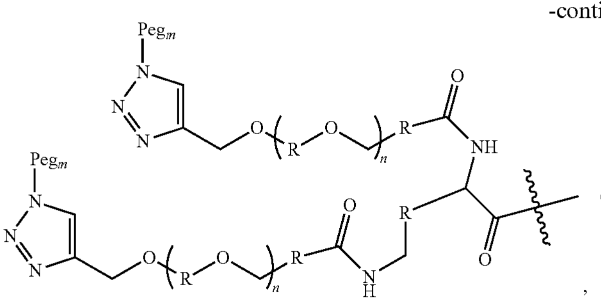

,

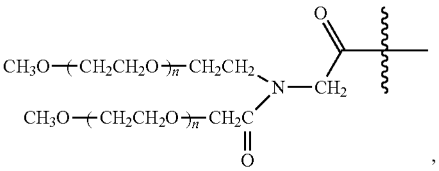

,

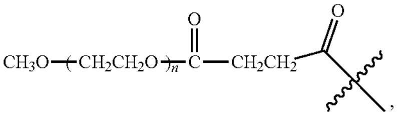

, and

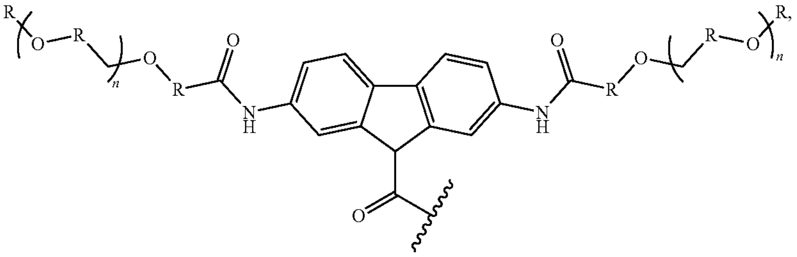

wherein each R is independently C1-4 alkyl; each n is independently an integer in a range of 1 to 30000 kDa; the polyethylene glycol or $peg_m$ is a polyethylene glycol having a molecular weight in a range of 44 to 132000 kDa; m represents the molecular weight of the polyethylene glycol; and the wave line indicates the position of R1 linking to R2.

3. The conjugate of the biomolecule of claim 1, wherein R1 is selected from the group consisting of:

R1-1

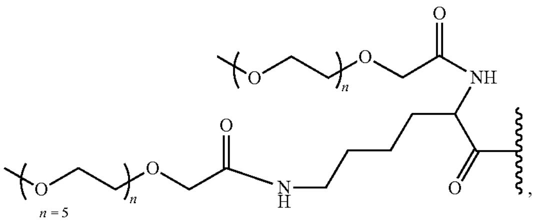

,

R1-2

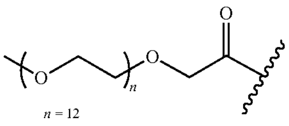

,

R1-3

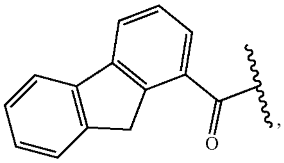

,

R1-4

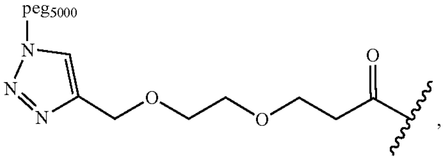

,

R1-5

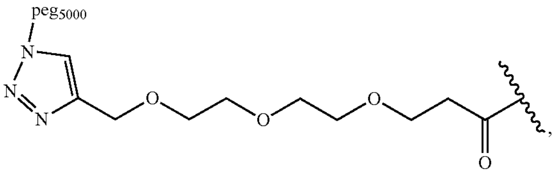

,

R1-6

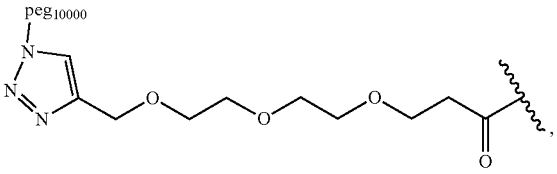

,

-continued
R1-7
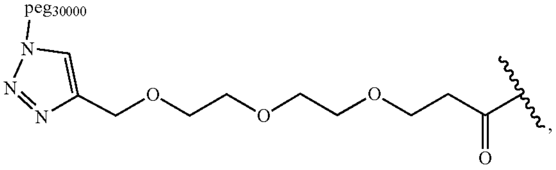
R1-8
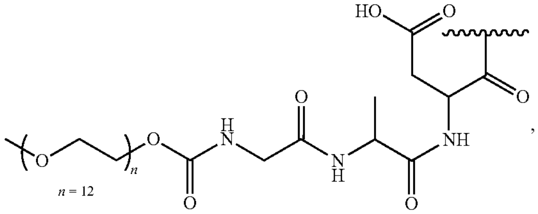
R1-9
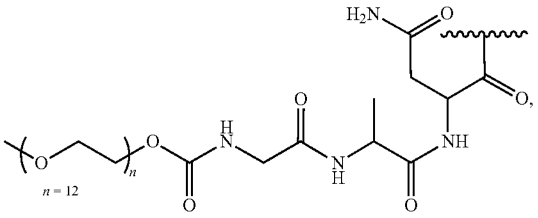
R1-10
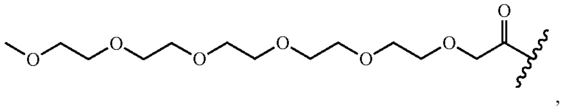
R1-11
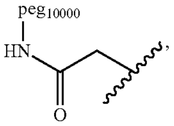
R1-12
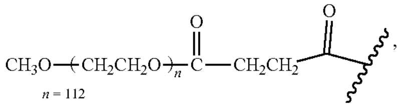
R1-13
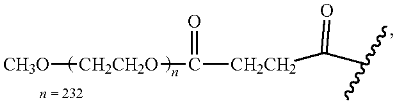
R1-14
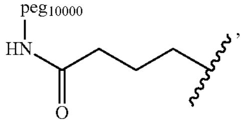
R1-15
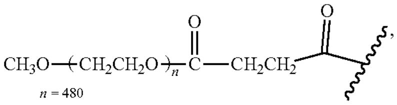
R1-16
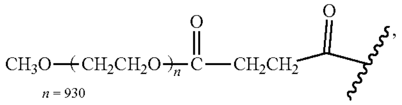
R1-17
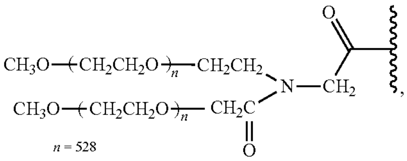
R1-18
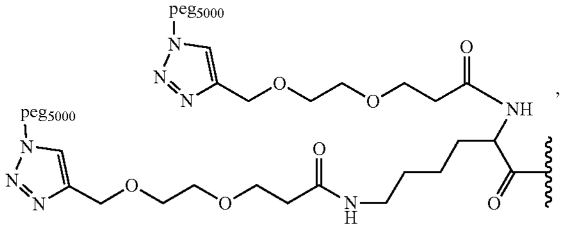
R1-19
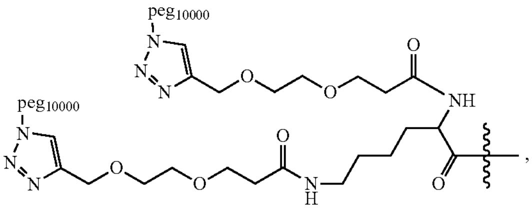
R1-20
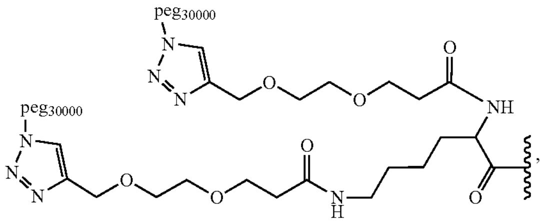

-continued
R1-21
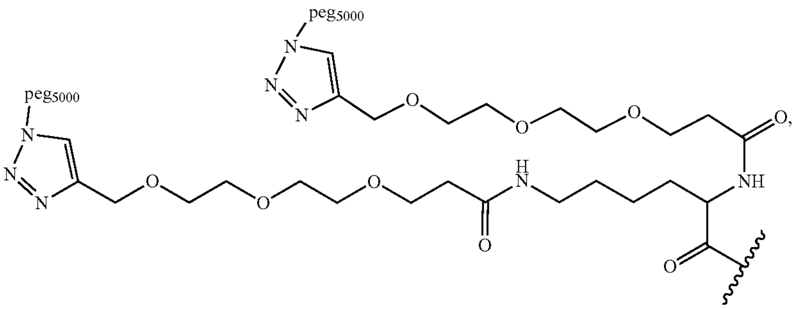
R1-22
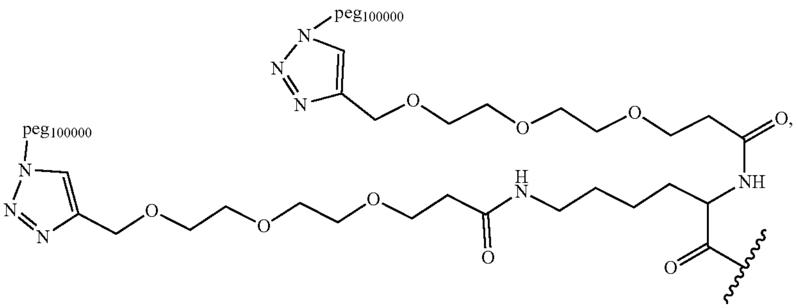
R1-23
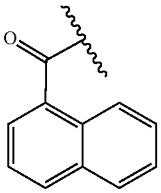
,
R1-24
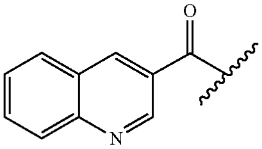
,
R1-25
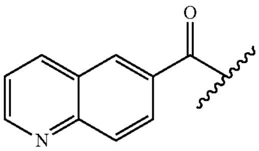
,
R1-26
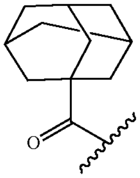
,
R1-27
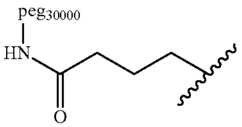
,
R1-28
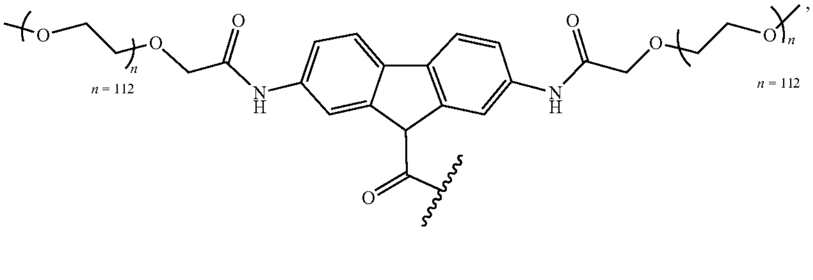
, -continued

R1-29

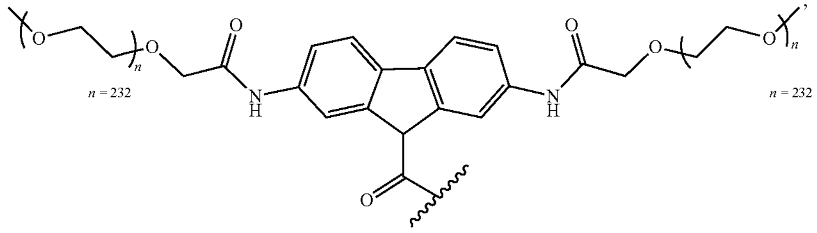

R1-30

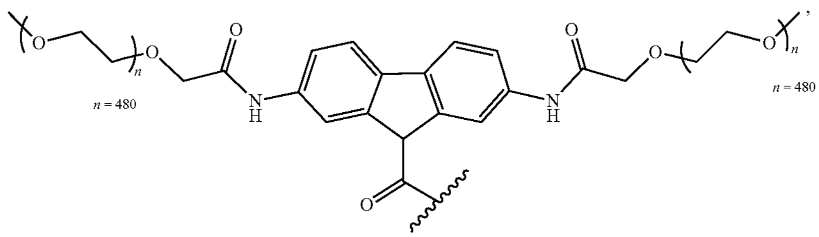

, and

R1-31

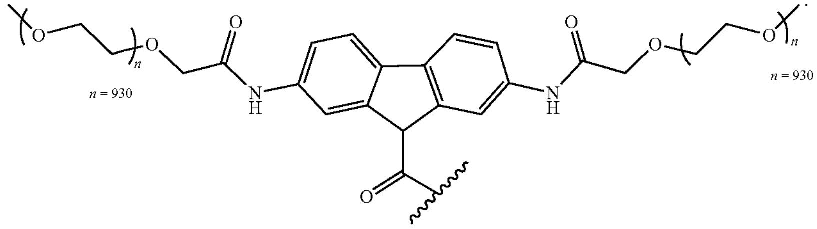

4. The conjugate of the biomolecule of claim 1, wherein R2 is a peptide capable of being activated or cleaved by one or multiple proteolytic enzyme, protease or peptidase, wherein the protease is selected from the group consisting of cysteine protease, asparagines protease, aspartate protease, glutamic acid protease, threonine protease, gelatinase, metallopro-teinase, or asparagine peptide lyase;

R2 is a peptide capable of being cleaved by at least one of enzymes selected from the group consisting of Legumain, granzyme, Cathepsin B, Cathepsin C, Cathepsin D, Cathepsin E, Cathepsin K, Cathepsin L, plasmin, collagenase, Type IV collagenase, astromelysin, Factor Xa, trypsin-like protease, elastase-like protease, subtilisin-like protease, actinidain, bromelain, calpain, caspase, caspase-3, Mirl-CP, papain, HIV-1 protease, HSV protease, CMV protease, chymosm, pepsm, matriptase, plasmepsm, nepenthesin, metalloexopeptidase, metalloendopeptidase, matrix metalloprotease (MMP), MMP1, MMP2, MMP3, MMP8, MMP9, MMPlO, MMP11, MMP12, MMPP13, MMPP14, urokinase plasminogen activator (uPA), prostate-specific antigen (PSA, hK3), interleukin-113 converting enzyme, thrombin, FAP (FAP-a), meprin, CD26.

5. The conjugate of the biomolecule of claim 1, wherein R2 is a peptide represented by -R2a-, -R2b-, -R2a-N—, -R2a-D-, -R2a-AAN—, -R2a-AAD-, or -R2a-R2b-; wherein R2a is a peptide capable of being cleaved at amide bond by one or more proteolytic enzymes; R2b is a peptide with its nitrogen in side chain forming a carbamate with R3, wherein the carbamate is capable of being cleaved by one or more proteolytic enzymes; A is alanine; N is asparagine with its nitrogen in side chain forming a carbamate with R3, wherein the carbamate is capable of being cleaved by Legumain; D is aspartic acid with its nitrogen in side chain forming a carbamate with R3 and the carbamate can be cleaved by Granzyme B;

R2 is a tripeptide, wherein the first amino acid residue of the tripeptide linked to R1 is selected from the group consisting of Ala, Thr, Val and Ile, the middle second amino acid residue is selected from the group consisting of Ala, Thr, Val and Asn, and the third amino acid residue linked to R3 is selected from the group consisting of Asn and Asp; and wherein R2 links to R1 via an amino group of the first amino acid residue in a linkage manner of amide, ester, carbamate, urea or hydrazone bond, and to R3 via a carboxyl group of the third amino acid residue in a linkage manner of amide, ester, carbamate, urea or hydrazone bond; the tripeptide is selected from the group consisting of Ala-Ala-Asn and Ala-Ala-Asp.

6. The conjugate of the biomolecule of claim 1, wherein R3 is selected from the group consisting of:

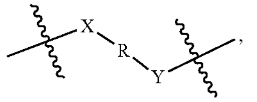

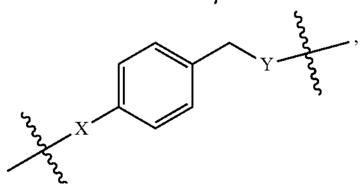

-continued

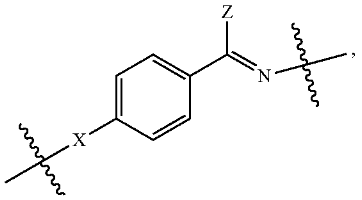

, and

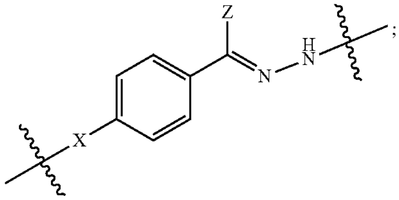

;

wherein X and Y are each independently NR' or 0, Z is H or $C_{1-10}$ alkyl, R is $C_{1-4}$ alkyl, and R' is H or $C_{1-4}$alkyl; and wherein R4 links to R3 via the Y or N in the above formulae in a linkage manner of amide, ester, carbamate, urea or hydrazone bond.

7. The conjugate of the biomolecule of claim 1, wherein R3 is selected from the group consisting of amide, ester, carbamate, urea and hydrazone bonds.

8. The conjugate of the biomolecule of claim 1, wherein R3 is selected from the group consisting of:

R3-1

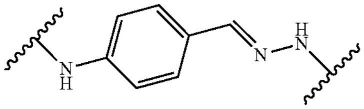

,

R3-2

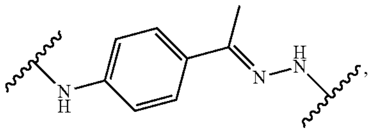

,

R3-3

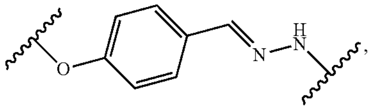

,

-continued

R3-4

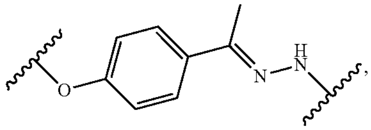

,

R3-5

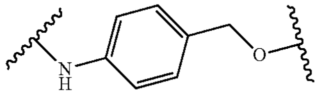

,

R3-6

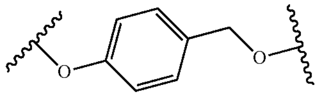

,

R3-7

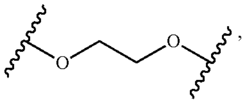

,

R3-8

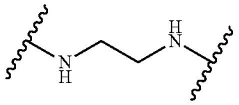

,

R3-9

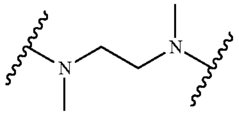

,

R3-10

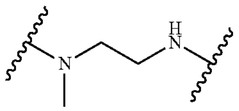

,

R3-11

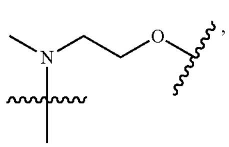

, and

R3-12

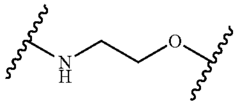

.

9. The conjugate of the biomolecule of claim 1, wherein R4 is selected from the group consisting of:

R4-1

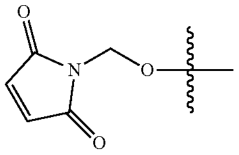

,

R4-2

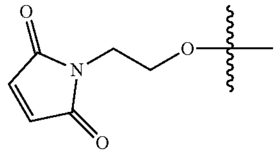

,

R4-3

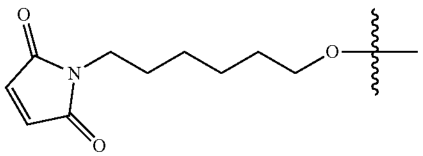

,

R4-4

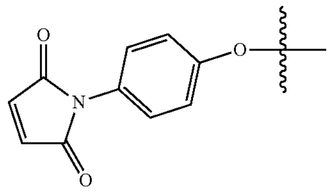

,

-continued
R4-5
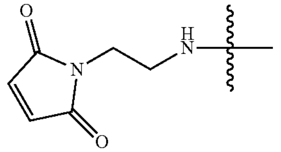
,
R4-6
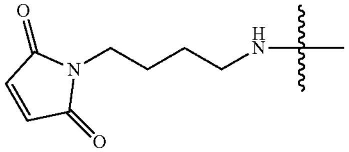
,
R4-7
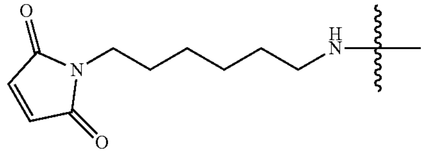
,
R4-8
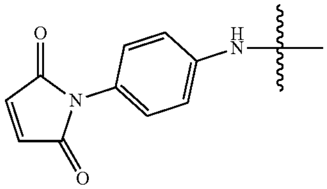
,
R4-9
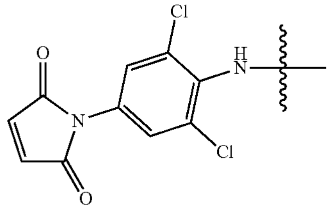
,
R4-10
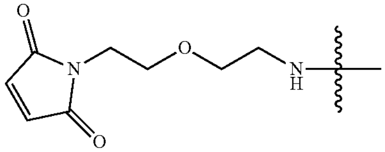
,
R4-11
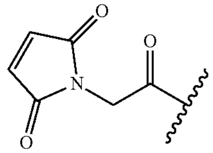
,
R4-12
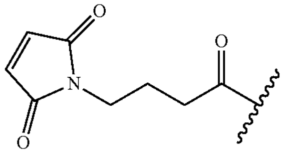
,
R4-13
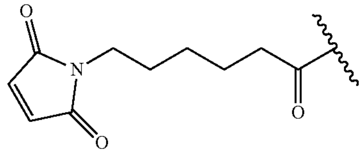
,
R4-14
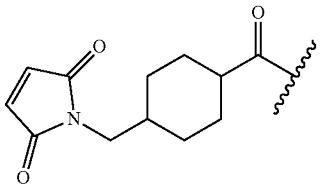
,
R4-15
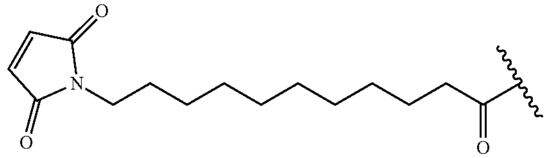
,
R4-16
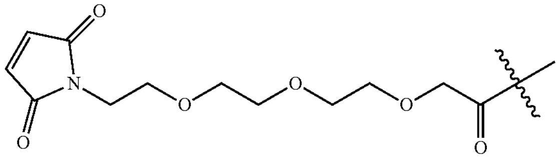
,
R4-17
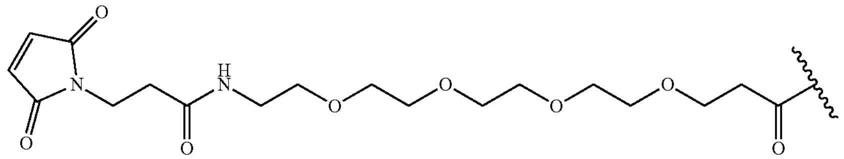
,
R4-18
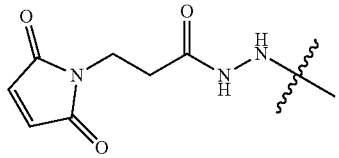
,
R4-19
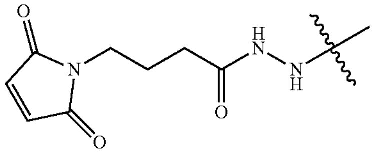
, -continued
R4-20
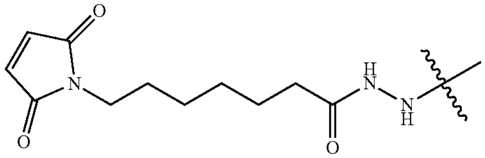
,
R4-21
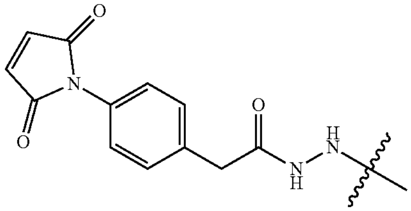
,
R4-22
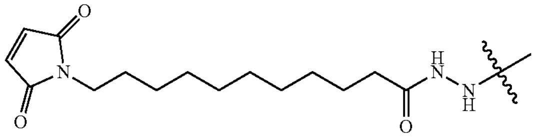
,
R4-23
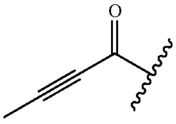
,
R4-24
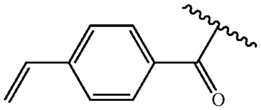
,
R4-25
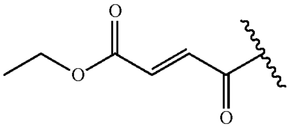
,
R4-26
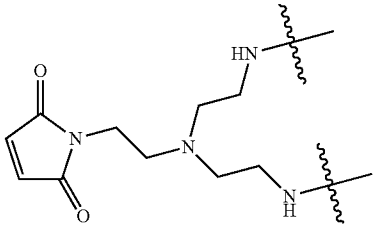
,
R4-27
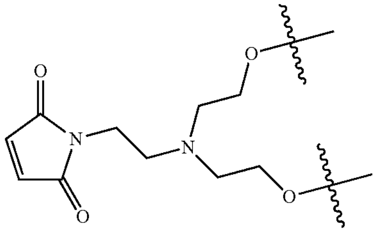
,
R4-28
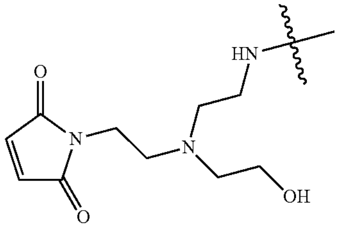
,
R4-29
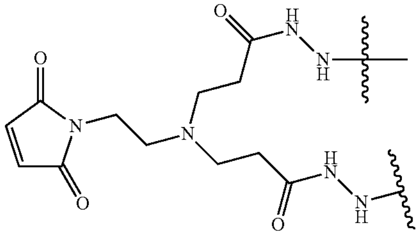
,
R4-30
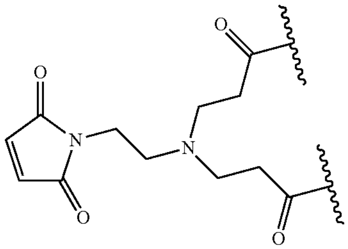
,
R4-31
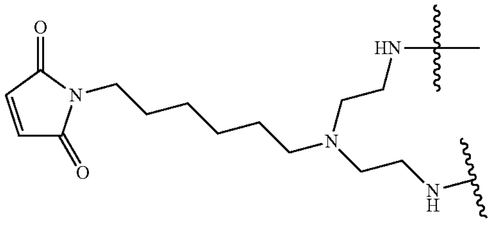
,
R4-32
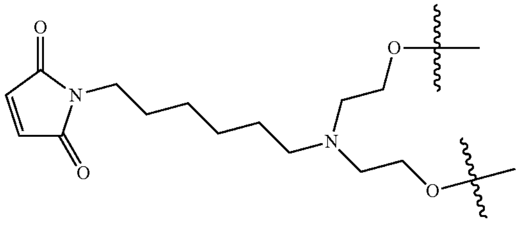
,
R4-33
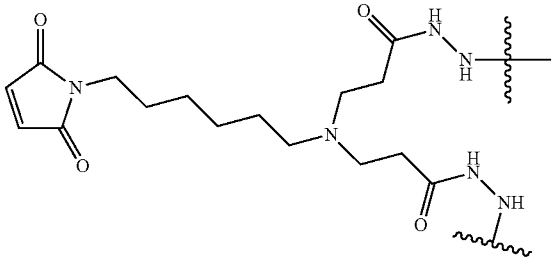
, -continued
R4-34
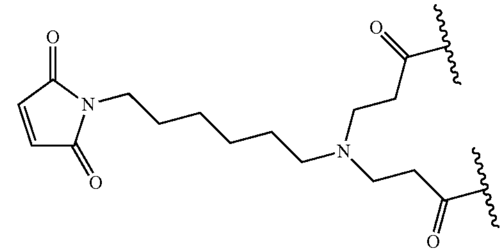
,
R4-35
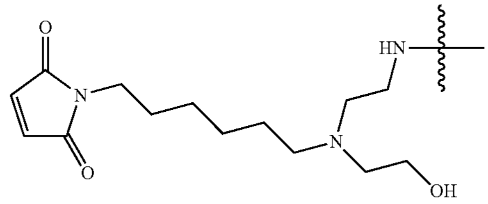
,
R4-36
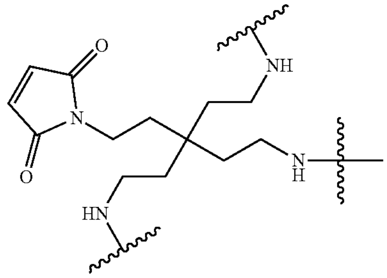
,
R4-37
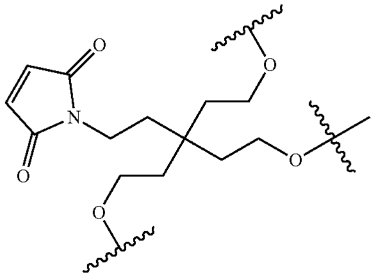
,
R4-38a
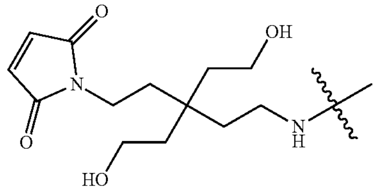
,
R4-38b
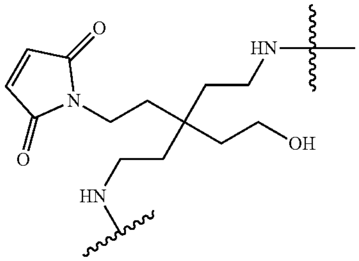
,
R4-39
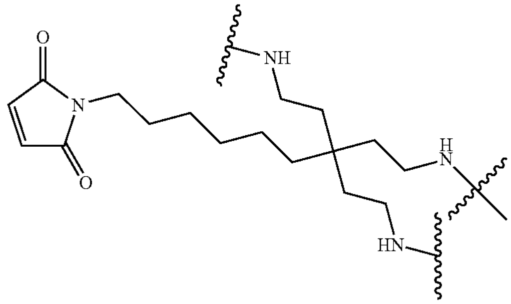
,
R4-40
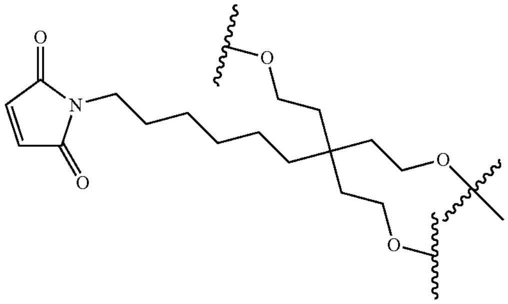
,
R4-41
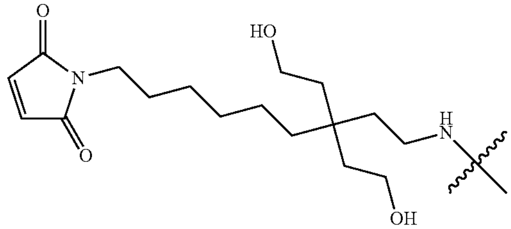
,
R4-42
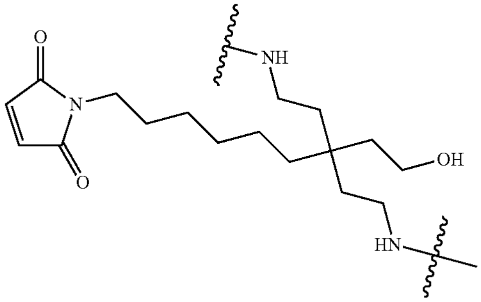
, -continued
R4-43
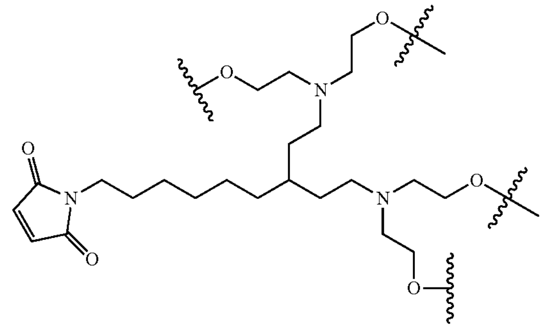
,
R4-44
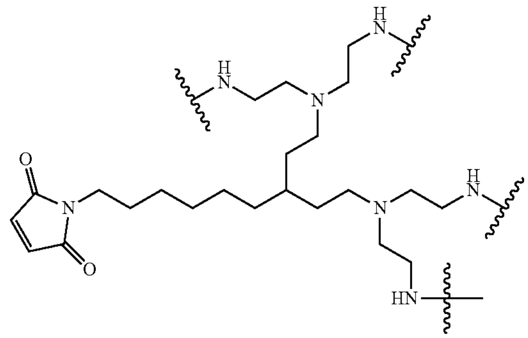
,
R4-45
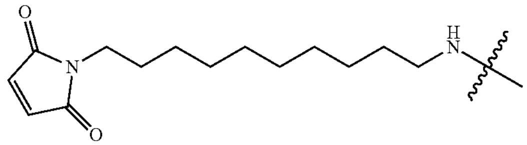
,
R4-46
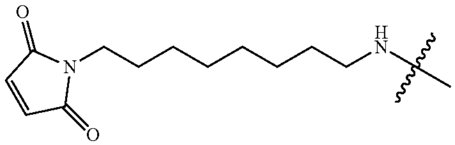
,
R4-47
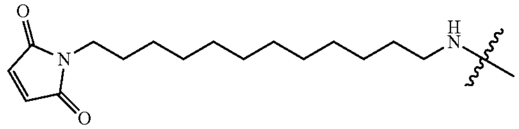
,
R4-48
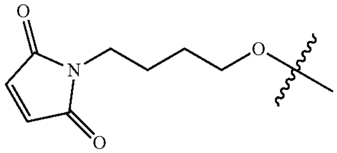
,
R4-49
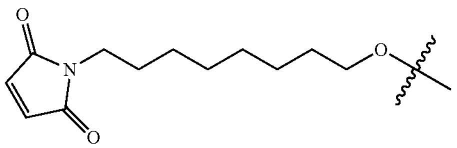
,
R4-50
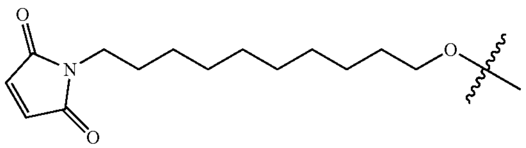
,
R4-51
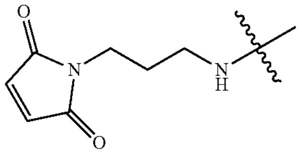
,
R4-52
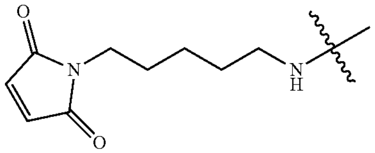
,
R4-53
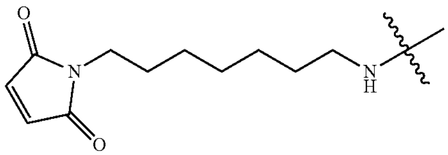
,
R4-54
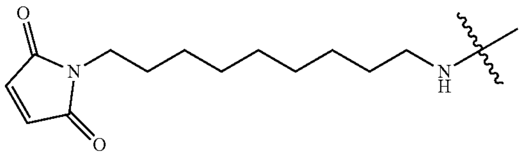
,
R4-55
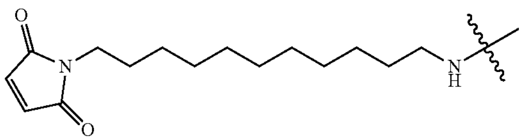
,
R4-56
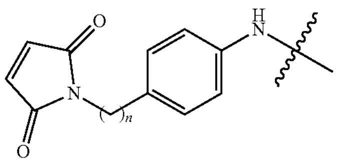
n = 1

-continued
R4-57
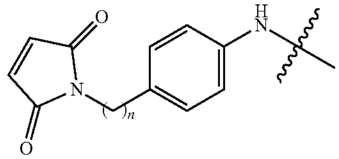
n = 2
R4-58
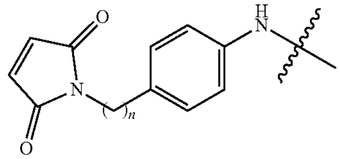
n = 3
R4-59
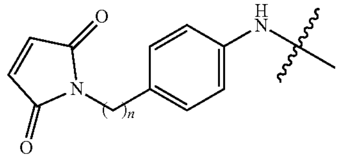,
n = 4
R4-60
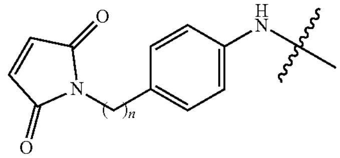,
n = 6
R4-61
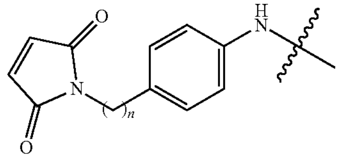,
n = 8
R4-62
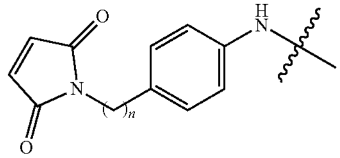,
n = 10
R4-63
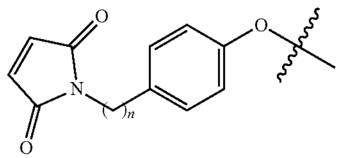,
n = 1
R4-64
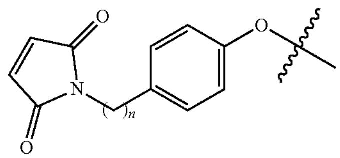,
n = 2
R4-65
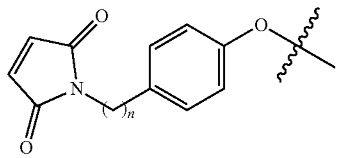,
n = 3
R4-66
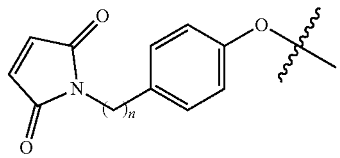,
n = 4
R4-67
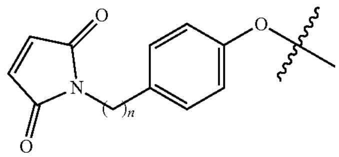,
n = 6
R4-68
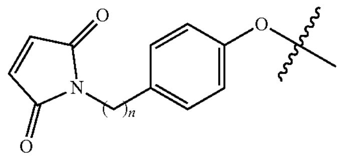,
n = 7
R4-69
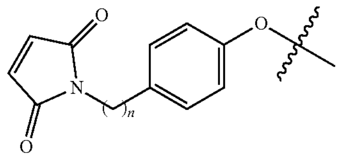,
n = 10
R4-70
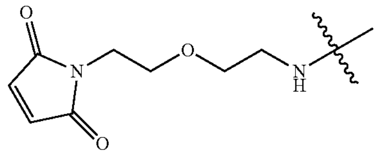,
R4-71
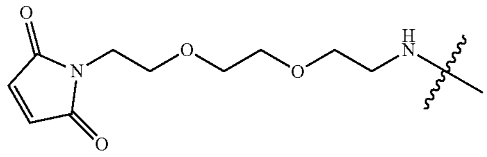,
R4-72
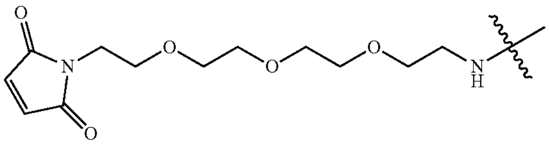, -continued

R4-73

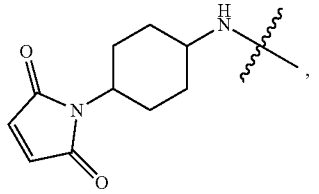

R4-74

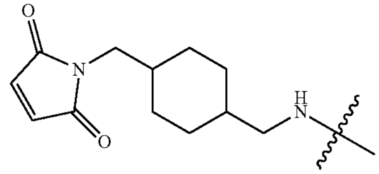

,

R4-75

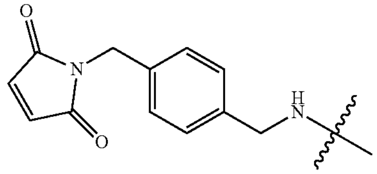

, and

R4-76

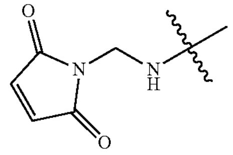

.

10. The conjugate of the biomolecule of claim 1, wherein R5 is a protein with one or more of its amino acids being mutated to cysteine, and R5 links to R4 via the thiol group of the cysteine;

R5 is an antibody with one or more of its amino acids being mutated to cysteine.

11. The conjugate of the biomolecule of claim 6, wherein R1-R2-R3-R4 is represented by any of the following structures:

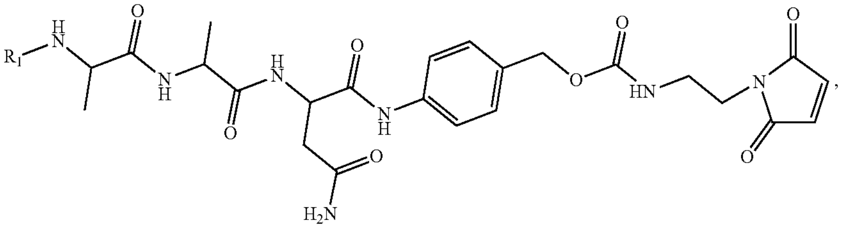

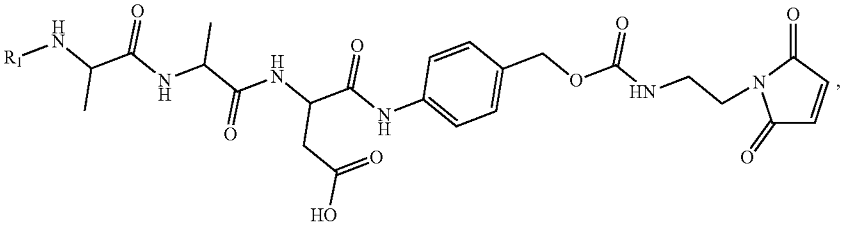

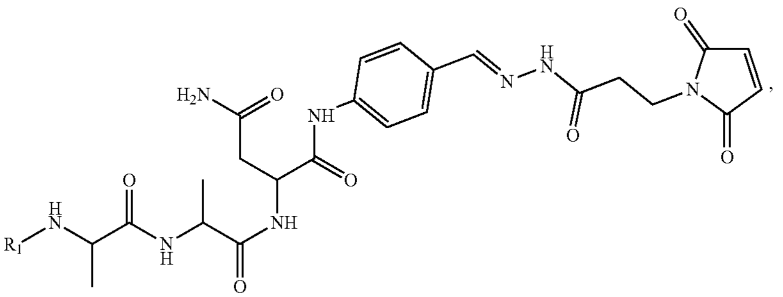

-continued
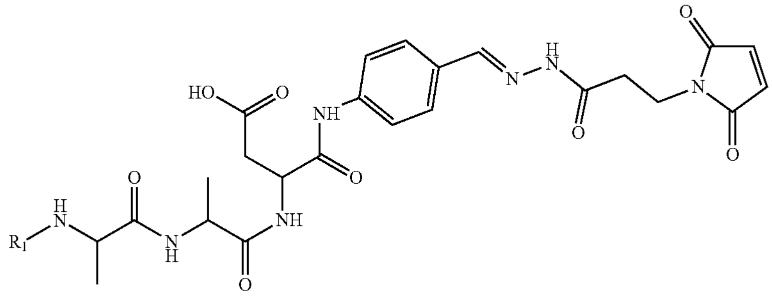
,
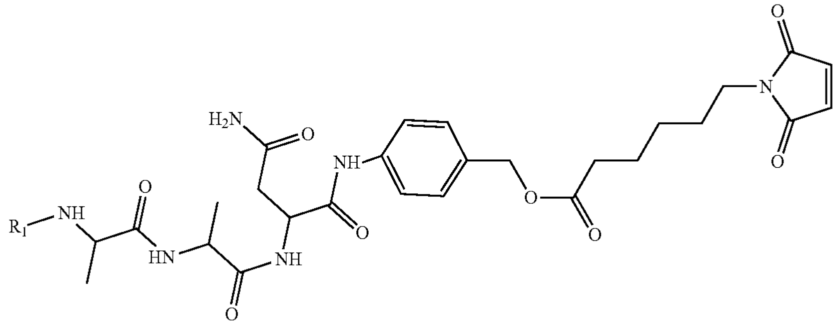
,
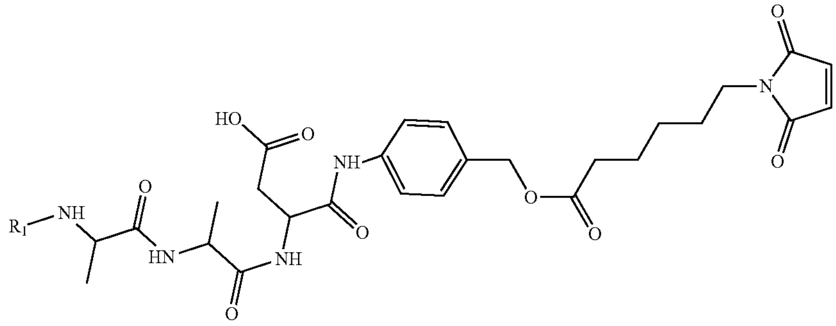
,
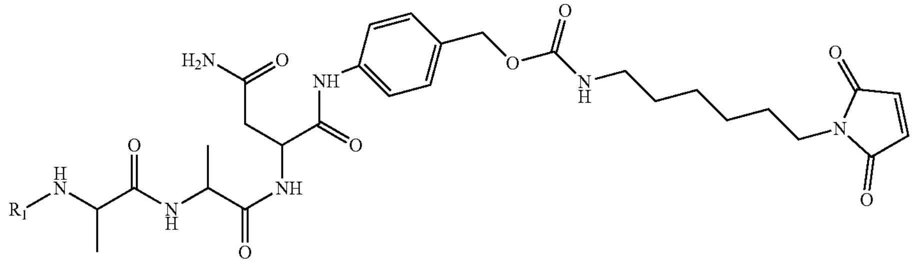
,
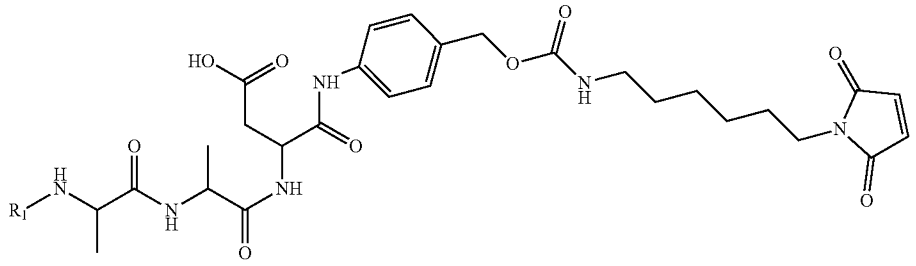
,
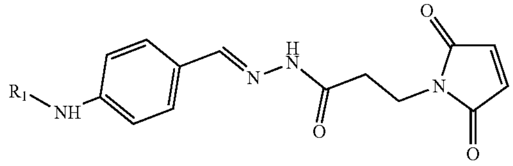
,
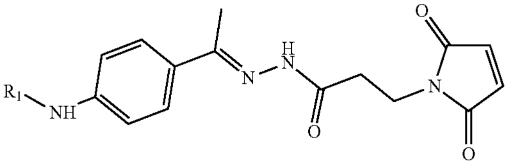
, -continued

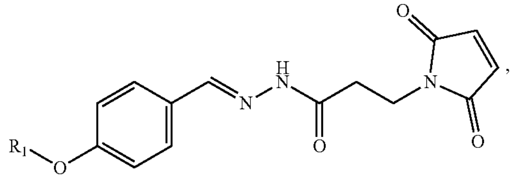

and

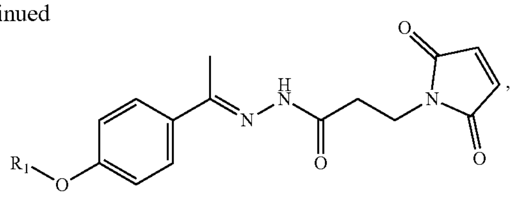

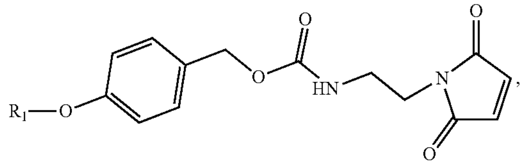

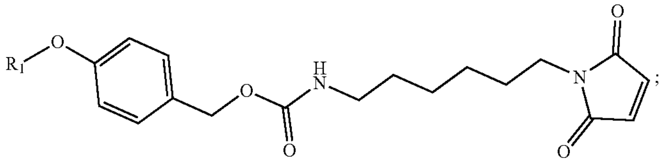

wherein R1 is defined as in claim 2 or 3.

12. The conjugate of the biomolecule of claim 1, wherein in the conjugate of biomolecule, R1-R2-R3-R4 is

S47

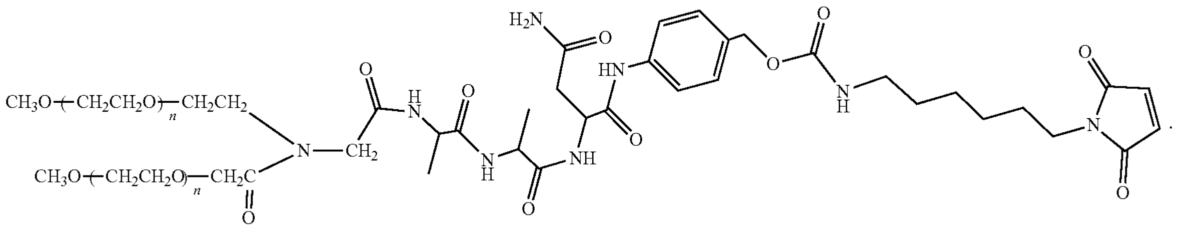

n = 528

13. A method for treating a tumor, comprising providing to a subject in need thereof a therapeutically effective amount of the conjugate of the biomolecule of claim 1.

14. The method of claim 13, wherein the tumor is a cancer in bladder, brain, breast, cervix, colon-rectum, esophagus, kidney, liver, lung, nasopharynx, pancreas, prostate, skin, stomach, uterus, ovary, testiculus or blood.

15. The conjugate of the biomolecule of claim 1, wherein R1-R2-R3-R4 of the structure are represented by:

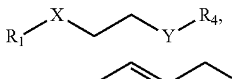

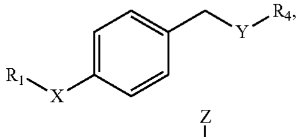

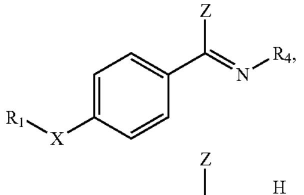

or

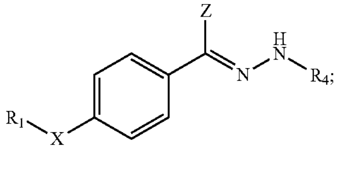

wherein X and Y are each independently NR' or O, Z is H or C1-10 alkyl, and R' is H or $C_{1-4}$alkyl; and wherein R1 links to X and R4 links to Y or N respectively in a linkage manner of amide, ester, carbamate, urea or hydrazone bond.

16. The conjugate of the biomolecule of claim 1, wherein R1-R2-R3-R4 of the structure are represented by:

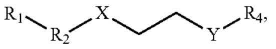

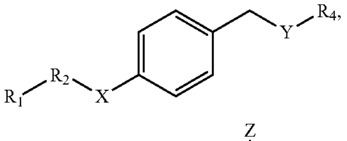

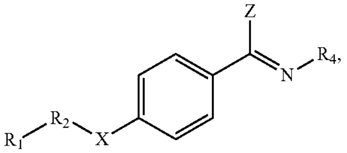

or

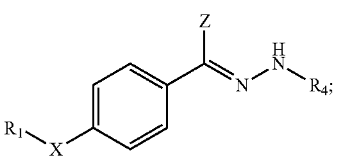

wherein X and Y are each independently NR' or O, Z is H or $C_{1-10}$ alkyl, and R' is H or $C_{1-4}$alkyl; and wherein R2 links to X and R4 links to Y or N respectively in a linkage manner of amide, ester, carbamate, urea or hydrazone bond.

17. A conjugate of a biomolecule of the structure:
S47
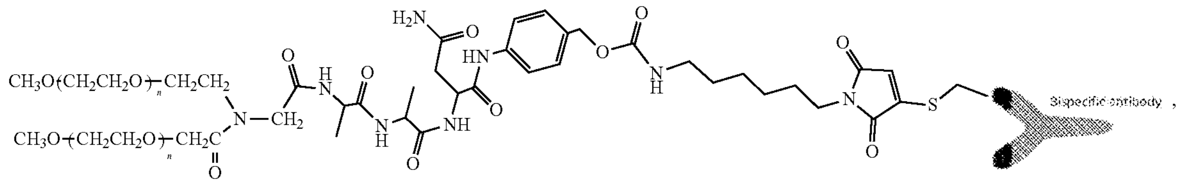
,
wherein antibody is selected from the group consisting of any of SEQ ID NO: 73, 74, 82 and 83.
* * * * *